(12) United States Patent
Bardiot et al.

(10) Patent No.: US 10,633,378 B2
(45) Date of Patent: Apr. 28, 2020

(54) VIRAL REPLICATION INHIBITORS

(71) Applicant: KATHOLIEKE UNIVERSITEIT LEUVEN, Leuven (BE)

(72) Inventors: Dorothée Bardiot, Leuven (BE); Gunter Carlens, Leuven (BE); Kai Dallmeier, Leuven (BE); Suzanne Kaptein, Leuven (BE); Mohamed Koukni, Leuven (BE); Arnaud Marchand, Leuven (BE); Johan Neyts, Leuven (BE); Wim Smets, Leuven (BE)

(73) Assignee: Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 14/777,765

(22) PCT Filed: Mar. 25, 2014

(86) PCT No.: PCT/EP2014/055946
§ 371 (c)(1),
(2) Date: Sep. 17, 2015

(87) PCT Pub. No.: WO2014/154682
PCT Pub. Date: Oct. 2, 2014

(65) Prior Publication Data
US 2016/0297810 A1  Oct. 13, 2016

Related U.S. Application Data

(60) Provisional application No. 61/805,054, filed on Mar. 25, 2013.

(30) Foreign Application Priority Data

Mar. 25, 2013 (GB) .................................. 1305376.4

(51) Int. Cl.
*C07D 471/04* (2006.01)
*C07D 401/14* (2006.01)
(Continued)

(52) U.S. Cl.
CPC ............ *C07D 471/04* (2013.01); *A61K 31/34* (2013.01); *A61K 31/381* (2013.01); *A61K 31/40* (2013.01); *A61K 31/415* (2013.01); *A61K 31/437* (2013.01); *A61K 31/4439* (2013.01); *A61K 45/06* (2013.01); *C07D 207/06* (2013.01); *C07D 207/323* (2013.01); *C07D 207/335* (2013.01); *C07D 211/06* (2013.01); *C07D 211/16* (2013.01); *C07D 223/04* (2013.01); *C07D 231/12* (2013.01); *C07D 241/04* (2013.01); *C07D 243/06* (2013.01); *C07D 243/08* (2013.01); *C07D 261/08* (2013.01); *C07D 263/32* (2013.01); *C07D 265/30* (2013.01); *C07D 267/10* (2013.01); *C07D 271/04* (2013.01); *C07D 271/08* (2013.01); *C07D 275/02* (2013.01); *C07D 277/28* (2013.01);
(Continued)

(58) Field of Classification Search
None
See application file for complete search history.

(56) References Cited

U.S. PATENT DOCUMENTS

2007/0167499 A1  7/2007  Stunkel et al.
2010/0048589 A1*  2/2010  Colburn ............... C07D 207/08
514/255.01
(Continued)

FOREIGN PATENT DOCUMENTS

| WO | 2010062821 A1 | 6/2010 |
| WO | 2011068715 A1 | 6/2011 |
| WO | 2012075908 A1 | 6/2012 |

OTHER PUBLICATIONS

PCT International Search Report dated Jul. 16, 2014 for PCT International Patent Application No. PCT/EP2014/055946, 5 pages.
(Continued)

*Primary Examiner* — Jared Barsky
(74) *Attorney, Agent, or Firm* — Amster, Rothenstein & Ebenstein LLP

(57) ABSTRACT

The present invention relates to a series of novel compounds, methods to prevent or treat viral infections in animals by using the novel compounds and to said novel compounds for use as a medicine, more preferably for use as a medicine to treat or prevent viral infections, particularly infections with RNA viruses, more particularly infections with viruses belonging to the family of the Flaviviridae, and yet more particularly infections with the Dengue virus. The present invention furthermore relates to pharmaceutical compositions or combination preparations of the novel compounds, to the compositions or preparations for use as a medicine, more preferably for the prevention or treatment of viral infections. The invention also relates to processes for preparation of the compounds.

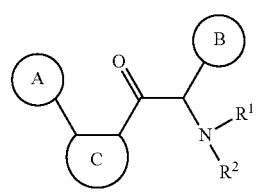

(A)

5 Claims, No Drawings
Specification includes a Sequence Listing.

(51) Int. Cl.
| | |
|---|---|
| C07D 405/14 | (2006.01) |
| C07D 413/14 | (2006.01) |
| C07D 223/04 | (2006.01) |
| C07D 231/12 | (2006.01) |
| C07D 333/22 | (2006.01) |
| C07D 401/04 | (2006.01) |
| C07D 401/06 | (2006.01) |
| C07D 403/04 | (2006.01) |
| C07D 405/04 | (2006.01) |
| C07D 405/06 | (2006.01) |
| C07D 409/04 | (2006.01) |
| C07D 409/06 | (2006.01) |
| C07D 409/14 | (2006.01) |
| C07D 413/04 | (2006.01) |
| C07D 413/06 | (2006.01) |
| C07D 417/04 | (2006.01) |
| C07D 417/06 | (2006.01) |
| C07D 417/12 | (2006.01) |
| C07D 417/14 | (2006.01) |
| C07D 261/08 | (2006.01) |
| C07D 207/06 | (2006.01) |
| C07D 265/30 | (2006.01) |
| C07D 267/10 | (2006.01) |
| C07D 275/02 | (2006.01) |
| C07D 498/04 | (2006.01) |
| C07D 279/12 | (2006.01) |
| A61K 31/415 | (2006.01) |
| C07D 409/12 | (2006.01) |
| A61K 31/34 | (2006.01) |
| A61K 31/381 | (2006.01) |
| A61K 31/40 | (2006.01) |
| C07D 207/323 | (2006.01) |
| C07D 403/06 | (2006.01) |
| C07D 405/12 | (2006.01) |
| C07D 407/06 | (2006.01) |
| C07D 271/04 | (2006.01) |
| C07D 285/06 | (2006.01) |
| A61K 31/4439 | (2006.01) |
| C07D 403/12 | (2006.01) |
| C07D 243/06 | (2006.01) |
| A61K 31/437 | (2006.01) |
| C07D 211/06 | (2006.01) |
| A61K 45/06 | (2006.01) |
| C07D 513/04 | (2006.01) |
| C07D 407/04 | (2006.01) |
| C07D 307/46 | (2006.01) |
| C07D 207/335 | (2006.01) |
| C07D 211/16 | (2006.01) |
| C07D 241/04 | (2006.01) |
| C07D 243/08 | (2006.01) |
| C07D 263/32 | (2006.01) |
| C07D 271/08 | (2006.01) |
| C07D 277/28 | (2006.01) |
| C07D 285/10 | (2006.01) |
| C07D 307/52 | (2006.01) |
| C07D 413/12 | (2006.01) |
| C07D 487/04 | (2006.01) |

(52) U.S. Cl.
CPC ......... *C07D 279/12* (2013.01); *C07D 285/06* (2013.01); *C07D 285/10* (2013.01); *C07D 307/46* (2013.01); *C07D 307/52* (2013.01); *C07D 333/22* (2013.01); *C07D 401/04* (2013.01); *C07D 401/06* (2013.01); *C07D 401/14* (2013.01); *C07D 403/04* (2013.01); *C07D 403/06* (2013.01); *C07D 403/12* (2013.01); *C07D 405/04* (2013.01); *C07D 405/06* (2013.01); *C07D 405/12* (2013.01); *C07D 405/14* (2013.01); *C07D 407/04* (2013.01); *C07D 407/06* (2013.01); *C07D 409/04* (2013.01); *C07D 409/06* (2013.01); *C07D 409/12* (2013.01); *C07D 409/14* (2013.01); *C07D 413/04* (2013.01); *C07D 413/06* (2013.01); *C07D 413/12* (2013.01); *C07D 413/14* (2013.01); *C07D 417/04* (2013.01); *C07D 417/06* (2013.01); *C07D 417/12* (2013.01); *C07D 417/14* (2013.01); *C07D 487/04* (2013.01); *C07D 498/04* (2013.01); *C07D 513/04* (2013.01); *Y02A 50/385* (2018.01); *Y02A 50/387* (2018.01)

(56) References Cited

U.S. PATENT DOCUMENTS

| | | |
|---|---|---|
| 2010/0215618 A1 | 8/2010 | Clive et al. |
| 2011/0224211 A1 | 9/2011 | Schmitz et al. |
| 2012/0136006 A1 | 5/2012 | Colburn et al. |
| 2013/0136719 A1 | 5/2013 | Chan Chun Kong et al. |
| 2013/0261139 A1 | 10/2013 | Zuo et al. |

OTHER PUBLICATIONS

PCT Notification Concerning Transmittal of International Preliminary Report on Patentability and Written Opinion of the International Searching Authority, dated Sep. 29, 2015 in connection with PCT International Patent Application No. PCT/EP2014/055946, 7 pages.

Examination Report dated Dec. 31, 2028 in connection with Indian Application No. 9801/DELNP/2015.

* cited by examiner

SEQUENCE LISTING

<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: DENV-For primer

<400> SEQUENCE: 1
tcggagccgg agtttacaaa					20

<210> SEQ ID NO 2
<211> LENGTH: 20
<212> TYPE: DNA
<213> ORGANISM: Artificial
<220> FEATURE:
<223> OTHER INFORMATION: DENV-Rev primer

<400> SEQUENCE: 2
tcttaacgtc cgcccatgat					20

<210> SEQ ID NO 3
<211> LENGTH: 19
<212> TYPE: DNA
<213> ORGANISM: Artificial
<220> FEATURE:
<223> OTHER INFORMATION: DENV probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (19)..(19)
<223> OTHER INFORMATION: minor groove binder

<400> SEQUENCE: 3
attccacaca atgtggcat					19

<210> SEQ ID NO 4
<211> LENGTH: 23
<212> TYPE: DNA
<213> ORGANISM: Artificial
<220> FEATURE:
<223> OTHER INFORMATION: DenS primer

<400> SEQUENCE: 4
ggatagacca gagatcctgc tgt					23

<210> SEQ ID NO 5
<211> LENGTH: 20
<212> TYPE: DNA
<213> ORGANISM: Artificial
<220> FEATURE:
<223> OTHER INFORMATION: DenAS1-3 primer

<400> SEQUENCE: 5
cattccattt tctggcgttc					20

<210> SEQ ID NO 6
<211> LENGTH: 20
<212> TYPE: DNA
<213> ORGANISM: Artificial
<220> FEATURE:
<223> OTHER INFORMATION: DenAS4 primer

<400> SEQUENCE: 6

```
caatccatct tgcggcgctc                                               20

<210> SEQ ID NO 7
<211> LENGTH: 20
<212> TYPE: DNA
<213> ORGANISM: Artificial
<220> FEATURE:
<223> OTHER INFORMATION: DEN_1-3 probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (20)..(20)
<223> OTHER INFORMATION: minor groove binder

<400> SEQUENCE: 7
cagcatcatt ccaggcacag                                               20

<210> SEQ ID NO 8
<211> LENGTH: 20
<212> TYPE: DNA
<213> ORGANISM: Artificial
<220> FEATURE:
<223> OTHER INFORMATION: DEN_4 probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (20)..(20)
<223> OTHER INFORMATION: minor groove binder

<400> SEQUENCE: 8
caacatcaat ccaggcacag                                               20

<210> SEQ ID NO 9
<211> LENGTH: 23
<212> TYPE: DNA
<213> ORGANISM: Artificial
<220> FEATURE:
<223> OTHER INFORMATION: YFV-For primer

<400> SEQUENCE: 9
tggcatattc cagtcaacct tct                                           23

<210> SEQ ID NO 10
<211> LENGTH: 22
<212> TYPE: DNA
<213> ORGANISM: Artificial
<220> FEATURE:
<223> OTHER INFORMATION: YFV-Rev primer

<400> SEQUENCE: 10
gaagcccaag atggaatcaa ct                                            22

<210> SEQ ID NO 11
<211> LENGTH: 19
<212> TYPE: DNA
<213> ORGANISM: Artificial
<220> FEATURE:
<223> OTHER INFORMATION: YFV-probe
<220> FEATURE:
<221> NAME/KEY: misc_feature
<222> LOCATION: (1)..(1)
<223> OTHER INFORMATION: 6-carboxyfluorescein
<220> FEATURE:
```

```
<221> NAME/KEY: misc_feature
<222> LOCATION: (19)..(19)
<223> OTHER INFORMATION: minor groove binder

<400> SEQUENCE: 11
ttccacacaa tgtggcatg                                     19
```

VIRAL REPLICATION INHIBITORS

CROSS-REFERENCE TO RELATED APPLICATIONS

This application is a U.S. national stage entry under 35 U.S.C. § 371 of PCT International Patent Application No. PCT/EP2014/055946, filed Mar. 25, 2014, which claims priority to Great Britain Application No. 1305376.4, filed Mar. 25, 2013 and the benefit of U.S. Provisional Patent Application No. 61/805,054, filed Mar. 25, 2013, the contents of which are incorporated herein by reference in their entirety.

FIELD OF THE INVENTION

The present invention relates to a series of novel compounds, methods to prevent or treat viral infections in animals by using the novel compounds and to said novel compounds for use as a medicine, more preferably for use as a medicine to treat or prevent viral infections, particularly infections with RNA viruses, more particularly infections with viruses belonging to the family of the Flaviviridae, and yet more particularly infections with the Dengue virus. The present invention furthermore relates to pharmaceutical compositions or combination preparations of the novel compounds, to the compositions or preparations for use as a medicine, more preferably for the prevention or treatment of viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known (DENV-1, -2, -3, and -4). Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control dengue disease, the only available methods at present are mosquito eradication strategies to control the vector. Although progress is being made in the development of vaccines for dengue, many difficulties are encountered. These include the existence of a phenomenon referred to as antibody-dependent enhancement (ADE).

Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titres. In both primary and secondary infections, higher viral titres are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyperendemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north. According to the United States (US) Centers for Disease Control and Prevention (CDC), both mosquitoes are currently omnipresent in southern Texas. The spread north of dengue-carrying mosquitoes is not confined to the US, but has also been observed in Europe.

Despite large efforts over the past 3 decades, there is currently no vaccine available to protect against dengue virus disease. The main problem is to develop a vaccine that offers protection against all four serotypes (a tetravalent vaccine) to the same extent. Furthermore, today, specific antiviral drugs for the treatment or prevention of dengue fever virus infection are not available. Clearly, there is still a great need for therapeutics for the prevention or treatment of viral infections in animals, more in particular in humans and especially for viral infections caused by Flaviviruses, more in particular Dengue virus. Therapeutics with good potency, no or low levels of less side-effects, a broad spectrum activity against multiple Dengue virus serotypes, a low toxicity and/or good pharmacokinetic or dynamic properties are very welcome. The present invention provides novel compounds which show activity against Flaviviruses, including Dengue virus. The prior art does not lead a person skilled in the art to the compounds of the present invention, nor to their use as antiviral compounds.

SUMMARY OF THE INVENTION

The present invention is based on the unexpected finding that at least one of the above-mentioned problems can be solved by a novel class of compounds.

The present invention provides new compounds which have been shown to possess antiviral activity. The present invention furthermore demonstrates that these compounds efficiently inhibit proliferation of viruses, especially Flaviviruses, more specifically Dengue virus (DENV) and Yellow Fever virus (YFV). Therefore, these compounds constitute a useful class of new potent compounds that can be used in the treatment and/or prevention of viral infections in animals, mammals and humans, more specifically for the treatment and/or prevention of infections with viruses belonging to the family of the Flaviviruses, and yet more particularly infections with Dengue viruses or yellow fever virus.

The present invention furthermore relates to the use of such compounds as medicines and to their use for the manufacture of medicaments for treating and/or preventing viral infections, in particular with viruses belonging to the family of the Flaviviruses, and yet more particularly infections with Dengue viruses or yellow fever virus, in animals or mammals, more in particular in humans. The present invention therefore relates to the compounds for use as medicines and to the compounds for use as medicaments for treating and/or preventing viral infections, in particular with viruses belonging to the family of the Flaviviruses, and yet more particularly infections with Dengue viruses or yellow fever virus, in animals or mammals, more in particular in humans. The invention also relates to methods for the preparation of all such compounds and to pharmaceutical compositions comprising them in an effective amount.

The present invention also relates to a method of treatment or prevention of viral infections in humans by the administration of one or more such compounds, optionally in combination with one or more other medicines, to a patient in need thereof. Particularly, the present invention also relates to a method of treatment or prevention of viral infections, especially Flaviviral infections, in humans by the administration of an effective amount of one or more such compounds or a pharmaceutically acceptable salt thereof, optionally in combination with one or more other medicines, to a patient in need thereof. More particularly, the present invention also relates to a method of treatment or prevention of infections by the Dengue virus or yellow fever virus in humans by the administration of an effective amount of one or more such compounds or a pharmaceutically acceptable salt thereof, optionally in combination with one or more other medicines, to a patient in need thereof.

One aspect of the invention is the provision of new compounds of formula (A),

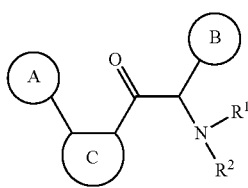

(A)

wherein,
cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, —NH$_2$, NH(alkyl), or N(alkyl)$_2$;
cycle C is a monocycle selected from

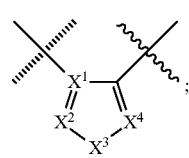

(a1)

(a2)

(a3)

wherein the wavy line ( $\sim$ ) indicates the point of attachment to the carbonyl of the main formula (A) and the hashed line ( $\|\|\|$ ) indicates the point of attachment to the cycle A of the main formula (A);
$X^1$ is selected from C; and N;
$X^2$ is selected from $CR^{12}$; $NR^{13}$; N; O; and S;
$X^3$ is selected from $CR^{14}$; $NR^{15}$; N; O; and S;
$X^4$ is selected from $CR^{16}$; $NR^{17}$; N; O; and S;
each $R^3$ and $R^9$ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;
each $R^4$ and $R^5$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;
$W^1$ is selected from $CR^{32}R^{32a}$; $NR^{33}$; O; S; and SO$_2$;
each p and q is independently selected from 1 and 2, whereby p+q is selected from 2 and 3;
cycle B is selected from aryl; and heterocycle; wherein said aryl and heterocycle can be unsubstituted or substituted with one or more $Z^{1a}$;
$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;
and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;
$R^2$ is selected from hydrogen; alkyl; cycloalkyl; alkenyl; cycloalkenyl; alkynyl; cycloalkynyl; heteroalkyl; heteroalkenyl; and heteroalkynyl;

and wherein said alkyl, cycloalkyl; alkenyl; cycloalkenyl; alkynyl; cycloalkynyl; heteroalkyl, heteroalkenyl, and heteroalkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)$Z^3$; —S(O)$_2Z^3$; —S(O)$_2$NZ$^4Z^5$; trifluoromethyl; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)$Z^3$; —S(O)$_2Z^3$; —S(O)$_2$NZ$^4Z^5$; trifluoromethyl; trifluoromethoxy; nitro; —NZ$^4Z^5$; —NZ$^4$S(O)$_2Z^2$; —NZ$^4$C(O)$Z^2$; —NZ$^4$C(O)NZ$^4Z^5$; cyano; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O) OH or NH$_2$;

each $Z^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein Z$^4$ and Z$^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof.

Preferably, the invention provides a compound of formula (A), wherein, cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, —NH$_2$, NH(alkyl), or N(alkyl)$_2$;

cycle C is a monocycle selected from

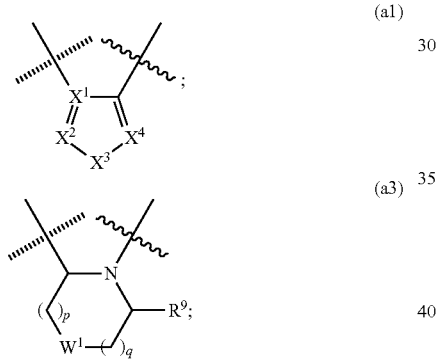

(a1)

(a3)

wherein the wavy line ($\sim$) indicates the point of attachment to the carbonyl of the main formula (A) and the hashed line ($\shortmid\shortmid\shortmid\shortmid$) indicates the point of attachment to the cycle A of the main formula (A);

X$^1$ is selected from C; and N;
X$^2$ is selected from CR$^{12}$; NR$^{13}$; N; O; and S;
X$^3$ is selected from CR$^{14}$; NR$^{15}$; N; O; and S;
X$^4$ is selected from CR$^{16}$; NR$^{17}$; N; O; and S;
each R$^9$ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;
W$^1$ is selected from CR$^{32}$R$^{32a}$; NR$^{33}$; O; S; and SO$_2$;
each p and q is independently selected from 1 and 2, whereby p+q is selected from 2 and 3;
cycle B is selected from aryl; and heterocycle; wherein said aryl and heterocycle can be unsubstituted or substituted with one or more Z$^{1a}$;
R$^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;
and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more Z$^{1b}$;
R$^2$ is selected from hydrogen; alkyl; cycloalkyl; alkenyl; cycloalkenyl; alkynyl; cycloalkynyl; heteroalkyl; heteroalkenyl; and heteroalkynyl;
and wherein said alkyl, cycloalkyl, alkenyl, cycloalkenyl, alkynyl, cycloalkynyl, heteroalkyl, heteroalkenyl, and heteroalkynyl, can be unsubstituted or substituted with one or more Z$^{1c}$;
each R$^{12}$, R$^{14}$, and R$^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;
wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;
R$^{13}$, R$^{15}$, and R$^{17}$ is independently selected from hydrogen; hydroxyl; sulfhydryl; —S(O)Z$^2$; —S(O)$_2$Z$^3$; —S(O)$_2$NZ$^4$Z$^5$; trifluoromethyl; —C(O)Z$^3$; —C(O)OZ$^2$; —C(O)NZ$^4$Z$^5$; —C(O)H; alkyl; cycloalkyl; alkenyl; cycloalkenyl; alkynyl; cycloalkynyl; heteroalkyl; heteroalkenyl; heteroalkynyl;
wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;
each R$^{32}$ and R$^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl;
and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;
each R$^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;
each Z$^{1a}$, Z$^{1b}$, and Z$^{1c}$ is independently selected from the group consisting of halogen; hydroxyl; sulfhydryl; —OZ$^2$; =O; —SZ$^2$; =S; —S(O)Z$^2$; —S(O)$_2$Z$^3$;

—S(O)$_2$NZ$^4$Z$^5$; trifluoromethyl; trifluoromethoxy; nitro; —NZ$^4$Z$^5$; —NZ$^4$S(O)$_2$Z$^2$; —NZ$^4$C(O)Z$^2$; —NZ$^4$C(O)NZ$^4$Z$^5$; cyano; —C(O)Z$^3$; —C(O)OZ$^2$; —C(O)NZ$^4$Z$^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each Z$^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each Z$^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each Z$^4$ and Z$^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein Z$^4$ and Z$^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof, with the proviso that said compound is not 2-anilino-2-(4-tert-butylphenyl)-1-(2-phenyl-1-piperidyl)ethanone;

2-anilino-1-(2-phenyl-1-piperidyl)-2-[4-(trifluoromethyl)phenyl]ethanone;

2-anilino-2-(4-tert-butylphenyl)-1-(2-phenylazepan-1-yl)ethanone.

DETAILED DESCRIPTION OF THE INVENTION

The present invention will be described with respect to particular embodiments but the invention is not limited thereto.

Preferred statements (features) and embodiments of the compounds and processes of this invention are set herein. Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Numbered statements of this invention are:
1. A compound of formula (A),

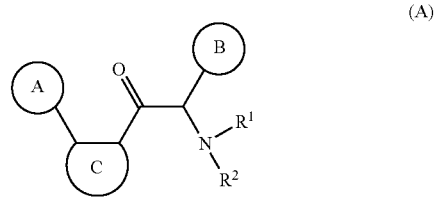

wherein,
cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, —NH$_2$, NH(alkyl), or N(alkyl)$_2$;

cycle C is a monocycle selected from

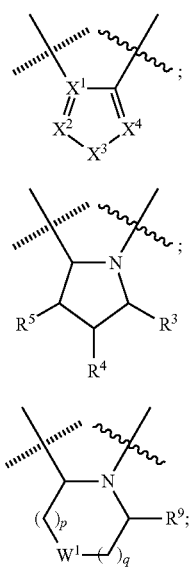

wherein the wavy line ( ∿ ) indicates the point of attachment to the carbonyl of the main formula (A) and the hashed line ( ⫶⫶⫶ ) indicates the point of attachment to the cycle A of the main formula (A);

$X^1$ is selected from C; and N;
$X^2$ is selected from $CR^{12}$; $NR^{13}$; N; O; and S;
$X^3$ is selected from $CR^{14}$; $NR^{15}$; N; O; and S;
$X^4$ is selected from $CR^{16}$; $NR^{17}$; N; O; and S;

each $R^3$ and $R^9$ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;

each $R^4$ and $R^5$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

$W^1$ is selected from $CR^{32}R^{32a}$; $NR^{33}$; O; S; and SO$_2$;

each p and q is independently selected from 1 and 2, whereby p+q is selected from 2 and 3;

cycle B is selected from aryl; and heterocycle; wherein said aryl and heterocycle can be unsubstituted or substituted with one or more $Z^{1a}$;

$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;

$R^2$ is selected from hydrogen; alkyl; cycloalkyl; alkenyl; cycloalkenyl; alkynyl; cycloalkynyl; heteroalkyl; heteroalkenyl; and heteroalkynyl;

and wherein said alkyl, cycloalkyl; alkenyl; cycloalkenyl; alkynyl; cycloalkynyl; heteroalkyl, heteroalkenyl, and heteroalkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)$Z^2$; —S(O)$_2Z^3$; —S(O)$_2NZ^4Z^5$; trifluoromethyl; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)$Z^2$; —S(O)$_2Z^3$;

—S(O)$_2$NZ$^4$Z$^5$; trifluoromethyl; trifluoromethoxy; nitro; —NZ$^4$Z$^5$; —NZ$^4$S(O)$_2$Z$^2$; —NZ$^4$C(O)Z$^2$; —NZ$^4$C(O)NZ$^4$Z$^5$; cyano; —C(O)Z$^3$; —C(O)OZ$^2$; —C(O)NZ$^4$Z$^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each Z$^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each Z$^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each Z$^4$ and Z$^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein Z$^4$ and Z$^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof.

2. The compound according to statement 1, wherein cycle C is selected from the following group of cycles

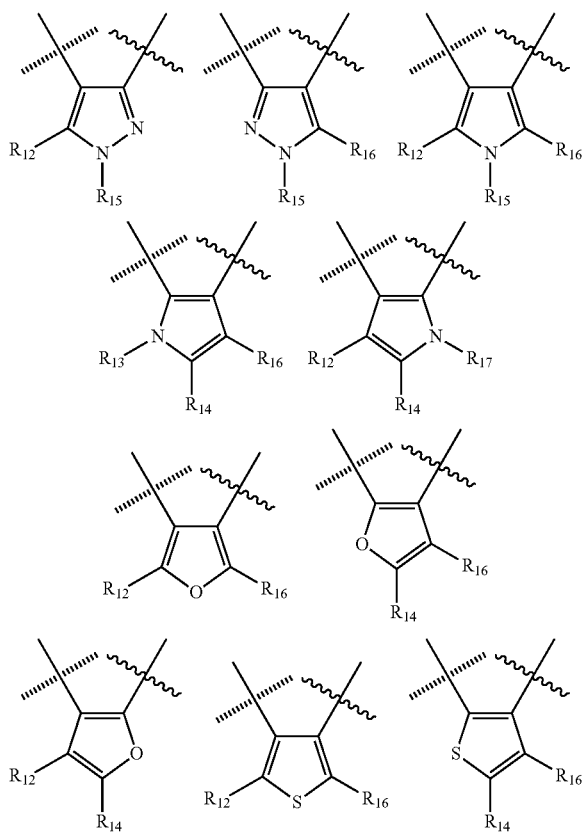

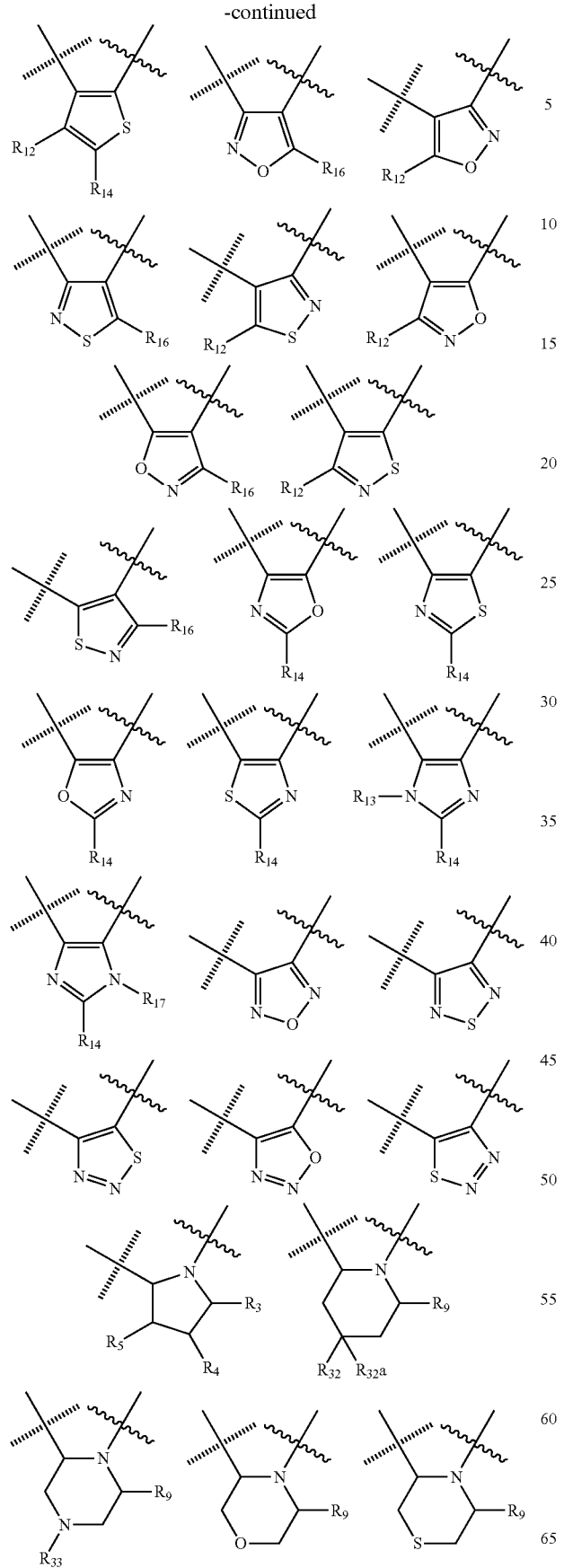
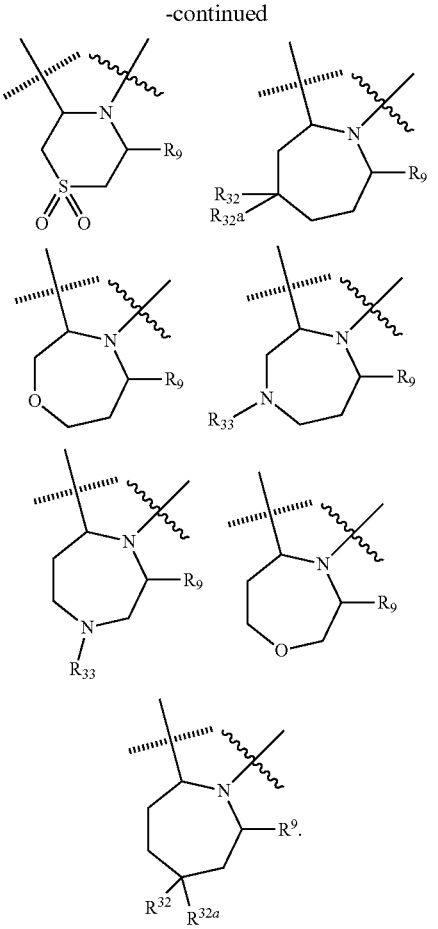
3. The compounds of according to statement 1 or 2, wherein cycle C is selected from the following group of cycles
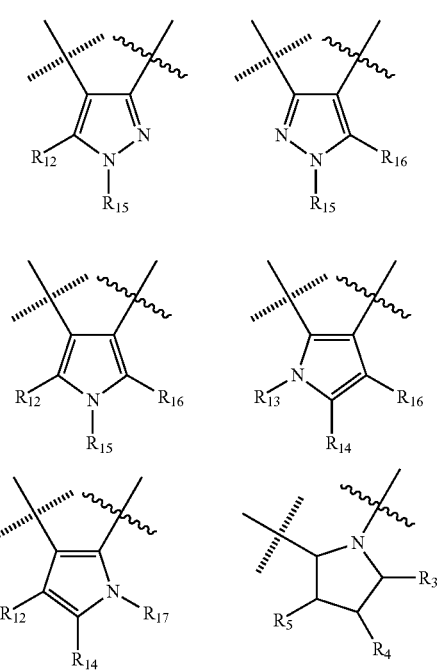

-continued
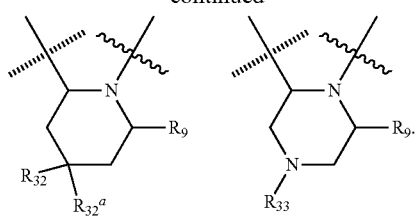
4. The compounds according to any one of statements 1 to 3, selected from the compounds of formula (C1), (C2), (C3), (C4), and (C5),
(C1)
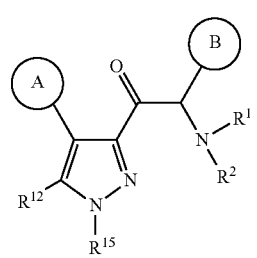
(C2)
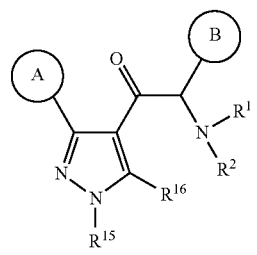
(C3)
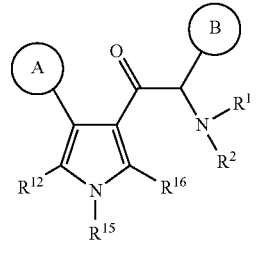
(C4)
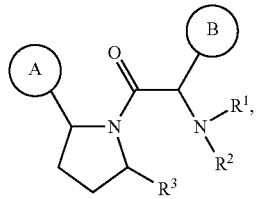
(C5)
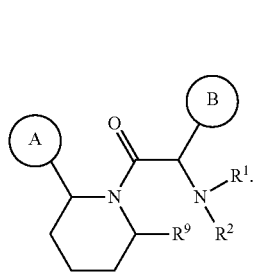
5. The compounds of according to statement 1, wherein, cycle C is a monocycle selected from
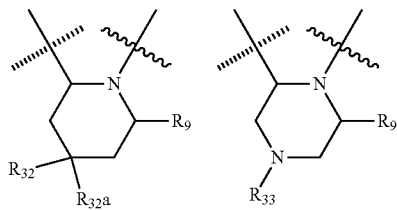
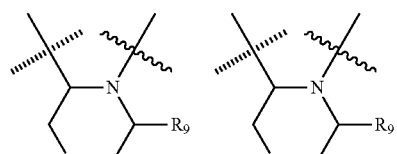
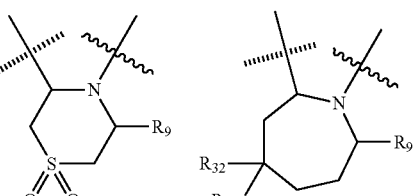
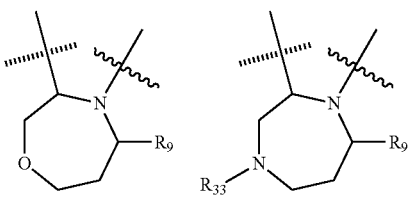
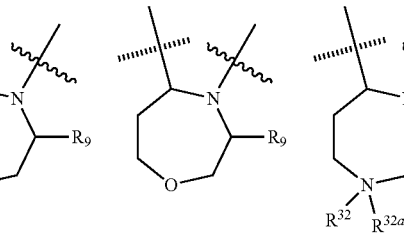
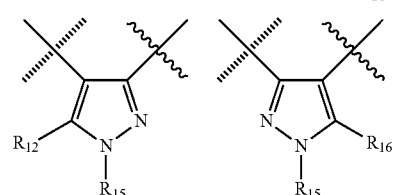
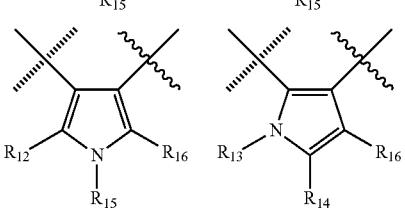
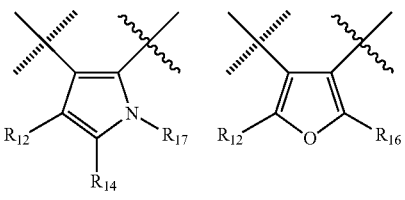

-continued

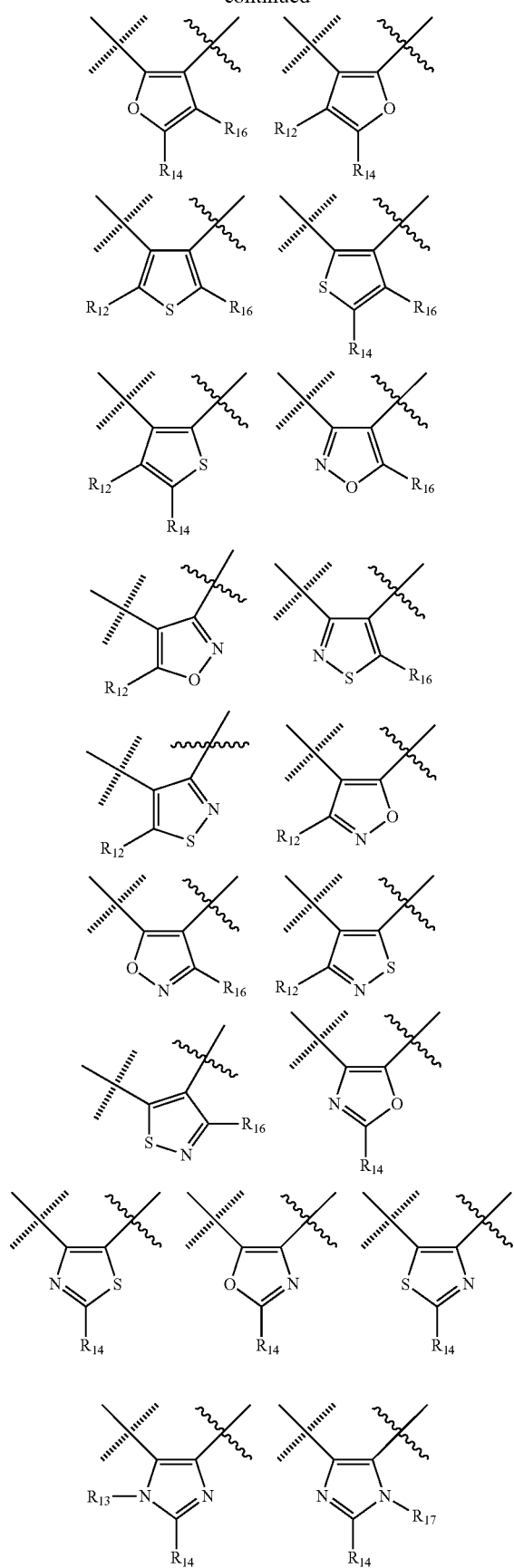
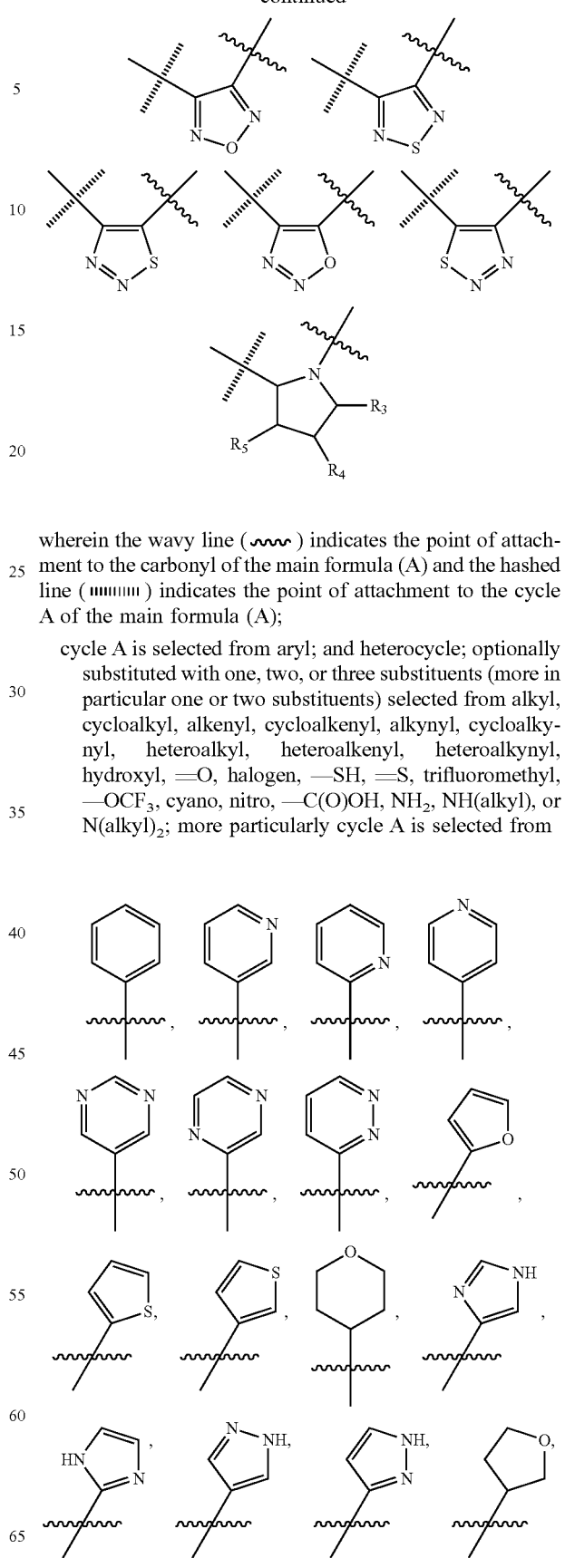

wherein the wavy line ( ~ ) indicates the point of attachment to the carbonyl of the main formula (A) and the hashed line ( ⦀ ) indicates the point of attachment to the cycle A of the main formula (A);

cycle A is selected from aryl; and heterocycle; optionally substituted with one, two, or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$; more particularly cycle A is selected from

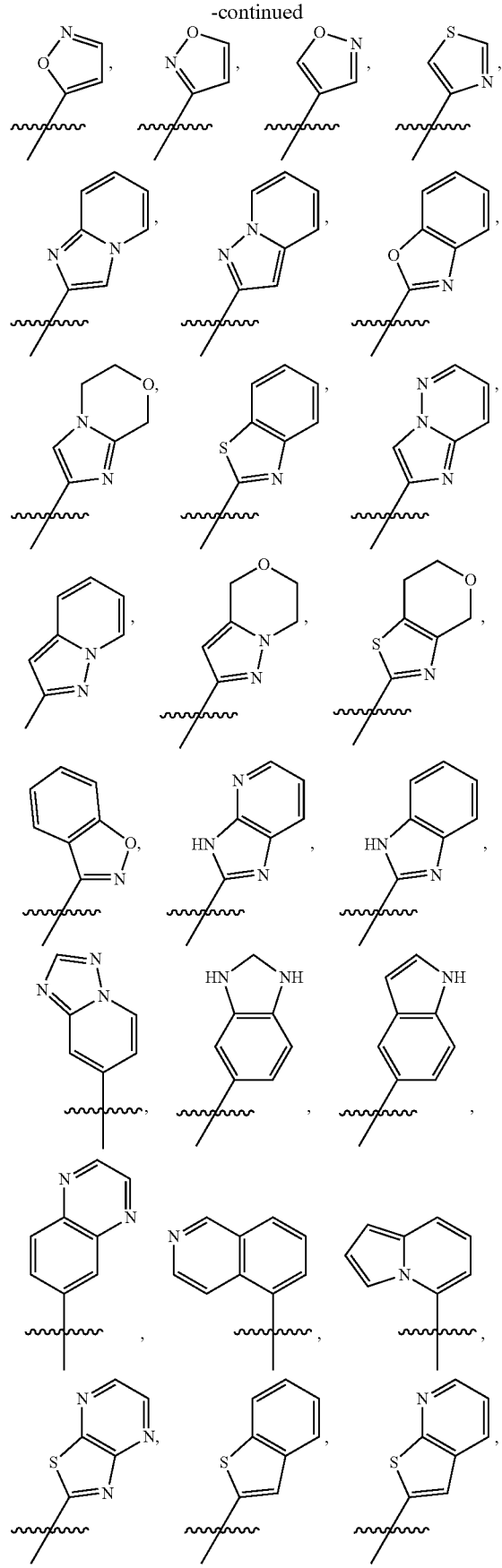

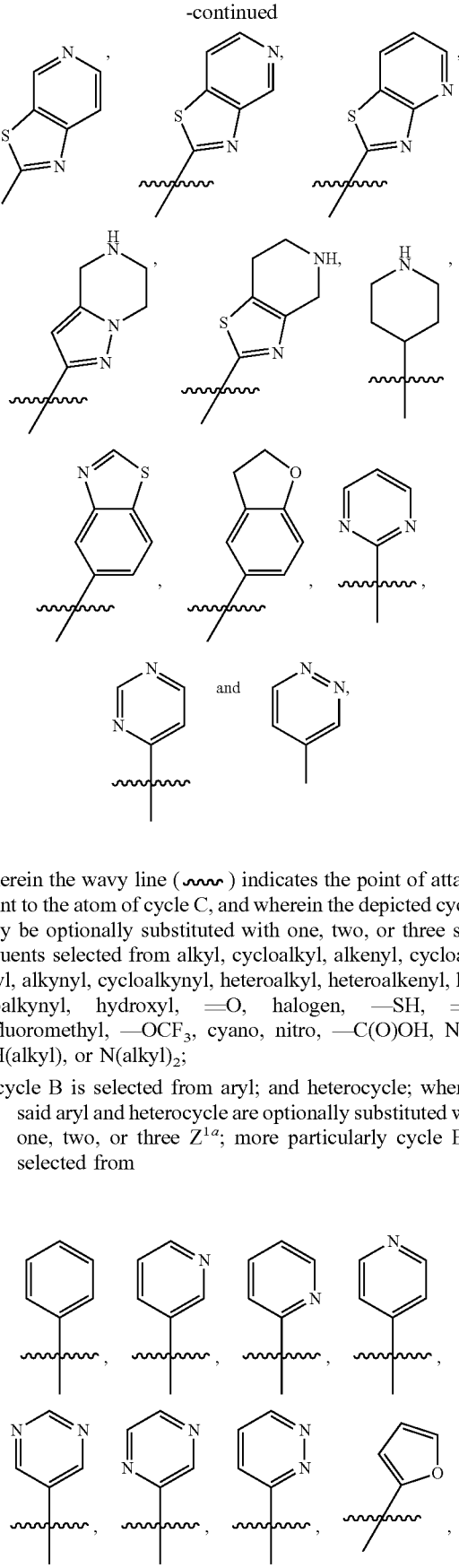

wherein the wavy line (∿∿∿) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$;

cycle B is selected from aryl; and heterocycle; wherein said aryl and heterocycle are optionally substituted with one, two, or three Z$^{1a}$; more particularly cycle B is selected from

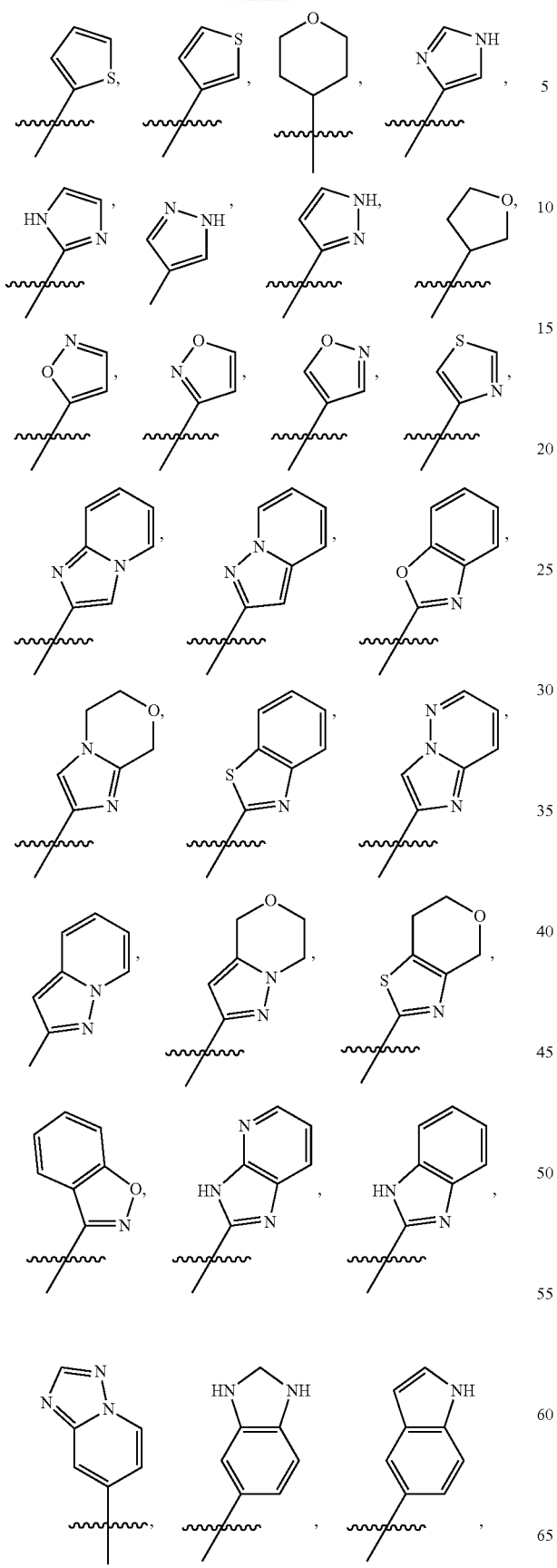
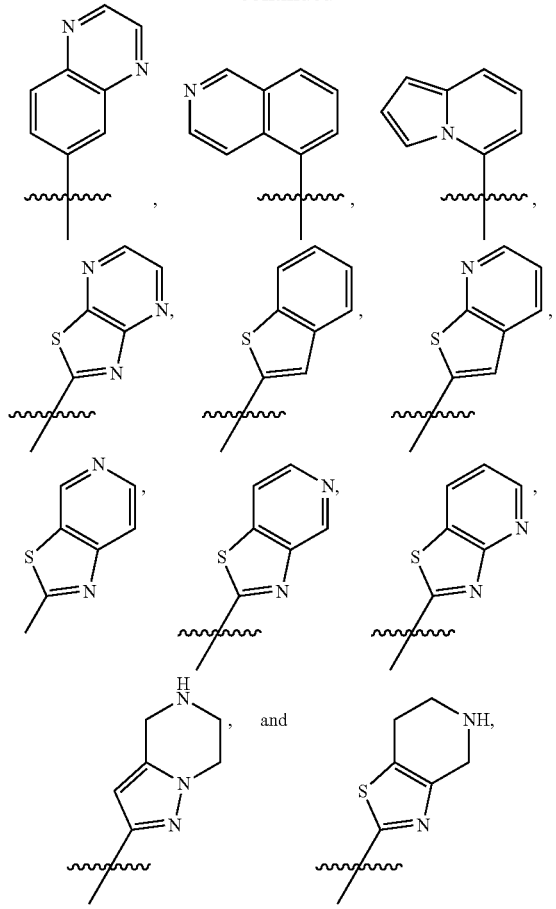

wherein the wavy line (⁓) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$ alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$ alkynyl, arylhetero$C_{1-6}$alkyl, arylhetero$C_{2-6}$ alkenyl, arylhetero$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$ alkenyl, and hetero$C_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$ alkynyl, are optionally substituted with one, two, or three $Z^{1c}$; preferably said $C_{1-6}$alkyl is optionally substituted with one, two, or three $Z^{1c}$;

$R^3$ is selected from hydrogen; $C_{1-6}$alkyl; heteroC$_{1-6}$alkyl; and =O;

each $R^4$ and $R^5$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; heteroC$_{1-6}$alkyl; heteroC$_{1-6}$alkenyl; and heteroC$_{1-6}$alkynyl;

$R^9$ is selected from hydrogen; $C_{1-6}$alkyl; heteroC$_{1-6}$alkyl; and =O;

each of $R^{12}$, $R^{14}$ and $R^{16}$ is independently selected from hydrogen; halogen; trifluoromethyl; cyano; $C_{1-6}$alkyl and $C_{1-6}$cycloalkyl;

each $R^{13}$, $R^{15}$ and $R^{17}$ is independently selected from hydrogen; $C_{1-6}$alkyl; and $C_{1-6}$cycloalkyl;

each $R^{32}$ and $R^{32a}$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero $C_{1-6}$alkyl; heteroC$_{2-6}$alkenyl; and hetero $C_{2-6}$alkynyl;

$R^{33}$ is independently selected from hydrogen and $C_{1-6}$alkyl;

each $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^1$, $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)$_2$Z$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, heteroC$_{1-6}$alkyl, aryl, heterocycle, and heterocycle-C$_{1-6}$alkyl; more preferably each $Z^1$, $Z^{1a}$, $Z^{1b}$, and $Z^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, $C_{1-6}$alkyl, heteroC$_{1-6}$alkyl, aryl, heterocycle, and heterocycle-C$_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, aryl heteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl; preferably said $C_{1-6}$alkyl, heteroC$_{1-6}$ alkyl, aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$ alkyl, —NH$_2$, —NHCH$_3$; —N(CH$_3$)$_2$, —NH—C (=O)O—C$_{1-4}$alkyl, morpholinyl, —S(O)$_2$C$_{1-4}$alkyl, and —O—C$_{1-6}$alkyl; more preferably said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$ C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-C$_{1-6}$alkyl; more preferably $Z^2$ is independently selected from $C_{1-6}$alkyl, aryl, and heterocycle-C$_{1-6}$alkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$ alkenyl, arylheteroC$_{2-6}$alkynyl, heterocycle-C$_{1-6}$ alkyl, heterocycle-C$_{2-6}$alkenyl, heterocycle-C$_{2-6}$ alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; preferably said $C_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$alkyl, —OCF$_3$, —S(=O)$_2$ C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^3$ is independently selected from hydroxyl, C$_{1-6}$alkyl, aryl, and heterocycle; more preferably Z$^3$ is independently selected from hydroxyl, C$_{1-6}$alkyl, and heterocycle;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each Z$^4$ and Z$^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each Z$^4$ and Z$^5$ is independently selected from hydrogen, C$_{1-6}$alkyl, aryl, C$_{3-7}$cycloalkyl, and heterocycle; more preferably each Z$^4$ and Z$^5$ is independently selected from hydrogen, C$_{1-6}$alkyl, and C$_{3-7}$cycloalkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH or —NH$_2$;

and wherein Z$^4$ and Z$^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$.

6. The compounds according to any one of statements 1 to 5, wherein each Z$^1$, Z$^{1a}$, Z$^{1b}$, and Z$^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, C$_{1-6}$alkyl, heteroC$_{1-6}$alkyl, aryl, heterocycle, and heterocycle-C$_{1-6}$alkyl;

and wherein said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl; —S(O)$_2$C$_{1-4}$alkyl, and —O—C$_{1-6}$alkyl;

each Z$^2$ is independently selected from C$_{1-6}$alkyl, aryl, and heterocycle-C$_{1-6}$alkyl;

wherein said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;

each Z$^3$ is independently selected from hydroxyl, C$_{1-6}$alkyl, and heterocycle;

wherein said C$_{1-6}$alkyl and heterocycle are optionally substituted with one, two, or three substituents selected from C$_{1-6}$alkyl and —N(CH$_3$)$_2$;

each Z$^4$ and Z$^5$ is independently selected from hydrogen, C$_{1-6}$alkyl, and C$_{3-7}$cycloalkyl.

7. A pharmaceutical composition comprising a pharmaceutically acceptable carrier, and as active ingredient an effective amount of the compound according to any one of statements 1 to 6 or a pharmaceutically acceptable salt thereof.

8. The compounds according to any one of statements 1 to 6, or a pharmaceutical composition according to statement 7, for use as a medicine.

9. The compounds according to any one of statements 1 to 6, or a pharmaceutical composition according to statement 7, for use in the prevention or treatment of a flavivirus infection in an animal, mammal or human.

10. The compounds according to according to statement 9, or a pharmaceutical composition according to statement 9, wherein the flavivirus infection is an infection with a Dengue virus or a yellow fever virus.

11. A method for the preparation of the compound according to any one of statements 1 to 6 comprising the step of reacting an imine with an aldehyde under umpolung conditions in the presence of a thiazolium catalyst to obtain the desired compounds of the invention.

In another embodiment, the invention relates to a method for the preparation of the compounds of the invention, comprising the steps of reacting a ketone derivative having a methylene adjacent to the carbonyl under halogenation conditions to obtain an alpha-halogenoketone, substitute the previously obtained alpha-halogenoketone with amines to obtain the desired compounds of the invention.

In another embodiment, the invention relates to a method for the preparation of the compounds of the invention, comprising the steps of reacting a heterocyclicamine with 2-halogeno-acetic acid halide to obtain an alpha-halogenoamide derivative, substitute the previously obtained alpha-halogenoamide with amines to obtain the desired compounds of the invention.

12. A method of treatment or prevention of Flaviviral infections, in humans by the administration of an effective amount of a compound according to any one of statements 1 to 6 or a pharmaceutically acceptable salt thereof, optionally in combination with one or more medicines, to a patient in need thereof.

13. The method according to statement 12, wherein the Flaviviral infection is an infection by the Dengue virus or yellow fever virus.

14. The compounds according to any one of statements 1 to 10, or a pharmaceutical composition according to any one of statements 7 to 10, wherein, cycle A is selected from the group consisting of $C_{3-7}$cycloalkyl; $C_{5-7}$cycloalkenyl; $C_{5-7}$cycloalkynyl; $C_{6-12}$aryl; and heterocycle; wherein said $C_{3-7}$cycloalkyl, $C_{5-7}$cycloalkenyl, $C_{5-7}$cycloalkynyl, $C_{6-12}$aryl and heterocycle, can be unsubstituted or substituted with one or more substituents selected from $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero $C_{1-6}$alkyl, hetero $C_{2-6}$alkenyl, hetero $C_{2-6}$alkynyl, hydroxyl, =O, halogen, —SH, =S, trifluoromethyl, —OCF$_3$, cyano, nitro, —C(O)OH, —NH$_2$, NH($C_{1-6}$alkyl), or N($C_{1-6}$alkyl)$_2$;

cycle C is a monocycle selected from

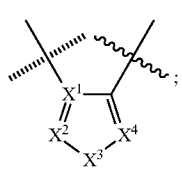
(a1)

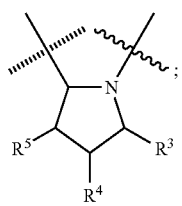
(a2)

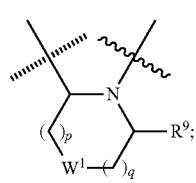
(a3)

wherein the wavy line (∿) indicates the point of attachment to the carbonyl of the main formula (A) and the hashed line (⫶) indicates the point of attachment to the cycle A of the main formula (A);

$X^1$ is selected from C; and N;
$X^2$ is selected from $CR^{12}$; $NR^{13}$; N; O; and S;
$X^3$ is selected from $CR^{14}$, $NR^{15}$; N; O; and S;
$X^4$ is selected from $CR^{16}$, $NR^{17}$; N; O; and S;

each $R^3$ and $R^9$ is independently selected from hydrogen; $C_{1-6}$alkyl; $C_{2-6}$alkenyl; $C_{2-6}$alkynyl; hetero$C_{1-6}$alkyl; hetero$C_{2-6}$alkenyl; hetero$C_{2-6}$alkynyl; =O; and =S; wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl can be unsubstituted or substituted with one or more substituents selected from hydroxyl, =O, halogen, —SH, =S, trifluoromethyl, —OCF$_3$, cyano, nitro, —C(O)OH or NH$_2$;

each $R^4$ and $R^5$ is independently selected from hydrogen; halogen; hydroxyl; sulfhydryl; =O; =S; trifluoromethyl; trifluoromethoxy; cyano; $C_{1-6}$alkyl; $C_{2-6}$alkenyl; $C_{2-6}$alkynyl; hetero$C_{1-6}$alkyl; hetero$C_{2-6}$alkenyl; and hetero$C_{2-6}$alkynyl; and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

$W^1$ is selected from $CR^{32}R^{32a}$; $NR^{33}$; O; S; and SO$_2$;
each p and q is independently selected from 1 and 2, whereby p+q is selected from 2 and 3;

cycle B is selected from aryl; and heterocycle; wherein said aryl and heterocycle can be unsubstituted or substituted with one or more $Z^{1a}$;

$R^1$ is selected from $C_{3-7}$cycloalkyl; $C_{5-7}$cycloalkenyl; $C_{5-7}$cycloalkynyl; $C_{6-12}$aryl; heterocycle; $C_{6-12}$aryl$C_{1-6}$alkyl; $C_{6-12}$aryl$C_{2-6}$alkenyl; $C_{6-12}$aryl$C_{2-6}$alkynyl; heterocycle-$C_{1-6}$alkyl; heterocycle-$C_{2-6}$alkenyl; heterocycle-$C_{2-6}$alkynyl; $C_{6-12}$arylhetero$C_{1-6}$alkyl; $C_{6-12}$arylhetero$C_{2-6}$alkenyl; $C_{6-12}$arylhetero$C_{2-6}$alkynyl; heterocycle-hetero$C_{1-6}$alkyl; heterocycle-hetero$C_{2-6}$alkenyl; heterocycle-hetero$C_{2-6}$alkynyl;

and wherein said $C_{3-7}$cycloalkyl; $C_{5-7}$cycloalkenyl; $C_{5-7}$cycloalkynyl; $C_{6-12}$aryl, heterocycle, $C_{6-12}$aryl$C_{1-6}$alkyl, $C_{6-12}$aryl$C_{2-6}$alkenyl, $C_{6-12}$aryl$C_{2-6}$alkynyl, heterocycle-$C_{1-6}$alkyl, heterocycle-$C_{2-6}$alkenyl, heterocycle-$C_{2-6}$alkynyl, $C_{6-12}$arylhetero$C_{1-6}$alkyl, $C_{6-12}$arylhetero$C_{2-6}$alkenyl, $C_{6-12}$arylhetero$C_{2-6}$alkynyl, heterocycle-hetero$C_{1-6}$alkyl, heterocycle-hetero$C_{2-6}$alkenyl and heterocycle-hetero$C_{2-6}$alkynyl can be unsubstituted or substituted with one or more $Z^{1b}$;

$R^2$ is selected from hydrogen; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; and hetero$C_{2-6}$alkynyl;

and wherein said $C_{1-6}$alkyl, $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl, hetero$C_{2-6}$alkenyl, and hetero$C_{2-6}$alkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; hetero$C_{2-6}$alkynyl;

wherein said $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero$C_{1-6}$alkyl, hetero$C_{2-6}$alkenyl, and hetero$C_{2-6}$alkynyl can be unsubstituted or substituted with one or more substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)Z$^2$; —S(O)$_2$Z$^3$; —S(O)$_2$NZ$^4$Z$^5$; trifluoromethyl; —C(O)Z$^3$; —C(O)OZ$^2$; —C(O)NZ$^4$Z$^5$; —C(O)H; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; hetero$C_{2-6}$alkynyl;

wherein said $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero$C_{1-6}$alkyl, hetero$C_{2-6}$alkenyl, or hetero$C_{2-6}$alkynyl can be unsubstituted or substituted with one or more substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; C$_{1-6}$alkyl; C$_{2-6}$alkenyl; C$_{2-6}$alkynyl; heteroC$_{1-6}$alkyl; heteroC$_{2-6}$alkenyl; and heteroC$_{2-6}$alkynyl; and wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; C$_{1-6}$alkyl; C$_{2-6}$alkenyl; C$_{2-6}$alkynyl; heteroC$_{1-6}$alkyl; heteroC$_{2-6}$alkenyl; and heteroC$_{2-6}$alkynyl; and wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)Z$^2$; —S(O)$_2$Z$^3$; —S(O)$_2$NZ$^4$Z$^5$; trifluoromethyl; trifluoromethoxy; nitro; —NZ$^4$Z$^5$; —NZ$^4$S(O)$_2$Z$^2$; —NZ$^4$C(O)Z$^2$; —NZ$^4$C(O)NZ$^4$Z$^5$; cyano; —C(O)Z$^3$; —C(O)OZ$^2$; —C(O)NZ$^4$Z$^5$; —C(O)H; C$_{1-6}$alkyl; C$_{3-7}$cycloalkyl; C$_{2-6}$alkenyl; C$_{5-7}$cycloalkenyl; C$_{2-6}$alkynyl; C$_{5-7}$cycloalkynyl; heteroC$_{1-6}$alkyl; heteroC$_{2-6}$alkenyl; heteroC$_{2-6}$alkynyl; C$_{6-12}$aryl; heterocycle; C$_{6-12}$arylC$_{1-6}$alkyl; C$_{6-12}$arylC$_{2-6}$alkenyl; C$_{6-12}$arylC$_{2-6}$alkynyl; C$_{6-12}$arylheteroC$_{1-6}$alkyl; C$_{6-12}$arylheteroC$_{2-6}$alkenyl; C$_{6-12}$arylheteroC$_{2-6}$alkynyl; heterocycle-C$_{1-6}$alkyl; heterocycle-C$_{2-6}$alkenyl; heterocycle-C$_{2-6}$alkynyl; heterocycle-heteroC$_{1-6}$alkyl, heterocycle-heteroC$_{2-6}$alkenyl; or heterocycle-heteroC$_{2-6}$alkynyl;

and wherein said C$_{1-6}$alkyl, C$_{3-7}$cycloalkyl, C$_{2-6}$alkenyl, C$_{5-7}$cycloalkenyl, C$_{2-6}$alkynyl, C$_{5-7}$cycloalkynyl, heteroC$_{1-6}$alkyl, heteroC$_{2-6}$alkenyl, heteroC$_{2-6}$alkynyl, C$_{6-12}$aryl, heterocycle, C$_{6-12}$arylC$_{1-6}$alkyl, C$_{6-12}$arylC$_{2-6}$alkenyl, C$_{6-12}$arylC$_{2-6}$alkynyl, C$_{6-12}$arylheteroC$_{1-6}$alkyl, C$_{6-12}$arylheteroC$_{2-6}$alkenyl, C$_{6-12}$arylheteroC$_{2-6}$alkynyl, heterocycle-alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, or heterocycle-heteroC$_{2-6}$alkynyl can be unsubstituted or substituted with one or more substituents selected from C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, cyano, nitro, —C(O)OH or NH$_2$;

each $Z^2$ is independently selected from C$_{1-6}$alkyl; C$_{3-7}$cycloalkyl; C$_{2-6}$alkenyl; C$_{5-7}$cycloalkenyl; C$_{2-6}$alkynyl; C$_{5-7}$cycloalkynyl; heteroC$_{1-6}$alkyl; heteroC$_{2-6}$alkenyl; heteroC$_{2-6}$alkynyl; C$_{6-12}$aryl; heterocycle; C$_{6-12}$arylC$_{1-6}$alkyl; C$_{6-12}$arylC$_{2-6}$alkenyl; C$_{6-12}$arylC$_{2-6}$alkynyl; C$_{6-12}$arylheteroC$_{1-6}$alkyl; C$_{6-12}$arylheteroC$_{2-6}$alkenyl; C$_{6-12}$arylheteroC$_{2-6}$alkynyl; heterocycle-C$_{1-6}$alkyl; heterocycle-C$_{2-6}$alkenyl; heterocycle-C$_{2-6}$alkynyl; heterocycle-heteroC$_{1-6}$alkyl; heterocycle-heteroC$_{2-6}$alkenyl; or heterocycle-heteroC$_{2-6}$alkynyl;

wherein said C$_{1-6}$alkyl, C$_{3-7}$cycloalkyl, C$_{2-6}$alkenyl, C$_{5-7}$cycloalkenyl, C$_{2-6}$alkynyl, C$_{5-7}$cycloalkynyl, heteroC$_{1-6}$alkyl, heteroC$_{2-6}$alkenyl, heteroC$_{2-6}$alkynyl, C$_{6-12}$aryl, heterocycle, C$_{6-12}$arylC$_{1-6}$alkyl, C$_{6-12}$arylC$_{2-6}$alkenyl, C$_{6-12}$arylC$_{2-6}$alkynyl, C$_{6-12}$arylheteroC$_{1-6}$alkyl, C$_{6-12}$arylheteroC$_{2-6}$alkenyl, C$_{6-12}$arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, or heterocycle-heteroC$_{2-6}$alkynyl can be unsubstituted or substituted with one or more substituents selected from C$_{1-6}$alkyl, C$_{2-6}$alkenyl, C$_{2-6}$alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; C$_{1-6}$alkyl; C$_{3-7}$cycloalkyl; C$_{2-6}$alkenyl; C$_{5-7}$cycloalkenyl; C$_{2-6}$alkynyl; C$_{5-7}$cycloalkynyl; heteroC$_{1-6}$alkyl; heteroC$_{2-6}$alkenyl; heteroC$_{2-6}$alkynyl; aryl; heterocycle; C$_{6-12}$arylC$_{1-6}$alkyl; C$_{6-12}$arylC$_{2-6}$alkenyl; C$_{6-12}$arylC$_{2-6}$alkynyl; C$_{6-12}$arylheteroC$_{1-6}$alkyl; C$_{6-12}$arylheteroC$_{2-6}$alkenyl; C$_{6-12}$arylheteroC$_{2-6}$alkynyl; heterocycle-C$_{1-6}$alkyl; heterocycle-C$_{2-6}$alkenyl; heterocycle-C$_{2-6}$alkynyl; heterocycle-heteroC$_{1-6}$alkyl; heterocycle-heteroC$_{2-6}$alkenyl; or heterocycle-heteroC$_{2-6}$alkynyl;

wherein said C$_{1-6}$alkyl, C$_{3-7}$cycloalkyl, C$_{2-6}$alkenyl, C$_{5-7}$cycloalkenyl, C$_{2-6}$alkynyl, C$_{5-7}$cycloalkynyl, heteroC$_{1-6}$alkyl, heteroC$_{2-6}$alkenyl, heteroC$_{2-6}$alkynyl, C$_{6-12}$aryl, heterocycle, C$_{6-12}$arylC$_{1-6}$alkyl, C$_{6-12}$arylC$_{2-6}$alkenyl, C$_{6-12}$arylC$_{2-6}$alkynyl, C$_{6-12}$arylheteroC$_{1-6}$alkyl, C$_{6-12}$arylheteroC$_{2-6}$alkenyl, C$_{6-12}$arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, or heterocycle-heteroC$_{2-6}$alkynyl can be unsubstituted or substituted with one or more substituents selected from C$_{1-6}$alkyl, C$_{2-6}$alkenyl, C$_{2-6}$alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; C$_{1-6}$alkyl; C$_{3-7}$cycloalkyl; C$_{2-6}$alkenyl; C$_{5-7}$cycloalkenyl; C$_{2-6}$alkynyl; C$_{5-7}$cycloalkynyl; heteroC$_{1-6}$alkyl; heteroC$_{2-6}$alkenyl; heteroC$_{2-6}$alkynyl; C$_{6-12}$aryl; heterocycle; C$_{6-12}$arylC$_{1-6}$alkyl; C$_{6-12}$arylC$_{2-6}$alkenyl; C$_{6-12}$arylC$_{2-6}$alkynyl; C$_{6-12}$arylheteroC$_{1-6}$alkyl; C$_{6-12}$arylheteroC$_{2-6}$alkenyl; C$_{6-12}$arylheteroC$_{2-6}$alkynyl; heterocycle-C$_{1-6}$alkyl; heterocycle-C$_{2-6}$alkenyl; heterocycle-C$_{2-6}$alkynyl; heterocycle-heteroC$_{1-6}$alkyl; heterocycle-heteroC$_{2-6}$alkenyl; or heterocycle-heteroC$_{2-6}$alkynyl;

wherein said C$_{1-6}$alkyl, C$_{3-7}$cycloalkyl, C$_{2-6}$alkenyl, C$_{5-7}$cycloalkenyl, C$_{2-6}$alkynyl, C$_{5-7}$cycloalkynyl, heteroC$_{1-6}$alkyl, heteroC$_{2-6}$alkenyl, heteroC$_{2-6}$alkynyl, C$_{6-12}$aryl, heterocycle, C$_{6-12}$arylC$_{1-6}$alkyl, C$_{6-12}$arylC$_{2-6}$alkenyl, C$_{6-12}$arylC$_{2-6}$alkynyl, C$_{6-12}$arylheteroC$_{1-6}$alkyl, C$_{6-12}$arylheteroC$_{2-6}$alkenyl, C$_{6-12}$arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, or heterocycle-heteroC$_{2-6}$alkynyl can be unsubstituted or substituted with one or more substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(O)OH or NH$_2$;

and wherein $Z^4$ and $Z^5$ can be taken together in order to form a (5-, 6-, or 7-membered) heterocycle which can be unsubstituted or substituted with C$_{1-6}$alkyl, C$_{3-7}$cycloalkyl, $C_{2-6}$alkenyl, $C_{5-7}$cycloalkenyl, $C_{2-6}$alkynyl, $C_{5-7}$cycloalkynyl, hydroxyl, halogen, —SH, trifluoromethyl, —O-alkyl, —OCF$_3$, cyano, nitro, —C(O)OH or —NH$_2$;

preferably wherein said heteroC$_{1-6}$alkyl as a group or part of a group is selected from —CO—O—C$_{1-5}$alkyl, —O—C$_{1-6}$alkyl, —NH—C$_{1-6}$alkyl, —N(C$_{1-6}$alkyl)$_2$, —S(=O)$_2$C$_{1-6}$alkyl, and —S—C$_{1-6}$alkyl;

and isomers (in particular stereo-isomers or tautomers), solvates, salts (in particular pharmaceutically acceptable salts) or prodrugs thereof.

15. The compounds according to any one of statements 1 to 10, 14, or a pharmaceutical composition according to any one of statements 7 to 10, wherein, cycle A is selected from the group consisting of $C_{3-7}$cycloalkyl; $C_{6-12}$aryl; and heterocycle; wherein said $C_{3-7}$cycloalkyl, $C_{6-12}$aryl and heterocycle, can be unsubstituted or substituted with one or more substituents selected from $C_{1-6}$alkyl, $C_{3-7}$cycloalkyl, hetero C$_{1-6}$alkyl, hetero C$_{2-6}$alkenyl, hetero C$_{2-6}$alkynyl, hydroxyl, =O, halogen, —SH, =S, trifluoromethyl, —OCF$_3$, cyano, nitro, —C(O)OH, —NH$_2$, NH(C$_{1-6}$alkyl), or N(C$_{1-6}$alkyl)$_2$;

cycle C is a monocycle selected from

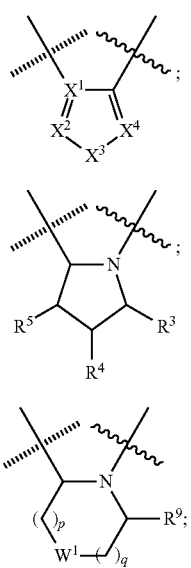

wherein the wavy line ( $\sim\!\!\sim$ ) indicates the point of attachment to the carbonyl of the main formula (A) and the hashed line ( ⫶⫶⫶⫶ ) indicates the point of attachment to the cycle A of the main formula (A);

$X^1$ is selected from C; and N;
$X^2$ is selected from CR$^{12}$; NR$^{13}$; N; O; and S;
$X^3$ is selected from CR$^{14}$; NR$^{15}$; N; O; and S;
$X^4$ is selected from CR$^{16}$; NR$^{17}$; N; O; and S;
each R$^3$ and R$^9$ is independently selected from hydrogen; C$_{1-6}$alkyl; heteroC$_{1-6}$alkyl; =O; and =S; wherein said C$_{1-6}$alkyl, and heteroC$_{1-6}$alkyl, can be unsubstituted or substituted with one or more substituents selected from hydroxyl, =O, halogen, —SH, =S, trifluoromethyl, —OCF$_3$, cyano, nitro, —C(O)OH or NH$_2$;
each R$^4$ and R$^5$ is independently selected from hydrogen; halogen; hydroxyl; sulfhydryl; =O; =S; trifluoromethyl; trifluoromethoxy; cyano; C$_{1-6}$alkyl; and heteroC$_{1-6}$alkyl; and wherein said C$_{1-6}$alkyl, heteroC$_{1-6}$alkyl, can be unsubstituted or substituted with one or more substituents selected from hydroxyl, =O, halogen, —SH, =S, trifluoromethyl, —OCF$_3$, cyano, nitro, —C(O)OH or NH$_2$;
$W^1$ is selected from CR$^{32}$R$^{32a}$; NR$^{33}$; O; S; and SO$_2$;
each p and q is independently selected from 1 and 2, whereby p+q is selected from 2 and 3;
cycle B is selected from aryl; and heterocycle; wherein said aryl and heterocycle can be unsubstituted or substituted with one or more $Z^{1a}$;
R$^1$ is selected from C$_{3-7}$cycloalkyl; C$_{6-12}$aryl; heterocycle; C$_{6-12}$arylC$_{1-6}$alkyl; heterocycle-C$_{1-6}$alkyl; C$_{6-12}$aryl-heteroC$_{1-6}$alkyl; heterocycle-heteroC$_{1-6}$alkyl;
and wherein said C$_{3-7}$cycloalkyl; C$_{6-12}$aryl, heterocycle, C$_{6-12}$arylC$_{1-6}$alkyl, heterocycle-C$_{1-6}$alkyl, C$_{6-12}$arylheteroC$_{1-6}$alkyl, and heterocycle-heteroC$_{1-6}$ alkyl, can be unsubstituted or substituted with one or more $Z^{1b}$;
R$^2$ is selected from hydrogen; C$_{1-6}$alkyl; C$_{3-7}$cycloalkyl; and heteroC$_{1-6}$alkyl;
and wherein said C$_{1-6}$alkyl, C$_{3-7}$cycloalkyl; and heteroC$_{1-6}$alkyl, can be unsubstituted or substituted with one or more $Z^{1c}$;
each R$^{12}$, R$^{14}$, and R$^{16}$ is independently selected from hydrogen; halogen; hydroxyl; sulfhydryl; trifluoromethyl; trifluoromethoxy; nitro; amino; cyano; C$_{1-6}$alkyl; C$_{3-7}$cycloalkyl; heteroC$_{1-6}$alkyl;
wherein said C$_{1-6}$alkyl, C$_{3-7}$cycloalkyl, and heteroC$_{1-6}$alkyl, can be unsubstituted or substituted with one or more substituents selected from C$_{1-6}$alkyl, heteroC$_{1-6}$ alkyl, hydroxyl, =O, halogen, —SH, =S, trifluoromethyl, —OCF$_3$, cyano, nitro, —C(O)OH or NH$_2$;
R$^{13}$, R$^{15}$, and R$^{17}$ is independently selected from hydrogen; hydroxyl; sulfhydryl; —S(O)Z$^2$; —S(O)$_2$Z$^3$; —S(O)$_2$NZ$^4$Z$^5$; trifluoromethyl; —C(O)Z$^3$; —C(O)OZ$^2$; —C(O)NZ$^4$Z$^5$; —C(O)H; C$_{1-6}$alkyl; C$_{3-7}$cycloalkyl; heteroC$_{1-6}$alkyl;
wherein said C$_{1-6}$alkyl, C$_{3-7}$cycloalkyl, heteroC$_{1-6}$alkyl, can be unsubstituted or substituted with one or more substituents selected from C$_{1-6}$alkyl, heteroC$_{1-6}$ alkyl, hydroxyl, =O, halogen, —SH, =S, trifluoromethyl, —OCF$_3$, cyano, nitro, —C(O)OH or NH$_2$;
each R$^{32}$ and R$^{32a}$ is independently selected from hydrogen; halogen; hydroxyl; sulfhydryl; =O; =S; trifluoromethyl; trifluoromethoxy; cyano; C$_{1-6}$alkyl; and heteroC$_{1-6}$alkyl; and wherein said C$_{1-6}$alkyl, heteroC$_{1-6}$ alkyl, can be unsubstituted or substituted with one or more substituents selected from hydroxyl, =O, halogen, —SH, =S, trifluoromethyl, —OCF$_3$, cyano, nitro, —C(O)OH or NH$_2$;
each R$^{33}$ is independently selected from hydrogen; C$_{1-6}$alkyl; and heteroC$_{1-6}$alkyl; wherein said C$_{1-6}$alkyl, heteroC$_{1-6}$alkyl, can be unsubstituted or substituted with one or more substituents selected from hydroxyl, =O, halogen, —SH, =S, trifluoromethyl, —OCF$_3$, cyano, nitro, —C(O)OH or NH$_2$;
each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)Z$^2$; —S(O)$_2$Z$^3$; —S(O)$_2$NZ$^4$Z$^5$; trifluoromethyl; trifluoromethoxy; nitro; —NZ$^4$Z$^5$; —NZ$^4$S(O)$_2$Z$^2$; —NZ$^4$C(O)Z$^2$; —NZ$^4$C(O)NZ$^4$Z$^5$; cyano; —C(O)Z$^3$; —C(O)OZ$^2$;

—C(O)NZ⁴Z⁵; —C(O)H; $C_{1-6}$alkyl; $C_{3-7}$cycloalkyl;heteroC$_{1-6}$alkyl; $C_{6-12}$aryl; heterocycle; $C_{6-12}$arylC$_{1-6}$alkyl; $C_{6-12}$arylheteroC$_{1-6}$alkyl; heterocycle-C$_{1-6}$ alkyl; or heterocycle-heteroC$_{1-6}$alkyl, and wherein said $C_{1-6}$alkyl, $C_{3-7}$cycloalkyl, heteroC$_{1-6}$ alkyl, $C_{6-12}$aryl, heterocycle, $C_{6-12}$arylC$_{1-6}$alkyl, $C_{6-12}$arylheteroC$_{1-6}$alkyl, heterocycle-C$_{1-6}$alkyl, or heterocycle-heteroC$_{1-6}$alkyl, can be unsubstituted or substituted with one or more substituents selected from $C_{1-6}$alkyl, heteroC$_{1-6}$alkyl, hydroxyl, =O, halogen, —SH, =S, trifluoromethyl, —OCF$_3$, cyano, nitro, —C(O)OH or NH$_2$;

each Z² is independently selected from $C_{1-6}$alkyl; $C_{3-7}$cycloalkyl; heteroC$_{1-6}$alkyl; $C_{6-12}$aryl; heterocycle; $C_{6-12}$arylC$_{1-6}$alkyl; $C_{6-12}$arylheteroC$_{1-6}$alkyl; heterocycle-C$_{1-6}$alkyl; or heterocycle-heteroC$_{1-6}$alkyl;

wherein said $C_{1-6}$alkyl, $C_{3-7}$cycloalkyl, heteroC$_{1-6}$ alkyl, $C_{6-12}$aryl, heterocycle, $C_{6-12}$arylC$_{1-6}$alkyl, $C_{6-12}$arylheteroC$_{1-6}$alkyl, heterocycle-C$_{1-6}$alkyl, or heterocycle-heteroC$_{1-6}$alkyl, can be unsubstituted or substituted with one or more substituents selected from $C_{1-6}$alkyl, hydroxyl, =O, halogen, —SH, =S, trifluoromethyl, —O-alkyl, —OCF$_3$, cyano, nitro, —C(O)OH or NH$_2$;

each Z³ is independently selected from hydroxyl; $C_{1-6}$alkyl; $C_{3-7}$cycloalkyl; heteroC$_{1-6}$alkyl; aryl; heterocycle; $C_{6-12}$arylC$_{1-6}$alkyl; $C_{6-12}$arylheteroC$_{1-6}$alkyl; heterocycle-C$_{1-6}$alkyl; or heterocycle-heteroC$_{1-6}$alkyl;

wherein said $C_{1-6}$alkyl, $C_{3-7}$cycloalkyl, heteroC$_{1-6}$ alkyl, $C_{6-12}$aryl, heterocycle, $C_{6-12}$arylC$_{1-6}$alkyl, $C_{6-12}$arylheteroC$_{1-6}$alkyl, heterocycle-C$_{1-6}$alkyl, or heterocycle-heteroC$_{1-6}$alkyl, can be unsubstituted or substituted with one or more substituents selected from $C_{1-6}$alkyl, hydroxyl, =O, halogen, —SH, =S, trifluoromethyl, —O-alkyl, —OCF$_3$, cyano, nitro, —C(O)OH or NH$_2$;

each Z⁴ and Z⁵ is independently selected from hydrogen; $C_{1-6}$alkyl; $C_{3-7}$cycloalkyl; heteroC$_{1-6}$alkyl; $C_{6-12}$aryl; heterocycle; $C_{6-12}$arylC$_{1-6}$alkyl; $C_{6-12}$arylheteroC$_{1-6}$ alkyl; heterocycle-C$_{1-6}$alkyl; or heterocycle-heteroC$_{1-6}$ alkyl;

wherein said $C_{1-6}$alkyl, $C_{3-7}$cycloalkyl, heteroC$_{1-6}$ alkyl, $C_{6-12}$aryl, heterocycle, $C_{6-12}$arylC$_{1-6}$alkyl, $C_{6-12}$arylheteroC$_{1-6}$alkyl, heterocycle-C$_{1-6}$alkyl, or heterocycle-heteroC$_{1-6}$alkyl, can be unsubstituted or substituted with one or more substituents selected from $C_{1-6}$alkyl, hydroxyl, =O, halogen, —SH, =S, trifluoromethyl, —O—C$_{1-6}$alkyl, —OCF$_3$, cyano, nitro, —C(O)OH or NH$_2$;

and wherein Z⁴ and Z⁵ can be taken together in order to form a (5-, 6-, or 7-membered) heterocycle which can be unsubstituted or substituted with $C_{1-6}$alkyl, $C_{3-7}$cycloalkyl, hydroxyl, halogen, —SH, trifluoromethyl, —O-alkyl, —OCF$_3$, cyano, nitro, —C(O)OH or —NH$_2$; and isomers (in particular stereoisomers or tautomers), solvates, salts (in particular pharmaceutically acceptable salts) or prodrugs thereof.

16. A compound of formula (A),

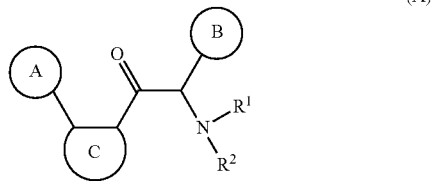

(A)

wherein,
cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, —NH$_2$, NH(alkyl), or N(alkyl)$_2$;

cycle C is a monocycle selected from

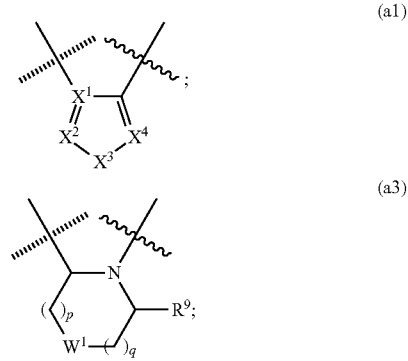

wherein the wavy line ($\sim$) indicates the point of attachment to the carbonyl of the main formula (A) and the hashed line ($\parallel$) indicates the point of attachment to the cycle A of the main formula (A);

X¹ is selected from C; and N;
X² is selected from CR¹²; NR¹³; N; O; and S;
X³ is selected from CR¹⁴, NR¹⁵; N; O; and S;
X⁴ is selected from CR¹⁶, NR¹⁷; N; O; and S;
each R⁹ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;

W¹ is selected from CR³²R$^{32a}$; NR³³; O; S; and SO$_2$;
each p and q is independently selected from 1 and 2, whereby p+q is selected from 2 and 3;
cycle B is selected from aryl; and heterocycle; wherein said aryl and heterocycle can be unsubstituted or substituted with one or more $Z^{1a}$;
R¹ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;

$R^2$ is selected from hydrogen; alkyl; cycloalkyl; alkenyl; cycloalkenyl; alkynyl; cycloalkynyl; heteroalkyl; heteroalkenyl; and heteroalkynyl;

and wherein said alkyl, cycloalkyl; alkenyl; cycloalkenyl; alkynyl; cycloalkynyl; heteroalkyl, heteroalkenyl, and heteroalkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)$Z^2$; —S(O)$_2Z^3$; —S(O)$_2$NZ$^4Z^5$; trifluoromethyl; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)$Z^2$; —S(O)$_2Z^3$; —S(O)$_2$NZ$^4Z^5$; trifluoromethyl; trifluoromethoxy; nitro; —NZ$^4Z^5$; —NZ$^4$S(O)$_2Z^2$; —NZ$^4$C(O)$Z^2$; —NZ$^4$C(O)NZ$^4Z^5$; cyano; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkynyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein Z$^4$ and Z$^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof, with the proviso that said compound is not
2-anilino-2-(4-tert-butylphenyl)-1-(2-phenyl-1-piperidyl)ethanone;
2-anilino-1-(2-phenyl-1-piperidyl)-2-[4-(trifluoromethyl)phenyl]ethanone;
2-anilino-2-(4-tert-butylphenyl)-1-(2-phenylazepan-1-yl)ethanone.

17. The compounds according to any one of statements 1-10, 14-16, or a pharmaceutical composition according to any one of statements 7 to 10, wherein cycle C is selected from the following group of cycles

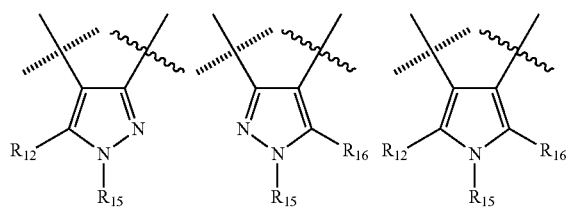

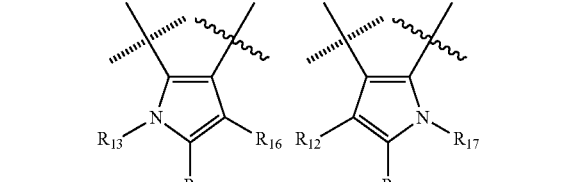

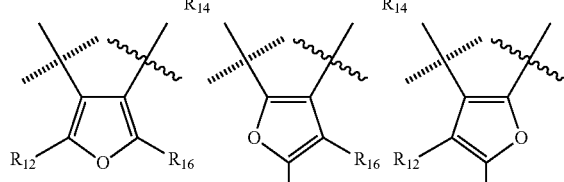

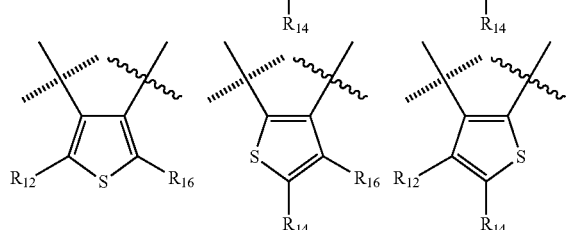

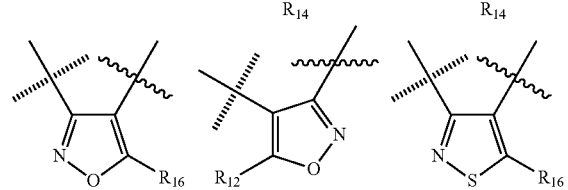

-continued

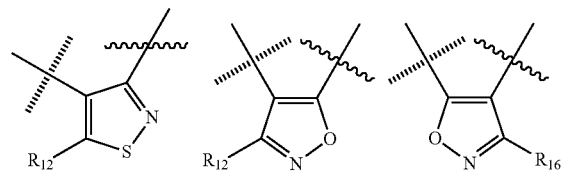

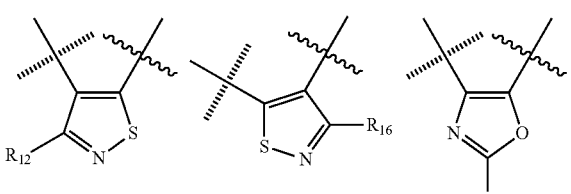

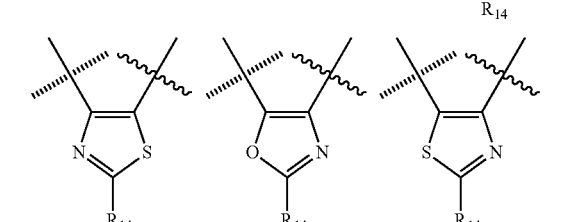

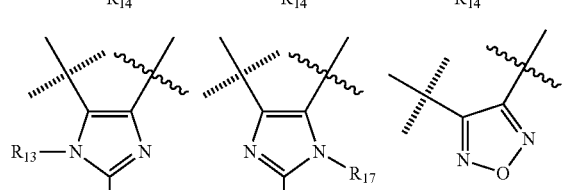

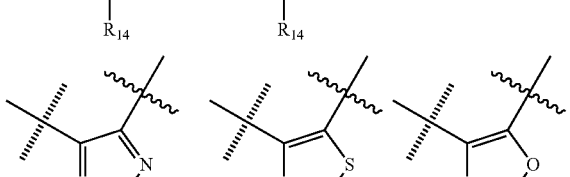

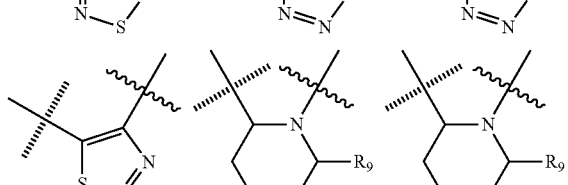

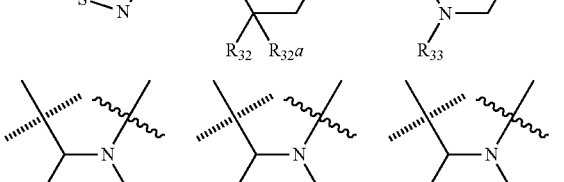

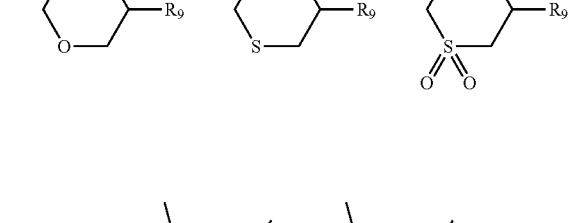

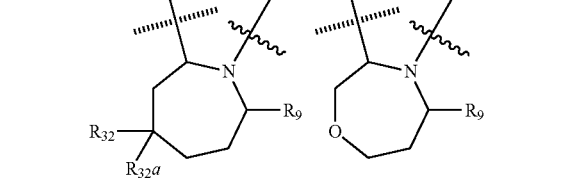

-continued

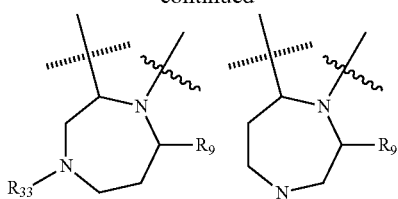

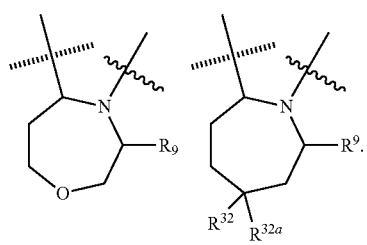

18. The compounds according to statement 17, wherein cycle C is selected from the following group of cycles

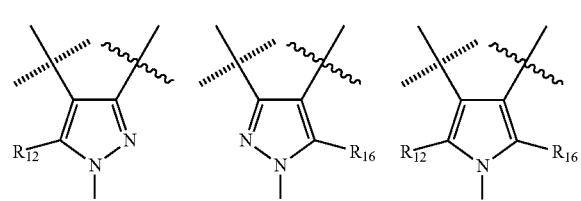

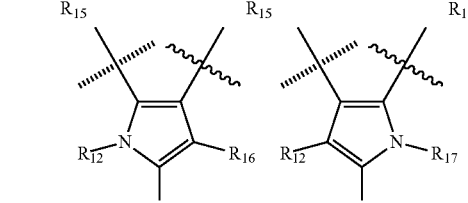

19. The compounds according to any one of statements 1-10, 14-18, or a pharmaceutical composition according to any one of statements 7 to 10, selected from the compounds of formula (C1), (C2), (C3), and (C5),

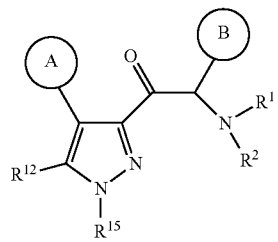
(C1)

-continued

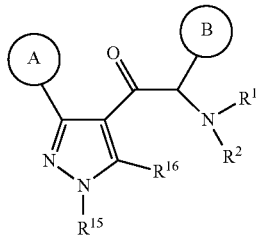
(C2)

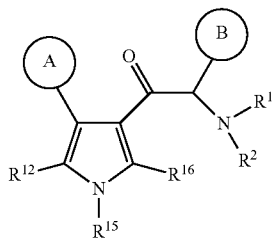
(C3)

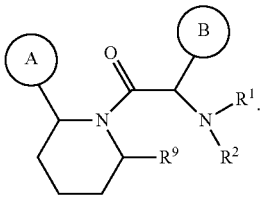
(C5)

20. The compounds according to any one of statements 1-10, 14-19, or a pharmaceutical composition according to any one of statements 7 to 10, wherein, cycle C is a monocycle selected from

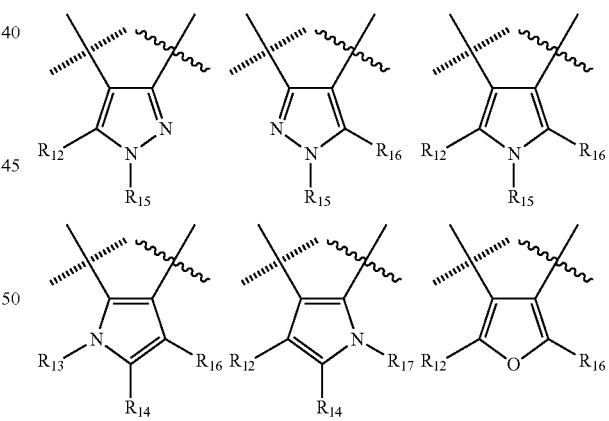

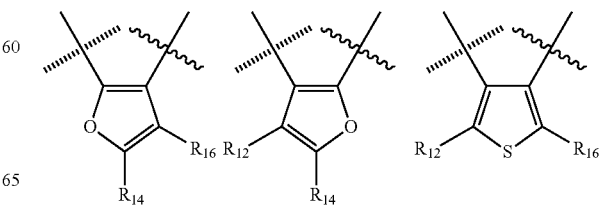

-continued

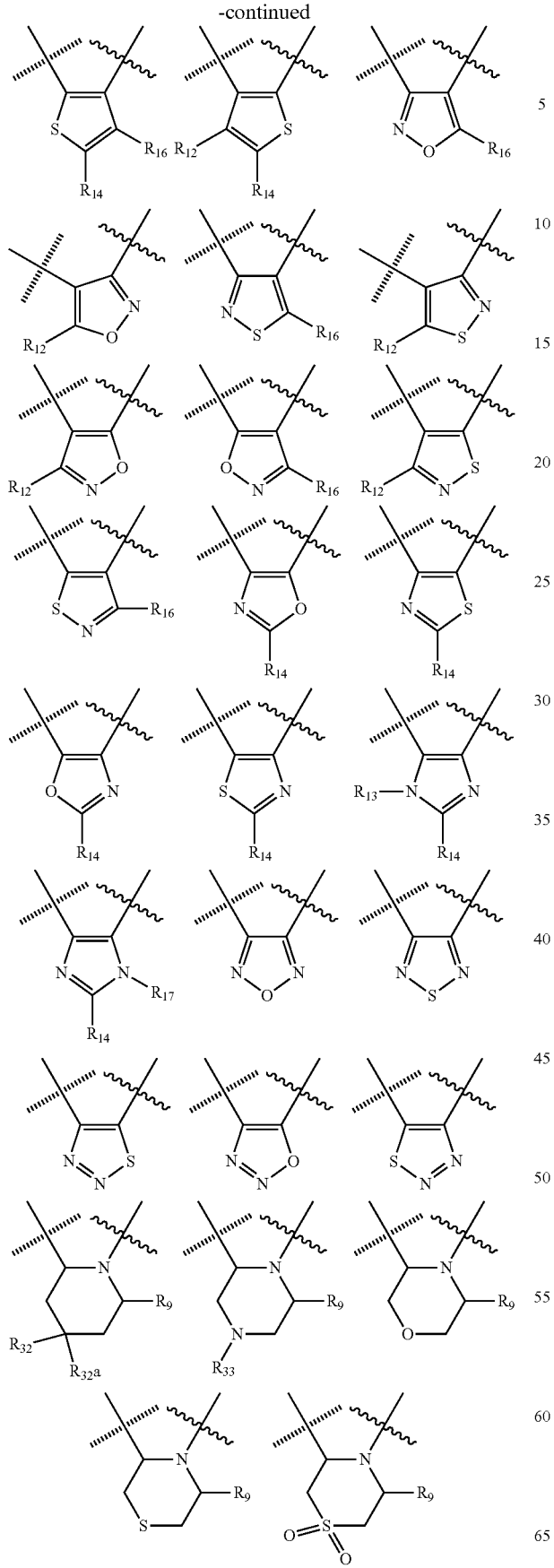

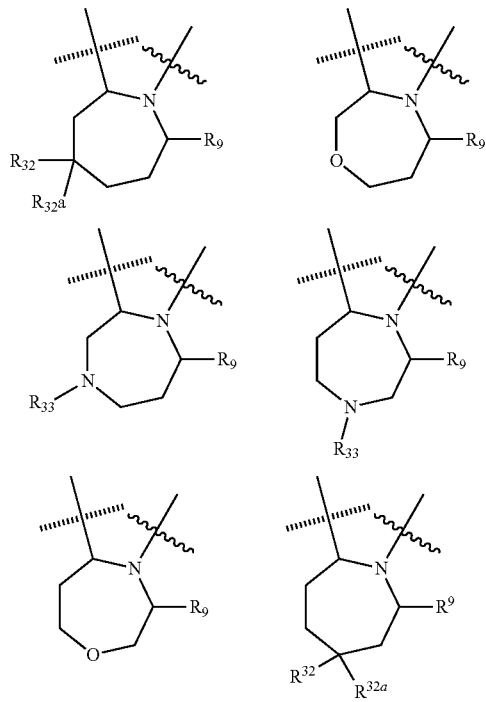

wherein the wavy line ( ～ ) indicates the point of attachment to the carbonyl of the main formula (A) and the hashed line ( ⁞⁞⁞ ) indicates the point of attachment to the cycle A of the main formula (A);

cycle A is selected from aryl; and heterocycle; optionally substituted with one, two, or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$; more particularly cycle A is selected from

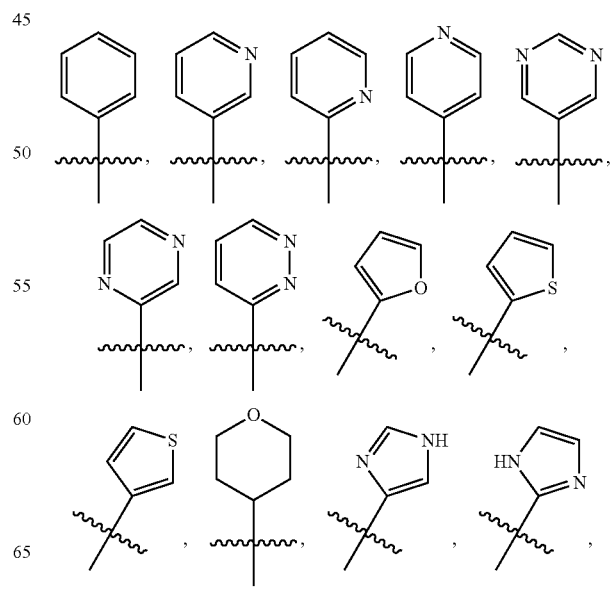

-continued

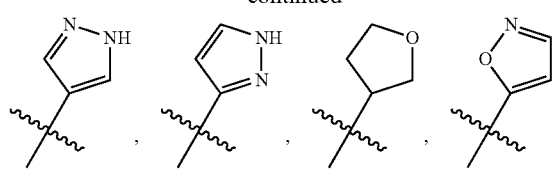
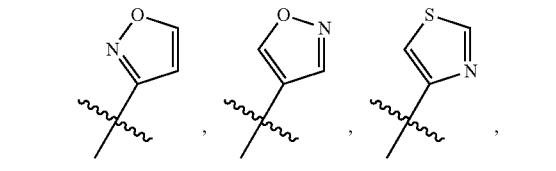
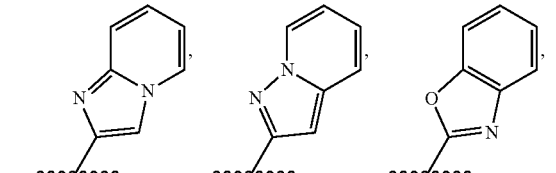
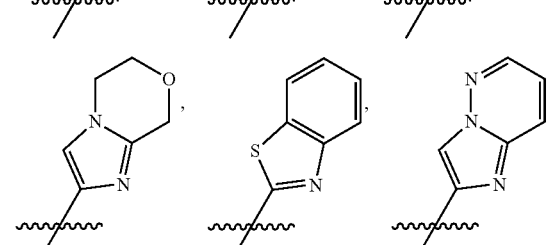
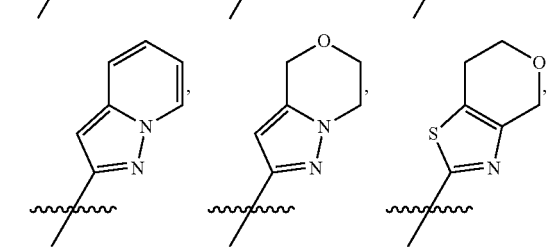
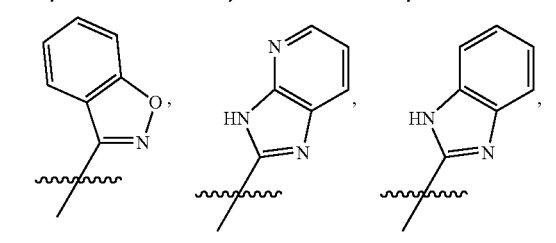
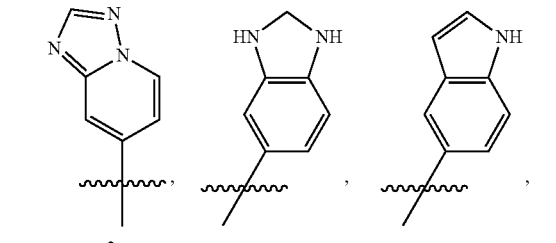
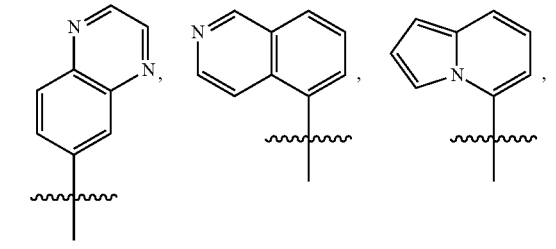

-continued

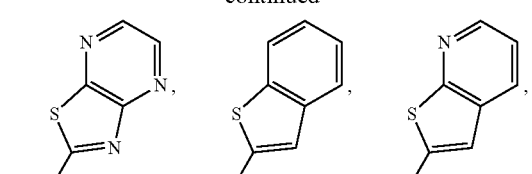
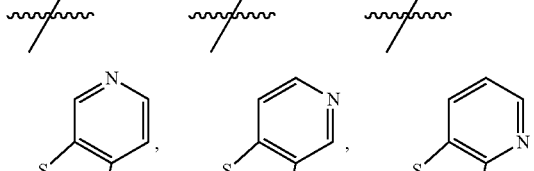
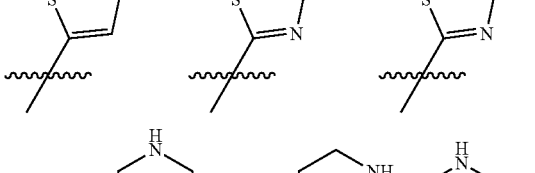
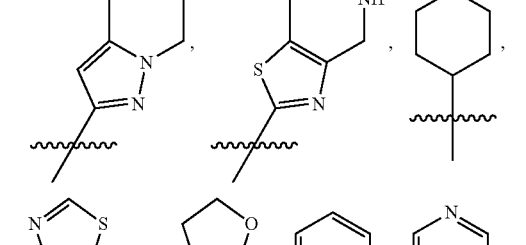
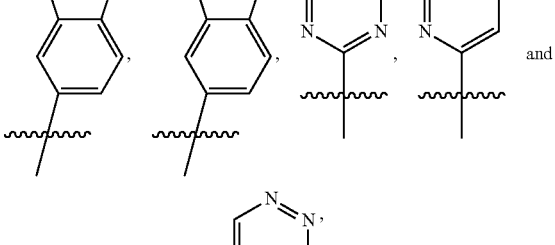

and

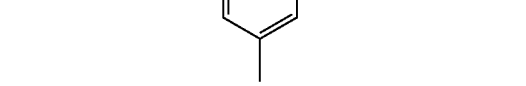

wherein the wavy line (∼∼∼) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$;

cycle B is selected from aryl; and heterocycle; wherein said aryl and heterocycle are optionally substituted with one, two, or three Z$^{1a}$; more particularly cycle B is selected from

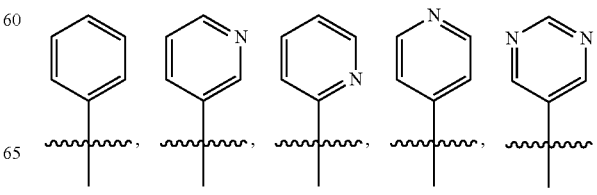

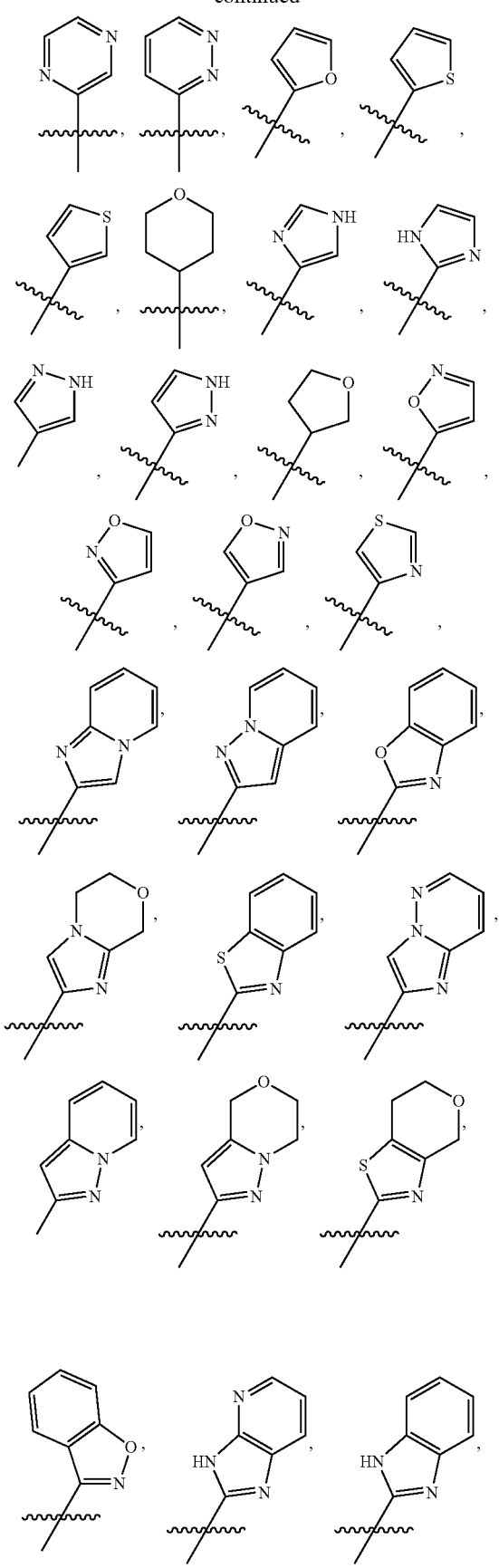
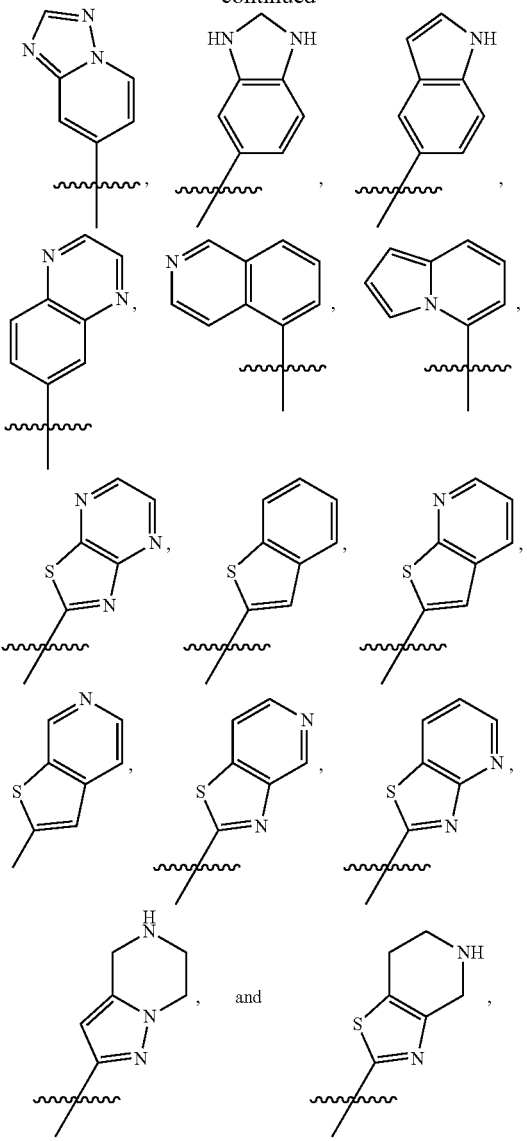

wherein the wavy line (⁓) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$ alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl, are optionally substituted with one, two, or three $Z^{1c}$; preferably said $C_{1-6}$alkyl is optionally substituted with one, two, or three $Z^{1c}$;

$R^9$ is selected from hydrogen; $C_{1-6}$alkyl; heteroC$_{1-6}$alkyl; and =O;

each of $R^{12}$, $R^{14}$ and $R^{16}$ is independently selected from hydrogen; halogen; trifluoromethyl; cyano; $C_{1-6}$alkyl and $C_{1-6}$cycloalkyl;

each $R^{13}$, $R^{15}$ and $R^{17}$ is independently selected from hydrogen; $C_{1-6}$alkyl; and $C_{1-6}$cycloalkyl;

each $R^{32}$ and $R^{32a}$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero $C_{1-6}$alkyl; heteroC$_{2-6}$alkenyl; and hetero $C_{2-6}$alkynyl;

$R^{33}$ is independently selected from hydrogen and $C_{1-6}$alkyl;

each $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-$C_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)$_2Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, heteroC$_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —O$Z^2$, —O—C(=O)$Z^3$, =O, —S(=O)$_2Z^3$, —S(=O)$_2$N$Z^4Z^5$, trifluoromethyl, trifluoromethoxy, —N$Z^4Z^5$, —N$Z^4$C(=O)$Z^2$, —N$Z^4$C(=O)—O$Z^2$, cyano, —C(=O)$Z^3$, —C(=O)O$Z^2$, —C(=O)N$Z^4Z^5$, $C_{1-6}$alkyl, heteroC$_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-$C_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl; preferably said $C_{1-6}$alkyl, heteroC$_{1-6}$ alkyl, aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$ alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$ C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-C$_{1-6}$alkyl; more preferably $Z^2$ is independently selected from $C_{1-6}$alkyl, aryl, and heterocycle-C$_{1-6}$alkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$ alkenyl, arylheteroC$_{2-6}$alkynyl, heterocycle-C$_{1-6}$ alkyl, heterocycle-C$_{2-6}$alkenyl, heterocycle-C$_{2-6}$ alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; preferably said $C_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$alkyl, —OCF$_3$, —S(=O)$_2$ C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$ alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^3$ is independently selected from hydroxyl, C$_{1-6}$alkyl, aryl, and heterocycle; more preferably Z$^3$ is independently selected from hydroxyl, C$_{1-6}$alkyl, and heterocycle;
wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;
each Z$^4$ and Z$^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each Z$^4$ and Z$^5$ is independently selected from hydrogen, C$_{1-6}$alkyl, aryl, C$_{3-7}$cycloalkyl, and heterocycle; more preferably each Z$^4$ and Z$^5$ is independently selected from hydrogen, C$_{1-6}$alkyl, and C$_{3-7}$cycloalkyl;
wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH or —NH$_2$;
and wherein Z$^4$ and Z$^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$.
21. The compound according to any one of statements 1-10, 14-20, or a pharmaceutical composition according to any one of statements 7 to 10, wherein
each Z$^1$, Z$^{1a}$, Z$^{1b}$, and Z$^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, C$_{1-6}$alkyl, heteroC$_{1-6}$alkyl, aryl, heterocycle, and heterocycle-C$_{1-6}$alkyl;
and wherein said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl; —S(O)$_2$C$_{1-4}$alkyl, and —O—C$_{1-6}$alkyl;
each Z$^2$ is independently selected from C$_{1-6}$alkyl, aryl, and heterocycle-C$_{1-6}$alkyl;
wherein said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;
each Z$^3$ is independently selected from hydroxyl, C$_{1-6}$alkyl, and heterocycle;
wherein said C$_{1-6}$alkyl and heterocycle are optionally substituted with one, two, or three substituents selected from C$_{1-6}$alkyl and —N(CH$_3$)$_2$;
each Z$^4$ and Z$^5$ is independently selected from hydrogen, C$_{1-6}$alkyl, and C$_{3-7}$cycloalkyl.
22. The compounds according to any one of statements 16-21, for use as a medicine.
23. The compounds according to statement 22, for use in the prevention or treatment of a flavivirus infection in an animal, mammal or human.
24. A compounds of formula (A), for use in the prevention or treatment of a flavivirus infection in an animal, mammal or human;

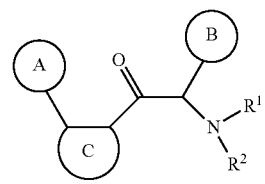

(A)

wherein,
cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, —NH$_2$, NH(alkyl), or N(alkyl)$_2$;
cycle C is a monocycle selected from

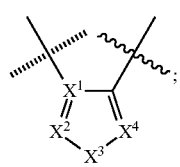

(a1)

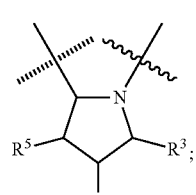

(a2)

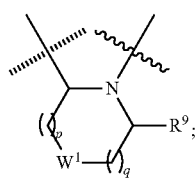

(a3)

wherein the wavy line ( ～ ) indicates the point of attachment to the carbonyl of the main formula (A) and the hashed line ( ⁞⁞⁞⁞⁞ ) indicates the point of attachment to the cycle A of the main formula (A);

$X^1$ is selected from C; and N;

$X^2$ is selected from $CR^{12}$; $NR^{13}$; N; O; and S;

$X^3$ is selected from $CR^{14}$, $NR^{15}$; N; O; and S;

$X^4$ is selected from $CR^{16}$, $NR^{17}$; N; O; and S;

each $R^3$ and $R^9$ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;

each $R^4$ and $R^5$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

$W^1$ is selected from $CR^{32}R^{32a}$; $NR^{33}$; O; S; and SO$_2$;

each p and q is independently selected from 1 and 2, whereby p+q is selected from 2 and 3;

cycle B is selected from aryl; and heterocycle; wherein said aryl and heterocycle can be unsubstituted or substituted with one or more $Z^{1a}$;

$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;

$R^2$ is selected from hydrogen; alkyl; cycloalkyl; alkenyl; cycloalkenyl; alkynyl; cycloalkynyl; heteroalkyl; heteroalkenyl; and heteroalkynyl;

and wherein said alkyl, cycloalkyl; alkenyl; cycloalkenyl; alkynyl; cycloalkynyl; heteroalkyl, heteroalkenyl, and heteroalkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)$Z^2$; —S(O)$_2Z^3$; —S(O)$_2$NZ$^4Z^5$; trifluoromethyl; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)$Z^2$; —S(O)$_2Z^3$; —S(O)$_2$NZ$^4Z^5$; trifluoromethyl; trifluoromethoxy; nitro; —NZ$^4Z^5$; —NZ$^4$S(O)$_2Z^2$; —NZ$^4$C(O)$Z^2$; —NZ$^4$C(O)NZ$^4Z^5$; cyano; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein $Z^4$ and $Z^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof.

25. The compounds according to statement 24, wherein cycle C is selected from the following group of cycles

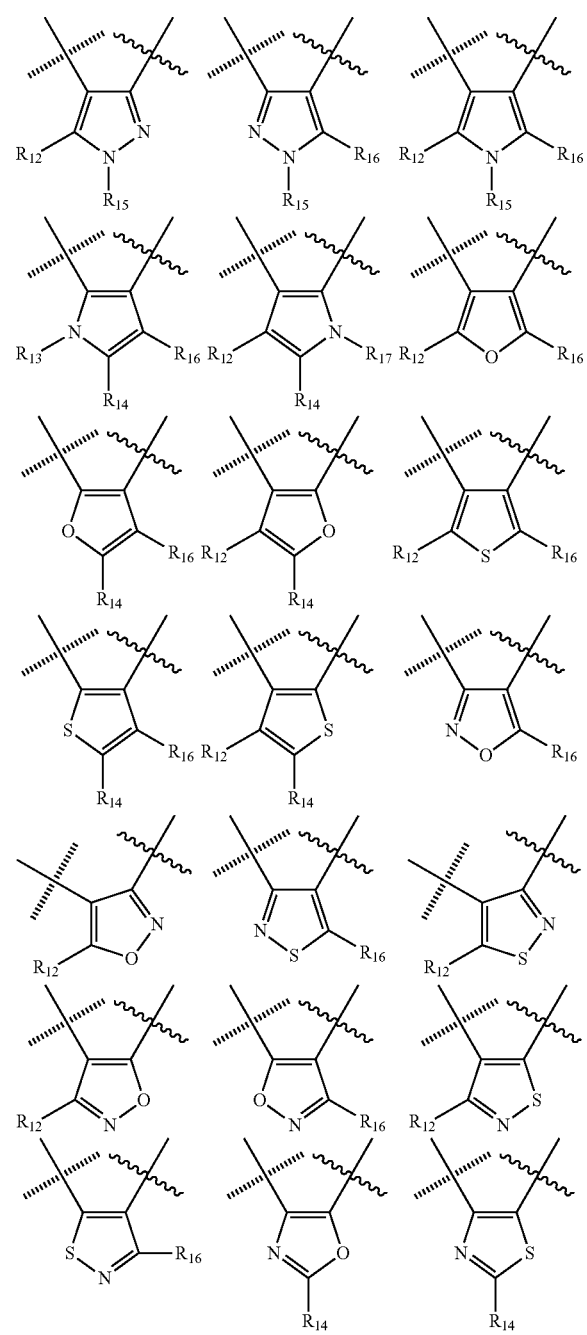

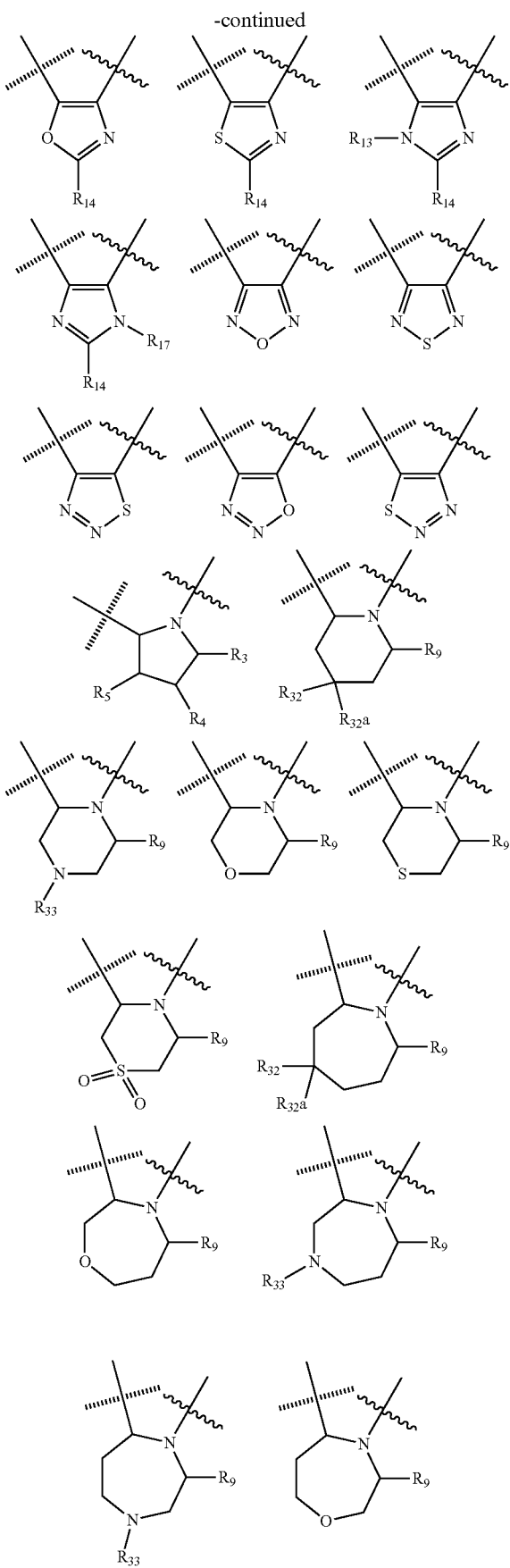
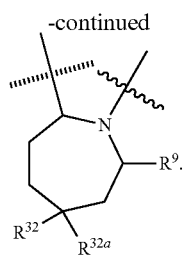
26. The compounds according to any one of statements 24 or 25, wherein cycle C is selected from the following group of cycles
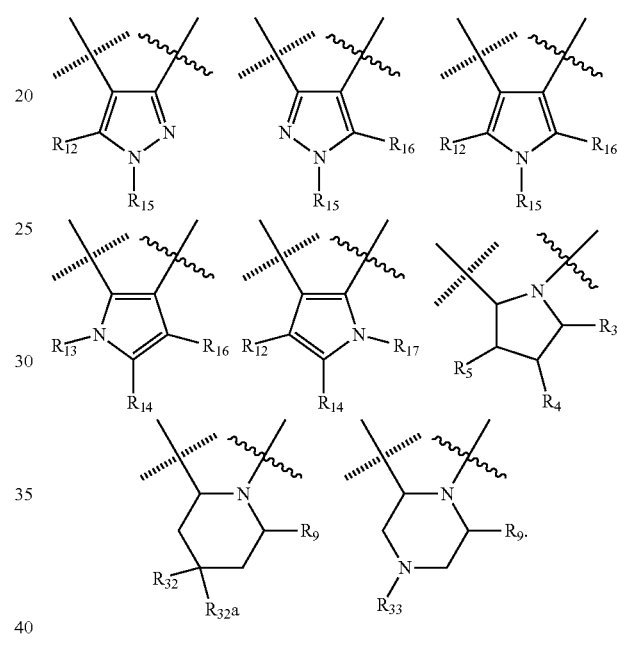
27. The compounds according to any one of statements 24 to 26, selected from the compounds of formula (C1), (C2), (C3), (C4), and (C5),
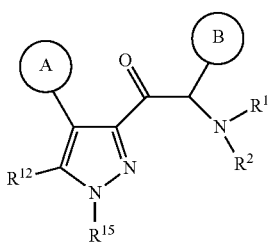
(C1)
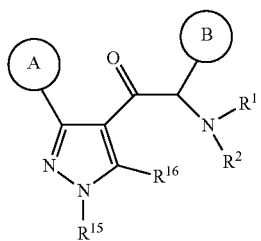
(C2)

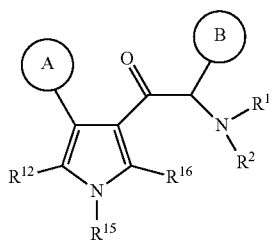
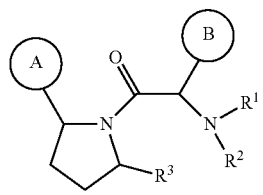
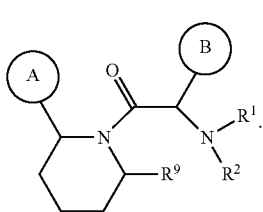
28. The compounds according to statement 27 wherein, cycle C is a monocycle selected from
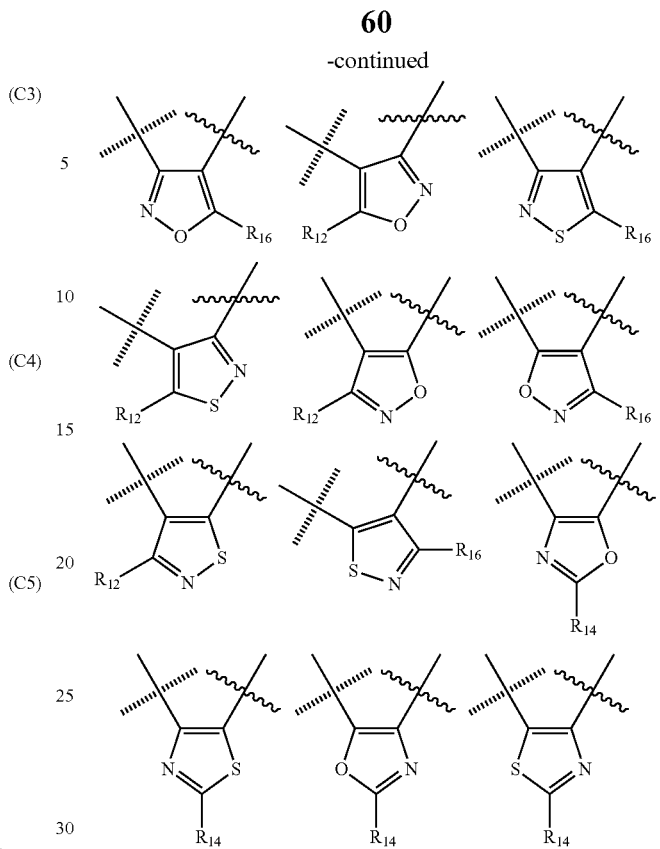
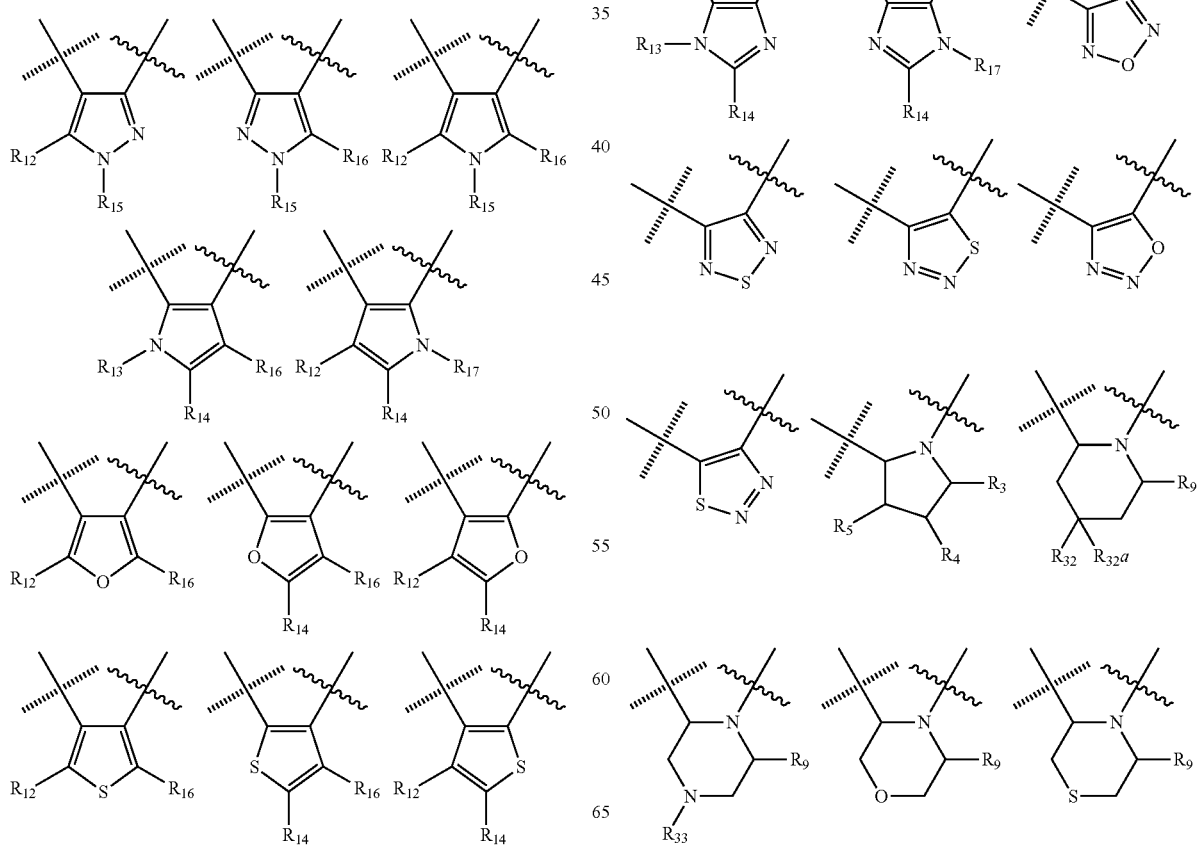

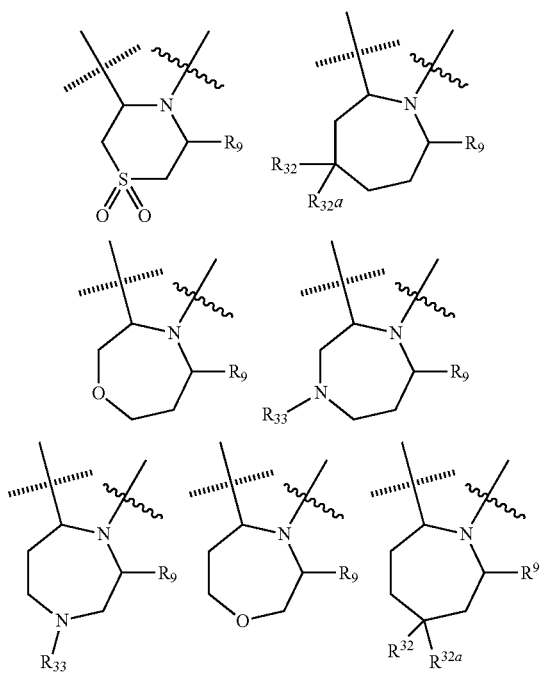

wherein the wavy line (∿) indicates the point of attachment to the carbonyl of the main formula (A) and the hashed line (⸽) indicates the point of attachment to the cycle A of the main formula (A);

cycle A is selected from aryl; and heterocycle; optionally substituted with one, two, or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$; more particularly cycle A is selected from

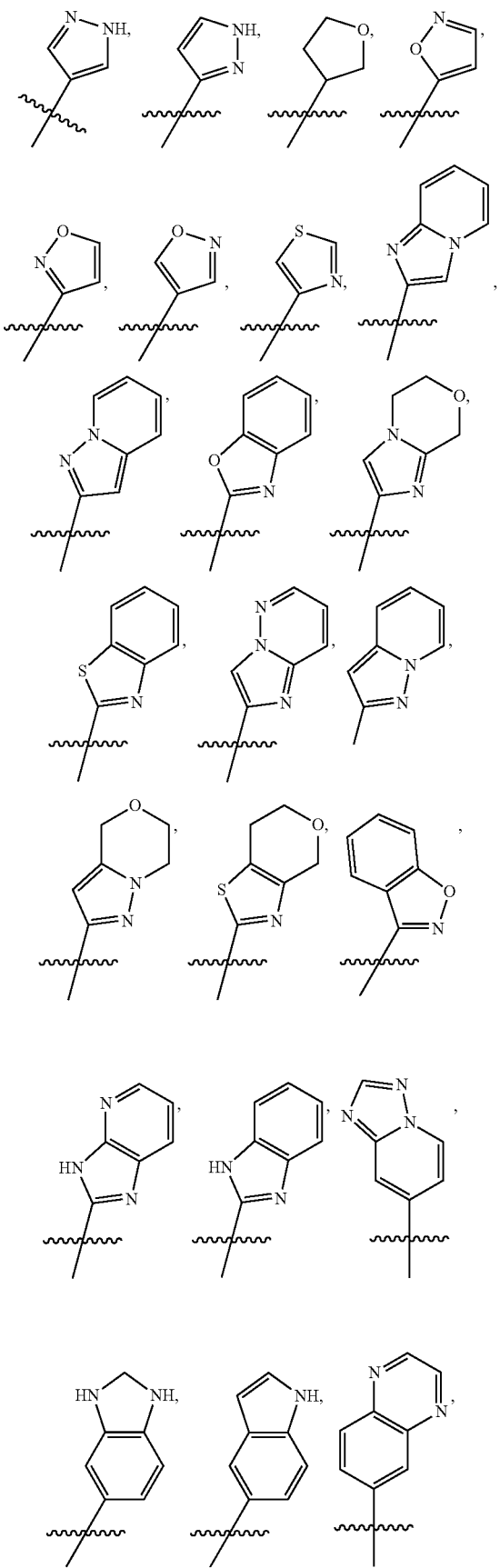

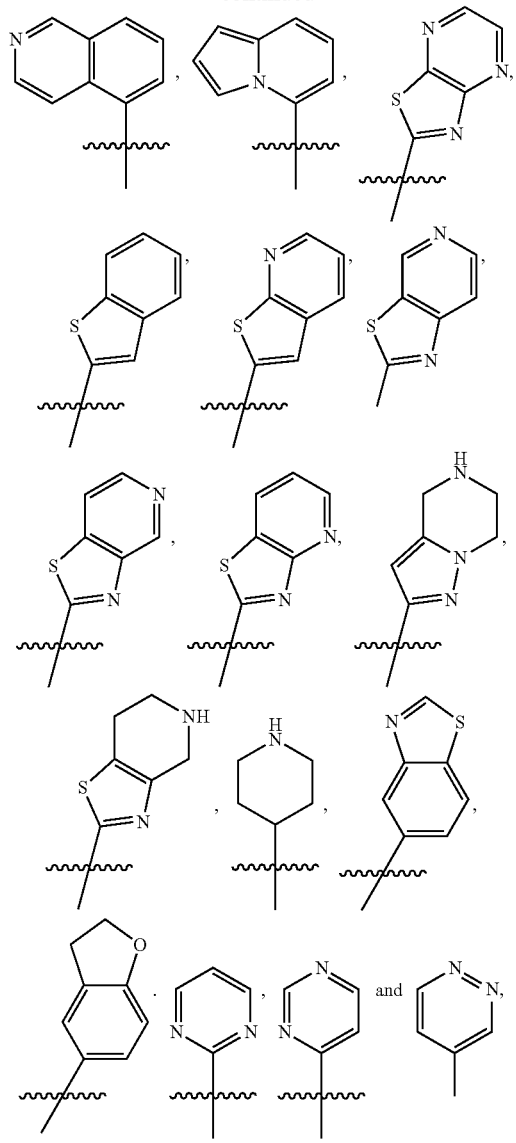

wherein the wavy line (∿) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$;

cycle B is selected from aryl; and heterocycle; wherein said aryl and heterocycle are optionally substituted with one, two, or three $Z^{1a}$; more particularly cycle B is selected from

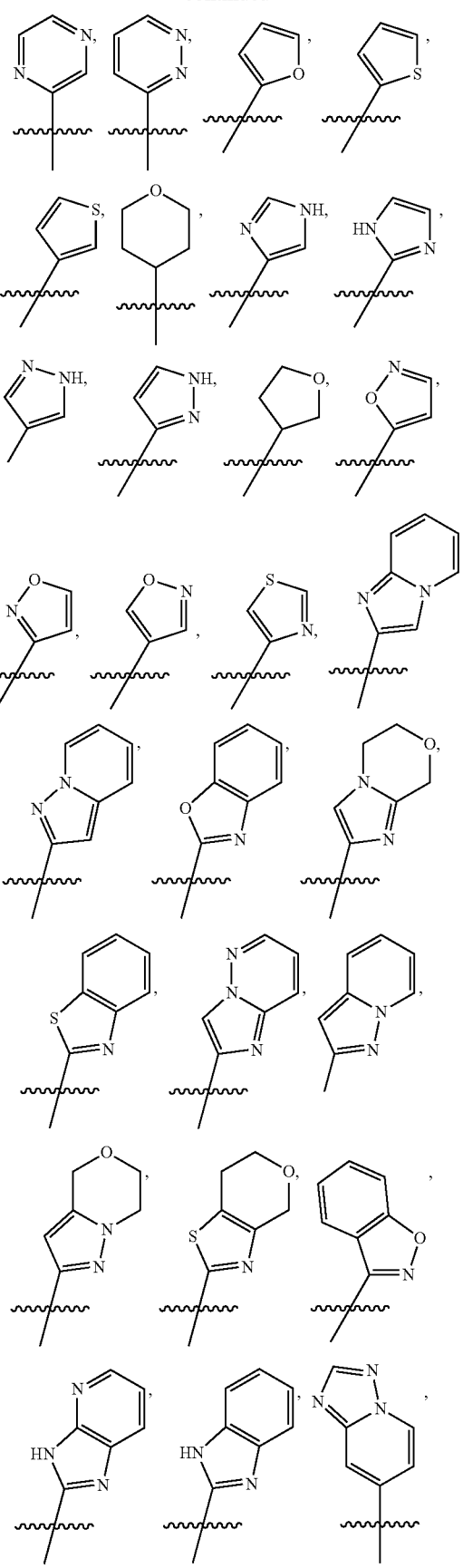

-continued

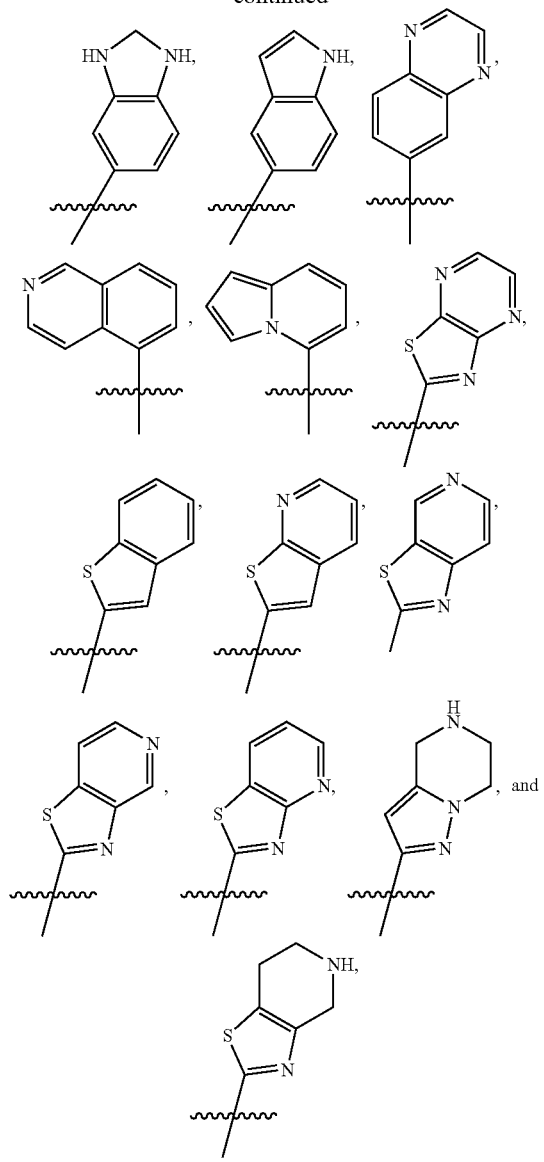

wherein the wavy line (~~~) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$ alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$ alkynyl, arylhetero$C_{1-6}$alkyl, arylhetero$C_{2-6}$ alkenyl, arylhetero$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$ alkenyl, and hetero$C_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$ alkynyl, are optionally substituted with one, two, or three $Z^{1c}$; preferably said $C_{1-6}$alkyl is optionally substituted with one, two, or three $Z^{1c}$;

$R^3$ is selected from hydrogen; $C_{1-6}$alkyl; hetero$C_{1-6}$alkyl; and =O;

each $R^4$ and $R^5$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero$C_{1-6}$alkyl; hetero$C_{1-6}$alkenyl; and hetero$C_{1-6}$ alkynyl;

$R^9$ is selected from hydrogen; $C_{1-6}$alkyl; hetero$C_{1-6}$alkyl; and =O;

each of $R^{12}$, $R^{14}$ and $R^{16}$ is independently selected from hydrogen; halogen; trifluoromethyl; cyano; $C_{1-6}$alkyl and $C_{1-6}$cycloalkyl;

each $R^{13}$, $R^{15}$ and $R^{17}$ is independently selected from hydrogen; $C_{1-6}$alkyl; and $C_{1-6}$cycloalkyl;

each $R^{32}$ and $R^{32a}$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero $C_{1-6}$alkyl; hetero$C_{2-6}$alkenyl; and hetero $C_{2-6}$alkynyl;

$R^{33}$ is independently selected from hydrogen and $C_{1-6}$alkyl;

each $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O) $Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$ alkynyl, aryl, heterocycle, aryl$C_{1-6}$alkyl, aryl$C_{2-6}$ alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$ alkyl, heterocycle-$C_{2-6}$alkenyl, heterocycle-$C_{2-6}$ alkynyl, heterocycle-hetero$C_{1-6}$alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)$_2Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —O$Z^2$, —O—C(=O)$Z^3$, =O, —S(=O)$_2Z^3$, —S(=O)$_2$ N$Z^4Z^5$, trifluoromethyl, trifluoromethoxy, —N$Z^4Z^5$, —N$Z^4$C(=O)$Z^2$, —N$Z^4$C(=O)—O$Z^2$, cyano, —C(=O)$Z^3$, —C(=O)O$Z^2$, —C(=O)N$Z^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl; preferably said C$_{1-6}$alkyl, heteroC$_{1-6}$ alkyl, aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$ C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-C$_{1-6}$alkyl; more preferably $Z^2$ is independently selected from $C_{1-6}$alkyl, aryl, and heterocycle-C$_{1-6}$alkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; preferably said C$_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$alkyl, —OCF$_3$, —S(=O)$_2$ C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; more preferably said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$ alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^3$ is independently selected from hydroxyl, C$_{1-6}$alkyl, aryl, and heterocycle; more preferably $Z^3$ is independently selected from hydroxyl, C$_{1-6}$alkyl, and heterocycle;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each $Z^4$ and $Z^5$ is independently selected from hydrogen, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, $C_{3-7}$cycloalkyl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^4$ and $Z^5$ is independently selected from hydrogen, C$_{1-6}$alkyl, aryl, C$_{3-7}$cycloalkyl, and heterocycle; more preferably each $Z^4$ and $Z^5$ is independently selected from hydrogen, C$_{1-6}$alkyl, and C$_{3-7}$cycloalkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—C$_{1-6}$alkyl, —OCF$_3$, cyano, nitro, —C(=O)OH or —NH$_2$;

and wherein $Z^4$ and $Z^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$.

29. The compound according to any one of statements 24 to 28, wherein
   each Z$^1$, Z$^{1a}$, Z$^{1b}$, and Z$^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, C$_{1-6}$alkyl, heteroC$_{1-6}$alkyl, aryl, heterocycle, and heterocycle-C$_{1-6}$alkyl;
   and wherein said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl; —S(O)$_2$C$_{1-4}$alkyl, and O—C$_{1-6}$alkyl;
   each Z$^2$ is independently selected from C$_{1-6}$alkyl, aryl, and heterocycle-C$_{1-6}$alkyl;
   wherein said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;
   each Z$^3$ is independently selected from hydroxyl, C$_{1-6}$alkyl, and heterocycle;
   wherein said C$_{1-6}$alkyl and heterocycle are optionally substituted with one, two, or three substituents selected from C$_{1-6}$alkyl and —N(CH$_3$)$_2$;
   each Z$^4$ and Z$^5$ is independently selected from hydrogen, C$_{1-6}$alkyl, and C$_{3-7}$cycloalkyl.

30. The compounds according to any one of statements 24 to 29, wherein the flavivirus infection is an infection with a Dengue virus or a yellow fever virus.

31. A pharmaceutical composition comprising a pharmaceutically acceptable carrier, and as active ingredient an effective amount of the compound according to any one of statements 16 to 29 or a pharmaceutically acceptable salt thereof.

32. A method for the preparation of the compound according to any one of statements 16 to 29 comprising the step of reacting an imine with an aldehyde under umpolung conditions in the presence of a thiazolium catalyst to obtain the desired compounds of the invention.

33. A method for the preparation of the compound according to any one of statements 16 to 29 comprising the step of reacting a ketone derivative having a methylene adjacent to the carbonyl under halogenation conditions to obtain an alpha-halogenoketone,
   substitute the previously obtained alpha-halogenoketone with amines to obtain the desired compounds of the invention.

34. A method for the preparation of the compound according to any one of statements 16 to 29 comprising the step of reacting a heterocyclicamine with 2-halogeno-acetic acid halide to obtain an alpha-halogenoamide derivative,
   substitute the previously obtained alpha-halogenoamide with amines to obtain the desired compounds of the invention.

35. A method of treatment or prevention of Flaviviral infections, in humans by the administration of an effective amount of a compound according to any one of statements 16 to 29 or a pharmaceutically acceptable salt thereof, optionally in combination with one or more other medicines, to a patient in need thereof.

36. The method according to statement 35, wherein the Flaviviral infection is an infection by the Dengue virus or yellow fever virus.

37. The compound according to any one of statements 1-10, 14-29, or a pharmaceutical composition according to any one of statements 7 to 10, wherein
   cycle C is a monocycle selected from

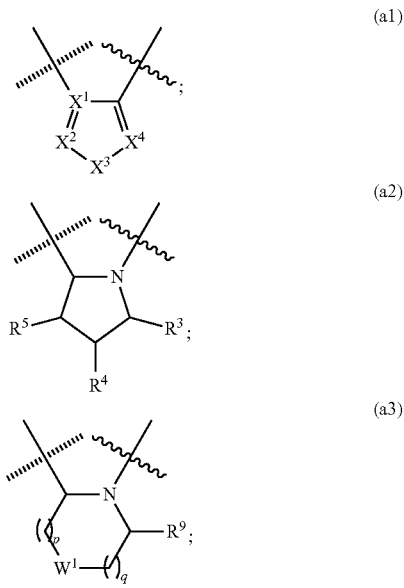

wherein the wavy line ( $\sim\!\sim$ ) indicates the point of attachment to the carbonyl of the main formula (A) and the hashed line ( ⫶⫶⫶ ) indicates the point of attachment to the cycle A of the main formula (A);
   X$^1$ is selected from C; and N;
   X$^2$ is selected from CR$^{12}$; NR$^{13}$; N; O; and S;
   X$^3$ is selected from CR$^{14}$, NR$^{15}$; N; O; and S;
   X$^4$ is selected from CR$^{16}$, NR$^{17}$; N; O; and S;
   each R$^3$ and R$^9$ is independently selected from hydrogen; C$_{1-6}$alkyl; C$_{2-6}$alkenyl; C$_{2-6}$alkynyl; heteroC$_{1-6}$alkyl; heteroC$_{2-6}$alkenyl; heteroC$_{2-6}$alkynyl; =O; and =S; wherein said C$_{1-6}$alkyl, C$_{2-6}$alkenyl, C$_{2-6}$alkynyl, heteroC$_{1-6}$alkyl, heteroC$_{2-6}$alkenyl, and heteroC$_{2-6}$alkynyl can be unsubstituted or substituted with one or more substituents selected from hydroxyl, =O, halogen, —SH, =S, trifluoromethyl, —OCF$_3$, cyano, nitro, —C(O)OH or NH$_2$;
   each R$^4$ and R$^5$ is independently selected from hydrogen; halogen; hydroxyl; sulfhydryl; =O; =S; trifluoromethyl; trifluoromethoxy; cyano; C$_{1-6}$alkyl; C$_{2-6}$alkenyl; C$_{2-6}$alkynyl; heteroC$_{1-6}$alkyl; heteroC$_{2-6}$alkenyl; and heteroC$_{2-6}$alkynyl; and wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, can be unsubstituted or substituted with one or more substituents selected from hydroxyl, =O, halogen, —SH, =S, trifluoromethyl, —OCF$_3$, cyano, nitro, —C(O)OH or NH$_2$;
   W$^1$ is selected from CR$^{32}$R$^{32a}$; NR$^{33}$; O; S; and SO$_2$;
   each p and q is independently selected from 1 and 2, whereby p+q is selected from 2 and 3;
   cycle A is selected from the group consisting of C$_{3-7}$cycloalkyl; C$_{5-7}$cycloalkenyl; C$_{5-7}$cycloalkynyl;

$C_{6-12}$aryl; and heterocycle; wherein said $C_{3-7}$cycloalkyl, $C_{5-7}$cycloalkenyl, $C_{5-7}$cycloalkynyl, $C_{6-12}$aryl and heterocycle, can be unsubstituted or substituted with one or more substituents selected from $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero $C_{1-6}$alkyl, hetero $C_{2-6}$alkenyl, hetero $C_{2-6}$alkynyl, hydroxyl, =O, halogen, —SH, =S, trifluoromethyl, —OCF$_3$, cyano, nitro, —C(O)OH, —NH$_2$, NH($C_{1-6}$alkyl), or N($C_{1-6}$alkyl)$_2$;

cycle B is selected from aryl; and heterocycle; wherein said aryl and heterocycle are optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)Z$^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)Z$^3$, and $C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

$R^3$ is selected from hydrogen; $C_{1-6}$alkyl; hetero$C_{1-6}$alkyl; and =O;

each $R^4$ and $R^5$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero$C_{1-6}$alkyl; hetero$C_{2-6}$alkenyl; and hetero$C_{2-6}$alkynyl;

$R^9$ is selected from hydrogen; $C_{1-6}$alkyl; hetero$C_{1-6}$alkyl; and =O;

each of $R^{12}$, $R^{14}$ and $R^{16}$ is independently selected from hydrogen; halogen; trifluoromethyl; cyano; $C_{1-6}$alkyl and $C_{1-6}$cycloalkyl;

each $R^{13}$, $R^{15}$ and $R^{17}$ is independently selected from hydrogen; $C_{1-6}$alkyl; and $C_{1-6}$cycloalkyl;

each $R^{32}$ and $R^{32a}$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero $C_{1-6}$alkyl; hetero$C_{2-6}$alkenyl; and hetero$C_{2-6}$alkynyl;

$R^{33}$ is independently selected from hydrogen and $C_{1-6}$alkyl;

each $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$ alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)$_2$Z$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$ alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$ alkynyl, are optionally substituted with one, two or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl; preferably said $C_{1-6}$alkyl, hetero$C_{1-6}$ alkyl, aryl, heterocycle, and heterocycle-$C_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$ alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$ C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl;

preferably Z² is independently selected from C₁₋₆alkyl, aryl, heterocycle, and heterocycle-C₁₋₆alkyl; more preferably Z² is independently selected from C₁₋₆alkyl, aryl, and heterocycle-C₁₋₆alkyl;
  wherein said C₁₋₆alkyl, C₂₋₆alkenyl, C₂₋₆alkynyl, heteroC₁₋₆alkyl, heteroC₂₋₆alkenyl, heteroC₂₋₆alkynyl, aryl, heterocycle, arylC₁₋₆alkyl, arylC₂₋₆alkenyl, arylC₂₋₆alkynyl, arylheteroC₁₋₆alkyl, arylheteroC₂₋₆alkenyl, arylheteroC₂₋₆alkynyl, heterocycle-C₁₋₆alkyl, heterocycle-C₂₋₆alkenyl, heterocycle-C₂₋₆alkynyl, heterocycle-heteroC₁₋₆alkyl, heterocycle-heteroC₂₋₆alkenyl, and heterocycle-heteroC₂₋₆ alkynyl, are optionally substituted with one, two, or three substituents selected from C₁₋₆alkyl, C₂₋₆alkenyl, C₂₋₆alkynyl, hydroxyl, =O, halogen, —SH, =S, trifluoromethyl, difluoromethyl, —O—C₁₋₆ alkyl, —OCF₃, —S(=O)₂C₁₋₄alkyl, cyano, nitro, —C(=O)OH, —C(=O)O—C₁₋₄alkyl, —NH₂, —N(CH₃)₂, pyrrolidinyl, piperidinyl, and piperazinyl; preferably said C₁₋₆alkyl, aryl, heterocycle, and heterocycle-C₁₋₆alkyl, are optionally substituted with one, two, or three substituents selected from hydroxyl, =O, halogen, —SH, =S, trifluoromethyl, difluoromethyl, —O—C₁₋₆alkyl, —OCF₃, —S(=O)₂ C₁₋₄alkyl, cyano, nitro, —C(=O)OH, —C(=O)O—C₁₋₄alkyl, —NH₂, —N(CH₃)₂, pyrrolidinyl, piperidinyl, and piperazinyl; more preferably said C₁₋₆alkyl, and aryl, are optionally substituted with one, two, or three substituents selected from hydroxyl, halogen, difluoromethyl, —O—C₁₋₆alkyl, —S(=O)₂C₁₋₄alkyl, —C(=O)OH, —C(=O)O—C₁₋₄alkyl, —NH₂, —N(CH₃)₂, pyrrolidinyl, piperidinyl, and piperazinyl;
each Z³ is independently selected from hydroxyl, C₁₋₆alkyl, C₂₋₆alkenyl, C₂₋₆alkynyl, heteroC₁₋₆alkyl, heteroC₂₋₆alkenyl, heteroC₂₋₆alkynyl, aryl, heterocycle, arylC₁₋₆alkyl, arylC₂₋₆alkenyl, arylC₂₋₆alkynyl, arylheteroC₁₋₆alkyl, arylheteroC₂₋₆alkenyl, arylheteroC₂₋₆alkynyl, heterocycle-C₁₋₆alkyl, heterocycle-C₂₋₆ alkenyl, heterocycle-C₂₋₆alkynyl, heterocycle-heteroC₁₋₆alkyl, heterocycle-heteroC₂₋₆alkenyl, and heterocycle-heteroC₂₋₆alkynyl; preferably Z³ is independently selected from hydroxyl, C₁₋₆alkyl, aryl, and heterocycle; more preferably Z³ is independently selected from hydroxyl, C₁₋₆alkyl, and heterocycle;
  wherein said C₁₋₆alkyl, C₂₋₆alkenyl, C₂₋₆alkynyl, heteroC₁₋₆alkyl, heteroC₂₋₆alkenyl, heteroC₂₋₆alkynyl, aryl, heterocycle, arylC₁₋₆alkyl, arylC₂₋₆alkenyl, arylC₂₋₆alkynyl, arylheteroC₁₋₆alkyl, arylheteroC₂₋₆alkenyl, arylheteroC₂₋₆alkynyl, heterocycle-C₁₋₆alkyl, heterocycle-C₂₋₆alkenyl, heterocycle-C₂₋₆alkynyl, heterocycle-heteroC₁₋₆alkyl, heterocycle-heteroC₂₋₆alkenyl, and heterocycle-heteroC₂₋₆ alkynyl, are optionally substituted with one, two, or three substituents selected from C₁₋₆alkyl, C₂₋₆alkenyl, C₂₋₆alkynyl, hydroxyl, =O, halogen, —SH, =S, trifluoromethyl, —O—C₁₋₆alkyl, —OCF₃, cyano, nitro, —C(=O)OH, —NH₂, and —N(CH₃)₂; preferably said C₁₋₆alkyl, aryl, and heterocycle are optionally substituted with one, two, or three substituents selected from C₁₋₆alkyl and —N(CH₃)₂; more preferably said C₁₋₆alkyl and heterocycle are optionally substituted with one, two, or three substituents selected from C₁₋₆alkyl and —N(CH₃)₂;
each Z⁴ and Z⁵ is independently selected from hydrogen, C₁₋₆alkyl, C₂₋₆alkenyl, C₂₋₆alkynyl, heteroC₁₋₆alkyl, heteroC₂₋₆alkenyl, heteroC₂₋₆alkynyl, aryl, C₃₋₇cycloalkyl, heterocycle, arylC₁₋₆alkyl, arylC₂₋₆alkenyl, arylC₂₋₆alkynyl, arylheteroC₁₋₆alkyl, arylheteroC₂₋₆alkenyl, arylheteroC₂₋₆alkynyl, heterocycle-C₁₋₆alkyl, heterocycle-C₂₋₆alkenyl, heterocycle-C₂₋₆alkynyl, heterocycle-heteroC₁₋₆alkyl, heterocycle-heteroC₂₋₆alkenyl, and heterocycle-heteroC₂₋₆alkynyl; preferably each Z⁴ and Z⁵ is independently selected from hydrogen, C₁₋₆alkyl, aryl, C₃₋₇cycloalkyl, and heterocycle; more preferably each Z⁴ and Z⁵ is independently selected from hydrogen, C₁₋₆alkyl, and C₃₋₇cycloalkyl;
  wherein said C₁₋₆alkyl, C₂₋₆alkenyl, C₂₋₆alkynyl, heteroC₁₋₆alkyl, heteroC₂₋₆alkenyl, heteroC₂₋₆alkynyl, aryl, heterocycle, arylC₁₋₆alkyl, arylC₂₋₆alkenyl, arylC₂₋₆alkynyl, arylheteroC₁₋₆alkyl, arylheteroC₂₋₆alkenyl, arylheteroC₂₋₆alkynyl, heterocycle-C₁₋₆alkyl, heterocycle-C₂₋₆alkenyl, heterocycle-C₂₋₆alkynyl, heterocycle-heteroC₁₋₆alkyl, heterocycle-heteroC₂₋₆alkenyl, and heterocycle-heteroC₂₋₆ alkynyl, are optionally substituted with one, two, or three substituents selected from C₁₋₆alkyl, C₂₋₆alkenyl, C₂₋₆alkynyl, hydroxyl, =O, halogen, —SH, =S, trifluoromethyl, —O—C₁₋₆alkyl, —OCF₃, cyano, nitro, —C(=O)OH or —NH₂;
  and wherein Z⁴ and Z⁵ can be taken together in order to form a (5-, 6-, or 7-membered) heterocycle which is optionally substituted with C₁₋₆alkyl, C₂₋₆alkenyl, C₂₋₆alkynyl, hydroxyl, halogen, —SH, trifluoromethyl, —O—C₁₋₆alkyl, —OCF₃, cyano, nitro, —C(=O)OH, or —NH₂;
preferably wherein said heteroC₁₋₆alkyl as a group or part of a group is selected from 00-O—C₁₋₅alkyl, —O—C₁₋₆ alkyl, —NH—C₁₋₆alkyl, —N(C₁₋₆alkyl)₂, —S(=O)₂ C₁₋₆alkyl, and —S—C₁₋₆alkyl.

38. The compound according to any one of statements 1-10, 14-29, 37 or a pharmaceutical composition according to any one of statements 7 to 10, wherein cycle B is selected from

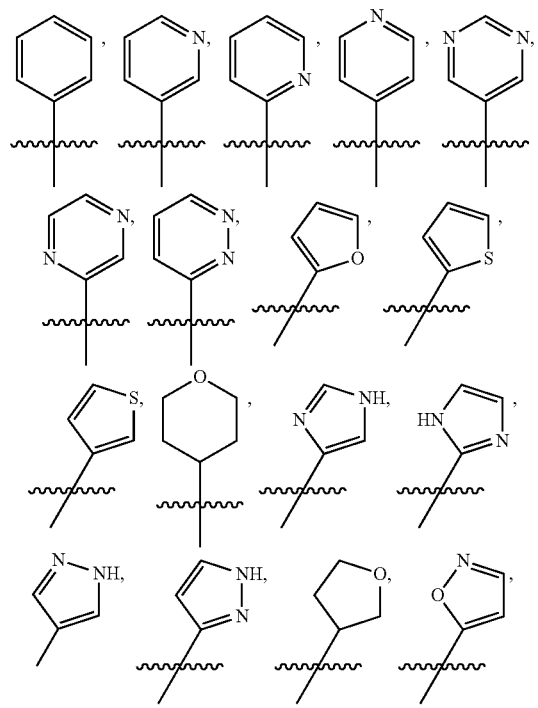

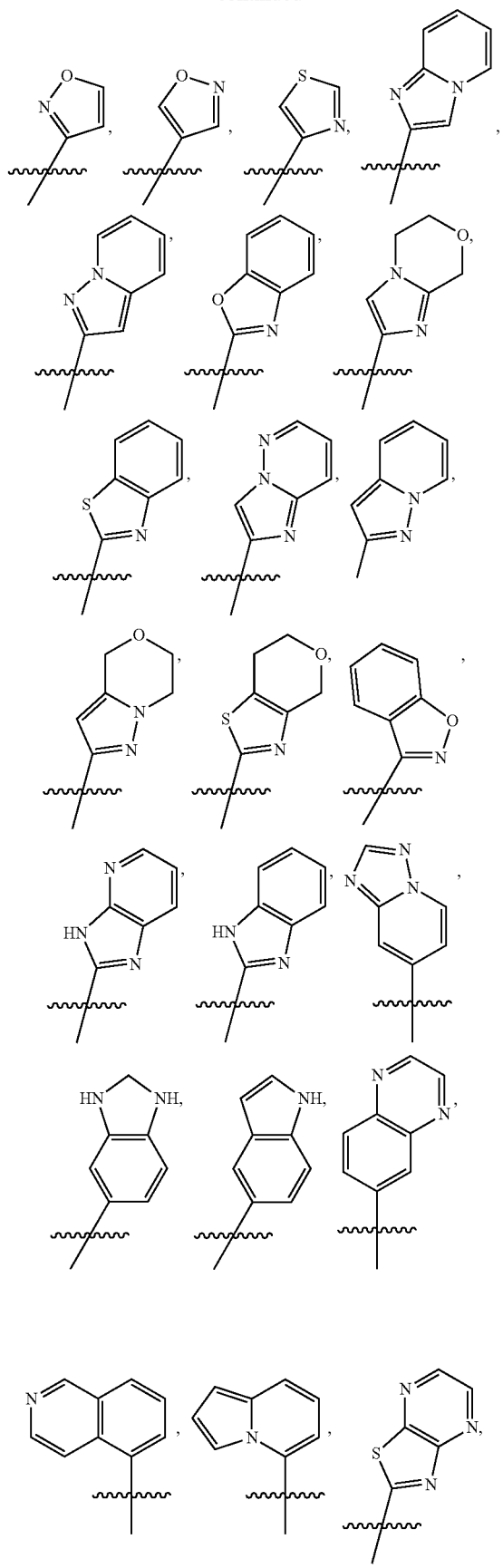
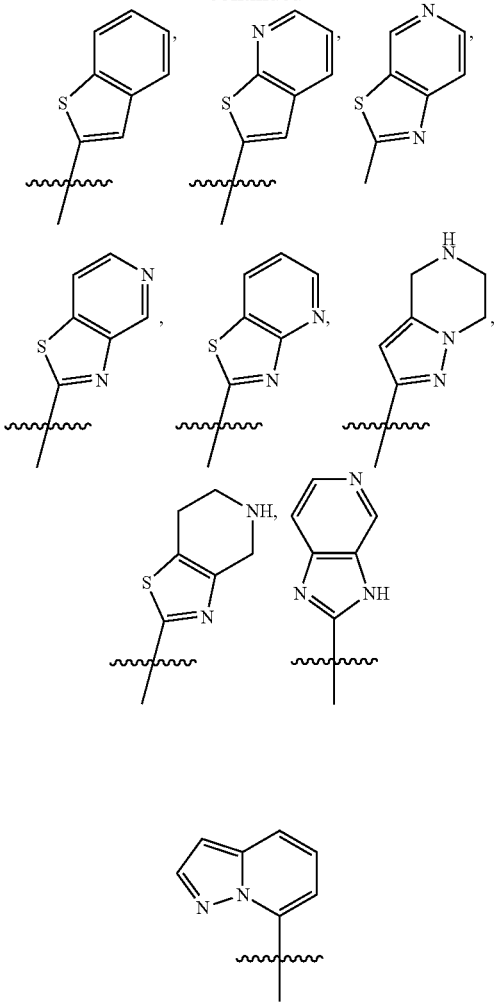

and wherein the wavy line (∿∿∿) indicates the point of attachment to the carbon atom of the main formula (A), and wherein the depicted cycles may be optionally substituted with one, two, or three $Z^{1a}$.

39. The compound according to any one of statements 1-10, 14-29, 37 or a pharmaceutical composition according to any one of statements 7 to 10, wherein B is selected from the group comprising unsubstituted or substituted with one or more $Z^{1a}$ (for example one, two or three $Z^{1a}$) phenyl, pyrazinyl, pyrazolo[1,5-a]pyridinyl; isoxazolyl; 6,8-dihydro-5H-imidazolo[2,1-c]1,4-oxazinyl; tetrahydropyranyl, thiophenyl, tetrahydrofuranyl, pyrimidinyl, furanyl, imidazo[1,2-a]pyridinyl; imidazolyl; quinoxalinyl, pyrazolyl; 1,3-dihydrobenzimidazolyl; isoquinolinyl; thiazolyl; indolyl; pyridazinyl; thiazolo[4,5-b]pyrazinyl; 1H-imidazo[4,5-b]pyridinyl; 1,3-benzoxazolyl; 1,3-benzothiazolyl; and 4,5,6,7-tetrahydropyrazolo[1,5-a]pyrazinyl.

40. The compound according to any one of statements 1-10, 14-29, 37-39; or a pharmaceutical composition according to any one of statements 7 to 10, wherein each $Z^{1a}$, is independently selected from the group consisting of halogen; hydroxyl; sulfhydryl; —$OZ^2$; =O; —$SZ^2$; =S; —$S(O)Z^2$; —$S(O)_2Z^3$; —$S(O)_2NZ^4Z^5$; trifluoromethyl; trifluoromethoxy; nitro; —$NZ^4Z^5$; —$NZ^4S(O)_2Z^2$; —$NZ^4C(O)Z^2$; —$NZ^4C(O)NZ^4Z^5$; cyano; —$C(O)Z^3$;

—C(O)OZ²; —C(O)NZ⁴Z⁵; —C(O)H; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; hetero$C_{2-6}$alkynyl; $C_{6-12}$aryl; heterocycle; $C_{6-12}$aryl$C_{1-6}$alkyl; $C_{6-12}$aryl$C_{2-6}$alkenyl; $C_{6-12}$aryl$C_{2-6}$alkynyl; $C_{6-12}$arylhetero$C_{1-6}$alkyl; $C_{6-12}$arylhetero$C_{2-6}$alkenyl; $C_{6-12}$arylhetero$C_{2-6}$alkynyl; heterocycle-$C_{1-6}$alkyl; heterocycle-$C_{2-6}$alkenyl; heterocycle-$C_{2-6}$alkynyl; heterocycle-hetero$C_{1-6}$alkyl, heterocycle-hetero$C_{2-6}$alkenyl; or heterocycle-hetero$C_{2-6}$alkynyl, and wherein said $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero$C_{1-6}$alkyl, hetero$C_{2-6}$alkenyl, hetero$C_{2-6}$alkynyl, $C_{6-12}$aryl, heterocycle, $C_{6-12}$aryl$C_{1-6}$alkyl, $C_{6-12}$aryl$C_{2-6}$ alkenyl, $C_{6-12}$aryl$C_{2-6}$alkynyl, $C_{6-12}$arylhetero$C_{1-6}$ alkyl, $C_{6-12}$arylhetero$C_{2-6}$alkenyl, $C_{6-12}$arylhetero$C_{2-6}$ alkynyl, heterocycle-alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, or heterocycle-hetero$C_{2-6}$alkynyl can be unsubstituted or substituted with one or more substituents selected from $C_{1-6}$alkyl, $C_{2-6}$alkenyl, $C_{2-6}$alkynyl, hetero$C_{1-6}$ alkyl, hetero$C_{2-6}$ alkenyl, hetero$C_{2-6}$alkynyl, hydroxyl, =O, halogen, —SH, =S, trifluoromethyl, —OCF₃, cyano, nitro, —C(O)OHNH₂; or —NZ⁴Z⁵;
preferably wherein said hetero$C_{1-6}$alkyl as a group or part of a group is selected from —CO—O—$C_{1-5}$alkyl, —O—$C_{1-6}$alkyl, —NH—$C_{1-6}$alkyl, —N($C_{1-6}$alkyl)₂, —S(=O)₂$C_{1-6}$alkyl, and —S—$C_{1-6}$alkyl.

41. The compound according to any one of statements 1-10, 14-29, 37-40; or a pharmaceutical composition according to any one of statements 7 to 10, wherein each $Z^{1b}$, is independently selected from the group consisting of halogen; hydroxyl; sulfhydryl; —OZ²; =O; —SZ²; =S; —S(O)Z²; —S(O)₂Z³; —S(O)₂NZ⁴Z⁵; trifluoromethyl; trifluoromethoxy; nitro; —NZ⁴Z⁵; —NZ⁴S(O)₂Z²; —NZ⁴C(O)Z²; —NZ⁴C(O)NZ⁴Z⁵; cyano; —C(O)Z³; —C(O)OZ²; —C(O)NZ⁴Z⁵; —C(O)H; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; hetero$C_{2-6}$alkynyl; $C_{6-12}$aryl; heterocycle; $C_{6-12}$aryl$C_{1-6}$alkyl; $C_{6-12}$aryl$C_{2-6}$alkenyl; $C_{6-12}$aryl$C_{2-6}$alkynyl; $C_{6-12}$arylhetero$C_{1-6}$alkyl; $C_{6-12}$arylhetero$C_{2-6}$alkenyl; $C_{6-12}$arylhetero$C_{2-6}$alkynyl; heterocycle-$C_{1-6}$alkyl; heterocycle-$C_{2-6}$alkenyl; heterocycle-$C_{2-6}$alkynyl; heterocycle-hetero$C_{1-6}$alkyl, heterocycle-hetero$C_{2-6}$alkenyl; or heterocycle-hetero$C_{2-6}$alkynyl, and wherein said $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero$C_{1-6}$alkyl, hetero$C_{2-6}$ alkenyl, hetero$C_{2-6}$alkynyl, $C_{6-12}$aryl, heterocycle, $C_{6-12}$aryl$C_{1-6}$alkyl, $C_{6-12}$aryl$C_{2-6}$alkenyl, $C_{6-12}$aryl$C_{2-6}$ alkynyl, $C_{6-12}$arylhetero$C_{1-6}$alkyl, $C_{6-12}$arylhetero$C_{2-6}$ alkenyl, $C_{6-12}$arylhetero$C_{2-6}$alkynyl, heterocycle-alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, or heterocycle-hetero$C_{2-6}$alkynyl can be unsubstituted or substituted with one or more substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF₃, cyano, nitro, —C(O)OHNH₂; or —NZ⁴Z⁵;
preferably wherein said hetero$C_{1-6}$alkyl as a group or part of a group is selected from —CO—O—$C_{1-5}$alkyl, —O—$C_{1-6}$alkyl, —NH—$C_{1-6}$alkyl, —N($C_{1-6}$alkyl)₂, —S(=O)₂$C_{1-6}$alkyl, and —S—$C_{1-6}$alkyl.

42. The compound according to any one of statements 1-10, 14-29, 37-41; or a pharmaceutical composition according to any one of statements 7 to 10, wherein each $Z^{1c}$, is independently selected from the group consisting of halogen; hydroxyl; sulfhydryl; —OZ²; =O; —SZ²; =S; —S(O)Z²; —S(O)₂Z³; —S(O)₂NZ⁴Z⁵; trifluoromethyl; trifluoromethoxy; nitro; —NZ⁴Z⁵; —NZ⁴S(O)₂Z²; —NZ⁴C(O)Z²; —NZ⁴C(O)NZ⁴Z⁵; cyano; —C(O)Z³; —C(O)OZ²; —C(O)NZ⁴Z⁵; —C(O)H; $C_{1-6}$alkyl; $C_{3-7}$cycloalkyl; $C_{2-6}$alkenyl; $C_{5-7}$cycloalkenyl; $C_{2-6}$alkynyl; $C_{5-7}$cycloalkynyl; hetero$C_{1-6}$alkyl; hetero$C_{2-6}$alkenyl; hetero$C_{2-6}$alkynyl; $C_{6-12}$aryl; heterocycle; $C_{6-12}$aryl$C_{1-6}$alkyl; $C_{6-12}$aryl$C_{2-6}$alkenyl; $C_{6-12}$aryl$C_{2-6}$alkynyl; $C_{6-12}$arylhetero$C_{1-6}$alkyl; $C_{6-12}$arylhetero$C_{2-6}$alkenyl; $C_{6-12}$arylhetero$C_{2-6}$alkynyl; heterocycle-$C_{1-6}$alkyl; heterocycle-$C_{2-6}$alkenyl; heterocycle-$C_{2-6}$alkynyl; heterocycle-hetero$C_{1-6}$alkyl, heterocycle-hetero$C_{2-6}$alkenyl; or heterocycle-hetero$C_{2-6}$alkynyl, and wherein said $C_{1-6}$alkyl, $C_{3-7}$cycloalkyl, $C_{2-6}$alkenyl, $C_{5-7}$cycloalkenyl, $C_{2-6}$alkynyl, $C_{5-7}$cycloalkynyl, hetero$C_{1-6}$alkyl, hetero$C_{2-6}$ alkenyl, hetero$C_{2-6}$alkynyl, $C_{6-12}$aryl, heterocycle, $C_{6-12}$aryl$C_{1-6}$alkyl, $C_{6-12}$aryl$C_{2-6}$alkenyl, $C_{6-12}$aryl$C_{2-6}$alkynyl, $C_{6-12}$arylhetero$C_{1-6}$alkyl, $C_{6-12}$arylhetero$C_{2-6}$alkenyl, $C_{6-12}$arylhetero$C_{2-6}$alkynyl, heterocycle-alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, or heterocycle-hetero$C_{2-6}$alkynyl can be unsubstituted or substituted with one or more substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF₃, cyano, nitro, —C(O)OHNH₂; or —NZ⁴Z⁵;
preferably wherein said hetero$C_{1-6}$alkyl as a group or part of a group is selected from —CO—O—$C_{1-5}$alkyl, —O—$C_{1-6}$alkyl, —NH—$C_{1-6}$alkyl, —N($C_{1-6}$alkyl)₂, —S(=O)₂$C_{1-6}$alkyl, and —S—$C_{1-6}$alkyl.

43. The compound according to any one of statements 1-10, 14-29, 37-42; or a pharmaceutical composition according to any one of statements 7 to 10, wherein, cycle A is selected from the group consisting of $C_{3-7}$cycloalkyl; $C_{5-7}$cycloalkenyl; $C_{5-7}$cycloalkynyl; $C_{6-12}$aryl; and heterocycle; wherein said $C_{3-7}$cycloalkyl, $C_{5-7}$cycloalkenyl, $C_{5-7}$cycloalkynyl, $C_{6-12}$aryl and heterocycle, can be unsubstituted or substituted with one or more substituents selected from $C_{1-6}$alkyl, $C_{3-7}$cycloalkyl, $C_{2-6}$alkenyl, $C_{6-7}$cycloalkenyl, $C_{2-6}$alkynyl, $C_{6-7}$cycloalkynyl, hetero$C_{1-6}$alkyl, hetero $C_{2-6}$alkenyl, hetero $C_{2-6}$alkynyl, hydroxyl, =O, halogen, —SH, =S, trifluoromethyl, —OCF₃, cyano, nitro, —C(O)OH, —NH₂, NH($C_{1-6}$ alkyl), or N($C_{1-6}$alkyl)₂; preferably wherein said hetero$C_{1-6}$alkyl as a group or part of a group is selected from —CO—O—$C_{1-6}$alkyl, —O—$C_{1-6}$alkyl, —NH—$C_{1-6}$ alkyl, —N($C_{1-6}$alkyl)₂, —S(=O)₂$C_{1-6}$alkyl, and S—$C_{1-6}$alkyl.

44. The compound according to any one of statements 1-10, 14-29, 37-43; or a pharmaceutical composition according to any one of statements 7 to 10, wherein cycle A is selected from

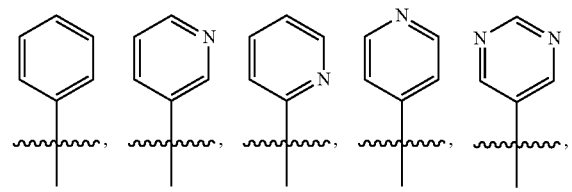

-continued
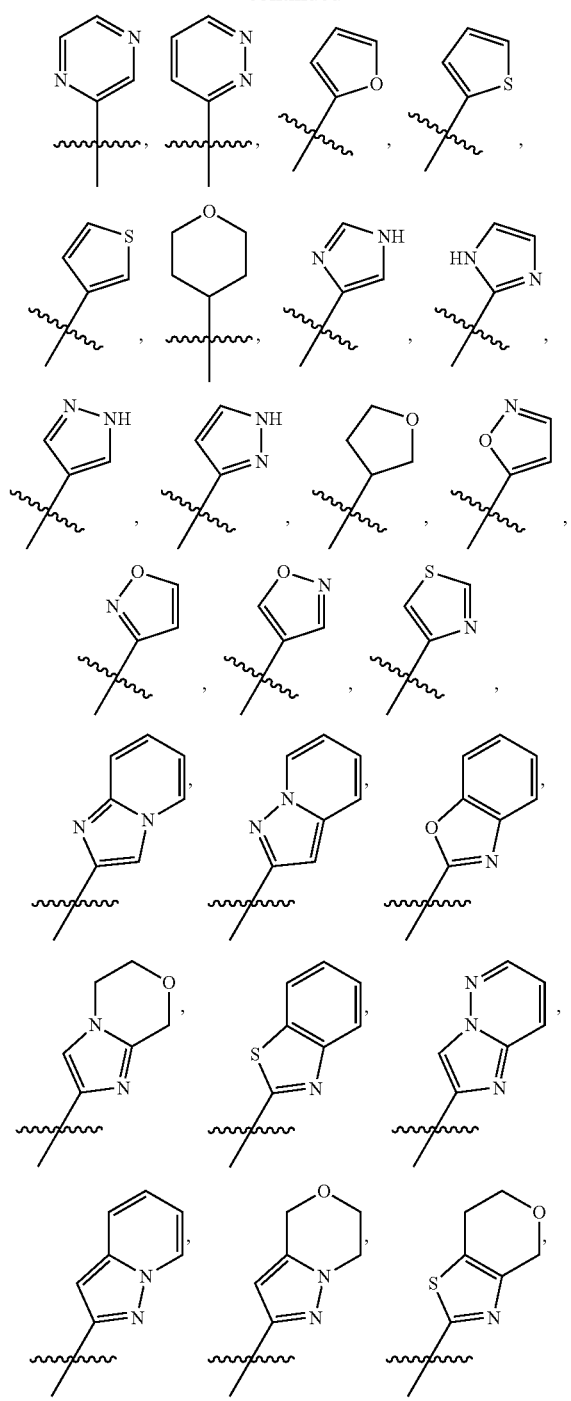
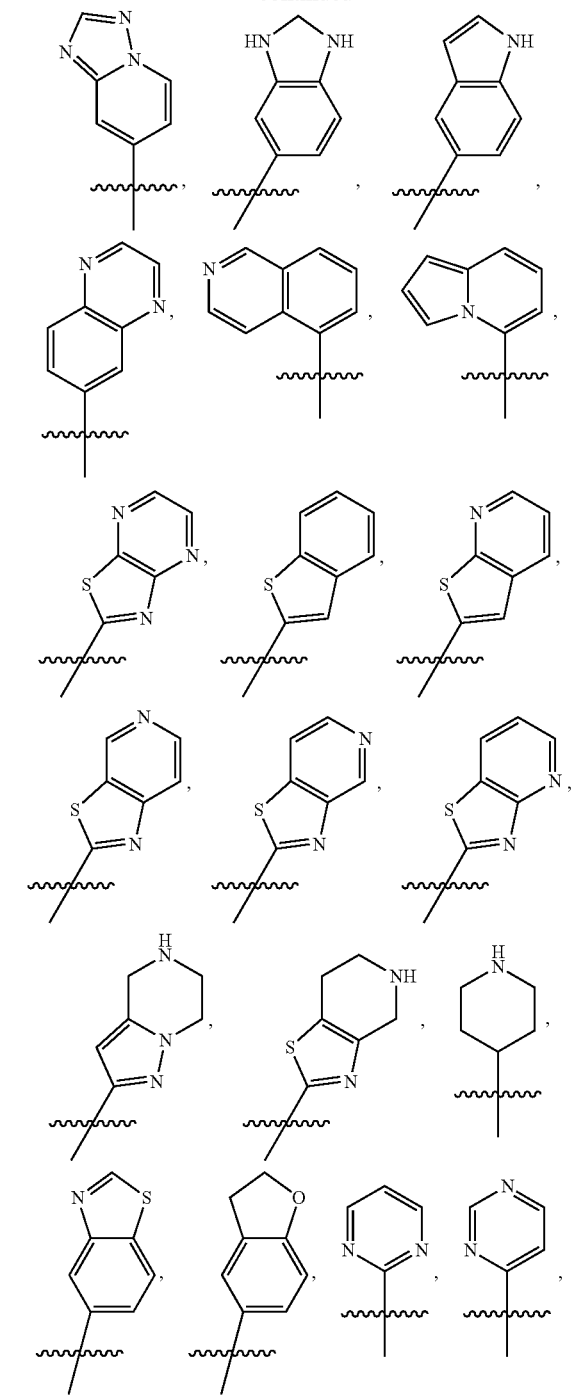
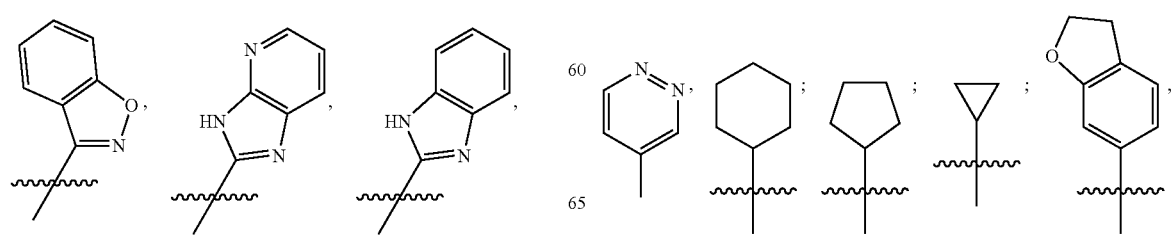

-continued

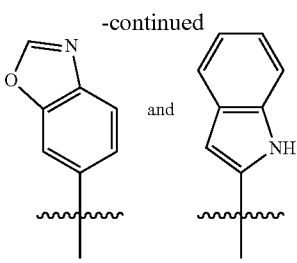
and wherein the wavy line (⌇) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$; preferably wherein said heteroC$_{1-6}$ alkyl as a group or part of a group is selected from —CO—O—C$_{1-5}$alkyl, —O—C$_{1-6}$alkyl, —NH—C$_{1-6}$alkyl, —N(C$_{1-6}$alkyl)$_2$, —S(=O)$_2$C$_{1-6}$alkyl, and —S—C$_{1-6}$alkyl.

45. The compound according to any one of statements 1-10, 14-29, 37-43; or a pharmaceutical composition according to any one of statements 7 to 10, wherein cycle A is selected from the group comprising unsubstituted or substituted with one or more substituents (for example one, two or three substituents) phenyl; pyrazolyl; pyrimidinyl; pyridinyl; thiophenyl; isoxazolyl; benzothiazolyl; furanyl; 1,3-benzoxazolyl; pyrazinyl; 2,3-dihydrobenzo[b]furanyl; indolyl; cyclopropyl; cyclopentyl; cyclohexyl; piperidinyl; tetrahydropyranyl; wherein said substituent can be each independently selected from C$_{1-6}$alkyl, C$_{3-7}$cycloalkyl, C$_{2-6}$alkenyl, C$_{5-7}$cycloalkenyl, C$_{2-6}$alkynyl, C$_{5-7}$cycloalkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, cyano, nitro, —C(O)OH, —NH$_2$, NH(alkyl), or N(alkyl)$_2$; preferably wherein said heteroC$_{1-6}$alkyl as a group or part of a group is selected from —CO—O—C$_{1-5}$alkyl, —O—C$_{1-6}$alkyl, —NH—C$_{1-6}$alkyl, —N(C$_{1-6}$alkyl)$_2$, —S(=O)$_2$C$_{1-6}$alkyl, and —S—C$_{1-6}$alkyl.

46. The compound according to any one of statements 1-10, 14-29, 37-45; or a pharmaceutical composition according to any one of statements 7 to 10, wherein
R$^1$ is selected from C$_{3-7}$cycloalkyl; C$_{6-12}$aryl; heterocycle; C$_{6-12}$arylC$_{1-6}$alkyl; heterocycle-C$_{1-6}$alkyl; C$_{6-12}$aryl-heteroC$_{1-6}$alkyl; heterocycle-heteroC$_{1-6}$alkyl;
and wherein said C$_{3-7}$cycloalkyl; C$_{6-12}$aryl, heterocycle, C$_{6-12}$arylC$_{1-6}$alkyl, heterocycle-C$_{1-6}$alkyl, C$_{6-12}$arylheteroC$_{1-6}$alkyl, heterocycle-heteroC$_{1-6}$alkyl, can be unsubstituted or substituted with one or more Z$^{1b}$;
each Z$^{1b}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, C$_{1-6}$alkyl, heteroC$_{1-6}$alkyl, C$_{6-12}$aryl, heterocycle, C$_{6-12}$arylC$_{1-6}$alkyl, C$_{6-12}$arylheteroC$_{1-6}$alkyl, heterocycle-C$_{1-6}$alkyl, and heterocycle-heteroC$_{1-6}$alkyl; preferably each Z$^{1b}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, C$_{1-6}$alkyl, heteroC$_{1-6}$alkyl, C$_{6-12}$aryl, heterocycle, and heterocycle-C$_{1-6}$alkyl;
and wherein said C$_{1-6}$alkyl, heteroC$_{1-6}$alkyl, C$_{6-12}$aryl, heterocycle, C$_{6-12}$arylC$_{1-6}$alkyl, C$_{6-12}$arylheteroC$_{1-6}$alkyl, heterocycle-C$_{1-6}$alkyl, and heterocycle-heteroC$_{1-6}$alkyl, are optionally substituted with one, two, or three substituents selected from C$_{1-6}$alkyl, heteroC$_{1-6}$alkyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; preferably said C$_{1-6}$alkyl, heteroC$_{1-6}$ alkyl, C$_{6-12}$aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$ alkyl, —NH$_2$, —NHCH$_3$; —N(CH$_3$)$_2$, —NH—C(=O)O—C$_{1-4}$alkyl, morpholinyl, —S(O)$_2$ C$_{1-4}$alkyl, and —O—C$_{1-6}$alkyl; more preferably said C$_{1-6}$alkyl, C$_{6-12}$aryl, and heterocycle are optionally substituted with one, two, or three substituents selected from hydroxyl, =O, —O—C(O)Me, cyano, —C(O)OH, —C(O)CO$_{1-6}$alkyl, —NH$_2$, —NHCH$_3$; —N(CH$_3$)$_2$, —NH—C(=O)O—C$_{1-4}$ alkyl, morpholinyl, —S(O)$_2$ C$_{1-4}$alkyl, and —O—C$_{1-6}$alkyl.

47. The compound according to any one of statements 1-10, 14-29, 37-46; or a pharmaceutical composition according to any one of statements 7 to 10, wherein
R$^1$ is selected from C$_{3-7}$cycloalkyl; C$_{6-12}$aryl; heterocycle; C$_{6-12}$arylC$_{1-6}$alkyl; heterocycle-C$_{1-6}$alkyl; C$_{6-12}$aryl-O—C$_{1-6}$alkyl-; heterocycle-O—C$_{1-6}$alkyl-;
and wherein said C$_{3-7}$cycloalkyl; C$_{6-12}$aryl, heterocycle, C$_{6-12}$arylC$_{1-6}$alkyl-, heterocycle-C$_{1-6}$alkyl-, C$_{6-12}$aryl-O—C$_{1-6}$alkyl-, heterocycle-O—C$_{1-6}$alkyl-, can be unsubstituted or substituted with one or more Z$^{1b}$;
each Z$^{1b}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, C$_{1-6}$alkyl, heteroC$_{1-6}$alkyl, C$_{6-12}$aryl, heterocycle, C$_{6-12}$arylC$_{1-6}$alkyl, C$_{6-12}$arylO—C$_{1-6}$alkyl-, heterocycle-C$_{1-6}$alkyl, and heterocycle-O—C$_{1-6}$alkyl-, preferably each Z$^{1b}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)$_2$Z$^2$, —NZ$^4$C(=O)NZ$^4$Z$^5$, cyano, —C(=O)Z³, —C(=O)OZ², —C(=O)NZ⁴Z⁵, —C(=O)H, C₁₋₆alkyl, heteroC₁₋₆alkyl, C₆₋₁₂aryl, heterocycle, and heterocycle-C₁₋₆alkyl; more preferably each $Z^{1b}$ is independently selected from the group consisting of halogen, hydroxyl, —OZ², —O—C(=O)Z³, =O, —S(=O)₂Z³, —S(=O)₂NZ⁴Z⁵, trifluoromethyl, trifluoromethoxy, —NZ⁴Z⁵, —NZ⁴C(=O)Z², —NZ⁴C(=O)—OZ², cyano, —C(=O)Z³, —C(=O)OZ², —C(=O)NZ⁴Z⁵, C₁₋₆alkyl, heteroC₁₋₆alkyl, C₆₋₁₂aryl, heterocycle, and heterocycle-C₁₋₆alkyl;

and wherein said C₁₋₆alkyl, heteroC₁₋₆alkyl, C₆₋₁₂aryl, heterocycle, C₆₋₁₂arylC₁₋₆alkyl, C₆₋₁₂aryl-O—C₁₋₆alkyl-, heterocycle-C₁₋₆alkyl, and heterocycle-O—C₁₋₆alkyl-, are optionally substituted with one, two, or three substituents selected from C₁₋₆alkyl, heteroC₁₋₆alkyl, hydroxyl, =O, halogen, —SH, =S, trifluoromethyl, —OCF₃, —O—C(O)Me, cyano, nitro, —C(O)OH, —C(O)OC₁₋₆alkyl, —NH₂, —NHCH₃; —N(CH₃)₂, —NH—C(=O)O—C₁₋₄alkyl, morpholinyl, —S(O)₂C₁₋₄alkyl, and —O—C₁₋₆alkyl; preferably said C₁₋₆alkyl, heteroC₁₋₆ alkyl, C₆₋₁₂aryl, heterocycle, and heterocycle-C₁₋₆ alkyl, are optionally substituted with one, two, or three substituents selected from hydroxyl, =O, halogen, —SH, =S, trifluoromethyl, —OCF₃, —O—C(O)Me, cyano, nitro, —C(O)OH, —C(O)OC₁₋₆ alkyl, —NH₂, —NHCH₃; —N(CH₃)₂, —NH—C(=O)O—C₁₋₄alkyl, morpholinyl, —S(O)₂ C₁₋₄alkyl, and —O—C₁₋₆alkyl; more preferably said C₁₋₆alkyl, C₆₋₁₂aryl, and heterocycle are optionally substituted with one, two, or three substituents selected from hydroxyl, =O, —O—C(O)Me, cyano, —C(O)OH, —C(O)CO₁₋₆alkyl, —NH₂, —NHCH₃; —N(CH₃)₂, —NH—C(=O)O—C₁₋₄alkyl, morpholinyl, —S(O)₂ C₁₋₄alkyl, and —O—C₁₋₆alkyl.

48. The compound according to any one of statements 1-10, 14-29, 37-47; or a pharmaceutical composition according to any one of statements 7 to 10, wherein said heteroalkyl as a group or part of a group is selected from —CO—O-alkyl, —O-alkyl, —NH-alkyl, —N(alkyl)₂, —S(=O)₂ alkyl, and —S-alkyl.

49. The compound according to any one of statements 1-10, 14-29, 37-48; or a pharmaceutical composition according to any one of statements 7 to 10, wherein said heteroC₁₋₆ alkyl as a group or part of a group is selected from —CO—O—C₁₋₆alkyl, —O—C₁₋₆alkyl, —NH—C₁₋₆alkyl, —N(C₁₋₆alkyl)₂, —S(=O)₂C₁₋₆alkyl, and —S—C₁₋₆alkyl.

A particular embodiment of the invention is the provision of new compounds of formula (B1), (B2), and (B3),

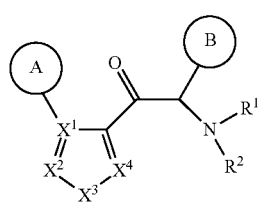
(B1)

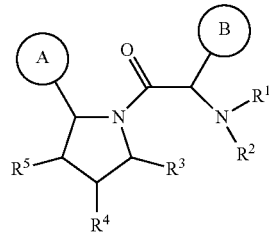
(B2)

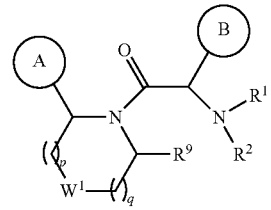
(B3)

wherein each of X¹, X², X³, X⁴, cycle A, cycle B, R¹, R², R³, R⁴, R⁵, R⁹, W¹, p and q are as described herein for formula (A) and particular embodiments described herein;

and isomers (in particular stereo-isomers or tautomers), solvates, salts (in particular pharmaceutically acceptable salts) or prodrugs thereof.

In another particular embodiment, the compounds have a structure according to formula (A), wherein cycle C is selected from the following group of cycles

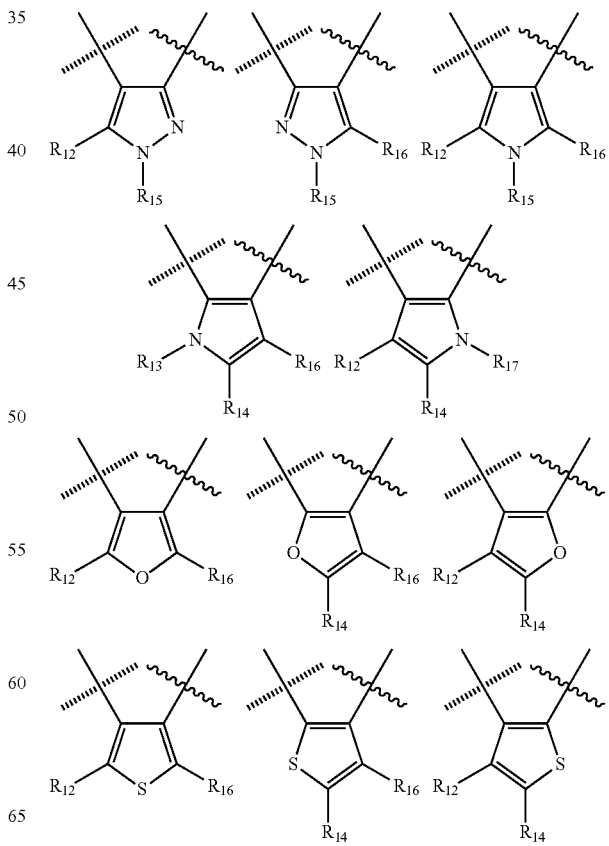

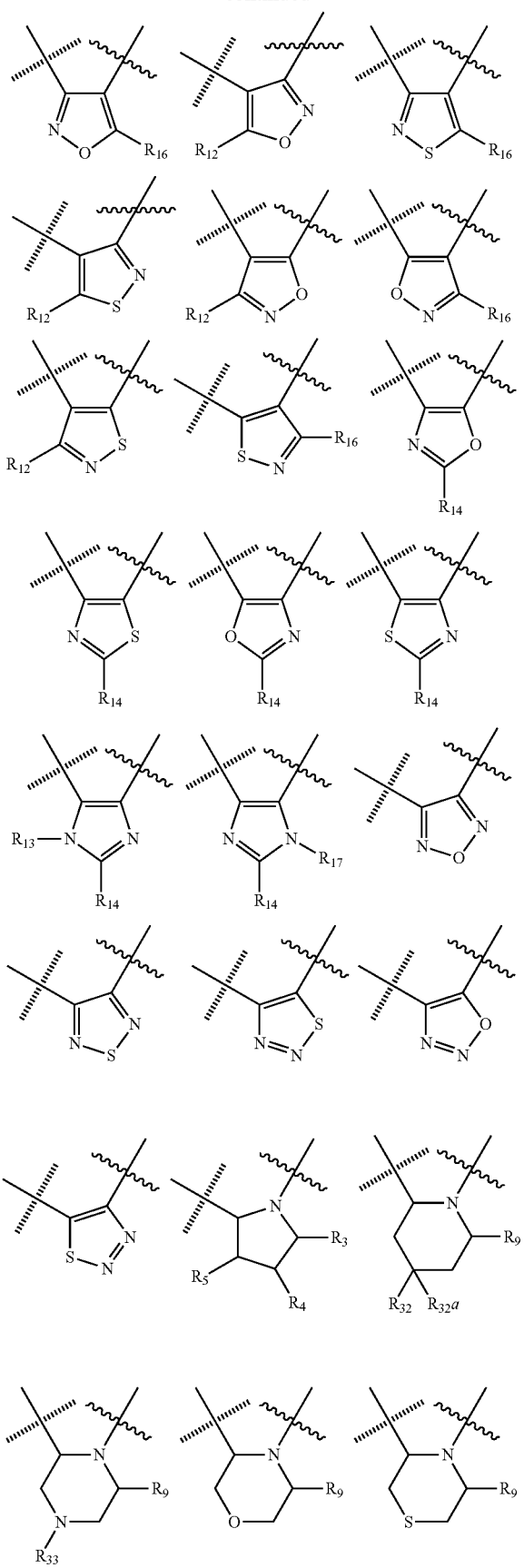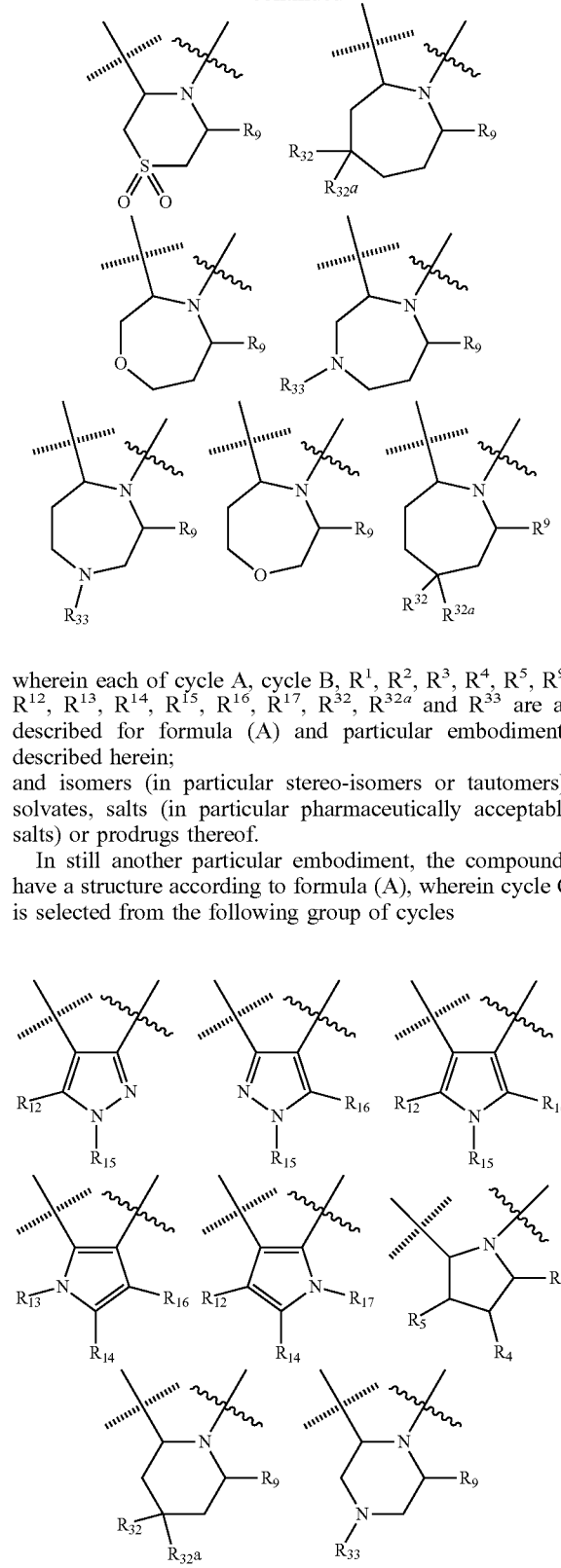

wherein each of cycle A, cycle B, $R^1$, $R^2$, $R^3$, $R^4$, $R^5$, $R^9$, $R^{12}$, $R^{13}$, $R^{14}$, $R^{15}$, $R^{16}$, $R^{17}$, $R^{32}$, $R^{32a}$ and $R^{33}$ are as described for formula (A) and particular embodiments described herein;

and isomers (in particular stereo-isomers or tautomers), solvates, salts (in particular pharmaceutically acceptable salts) or prodrugs thereof.

In still another particular embodiment, the compounds have a structure according to formula (A), wherein cycle C is selected from the following group of cycles

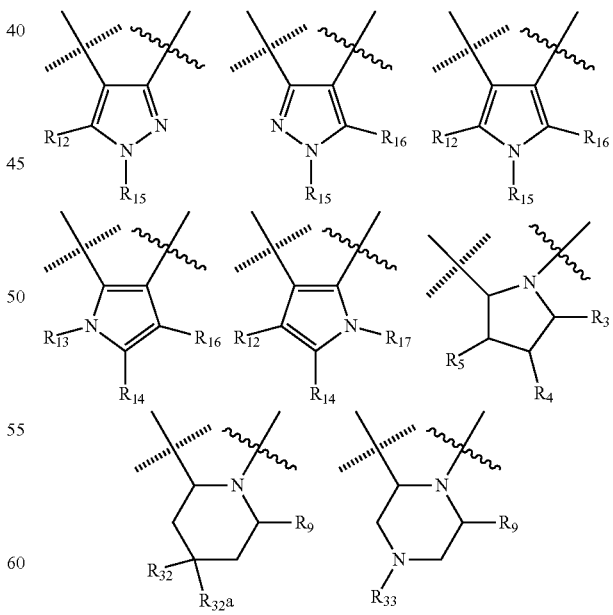

wherein each of cycle A, cycle B, $R^1$, $R^2$, $R^3$, $R^4$, $R^5$, $R^9$, $R^{12}$, $R^{13}$, $R^{14}$, $R^{15}$, $R^{16}$, $R^{17}$, $R^{32}$, $R^{32a}$ and $R^{33}$ are as described for formula (A) and particular embodiments described herein; and isomers (in particular stereo-isomers or tautomers), solvates, salts (in particular pharmaceutically acceptable salts) or prodrugs thereof.

In another embodiment, $X^1$ is C.

In another particular embodiment, $X^2$ is selected from $CR^{12}$; $NR^{13}$; and N.

In a particular embodiment, $R^{12}$ is selected from hydrogen; halogen; trifluoromethyl; cyano; alkyl and cycloalkyl. In a more particular embodiment, $R^{12}$ is selected from hydrogen; halogen; trifluoromethyl; cyano; $C_{1-6}$alkyl and $C_{3-7}$cycloalkyl. In a more particular embodiment, $R^{12}$ is selected from hydrogen; F; Cl; trifluoromethyl; cyano; and $C_{1-3}$alkyl.

In a particular embodiment, $R^{13}$ is selected from hydrogen; alkyl; and cycloalkyl. In a more particular embodiment, $R^{13}$ is selected from hydrogen; $C_{1-6}$alkyl and $C_{3-7}$cycloalkyl. In a more particular embodiment, $R^{13}$ is selected from hydrogen; and $C_{1-3}$alkyl; more in particular hydrogen and methyl.

In another particular embodiment, $X^3$ is selected from $CR^{14}$, $NR^{15}$; and N.

In a particular embodiment, $R^{14}$ is selected from hydrogen; halogen; trifluoromethyl; cyano; alkyl and cycloalkyl. In a more particular embodiment, $R^{14}$ is selected from hydrogen; halogen; trifluoromethyl; cyano; $C_{1-6}$alkyl and $C_{3-7}$cycloalkyl. In a more particular embodiment, $R^{14}$ is selected from hydrogen; F; Cl; trifluoromethyl; cyano; and $C_{1-3}$alkyl.

In a particular embodiment, $R^{15}$ is selected from hydrogen; alkyl; and cycloalkyl. In a more particular embodiment, $R^{15}$ is selected from hydrogen; $C_{1-6}$alkyl and $C_{3-7}$cycloalkyl. In a more particular embodiment, $R^{15}$ is selected from hydrogen; and $C_{1-3}$alkyl; more in particular selected from hydrogen and methyl.

In another particular embodiment, $X^4$ is selected from $CR^{16}$, $NR^{17}$; and N.

In a particular embodiment, $R^{16}$ is selected from hydrogen; halogen; trifluoromethyl; cyano; alkyl and cycloalkyl. In a more particular embodiment, $R^{16}$ is selected from hydrogen; halogen; trifluoromethyl; cyano; $C_{1-6}$alkyl and $C_{3-7}$cycloalkyl. In a more particular embodiment, $R^{16}$ is selected from hydrogen; F; Cl; trifluoromethyl; cyano; and $C_{1-3}$alkyl.

In a particular embodiment, $R^{17}$ is selected from hydrogen; alkyl; and cycloalkyl. In a more particular embodiment, $R^{17}$ is selected from hydrogen; $C_{1-6}$alkyl and $C_{3-7}$cycloalkyl. In a more particular embodiment, $R^{17}$ is selected from hydrogen; and $C_{1-3}$alkyl; more in particular selected from hydrogen and methyl.

In a particular embodiment, $R^3$ is selected from hydrogen; alkyl; heteroalkyl; and =O. In a more particular embodiment, $R^3$ is selected from hydrogen and alkyl; more in particular from hydrogen and $C_{1-6}$alkyl; yet more in particular from hydrogen and $C_{1-3}$alkyl; yet more in particular from hydrogen and methyl. In a particular embodiment, $R^3$ is selected from hydrogen; $C_{1-4}$alkyl; $C_{1-4}$alkoxycarbonyl; aminocarbonyl; $C_{1-4}$alkylaminocarbonyl; di($C_{1-4}$alkyl)aminocarbonyl; or hydroxymethyl.

In a particular embodiment, each $R^4$ and $R^5$ is independently selected from hydrogen; halogen; hydroxyl; sulfhydryl; trifluoromethyl; trifluoromethoxy; cyano; alkyl; alkenyl; alkynyl; heteroalkyl; heteroalkenyl; and heteroalkynyl. In a more particular embodiment, each $R^4$ and $R^5$ is independently selected from hydrogen; halogen; and alkyl. In a more particular embodiment, each $R^4$ and $R^5$ is independently selected from hydrogen; F; Cl; and $C_{1-6}$alkyl (more in particular $C_{1-3}$alkyl, more in particular methyl). In a more particular embodiment, at least one of $R^4$ and $R^5$ is hydrogen. In a particular embodiment, each $R^4$ and $R^5$ is independently selected from hydrogen; halogen; $C_{1-4}$alkyl; $C_{1-4}$alkoxy; cyano; hydroxy; $C_{1-4}$alkylthio; trifluoromethyl; amino; $C_{1-4}$alkylamino; di($C_{1-4}$alkyl)amino; carboxy; $C_{1-4}$alkoxycarbonyl; $C_{1-4}$alkylsulfonyl; $C_{1-4}$alkoxycarbonylamino; trifluoromethanesulfonyl; trifluoromethoxy; and hydroxy$C_{1-4}$alkyl; provided that one of $R^4$ and $R^5$ is hydrogen.

In a particular embodiment, $R^9$ is selected from hydrogen; alkyl; heteroalkyl; and =O. In a more particular embodiment, $R^9$ is selected from hydrogen and alkyl; more in particular from hydrogen and $C_{1-6}$alkyl; yet more in particular from hydrogen and $C_{1-3}$alkyl; yet more in particular from hydrogen and methyl.

In a particular embodiment, $W^1$ is selected from $CR^{32}R^{32a}$ and $NR^{33}$. In another particular embodiment, $W^1$ is selected from $CHR^{32a}$ and $NR^{33}$. In another particular embodiment, $W^1$ is selected from $CH_2$ and NH.

In a particular embodiment, each $R^{32}$ and $R^{32a}$ is independently selected from hydrogen; halogen; hydroxyl; sulfhydryl; trifluoromethyl; trifluoromethoxy; cyano; alkyl; alkenyl; alkynyl; heteroalkyl; heteroalkenyl; and heteroalkynyl. In a particular embodiment, it is provided that one of $R^{32}$ or $R^{32a}$ is hydrogen, except that both $R^{32}$ or $R^{32a}$ can be alkyl at the same time. In a more particular embodiment, each $R^{32}$ and $R^{32a}$ is independently selected from hydrogen; halogen; and alkyl. In a more particular embodiment, each $R^{32}$ and $R^{32a}$ is independently selected from hydrogen; F; Cl; and $C_{1-6}$alkyl (more in particular $C_{1-3}$alkyl, more in particular methyl). In a more particular embodiment, at least one of $R^{32}$ and $R^{32a}$ is hydrogen.

In a particular embodiment, $R^{33}$ is independently selected from hydrogen and alkyl. In a particular embodiment, $R^{33}$ is independently selected from hydrogen and $C_{1-6}$alkyl (more in particular $C_{1-3}$alkyl, more in particular methyl).

In a particular embodiment, p and q are 1.

In still another particular embodiment, the compounds have a structure according to formula (C1), (C2), (C3), (C4), and (C5),

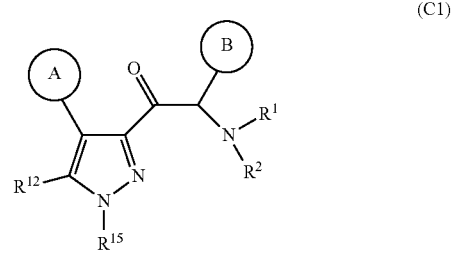

(C1)

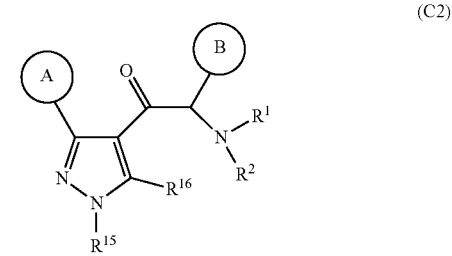

(C2)

-continued (C3)
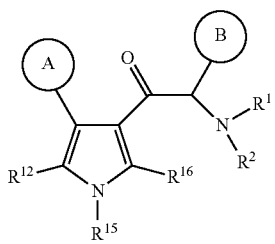

(C4)
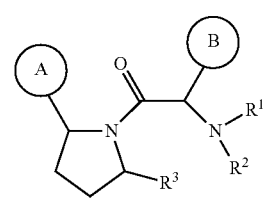

(C5)
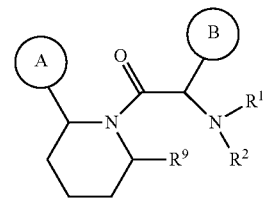

wherein each of cycle A, cycle B, $R^1$, $R^2$, $R^3$, $R^9$, and $R^{15}$, are as described for formula (A) and particular embodiments described herein; and isomers (in particular stereo-isomers or tautomers), solvates, salts (in particular pharmaceutically acceptable salts) or prodrugs thereof.

In still another particular embodiment, the compounds have a structure according to formula (D1), (D2), (D3), (D4), and (D5), (D1)
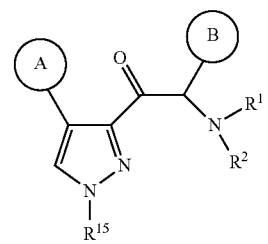

(D2)
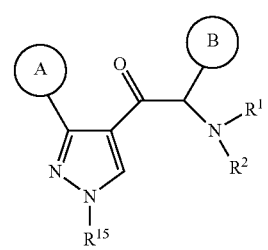

-continued (D3)
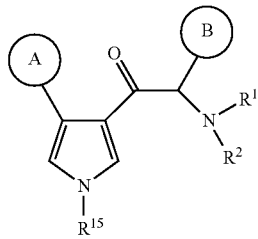

(D4)
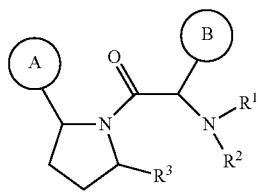

(D5)
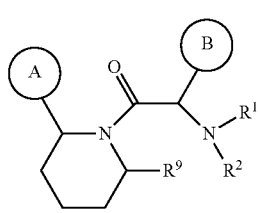

wherein each of cycle A, cycle B, $R^1$, $R^2$, $R^3$, $R^9$, and $R^{15}$, are as described for formula (A) and particular embodiments described herein; and isomers (in particular stereo-isomers or tautomers), solvates, salts (in particular pharmaceutically acceptable salts) or prodrugs thereof.

In a particular embodiment, cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one, two or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$. In another particular embodiment, cycle A is selected from the group consisting of aryl; and heterocycle (more in particular heteroaryl); wherein said aryl and heterocycle (more in particular heteroaryl), can be unsubstituted or substituted with one, two or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$. In another particular embodiment, cycle A is selected from aryl; and heterocycle selected from

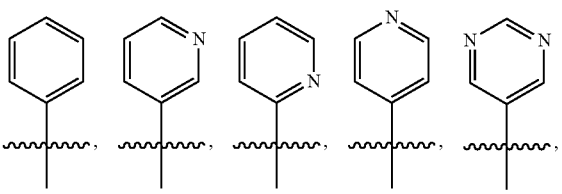

-continued

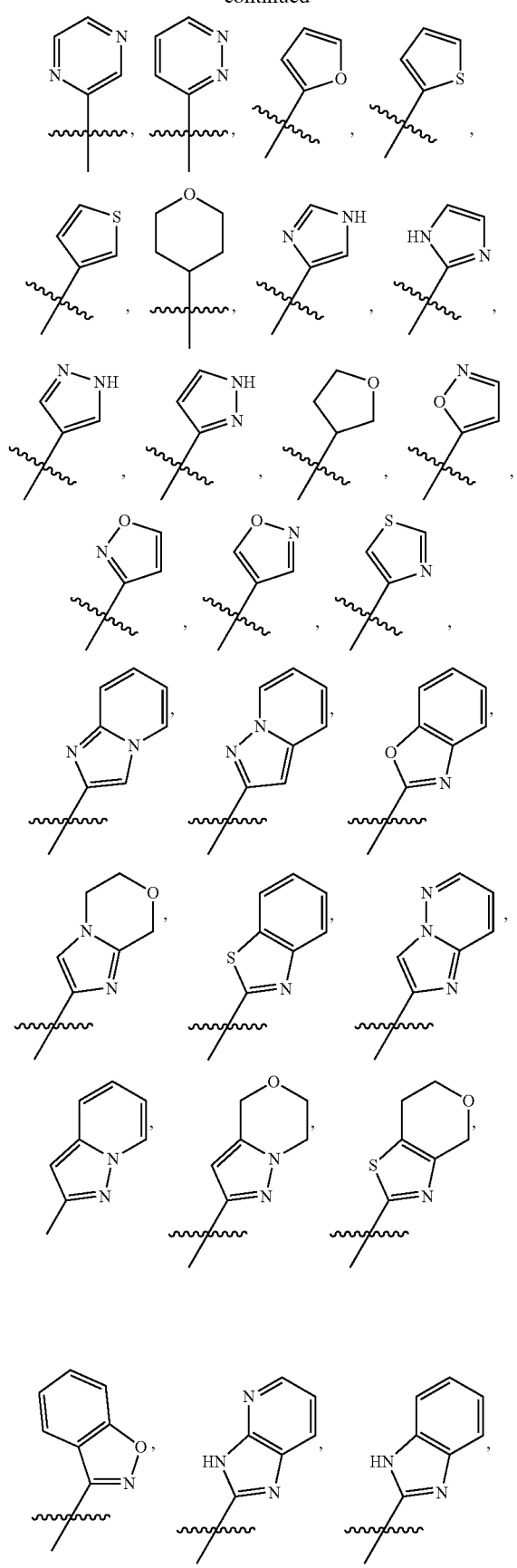

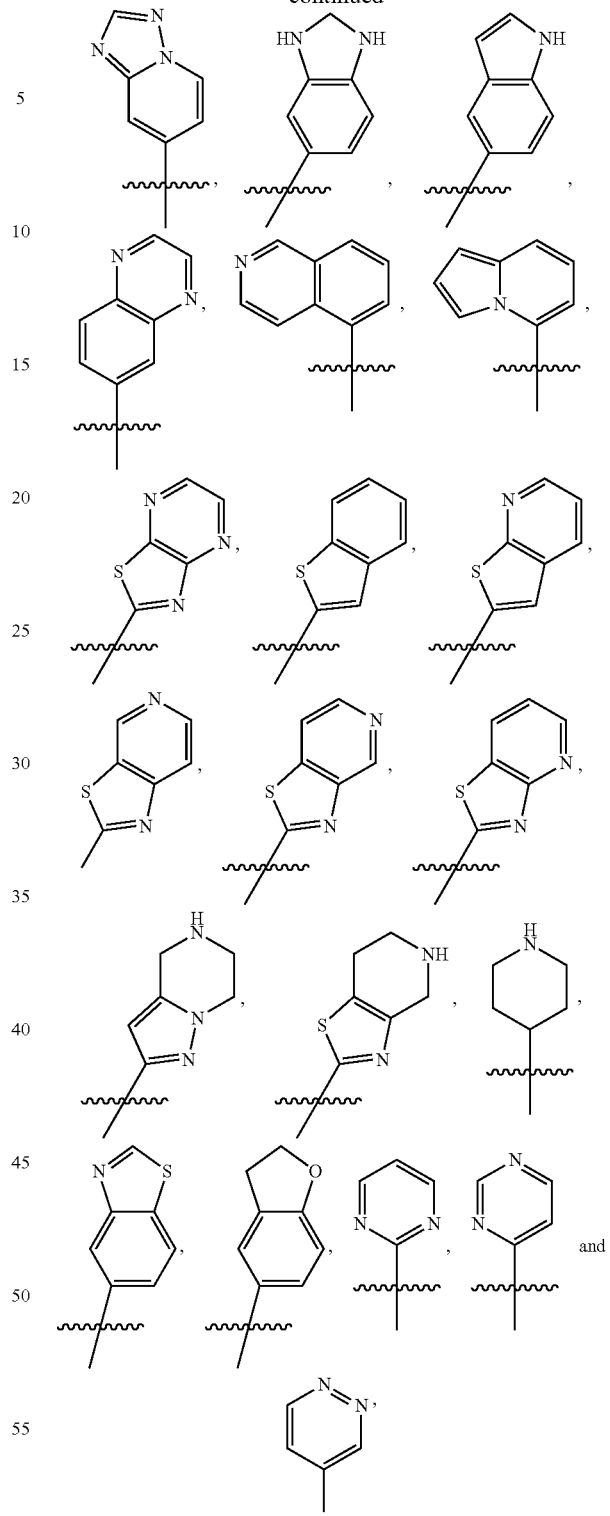

wherein the wavy line (⁓) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$. In another particular embodiment, cycle A is selected from aryl; and heteroaryl selected from

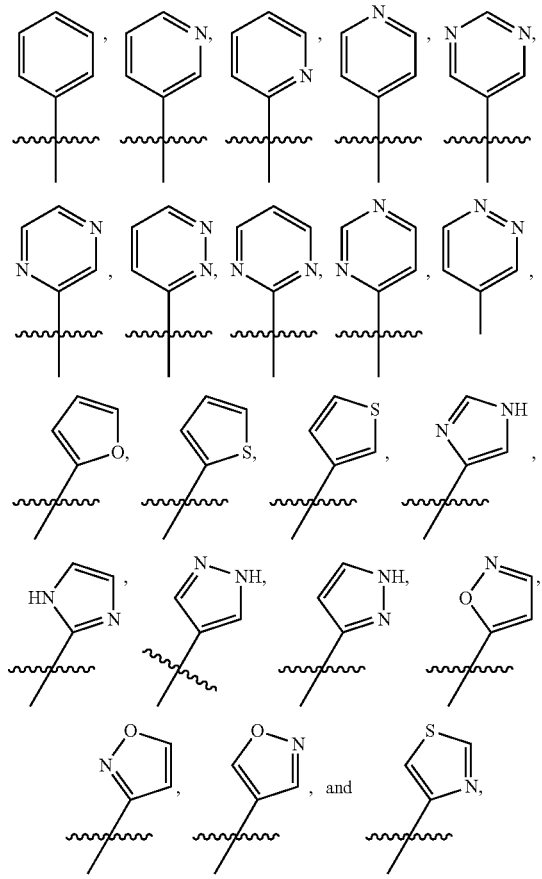

wherein the wavy line ( ) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$. In another particular embodiment, cycle A is selected from

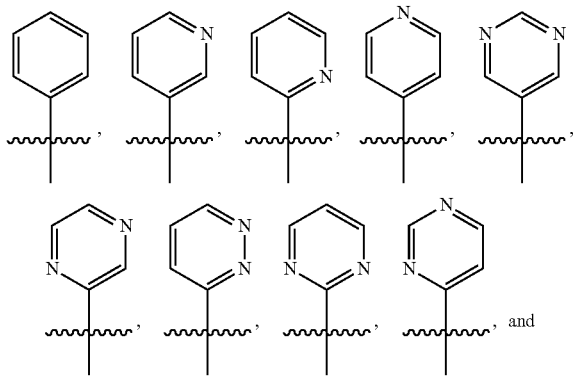

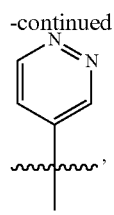

wherein the wavy line ( ) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$. In yet another particular embodiment, cycle A is selected from phenyl optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, halogen, —SH, trifluoromethyl, —OCF$_3$, cyano, nitro, —C(O)OH, NH$_2$, NH(alkyl), or N(alkyl)$_2$. In yet another particular embodiment, cycle A is phenyl optionally substituted with one, two, or three substituents selected from alkyl, alkenyl, alkynyl, heteroalkyl, heteroalkenyl, heteroalkynyl, hydroxyl, halogen, —SH, trifluoromethyl, —OCF$_3$, cyano, nitro, —C(O)OH, NH$_2$, NH(alkyl), or N(alkyl)$_2$. In yet another particular embodiment, cycle A is phenyl optionally substituted with one, two, or three substituents selected from alkyl, alkoxy, halogen, trifluoromethyl, —OCF$_3$, or cyano. In a particular embodiment, the cycles encompassed by cycle A are unsubstituted or substituted one, two or three substituents (more in particular one or two substituents) selected from $C_{1-6}$alkyl, $C_{3-7}$cycloalkyl, $C_{2-6}$alkenyl, $C_{3-7}$cycloalkenyl, $C_{3-6}$alkynyl, $C_{3-7}$cycloalkynyl, $C_{1-6}$heteroalkyl, $C_{2-6}$heteroalkenyl, $C_{3-6}$heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$.

In another particular embodiment, cycle B is selected from unsubstituted or substituted with one or more $Z^{1a}$ (in particular one, two or three $Z^{1a}$) phenyl; pyridyl, pyridazinyl, pyrimidinyl, pyrazinyl, triazinyl, oxazolyl, imidazolyl, thiazolyl, isoxazolyl, pyrazolyl, isothiazolyl, furyl, thienyl, pyrrolyl, benzofuranyl, indolyl, quinolinyl, isoquinolinyl, benzimidazolyl, pyridinimidazolyl, pyridinpyrolyl, pyrazolepyridinyl, benzpyrolyl, triazinyl, purinyl, quinoxalinyl, quinazolinyl, dihydroimidazooxazinyl and pteridinyl. In yet another particular embodiment, cycle B is selected from unsubstituted or substituted with one or more $Z^{1a}$ (in particular one, two or three $Z^{1a}$) phenyl; and pyridyl. In another particular embodiment, cycle B is a heterocycle which can be unsubstituted or substituted with one or more $Z^{1a}$ (in particular one, two or three $Z^{1a}$). In another particular embodiment, cycle B is selected from unsubstituted or substituted with one or more $Z^{1a}$ (in particular one, two or three $Z^{1a}$) aryl and heteroaryl. In a more particular embodiment cycle B is a heteroaryl which can be unsubstituted or substituted with one or more $Z^{1a}$ (in particular one, two or three $Z^{1a}$). In a yet more particular embodiment, cycle B is selected from unsubstituted or substituted with one or more $Z^{1a}$ (in particular one, two or three $Z^{1a}$) pyridyl, pyridazinyl, pyrimidinyl, pyrazinyl, triazinyl, oxazolyl, imidazolyl, thiazolyl, isoxazolyl, pyrazolyl, isothiazolyl, furyl, thienyl, pyrrolyl, benzofuranyl, indolyl, quinolinyl, isoquinolinyl, benzimidazolyl, pyridinimidazolyl, pyridinpyrolyl, pyrazolepyridinyl, benzpyrolyl, triazinyl, purinyl, quinoxalinyl, quinazolinyl, and pteridinyl. In a still more particular embodiment, cycle B is selected from unsubstituted or substituted with one or more $Z^{1a}$ (in particular one, two or three $Z^{1a}$) pyridyl, pyrazinyl, pyrimidyl, imidazolyl, isoxazolyl, pyrazolyl, furyl, thienyl, isoquinolinyl, benzimidazolyl, pyridinimidazolyl, benzpyrolyl, pyrazolepyridinyl and quinoxalinyl. In a particular embodiment, cycle B is not an unsubstituted phenyl.

In a particular embodiment, cycle B is selected from aryl and heterocycle, wherein said aryl and heterocycle are optionally substituted with one, two, or three $Z^{1a}$; preferably cycle B is selected from

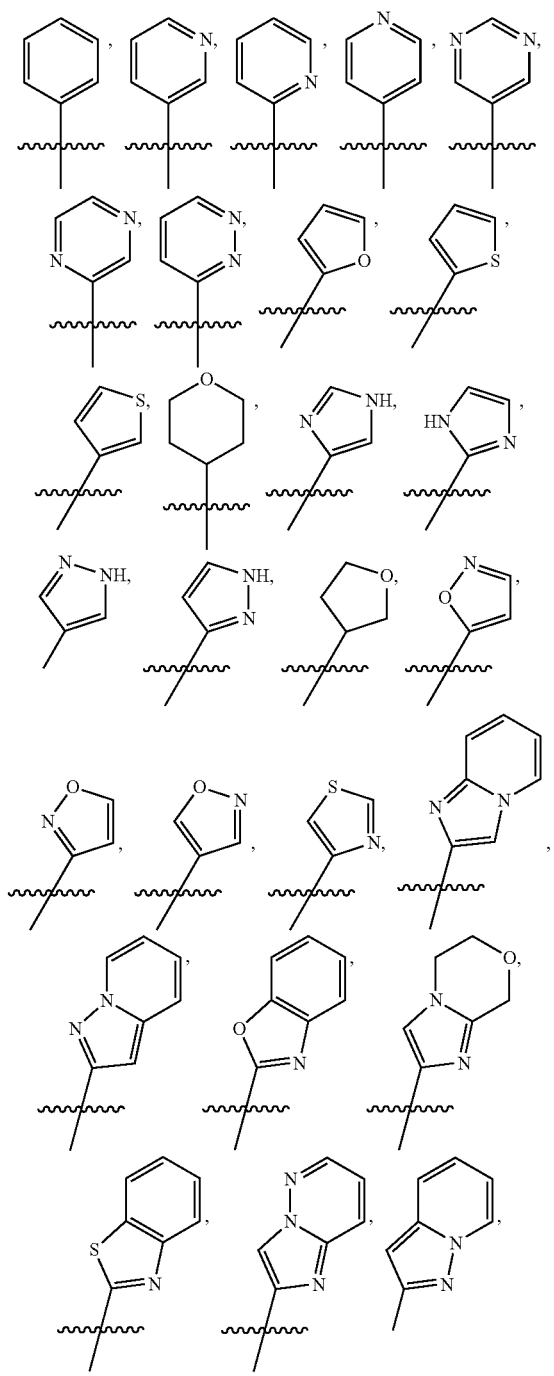

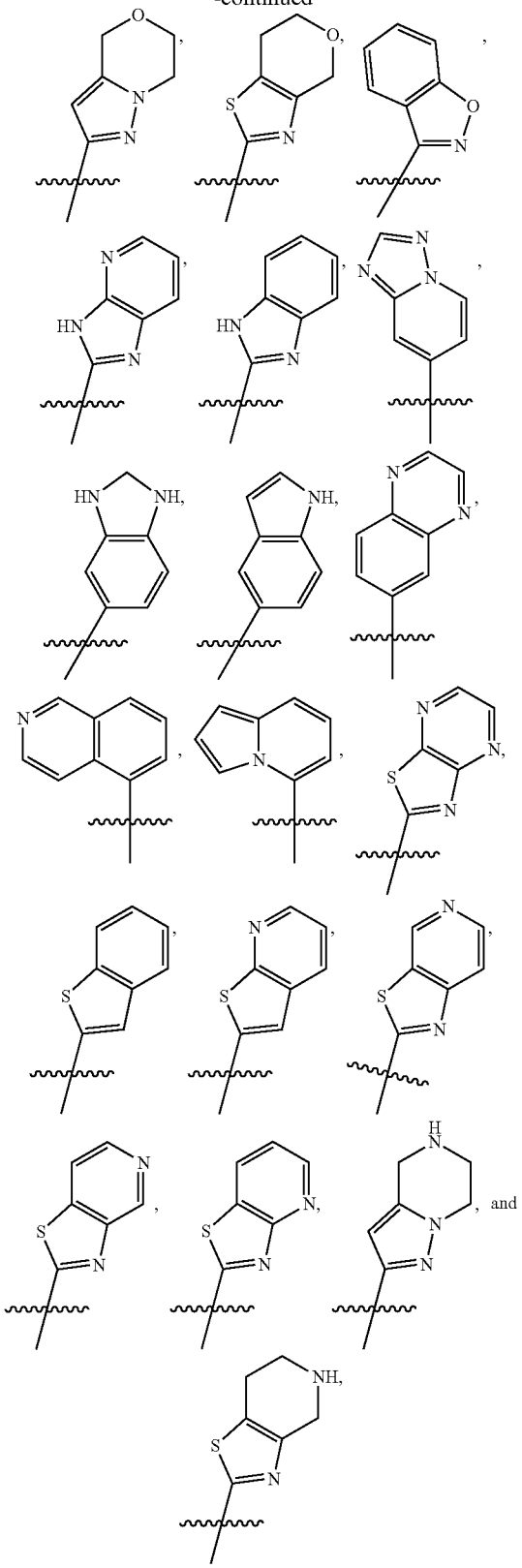

wherein the wavy line (∿) indicates the point of attachment to the carbon atom of the main formula (A), and wherein the depicted cycles may be optionally substituted with one, two, or three $Z^{1a}$.

In another embodiment, $R^2$ is selected from hydrogen and unsubstituted or substituted with one or more $Z^{1c}$ (in particular one or two $Z^{1c}$) alkyl. In another particular embodiment, $R^2$ is selected from hydrogen and alkyl (more in particular $C_{1-3}$alkyl). In yet another particular embodiment, $R^2$ is selected from hydrogen, methyl, ethyl, and propyl.

In another embodiment, $R^1$ is selected from aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl; and wherein said aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$ (in particular one, two or three $Z^{1b}$). In another embodiment, $R^1$ is selected from aryl; heterocycle; W-aryl; and W-heterocycle; wherein said aryl, heterocycle, W-aryl, and W-heterocycle can be unsubstituted or substituted with one or more $Z^{1b}$ (in particular one, two or three $Z^{1b}$); and wherein W is selected from $C_{1-3}$alkyl, $C_{1-3}$alkenyl, $C_{1-3}$alkynyl, $C_{1-3}$ heteroalkyl, $C_{1-3}$ heteroalkenyl and $C_{1-3}$ heteroalkynyl. In another particular embodiment, $R^1$ is selected from aryl; heterocycle; W-aryl; and W-heterocycle; wherein said aryl, heterocycle, W-aryl, and W-heterocycle can be unsubstituted or substituted with one or more $Z^{1b}$ (in particular one, two or three $Z^{1b}$); and wherein W is selected from $C_{1-3}$alkyl. In yet another particular embodiment, $R^1$ is selected from aryl; heterocycle; —$CH_2$-aryl; and —$CH_2$-heterocycle; wherein said aryl, heterocycle, —$CH_2$-aryl and —$CH_2$-heterocycle can be unsubstituted or substituted with one or more $Z^{1b}$ (in particular one, two or three $Z^{1b}$). In another embodiment, $R^1$ is selected from aryl; and heterocycle; wherein said aryl and heterocycle can be unsubstituted or substituted with one or more $Z^{1b}$ (in particular one, two or three $Z^{1b}$). In yet a more particular embodiment, $R^1$ is selected from phenyl and pyridyl, unsubstituted or substituted with one or more $Z^{1b}$ (in particular one, two or three $Z^{1b}$). In still a more particular embodiment, $R^1$ is selected from phenyl and

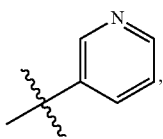

unsubstituted or substituted with one or more $Z^{1b}$ (in particular one, two or three $Z^{1b}$).

In a particular embodiment, each $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4S(=O)_2Z^2$, —$NZ^4C(=O)Z^2$, —$NZ^4C(=O)$—$OZ^2$, —$NZ^4C(=O)NZ^4Z^5$, cyano, —C(=O)$Z^3$, —C(=O)$OZ^2$, —C(=O)$NZ^4Z^5$, —C(=O)H, $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably each $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4S(=O)_2Z^2$, —$NZ^4C(=O)Z^2$, —$NZ^4C(=O)_2Z^2$, —$NZ^4C(=O)NZ^4Z^5$, cyano, —C(=O)$Z^3$, —C(=O)$OZ^2$, —C(=O)$NZ^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4C(=O)Z^2$, —$NZ^4C(=O)$—$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, hydroxyl, =O, halogen, —SH, =S, trifluoromethyl, —$OCF_3$, —O—C(O)Me, cyano, nitro, —C(O)OH, —C(O)$OC_{1-6}$alkyl, —$NH_2$, —$NHCH_3$; —$N(CH_3)_2$, —NH—C(=O)O—$C_{1-4}$alkyl, morpholinyl, —S(O)$_2C_{1-4}$alkyl, and —O—$C_{1-6}$alkyl; preferably said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, —$OCF_3$, —O—C(O)Me, cyano, nitro, —C(O)OH, —C(O)$OC_{1-6}$alkyl, —$NH_2$, —$NHCH_3$; —$N(CH_3)_2$, —NH—C(=O)O—$C_{1-4}$alkyl, morpholinyl, —S(O)$_2C_{1-4}$alkyl, and —O—$C_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)$OC_{1-6}$alkyl, —$NH_2$, —$NHCH_3$; —$N(CH_3)_2$, —NH—C(=O)O—$C_{1-4}$alkyl, morpholinyl, —S(O)$_2C_{1-4}$alkyl, and —O—$C_{1-6}$alkyl.

In a particular embodiment, each $Z^2$ is independently selected from $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{1-6}$alkenyl, arylhetero$C_{1-6}$ alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$ alkynyl; preferably $Z^2$ is independently selected from $C_{1-6}$alkyl, aryl, heterocycle, and heterocycle-$C_{1-6}$alkyl; more preferably $Z^2$ is independently selected from $C_{1-6}$alkyl, aryl, and heterocycle-$C_{1-6}$alkyl;

wherein said $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—$C_{1-6}$alkyl, —OCF$_3$, —S(=O)$_2$$C_{1-4}$alkyl, cyano, nitro, —C(=O)OH, —C(=O)O—$C_{1-4}$alkyl, —NH$_2$, —N(CH$_3$)$_2$, pyrrolidinyl, piperidinyl, and piperazinyl; preferably said $C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, difluoromethyl, —O—$C_{1-6}$alkyl, —OCF$_3$, —S(=O)$_2$$C_{1-4}$alkyl, cyano, nitro, —C(=O)OH, —C(=O)O—$C_{1-4}$alkyl, —NH$_2$, —N(CH$_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—$C_{1-6}$alkyl, —S(=O)$_2$$C_{1-4}$alkyl, —C(=O)OH, —C(=O)O—$C_{1-4}$alkyl, —NH$_2$, —N(CH$_3$)$_2$, pyrrolidinyl, piperidinyl, and piperazinyl.

In a particular embodiment, each $Z^3$ is independently selected from hydroxyl, $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^3$ is independently selected from hydroxyl, $C_{1-6}$alkyl, aryl, and heterocycle; more preferably $Z^3$ is independently selected from hydroxyl, $C_{1-6}$alkyl, and heterocycle;

wherein said $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, —C(=O)OH, —NH$_2$, and —N(CH$_3$)$_2$; preferably said $C_{1-6}$alkyl, aryl, and heterocycle are optionally substituted with one, two, or three substituents selected from $C_{1-6}$alkyl and —N(CH$_3$)$_2$; more preferably said $C_{1-6}$alkyl and heterocycle are optionally substituted with one, two, or three substituents selected from $C_{1-6}$alkyl and —N(CH$_3$)$_2$.

In a particular embodiment, each $Z^4$ and $Z^5$ is independently selected from hydrogen, $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^4$ and $Z^5$ is independently selected from hydrogen, $C_{1-6}$alkyl, aryl, $C_{3-7}$cycloalkyl, and heterocycle; more preferably each $Z^4$ and $Z^5$ is independently selected from hydrogen, $C_{1-6}$alkyl, and $C_{3-7}$cycloalkyl;

wherein said $C_{1-6}$alkyl, $C_{1-6}$alkyl, $C_{3-7}$cycloalkyl, $C_{2-6}$alkenyl, $C_{3-7}$cycloalkenyl, $C_{2-6}$alkynyl, $C_{3-7}$cycloalkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, —C(=O)OH or —NH$_2$, and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—$C_{1-6}$alkyl, —OCF$_3$, cyano, nitro, —C(=O)OH, or —NH$_2$.

A second aspect of the invention relates to the compounds of formula (A) for use as a medicine,

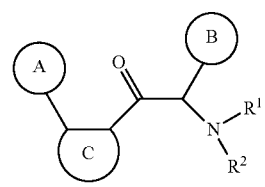

(A)

wherein,
cycle A is selected from the group consisting of cycloalkyl; cycloalkenyl; cycloalkynyl; aryl; and heterocycle; wherein said cycloalkyl, cycloalkenyl, cycloalkynyl, aryl and heterocycle, can be unsubstituted or substituted with one or more substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;
cycle C is a monocycle selected from

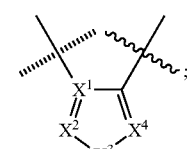

(a1)

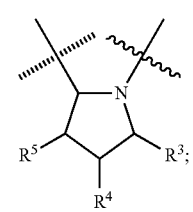

(a2)

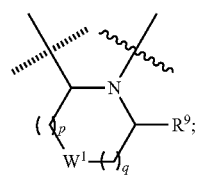

(a3)

wherein the wavy line (∿) indicates the point of attachment to the carbonyl of the main formula (A) and the hashed line (⫶⫶⫶) indicates the point of attachment to the cycle A of the main formula (A);

$X^1$ is selected from C; and N;

$X^2$ is selected from $CR^{12}$; $NR^{13}$; N; O; and S;

$X^3$ is selected from $CR^{14}$; $NR^{15}$; N; O; and S;

$X^4$ is selected from $CR^{16}$; $NR^{17}$; N; O; and S;

each $R^3$ and $R^9$ is independently selected from hydrogen; alkyl; alkenyl; alkynyl; heteroalkyl; heteroalkenyl; heteroalkynyl; =O; and =S; wherein said alkyl, alkenyl, alkynyl, heteroalkyl, heteroalkenyl, and heteroalkynyl can be unsubstituted or substituted with one or more substituents selected from hydroxyl, =O, halogen, —SH, =S, trifluoromethyl, —OCF$_3$, cyano, nitro, —C(O)OH or NH$_2$;

each $R^4$ and $R^5$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

$W^1$ is selected from $CR^{32}R^{32a}$; $NR^{33}$; O; S; and SO$_2$;

each p and q is independently selected from 1 and 2, whereby p+q is selected from 2 and 3;

cycle B is selected from aryl; and heterocycle; wherein said aryl and heterocycle can be unsubstituted or substituted with one or more $Z^{1a}$;

$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;

$R^2$ is selected from hydrogen; alkyl; cycloalkyl; alkenyl; cycloalkenyl; alkynyl; cycloalkynyl; heteroalkyl; heteroalkenyl; and heteroalkynyl;

and wherein said alkyl, cycloalkyl; alkenyl; cycloalkenyl; alkynyl; cycloalkynyl; heteroalkyl; heteroalkenyl, and heteroalkynyl, can be unsubstituted or substituted with one or more $Z^{1c}$;

each $R^{12}$, $R^{14}$, and $R^{16}$ is independently selected from hydrogen; halogen; hydroxyl; sulfhydryl; trifluoromethyl; trifluoromethoxy; nitro; amino; cyano; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, and heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

$R^{13}$, $R^{15}$, and $R^{17}$ is independently selected from hydrogen; hydroxyl; sulfhydryl; —S(O)$Z^2$; —S(O)$_2Z^3$; —S(O)$_2NZ^4Z^5$; trifluoromethyl; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl;

wherein said alkyl, cycloalkyl, alkenyl, cycloalkenyl, alkynyl, cycloalkynyl, heteroalkyl, heteroalkenyl, or heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $R^{32}$ and $R^{32a}$ is independently selected from hydrogen; halogen; hydroxyl; sulfhydryl; =O; =S; trifluoromethyl; trifluoromethoxy; cyano; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $R^{33}$ is independently selected from hydrogen; alkyl; alkenyl; alkynyl; heteroalkyl; heteroalkenyl; and heteroalkynyl; and wherein said alkyl, alkenyl, alkynyl, cycloalkynyl, heteroalkyl, heteroalkenyl, heteroalkynyl, can be unsubstituted or substituted with one or more substituents selected from hydroxyl, =O, halogen, —SH, =S, trifluoromethyl, —OCF$_3$, cyano, nitro, —C(O)OH or NH$_2$;

each $Z^{1a}$, $Z^{1b}$, and $Z^{1c}$ is independently selected from the group consisting of halogen; hydroxyl; sulfhydryl; —OZ$^2$; =O; —SZ$^2$; =S; —S(O)$Z^2$; —S(O)$_2Z^3$; —S(O)$_2NZ^4Z^5$; trifluoromethyl; trifluoromethoxy; nitro; —NZ$^4Z^5$; —NZ$^4$S(O)$_2Z^2$; —NZ$^4$C(O)$Z^2$; —NZ$^4$C(O)NZ$^4Z^5$; cyano; —C(O)$Z^3$; —C(O)OZ$^2$; —C(O)NZ$^4Z^5$; —C(O)H; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^2$ is independently selected from alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; cycloalkyl; alkenyl; cycloalkenyl; alkynyl; cycloalkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, cycloalkyl, alkenyl, cycloalkenyl, alkynyl, cycloalkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein $Z^4$ and $Z^5$ can be taken together in order to form a (5-, 6-, or 7-membered) heterocycle which can be unsubstituted or substituted with alkyl, cycloalkyl, alkenyl, cycloalkenyl, alkynyl, cycloalkynyl, hydroxyl, halogen, —SH, trifluoromethyl, —O-alkyl, —OCF$_3$, cyano, nitro, —C(O)OH or —NH$_2$;

and isomers (in particular stereo-isomers or tautomers), solvates, salts (in particular pharmaceutically acceptable salts) or prodrugs thereof.

A particular embodiment of this aspect of the invention relates to the compounds of formula (A), (B1), (B2), (B3), (C1), (C2), (C3), (C4), (C5), (D1), (D2), (D3), (D4), and (D5), and to compounds according to any of the particular embodiments thereof described herein for use as a medicine.

A third aspect of the invention relates to the compounds of formula (A), (B1), (B2), (B3), (C1), (C2), (C3), (C4), (C5), (D1), (D2), (D3), (D4), and (D5), and to compounds according to any of the particular embodiments thereof described herein for use as a medicament for the prevention or treatment of a viral infection in an animal (including a human).

In one embodiment, the viral infection is an infection with Flavivirus. In a further embodiment, the Flavivirus is Dengue virus.

The present invention further relates to a pharmaceutical composition comprising the compounds of formula (A), (B1), (B2), (B3), C1), (C2), (C3), (C4), (C5), (D1), (D2), (D3), (D4), or (D5) or compounds according to any of the particular embodiments thereof as described herein in combination with a pharmaceutically acceptable carrier.

The present invention further relates to a method for the prevention or treatment of a viral infection in an animal comprising administering said animal (including a human) in need for such prevention or treatment an effective dose of a compound of formula (A), (B1), (B2), (B3), C1), (C2), (C3), (C4), (C5), (D1), (D2), (D3), (D4), or (D5) or a compound according to any of the particular embodiments thereof as described herein.

The present invention further relates a method for the preparation of the compounds of formula (A), (B1), (B2), (B3), (C1), (C2), (C3), (C4), (C5), (D1), (D2), (D3), (D4), and (D5), and of compounds according to any of the particular embodiments thereof described herein, comprising the steps of:

reacting an imine with an aldehyde under umpolung conditions in the presence of a thiazolium catalyst to obtain the desired compounds of the invention.

In another embodiment, the invention relates to a method for the preparation of the compounds of the invention, comprising the steps of reacting a ketone derivative having a methylene adjacent to the carbonyl under halogenation conditions to obtain an alpha-halogenoketone, substitute the previously obtained alpha-halogenoketone with amines to obtain the desired compounds of the invention.

In another embodiment, the invention relates to a method for the preparation of the compounds of the invention, comprising the steps of reacting a heterocyclicamine with 2-halogeno-acetic acid halide to obtain an alpha-halogenoamide derivative, substitute the previously obtained alpha-halogenoamide with amines to obtain the desired compounds of the invention.

More in particular, one aspect of the invention is the provision of compounds of formula (A),

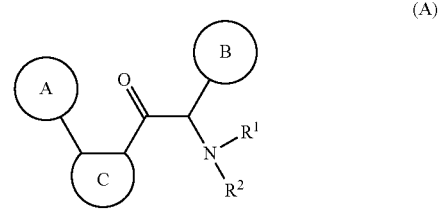

(A)

wherein,
cycle C is a monocycle selected from

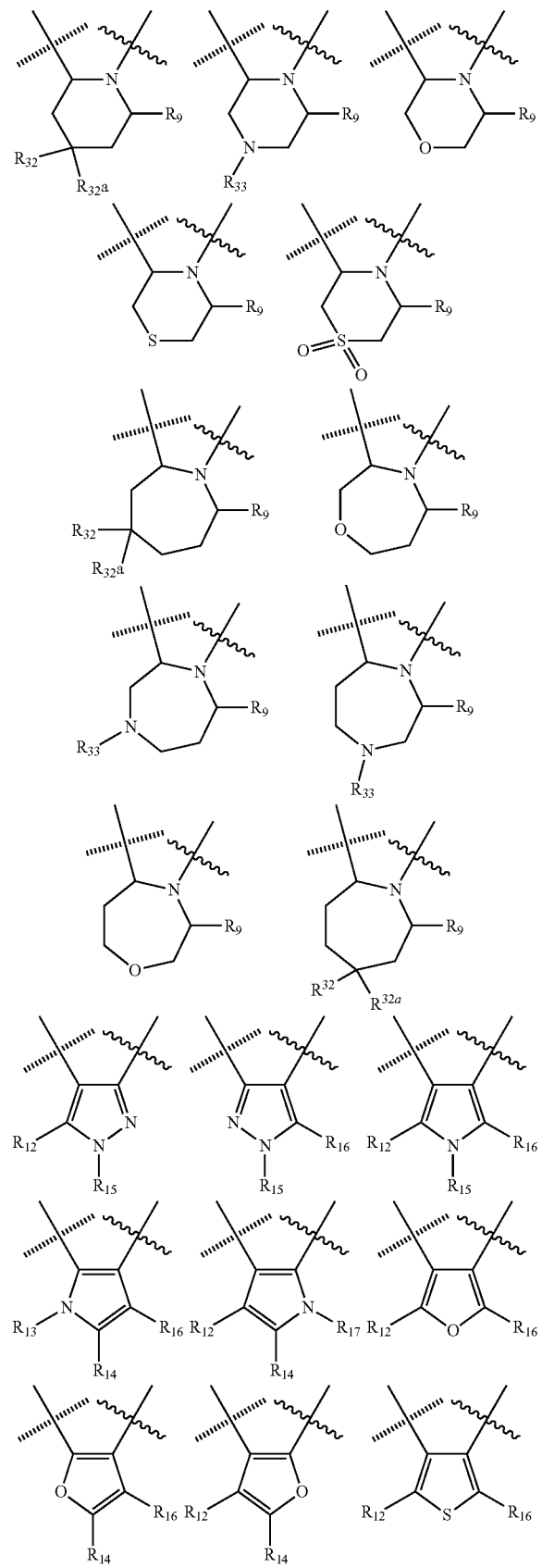

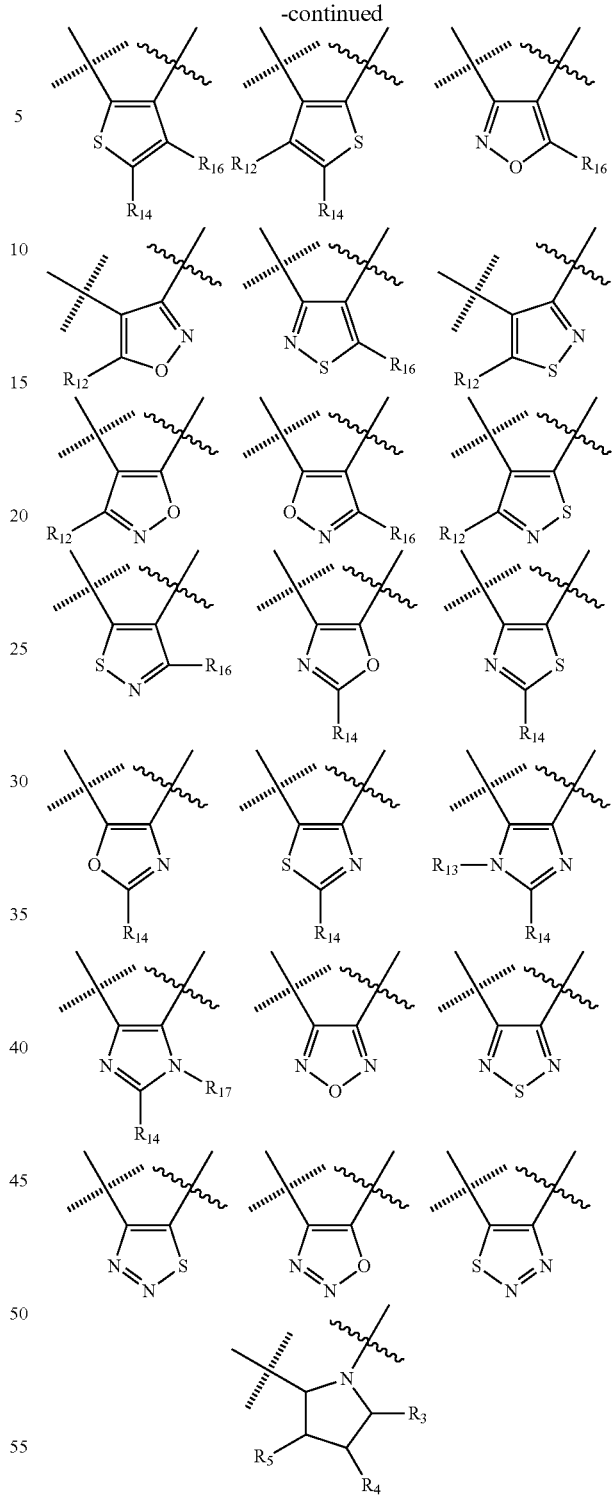

wherein the wavy line (~~~) indicates the point of attachment to the carbonyl of the main formula (A) and the hashed line (||||||||) indicates the point of attachment to the cycle A of the main formula (A);

cycle A is selected from aryl; and heterocycle; optionally substituted with one, two, or three substituents (more in particular one or two substituents) selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF₃, cyano, nitro, —C(O)OH, NH₂, NH(alkyl), or N(alkyl)₂; more particularly cycle A is selected from
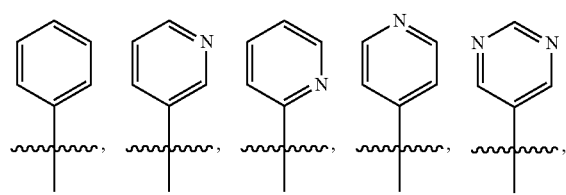
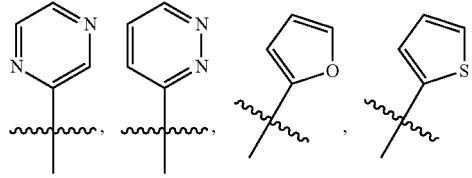
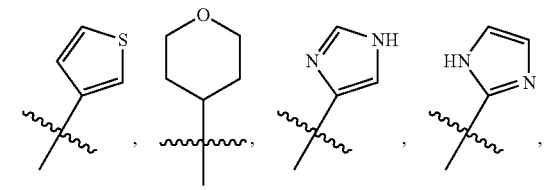
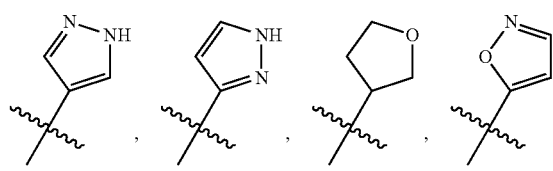
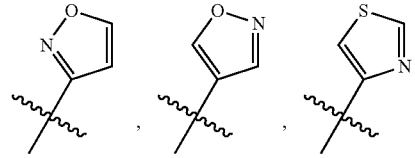
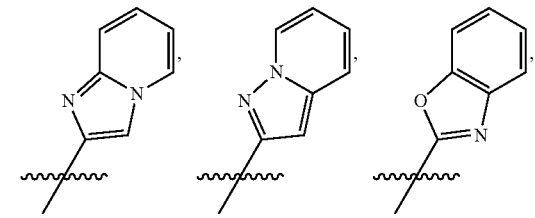
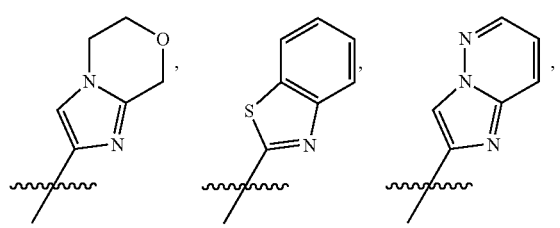
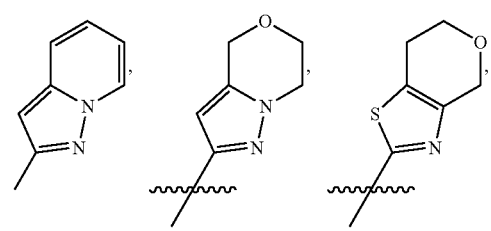
-continued
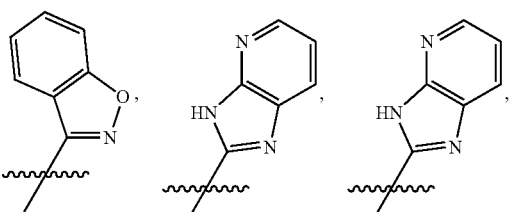
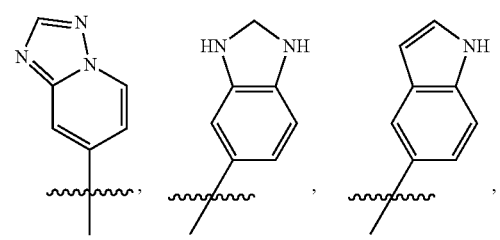
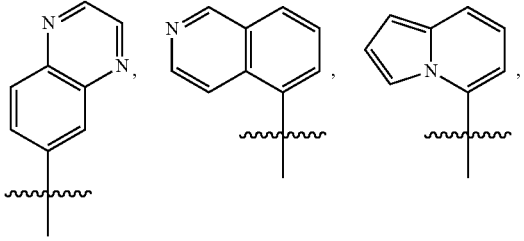
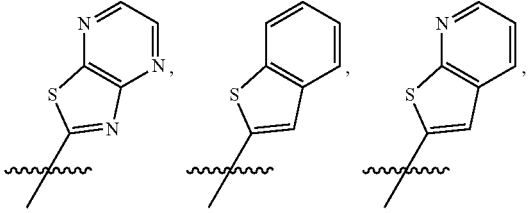
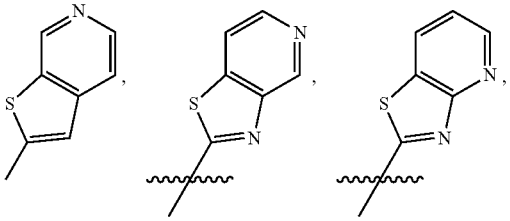
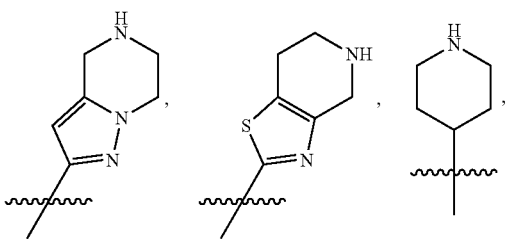
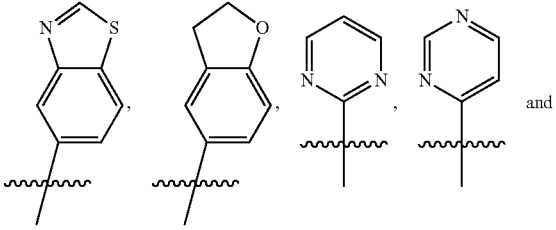
and -continued

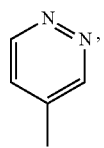

wherein the wavy line (~~~) indicates the point of attachment to the atom of cycle C, and wherein the depicted cycles may be optionally substituted with one, two, or three substituents selected from alkyl, cycloalkyl, alkenyl, cycloalkenyl, alkynyl, cycloalkynyl, heteroalkyl, heteroalkenyl, heteroalkynyl, hydroxyl, =O, halogen, —SH, =S, trifluoromethyl, —OCF$_3$, cyano, nitro, —C(O)OH, NH$_2$, NH(alkyl), or N(alkyl)$_2$;

cycle B is selected from aryl; and heterocycle; wherein said aryl and heterocycle are optionally substituted with one, two, or three $Z^{1a}$; more particularly cycle B is selected from

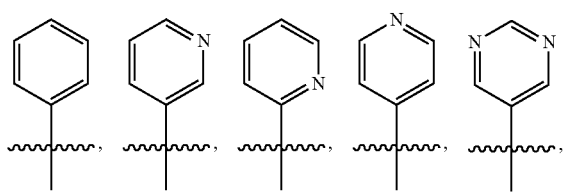

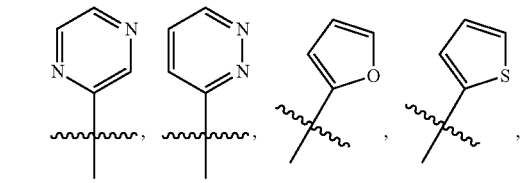

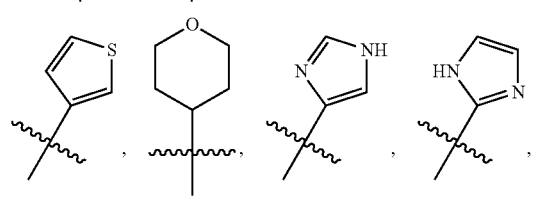

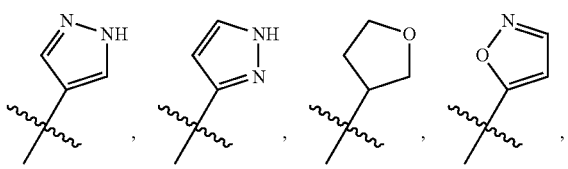

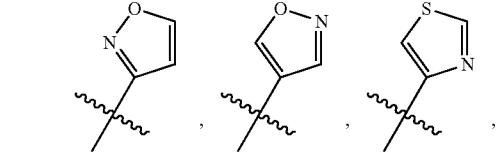

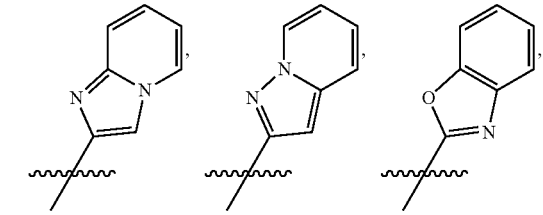

-continued

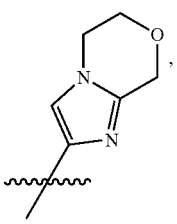 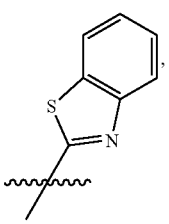 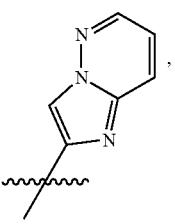

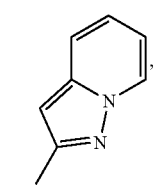 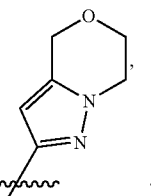 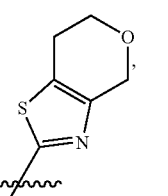

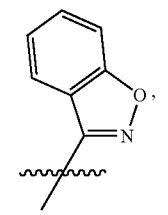 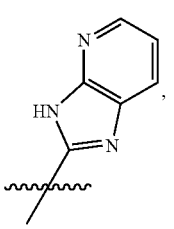 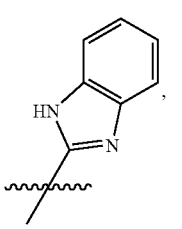

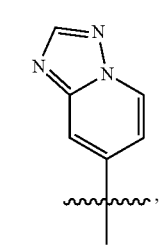 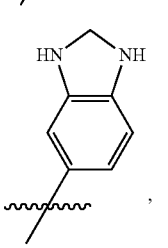 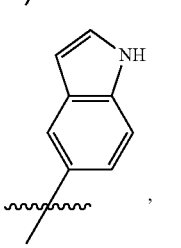

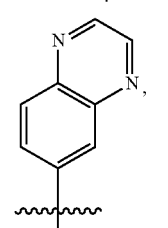 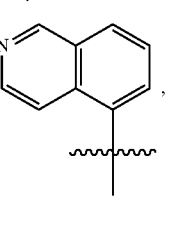 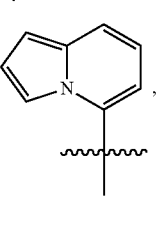

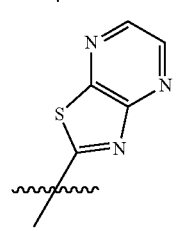 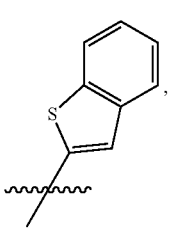 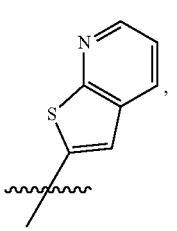

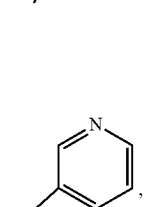 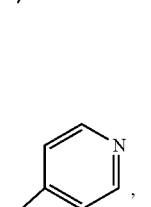 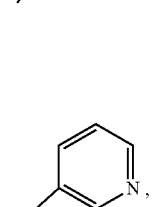

-continued

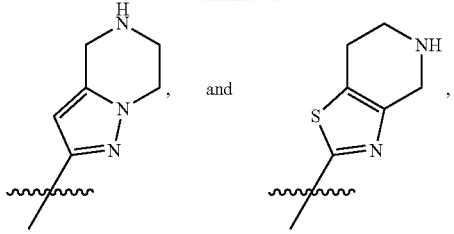

wherein the wavy line (∿∿∿) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$ alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$ alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

$R^3$ is selected from hydrogen; $C_{1-6}$alkyl; hetero$C_{1-6}$alkyl; and =O;

each $R^4$ and $R^5$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero$C_{1-6}$alkyl; hetero$C_{1-6}$alkenyl; and hetero$C_{1-6}$alkynyl;

$R^9$ is selected from hydrogen; $C_{1-6}$alkyl; hetero$C_{1-6}$alkyl; and =O;

each of $R^{12}$, $R^{14}$ and $R^{16}$ is independently selected from hydrogen; halogen; trifluoromethyl; cyano; $C_{1-6}$alkyl and $C_{1-6}$cycloalkyl;

each $R^{13}$, $R^{15}$ and $R^{17}$ is independently selected from hydrogen; $C_{1-6}$alkyl; and $C_{1-6}$cycloalkyl;

each $R^{32}$ and $R^{32a}$ is independently selected from hydrogen; halogen; hydroxyl; sulfhydryl; trifluoromethyl; trifluoromethoxy; cyano; $C_{1-6}$alkyl; $C_{2-6}$alkenyl; $C_{2-6}$alkynyl; hetero $C_{1-6}$alkyl; hetero$C_{2-6}$alkenyl; and hetero $C_{2-6}$alkynyl;

$R^{33}$ is independently selected from hydrogen and $C_{1-6}$alkyl;

each $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O) $Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O) N$Z^4Z^5$, cyano, —C(=O)$Z^3$, —C(=O)O$Z^2$, —C(=O) N$Z^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$ alkynyl, aryl, heterocycle, aryl$C_{1-6}$alkyl, aryl$C_{2-6}$ alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$ alkyl, heterocycle-$C_{2-6}$alkenyl, heterocycle-$C_{2-6}$ alkynyl, heterocycle-hetero$C_{1-6}$alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2$ N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)$_2Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —$OZ^2$, —O—C(=O)$Z^3$, =O, —S(=O)$_2Z^3$, —S(=O)$_2$ N$Z^4Z^5$, trifluoromethyl, trifluoromethoxy, —N$Z^4Z^5$, —N$Z^4$C(=O)$Z^2$, —N$Z^4$C(=O)—O$Z^2$, cyano, —C(=O)$Z^3$, —C(=O)O$Z^2$, —C(=O)N$Z^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$ alkenyl, arylhetero$C_{2-6}$alkynyl, heterocycle-$C_{1-6}$ alkyl, heterocycle-$C_{2-6}$alkenyl, heterocycle-$C_{2-6}$ alkynyl, heterocycle-hetero$C_{1-6}$alkyl, heterocycle-hetero$C_{2-6}$alkenyl, and heterocycle-hetero$C_{2-6}$ alkynyl, are optionally substituted with one, two or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, —O—C(O)Me, cyano, nitro, —C(O)OH, —C(O)O$C_{1-6}$alkyl, —NH$_2$, —NHCH$_3$; —N(CH$_3$)$_2$, —NH—C(=O)O—$C_{1-4}$ alkyl, morpholinyl, —S(O)$_2C_{1-4}$alkyl, and —O—$C_{1-6}$alkyl; preferably said $C_{1-6}$alkyl, hetero$C_{1-6}$ alkyl, aryl, heterocycle, and heterocycle-$C_{1-6}$ alkyl, are optionally substituted with one, two, or three substituents selected from hydroxyl, =O, halogen, —SH, =S, trifluoromethyl, —OCF$_3$, —O—C (O)Me, cyano, nitro, —C(O)OH, —C(O)O$C_{1-6}$ alkyl, —NH$_2$, —NHCH$_3$; —N(CH$_3$)$_2$, —NH—C (=O)O—$C_{1-4}$alkyl, morpholinyl, —S(O)$_2C_{1-4}$alkyl, and —O—$C_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)O$C_{1-6}$alkyl, —NH$_2$, —NHCH$_3$; —N(CH$_3$)$_2$, —NH—C(=O)O—$C_{1-4}$alkyl, morpholinyl, —S(O)$_2$ $C_{1-4}$alkyl, and —O—$C_{1-6}$alkyl;

each $Z^2$ is independently selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, arylC$_{2-6}$alkenyl, arylC$_{2-6}$alkynyl, arylheteroC$_{1-6}$alkyl, arylheteroC$_{1-6}$alkenyl, arylheteroC$_{1-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^2$ is independently selected from C$_{1-6}$alkyl, aryl, heterocycle, and heterocycle-C$_{1-6}$alkyl; more preferably Z$^2$ is independently selected from C$_{1-6}$alkyl, aryl, and heterocycle-C$_{1-6}$alkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; preferably said C$_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$alkyl, —OCF$_3$, —S(=O)$_2$ C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; more preferably said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl;

each Z$^3$ is independently selected from hydroxyl, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$ alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^3$ is independently selected from hydroxyl, C$_{1-6}$alkyl, aryl, and heterocycle; more preferably Z$^3$ is independently selected from hydroxyl, C$_{1-6}$alkyl, and heterocycle;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$ alkyl, heterocycle-C$_{2-6}$alkenyl, heterocycle-C$_{2-6}$ alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each Z$^4$ and Z$^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$ alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each Z$^4$ and Z$^5$ is independently selected from hydrogen, C$_{1-6}$alkyl, aryl, C$_{3-7}$cycloalkyl, and heterocycle; more preferably each Z$^4$ and Z$^5$ is independently selected from hydrogen, C$_{1-6}$alkyl, and C$_{3-7}$cycloalkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$ alkenyl, arylheteroC$_{2-6}$alkynyl, heterocycle-C$_{1-6}$ alkyl, heterocycle-C$_{2-6}$alkenyl, heterocycle-C$_{2-6}$ alkynyl, heterocycle-heteroC$_{1-6}$alkyl, heterocycle-heteroC$_{2-6}$alkenyl, and heterocycle-heteroC$_{2-6}$ alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH or —NH$_2$;

and wherein Z$^4$ and Z$^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof.

One aspect of the invention relates to the compounds of formula (A) for use as a medicine, more in particular for use in the prevention or treatment of a flavivirus infection in an animal, mammal or human, preferably an infection with dengue virus or yellow fever virus.

In a particular embodiment of the different aspects of the invention, the compounds have a structure according to formula (C1), (C2), (C3), (C4) or (C5),

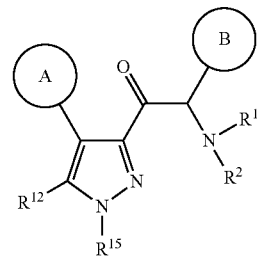

(C1)

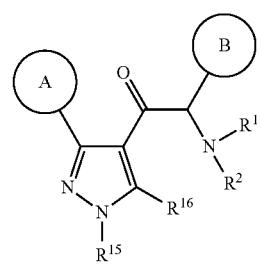

(C2)

(C3)

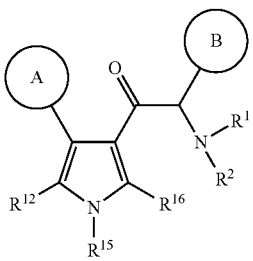

(C4)

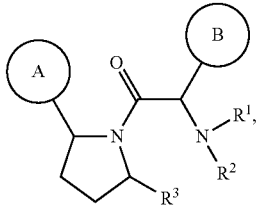

(C5)

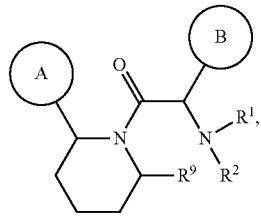

wherein cycle A, cycle B, $R^1$, $R^2$, $R^3$, $R^9$, $R^{12}$, $R^{15}$, and $R^{16}$ are as defined in formulae A or any of the embodiments described herein; and isomers (in particular stereo-isomers or tautomers), solvates, salts (in particular pharmaceutically acceptable salts) or prodrugs thereof.

In another particular embodiment, the compounds have a structure according to formula (E1), (E2), (E3), (E4), and (E5), (E1)

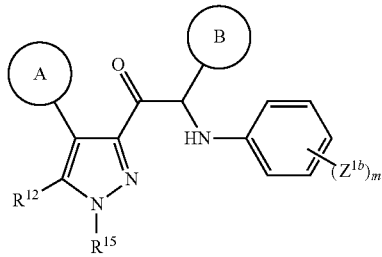

(E2)

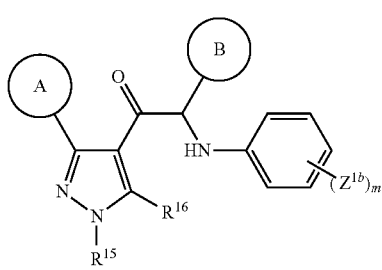

(E3)

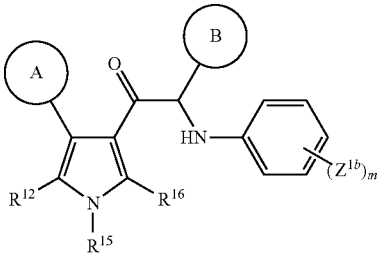

(E4)

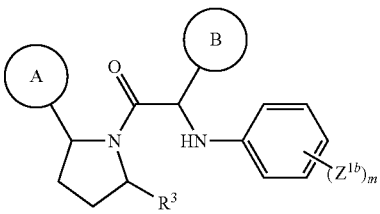

(E5)

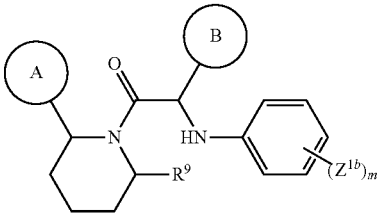

wherein each of cycle A, cycle B, $R^3$, $R^9$, $R^{12}$, $R^{15}$, $R^{16}$, and $Z^{1b}$ are as described for formula (A) and particular embodiments described herein and m is selected from 0, 1, 2 or 3; or more in particular wherein cycle B is selected from aryl and heteroaryl; more preferably cycle B is selected from

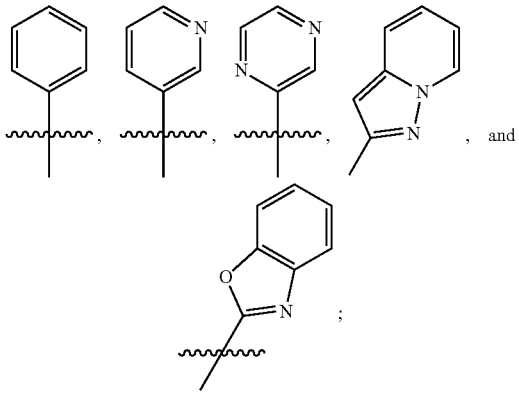

wherein said aryl, heteroaryl, and the depicted cycles may optionally be substituted with halogen, $C_{1-4}$alkyl, or $C_{1-4}$alkoxy; more preferably said aryl is substituted with halogen, $C_{1-4}$alkyl, or $C_{1-4}$alkoxy;

preferably $Z^{1b}$ is $C_{1-4}$alkoxy, —OCH$_2$CH$_2$OH, hydrogen, —CH$_2$—OH;

m is selected from 0, 1, 2, and 3; preferably m is selected from 1 and 2;

and isomers (in particular stereo-isomers or tautomers), solvates, salts (in particular pharmaceutically acceptable salts) or prodrugs thereof.

In another particular embodiment, $R^1$ has a structure according to formula (F),

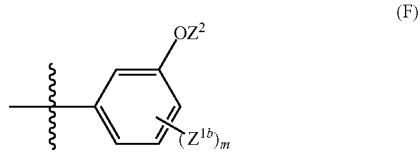

(F)

wherein the wavy line (∿∿) indicates the point of attachment to the amino atom of the main formula (A) and $Z^2$, $Z^{1b}$ and m are as described herein, as more in particular for formula (E1), (E2), (E3), (E4) or (E5).

The compounds of the present invention present at least one asymmetric center at the carbon atom substituted with cycle B, as shown below with an asterisk on formula (A). This asymmetric center can occur in its R or S configuration. In one preferred embodiment, said asymmetric center is in the R configuration. In another preferred embodiment, said asymmetric center is in the S configuration.

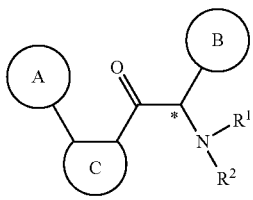

A very particular embodiment of the invention relates to the single compounds selected from the compounds in Table 1. The present invention therefore also relates and encompasses every single compounds listed in Table 1.

The term "treat" or "treating" as used herein is intended to refer to administration of a compound or composition of the invention to a subject for the purpose of effecting a therapeutic or prophylactic benefit through inhibition of a viral infection. Treating includes reversing, ameliorating, alleviating, inhibiting the progress of, lessening the severity of, or preventing a disease, disorder, or condition, or one or more symptoms of such disease, disorder or condition mediated through the inhibition of the viral infection. The term "subject" refers to an animal or mammalian patient in need of such treatment, such as a human.

It is to be noticed that the term "comprising", used in the claims, should not be interpreted as being restricted to the means listed thereafter; it does not exclude other elements or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Also embodiments described for an aspect of the invention may be used for another aspect of the invention and can be combined. Where an indefinite or definite article is used when referring to a singular noun e.g. "a" or "an", "the", this includes a plural of that noun unless something else is specifically stated.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "hydrocarbyl", "$C_{1-18}$ hydrocarbyl", "hydrocarbyl group" or "$C_{1-18}$ hydrocarbyl group" as used herein refers to $C_1$-$C_{18}$ normal, secondary, tertiary, unsaturated or saturated, non-aromatic, acyclic or cyclic, hydrocarbons and combinations thereof. This term therefore comprises alkyl, alkenyl, alkynyl, cycloalkyl, cycloalkenyl and cycloalkynyl.

The terminology "heterohydrocarbyl", "hetero $C_{1-18}$ hydrocarbyl", "heterohydrocarbyl group", "hetero $C_{1-18}$ hydrocarbyl group" or "hydrocarbyl group which optionally includes one or more heteroatoms, said heteroatoms being selected from the atoms consisting of O, S, and N" as used herein, refers to a hydrocarbyl group where one or more carbon atoms are replaced by an oxygen, nitrogen or sulphur atom(s) and thus includes heteroalkyl, heteroalkenyl, heteroalkynyl and non-aromatic heterocycle. This term therefore comprises as an example alkoxy, alkenyloxy, $C_w$alkyl-O—$C_{18-w}$alkyl, $C_w$alkenyl-O-alkyl, $C_w$alkyl-NH—$C_{18-w}$alkenyl, among others, wherein w is selected from any number between 1 and 18.

The term "alkyl" or "$C_{1-18}$ alkyl" as used herein means $C_1$-$C_{18}$ normal, secondary, or tertiary, linear, branched or straight hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl. In a particular embodiment, the term alkyl refers to $C_{1-12}$ hydrocarbons, yet more in particular to $C_{1-6}$ hydrocarbons, yet more in particular to $C_{1-3}$ hydrocarbons as further defined herein above. A preferred alkyl is $C_{1-8}$alkyl. Another preferred alkyl is $C_{1-4}$alkyl.

The term "cycloalkyl" or "$C_{3-18}$ cycloalkyl" as used herein and unless otherwise stated means a saturated hydrocarbon monovalent radical having from 3 to 18 carbon atoms consisting of or comprising a $C_{3-10}$ monocyclic or $C_{7-18}$ polycyclic saturated hydrocarbon, such as for instance cyclopropyl, cyclopropylmethylene, cyclobutyl, cyclopentyl, cyclopentylmethylene, cyclopropylethylene, methylcyclopropylene, cyclohexyl, cycloheptyl, cyclooctyl, isopropoylcyclooctyl, cyclooctylmethylene, norbornyl, fenchyl, trimethyltricycloheptyl, decalinyl, adamantyl and the like. For the avoidance of doubt and as an example, cyclopentylmethylene refers to

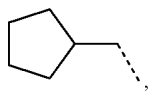

whereby the methyl group on the cyclopentyl is coupled to another group. Furthermore, for the avoidance of doubt and as an example, methylcyclopropylene refers to

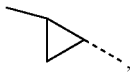

whereby the cyclopropyl of the methylcyclopropyl is coupled to another group. A preferred cycloalkyl is $C_{3-7}$cycloalkyl.

The term "alkenyl" or "$C_{2-18}$alkenyl" as used herein is $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$), and 5-hexenyl (—CH$_2$CH$_2$CH$_2$CH$_2$CH=CH$_2$). The double bond may be in the cis or trans configuration. In a particular embodiment, the term alkenyl refers to $C_{2-12}$ hydrocarbons, yet more in particular to $C_{2-6}$ hydrocarbons as further defined herein above. A preferred alkenyl is $C_{2-6}$alkenyl.

The term "cycloalkenyl" as used herein refers to a non-aromatic hydrocarbon radical having from 3 to 18 carbon atoms with at least one site (usually 1 to 3, preferably 1) of unsaturation, namely a carbon-carbon, sp2 double bond and consisting of or comprising a $C_{3-10}$ monocyclic or $C_{7-18}$ polycyclic hydrocarbon. Examples include, but are not limited to: cyclopentenyl (—$C_6H_7$), cyclopentenylpropylene, methylcyclohexenylene and cyclohexenyl (—$C_6H_9$). The double bond may be in the cis or trans configuration.

The term "alkynyl" or "$C_{2-18}$alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: ethynyl (—C≡CH), and 1-propynyl (propargyl, —CH$_2$C≡CH). In a particular embodiment, the term alkynyl refers to $C_{2-12}$ hydrocarbons, yet more in particular to $C_{2-6}$ hydrocarbons as further defined herein above. A preferred alkynyl is $C_{2-6}$alkynyl.

The term "cycloalkynyl" as used herein refers to a non-aromatic hydrocarbon radical having from 3 to 18 carbon atoms with at least one site (usually 1 to 3, preferably 1) of unsaturation, namely a carbon-carbon, sp triple bond and consisting of or comprising a $C_{3-10}$ monocyclic or $C_{7-18}$ polycyclic hydrocarbon. Examples include, but are not limited to: cyclohept-1-yne, 3-ethyl-cyclohept-1-ynylene, 4-cyclohept-1-yn-methylene and ethylene-cyclohept-1-yne.

The term "alkylene" as used herein each refer to a saturated, branched or straight chain hydrocarbon radical of 1-18 carbon atoms (more in particular $C_{1-12}$ or $C_{1-6}$ carbon atoms), and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "alkenylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp2 double bond, and having two monovalent radical centers derived by the removal of two hydrogen atoms from the same or two different carbon atoms of a parent alkene.

The term "alkynylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp triple bond, and having two monovalent radical centers derived by the removal of two hydrogen atoms from the same or two different carbon atoms of a parent alkyne.

The term "heteroalkyl" as used herein refers to an alkyl wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkyl can be replaced by NH$_2$ and/or that one or more —CH$_2$— of said acyclic alkyl can be replaced by —NH—, —O— or —S—. The S atoms in said chains may be optionally oxidized with one or two oxygen atoms, to afford sulfoxides and sulfones, respectively. Furthermore, the heteroalkyl groups in the compounds of the present invention can contain an oxo or thio group at any carbon or heteroatom that will result in a stable compound. The C atoms in said chains may be optionally oxidized with one oxygen atom, to afford for example carbonyl and carbonyloxy groups, respectively. Exemplary heteroalkyl groups include, but are not limited to, alcohols, alkyl ethers, primary, secondary, and tertiary alkyl amines, amides, ketones, esters, alkyl sulfides, and alkyl sulfones. In some embodiments, the term heteroalkyl thus comprises —CO—O-alkyl, —O-alkyl, —NH-alkyl, —N(alkyl)$_2$, —S(=O)$_2$alkyl, and —S-alkyl. In some embodiments, said heteroC$_{1-6}$alkyl as a group or part of a group is selected from —CO—O—C$_{1-5}$alkyl, —O—C$_{1-6}$alkyl, —NH—C$_{1-6}$alkyl, —N(C$_{1-6}$ alkyl)$_2$, —S(=O)$_2$C$_{1-6}$alkyl, and —S—C$_{1-6}$alkyl.

The term "heteroalkenyl" as used herein refers to an alkenyl wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkenyl can be replaced by NH$_2$, that one or more —CH$_2$— of said acyclic alkenyl can be replaced by —NH—, —O— or —S— and/or that one or more —CH= of said acyclic alkynyl can be replaced by —N=. The S atoms in said chains may be optionally oxidized with one or two oxygen atoms, to afford sulfoxides and sulfones, respectively. Furthermore, the heteroalkyl groups in the compounds of the present invention can contain an oxo or thio group at any carbon or heteroatom that will result in a stable compound. The term heteroalkenyl thus comprises imines, —O-alkenyl, —NH-alkenyl, —N(alkenyl)$_2$, —N(alkyl)(alkenyl), and —S-alkenyl.

The term "heteroalkynyl" as used herein refers to an alkynyl wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkynyl can be replaced by —NH$_2$, that one or more —CH$_2$— of said alkynyl can be replaced by —NH—, —O— or —S—, that one or more —CH= of said acyclic alkynyl can be replaced by —N= and/or that one or more ≡CH of said acyclic alkynyl can be replaced by ≡N. The S atoms in said chains may be optionally oxidized with one or two oxygen atoms, to afford sulfoxides and sulfones, respectively. Furthermore, the heteroalkynyl groups in the compounds of the present invention can contain an oxo or thio group at any carbon or heteroatom that will result in a stable compound. The term heteroalkynyl thus comprises —O-alkynyl, —NH-alkynyl, —N(alkynyl)$_2$, —N(alkyl)(alkynyl), —N(alkenyl)(alkynyl), and S-alkynyl.

The term "heteroalkylene" as used herein refers to an alkylene wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkylene can be replaced by —NH$_2$ and/or that one or more —CH$_2$— of said alkylene can be replaced by —NH—, —O— or —S—. The S atoms in said chains may be optionally oxidized with one or two oxygen atoms, to afford sulfoxides and sulfones, respectively. Furthermore, the heteroalkylene groups in the compounds of the present invention can contain an oxo or thio group at any carbon or heteroatom that will result in a stable compound.

The term "heteroalkenylene" as used herein refers to an alkenylene wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkenylene can be replaced by —NH$_2$, that one or more —CH$_2$— of said alkenylene can be replaced by —NH—, —O— or —S— and/or that one or more —CH= of said alkynylene can be replaced by —N=. The S atoms in said chains may be optionally oxidized with one or two oxygen atoms, to afford sulfoxides and sulfones, respectively. Furthermore, the heteroalkenylene groups in the compounds of the present invention can contain an oxo or thio group at any carbon or heteroatom that will result in a stable compound.

The term "heteroalkynylene" as used herein refers to an alkynylene wherein one or more carbon atoms (usually 1, 2 or 3) are replaced by an oxygen, nitrogen or sulphur atom, with the proviso that said chain may not contain two adjacent O atoms or two adjacent S atoms. This means that one or more —CH$_3$ of said alkynylene can be replaced by —NH$_2$, that one or more —CH$_2$— of said alkynylene can be replaced by —NH—, —O— or —S—, that one or more —CH= of said alkynylene can be replaced by —N= and/or that one or more ≡CH of said alkynylene can be replaced by ≡N. The S atoms in said chains may be optionally oxidized with one or two oxygen atoms, to afford sulfoxides and sulfones, respectively. Furthermore, the heteroalkynylene groups in the compounds of the present invention can contain an oxo or thio group at any carbon or heteroatom that will result in a stable compound.

The term "aryl" as used herein means an aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. The term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like. Particular aryl groups are phenyl and naphthyl, especially phenyl.

The term "arylalkyl" or "arylalkyl-" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethyl, and the like. The arylalkyl group comprises 6 to 20 carbon atoms, e.g. the alkyl moiety of the arylalkyl group is 1 to 6 carbon atoms and the aryl moiety is 5 to 14 carbon atoms.

The term "arylalkenyl" or "arylalkenyl-" as used herein refers to an alkenyl radical in which one of the hydrogen atoms bonded to a carbon atom, is replaced with an aryl radical. The arylalkenyl group comprises 6 to 20 carbon atoms, e.g. the alkenyl moiety of the arylalkenyl group is 1 to 6 carbon atoms and the aryl moiety is 5 to 14 carbon atoms.

The term "arylalkynyl" or "arylalkynyl-" as used herein refers to an alkynyl radical in which one of the hydrogen atoms bonded to a carbon atom, is replaced with an aryl radical. The arylalkynyl group comprises 6 to 20 carbon atoms, e.g. the alkynyl moiety of the arylalkynyl group is 1 to 6 carbon atoms and the aryl moiety is 5 to 14 carbon atoms.

The term "arylheteroalkyl" or "arylheteroalkyl-" as used herein refers to a heteroalkyl radical in which one of the hydrogen atoms bonded to a carbon atom, typically a terminal or sp3 carbon atom, is replaced with an aryl radical. The arylheteroalkyl group comprises 6 to 20 carbon atoms, e.g. the heteroalkyl moiety of the arylheteroalkyl group is 1 to 6 carbon atoms and the aryl moiety is 5 to 14 carbon atoms.

The term "arylheteroalkenyl" or "arylheteroalkenyl-" as used herein refers to a heteroalkenyl radical in which one of the hydrogen atoms bonded to a carbon atom, is replaced with an aryl radical. The arylheteroalkenyl group comprises 6 to 20 carbon atoms, e.g. the heteroalkenyl moiety of the arylheteroalkenyl group is 1 to 6 carbon atoms and the aryl moiety is 5 to 14 carbon atoms.

The term "arylheteroalkynyl" or "arylheteroalkynyl-" as used herein refers to a heteroalkynyl radical in which one of the hydrogen atoms bonded to a carbon atom, is replaced with an aryl radical. The arylheteroalkynyl group comprises 6 to 20 carbon atoms, e.g. the heteroalkynyl moiety of the arylheteroalkynyl group is 1 to 6 carbon atoms and the aryl moiety is 5 to 14 carbon atoms.

The term "heterocycle" as used herein means a saturated, unsaturated or aromatic ring system of 3 to 18 atoms including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

The term "heteroaryl" means an aromatic ring system of 5 to 18 atoms including at least one N, O, S, or P and thus refers to aromatic heterocycles. Examples of heteroaryl include but are not limited to pyridyl, pyridazinyl, pyrimidinyl, pyrazinyl, s-triazinyl, oxazolyl, imidazolyl, thiazolyl, isoxazolyl, pyrazolyl, isothiazolyl, furyl, thienyl, and pyrrolyl.

The term "non-aromatic heterocycle" as used herein means a saturated or unsaturated non-aromatic ring system of 3 to 18 atoms including at least one N, O, S, or P.

The term "heterocycle-alkyl" or "heterocycle-alkyl-" as used herein refers to an alkyl radical in which one of the hydrogen atoms bonded to a carbon atom, typically a terminal or sp3 carbon atom, is replaced with a heterocycle radical. An example of a heterocycle-alkyl group is 2-pyridyl-methylene. The heterocycle-alkyl group comprises 6 to 20 atoms, e.g. the alkyl moiety of the heterocycle-alkyl group is 1 to 6 carbon atoms and the heterocycle moiety is 3 to 14 atoms.

The term "heterocycle-alkenyl" or "heterocycle-alkenyl-" as used herein refers to an alkenyl radical in which one of the hydrogen atoms bonded to a carbon atom, is replaced with an heterocycle radical. The heterocycle-alkenyl group comprises 6 to 20 atoms, e.g. the alkenyl moiety of the heterocycle-alkenyl group is 1 to 6 carbon atoms and the heterocycle moiety is 3 to 14 atoms.

The term "heterocycle-alkynyl" or "heterocycle-alkynyl-" as used herein refers to an alkynyl radical in which one of the hydrogen atoms bonded to a carbon atom, is replaced with a heterocycle radical. The heterocycle-alkynyl group comprises 6 to 20 atoms, e.g. the alkynyl moiety of the heterocycle-alkynyl group is 1 to 6 carbon atoms and the heterocycle moiety is 3 to 14 atoms.

The term "heterocycle-heteroalkyl" or "heterocycle-heteroalkyl-" as used herein refers to a heteroalkyl radical in which one of the hydrogen atoms bonded to a carbon atom, typically a terminal or sp3 carbon atom, is replaced with a heterocycle radical. The heterocycle-heteroalkyl group comprises 6 to 20 atoms, e.g. the heteroalkyl moiety of the heterocycle-heteroalkyl group is 1 to 6 carbon atoms and the heterocycle moiety is 3 to 14 atoms.

The term "heterocycle-heteroalkenyl" or "heterocycle-heteroalkenyl-" as used herein refers to a heteroalkenyl radical in which one of the hydrogen atoms bonded to a carbon atom, is replaced with an heterocycle radical. The heterocycle-heteroalkenyl group comprises 6 to 20 atoms, e.g. the heteroalkenyl moiety of the heterocycle-heteroalkenyl group is 1 to 6 carbon atoms and the heterocycle moiety is 3 to 14 atoms.

The term "heterocycle-heteroalkynyl" or "heterocycle-heteroalkynyl-" as used herein refers to a heteroalkynyl radical in which one of the hydrogen atoms bonded to a carbon atom, is replaced with a heterocycle radical. The heterocycle-heteroalkynyl group comprises 6 to 20 atoms, e.g. the heteroalkynyl moiety of the heterocycle-heteroalkynyl group is 1 to 6 carbon atoms and the heterocycle moiety is 3 to 14 atoms.

The term "heteroaryl-alkyl" or "heteroaryl-alkyl-" as used herein refers to an alkyl radical in which one of the hydrogen atoms bonded to a carbon atom, typically a terminal or sp3 carbon atom, is replaced with a heteroaryl radical. An example of a heteroaryl-alkyl group is 2-pyridyl-methylene. The heteroaryl-alkyl group comprises 6 to 20 atoms, e.g. the alkyl moiety of the heteroaryl-alkyl group is 1 to 6 carbon atoms and the heteroaryl moiety is 5 to 14 atoms.

The term "heteroaryl-alkenyl" or "heteroaryl-alkenyl-" as used herein refers to an alkenyl radical in which one of the hydrogen atoms bonded to a carbon atom, is replaced with an heteroaryl radical. The heteroaryl-alkenyl group comprises 6 to 20 atoms, e.g. the alkenyl moiety of the heteroaryl-alkenyl group is 1 to 6 carbon atoms and the heteroaryl moiety is 5 to 14 atoms.

The term "heteroaryl-alkynyl" or "heteroaryl-alkynyl-" as used herein refers to an alkynyl radical in which one of the hydrogen atoms bonded to a carbon atom, is replaced with a heteroaryl radical. The heteroaryl-alkynyl group comprises 6 to 20 atoms, e.g. the alkynyl moiety of the heteroaryl-alkynyl group is 1 to 6 carbon atoms and the heteroaryl moiety is 5 to 14 atoms.

The term "heteroaryl-heteroalkyl" or "heteroaryl-heteroalkyl-" as used herein refers to a heteroalkyl radical in which one of the hydrogen atoms bonded to a carbon atom, typically a terminal or sp3 carbon atom, is replaced with a heterocycle radical. The heteroaryl-heteroalkyl group comprises 6 to 20 atoms, e.g. the heteroalkyl moiety of the heteroaryl-heteroalkyl group is 1 to 6 carbon atoms and the heteroaryl moiety is 5 to 14 atoms.

The term "heteroaryl-heteroalkenyl" or "heteroaryl-heteroalkenyl-" as used herein refers to a heteroalkenyl radical in which one of the hydrogen atoms bonded to a carbon atom, is replaced with an heteroaryl radical. The heteroaryl-heteroalkenyl group comprises 6 to 20 atoms, e.g. the heteroalkenyl moiety of the heteroaryl-heteroalkenyl group is 1 to 6 carbon atoms and the heteroaryl moiety is 5 to 14 atoms.

The term "heteroaryl-heteroalkynyl" or "heteroaryl-heteroalkynyl-" as used herein refers to a heteroalkynyl radical in which one of the hydrogen atoms bonded to a carbon atom, is replaced with a heteroaryl radical. The heteroaryl-heteroalkynyl group comprises 6 to 20 atoms, e.g. the heteroalkynyl moiety of the heteroaryl-heteroalkynyl group is 1 to 6 carbon atoms and the heteroaryl moiety is 5 to 14 atoms.

The term "non-aromatic heterocycle-alkyl" or "non-aromatic heterocycle-alkyl-" as used herein refers to an acyclic alkyl radical in which one of the hydrogen atoms bonded to a carbon atom, typically a terminal or sp3 carbon atom, is replaced with a non-aromatic heterocycle radical. The non-aromatic heterocycle-alkyl group comprises 6 to 20 atoms, e.g. the alkyl moiety of the non-aromatic heterocycle-alkyl group is 1 to 6 carbon atoms and the non-aromatic heterocycle moiety is 3 to 14 atoms.

The term "non-aromatic heterocycle-alkenyl" or "non-aromatic heterocycle-alkenyl-" as used herein refers to an acyclic alkenyl radical in which one of the hydrogen atoms bonded to a carbon atom, is replaced with an non-aromatic heterocycle radical. The non-aromatic heterocycle-alkenyl group comprises 6 to 20 atoms, e.g. the alkenyl moiety of the non-aromatic heterocycle-alkenyl group is 1 to 6 carbon atoms and the non-aromatic heterocycle moiety is 3 to 14 atoms.

The term "non-aromatic heterocycle-alkynyl" or "non-aromatic heterocycle-alkynyl-" as used herein refers to an acyclic alkynyl radical in which one of the hydrogen atoms bonded to a carbon atom, is replaced with a non-aromatic heterocycle radical. The non-aromatic heterocycle-alkynyl group comprises 6 to 20 atoms, e.g. the alkynyl moiety of the non-aromatic heterocycle-alkynyl group is 1 to 6 carbon atoms and the non-aromatic heterocycle moiety is 3 to 14 atoms.

The term "non-aromatic heterocycle-heteroalkyl" or "non-aromatic heterocycle-heteroalkyl-" as used herein refers to a heteroalkyl radical in which one of the hydrogen atoms bonded to a carbon atom, typically a terminal or sp3 carbon atom, is replaced with a heterocycle radical. The non-aromatic heterocycle-heteroalkyl group comprises 6 to 20 atoms, e.g. the heteroalkyl moiety of the non-aromatic heterocycle-heteroalkyl group is 1 to 6 carbon atoms and the non-aromatic heterocycle moiety is 3 to 14 atoms.

The term "non-aromatic heterocycle-heteroalkenyl" or "non-aromatic heterocycle-heteroalkenyl-" as used herein refers to a heteroalkenyl radical in which one of the hydrogen atoms bonded to a carbon atom, is replaced with an non-aromatic heterocycle radical. The non-aromatic heterocycle-heteroalkenyl group comprises 6 to 20 atoms, e.g. the heteroalkenyl moiety of the non-aromatic heterocycle-heteroalkenyl group is 1 to 6 carbon atoms and the non-aromatic heterocycle moiety is 3 to 14 atoms.

The term "non-aromatic heterocycle-heteroalkynyl" or "non-aromatic heterocycle-heteroalkynyl-" as used herein refers to a heteroalkynyl radical in which one of the hydrogen atoms bonded to a carbon atom, is replaced with a non-aromatic heterocycle radical. The non-aromatic heterocycle-heteroalkynyl group comprises 6 to 20 atoms, e.g. the heteroalkynyl moiety of the non-aromatic heterocycle-heteroalkynyl group is 1 to 6 carbon atoms and the non-aromatic heterocycle moiety is 3 to 14 atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cyclo-alkoxy", "aryloxy", "arylalkyloxy", "heterocycleoxy", "alkylthio", "cycloalkylthio", "arylthio", "arylalkylthio" and "heterocyclethio" refer to substituents wherein an alkyl group, respectively a cycloalkyl, aryl, arylalkyl or heterocycle (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals instead of alkyl. A preferred alkoxy is $C_{1-6}$alkoxy; another preferred alkoxy is $C_{1-4}$alkoxy.

As used herein and unless otherwise stated, the term halogen means any atom selected from the group consisting of fluorine (F), chlorine (Cl), bromine (Br) and iodine (I).

As used herein with respect to a substituting group, and unless otherwise stated, the terms "substituted" such as in "substituted alkyl", "substituted alkenyl", substituted alkynyl", "substituted aryl", "substituted heterocycle", "substituted arylalkyl", "substituted heterocycle-alkyl" and the like refer to the chemical structures defined herein, and wherein the said hydrocarbyl, heterohydrocarbyl group and/or the said aryl or heterocycle may be optionally substituted with one or more substituents (preferable 1, 2, 3, 4, 5 or 6), meaning that one or more hydrogen atoms are each independently replaced with a substituent. Typical substituents include, but are not limited to and in a particular embodiment said substituents are being independently selected from the group consisting of halogen, amino, hydroxyl, sulfhydryl, alkyl, alkoxy, alkenyl, alkenyloxy, alkynyl, alkynyloxy, cycloalkyl, cycloalkenyl, cycloalkynyl, heteroalkyl, heteroalkenyl, heteroalkynyl, aryl, heterocycle, arylalkyl, arylalkenyl, arylalkynyl, heterocycle-alkyl, heterocycle-alkenyl and heterocycle-alkynyl, —X, —Z, —O⁻, —OZ, =O, —SZ, —S⁻, =S, —NZ$_2$, —N⁺Z$_3$, =NZ, =N—OZ, —CX$_3$ (e.g. trifluoromethyl), —CN, —OCN, —SCN, —N=C=O, —N=C=S, —NO, —NO$_2$, =N$_2$, —N$_3$, —NZC(O)Z, —NZC(S)Z, —NZC(O)O⁻, —NZC(O)OZ, —NZC(S)OZ, —NZC(O)NZZ, NZC(NZ)Z, NZC(NZ)NZZ, —C(O)NZZ, —C(NZ)Z, —S(O)$_2$O⁻, —S(O)$_2$OZ, —S(O)$_2$Z, —OS(O)$_2$OZ, —OS(O)$_2$Z, —OS(O)$_2$O⁻, —S(O)$_2$NZ, —S(O)Z, —OP(O)(OZ)$_2$, —P(O)(OZ)$_2$, —P(O)(O)$_2$, —P(O)(OZ)(O), —P(O)(OH)$_2$, —C(O)Z, —C(O)X, —C(S)Z, —C(O)OZ, —C(O)O⁻, —C(S)OZ, —C(O)SZ, —C(S)SZ, —C(O)NZZ, —C(S)NZZ, —C(NZ)NZZ, —OC(O)Z, —OC(S)Z, —OC(O)O⁻, —OC(O)OZ, —OC(S)OZ, wherein each X is independently a halogen selected from F, Cl, Br, or I; and each Z is independently —H, alkyl, alkenyl, alkynyl, heteroalkyl, heteroalkenyl, heteroalkynyl, aryl, heterocycle, protecting group or prodrug moiety, while two Z bonded to a nitrogen atom can be taken together with the nitrogen atom to which they are bonded to form a heterocycle. Alkyl(ene), alkenyl(ene), and alkynyl(ene) groups may also be similarly substituted.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

The term "heteroatom(s)" as used herein means an atom selected from nitrogen, which can be quaternized; oxygen; and sulfur, including sulfoxide and sulfone.

The term "hydroxy" as used herein means —OH.

The term "carbonyl" as used herein means carbon atom bonded to oxygen with a double bond, i.e., C=O.

The term "amino" as used herein means the —NH$_2$ group.

The compounds of the invention are employed for the treatment or prophylaxis of viral infections, more particularly Flaviviral infections.

Flavivirus is a genus of the family (see http://en.wikipedia.org/wiki/Flaviviridae). This genus includes the West Nile virus, dengue virus, tick-borne encephalitis virus, yellow fever virus, and several other viruses which may cause encephalitis. Flaviviruses share a common size (40-65 nm), symmetry (enveloped, icosahedral nucleocapsid), nucleic acid (positive-sense, single stranded RNA approximately 10,000-11,000 bases), and appearance in the electron microscope. These viruses are transmitted by the bite from an infected arthropod (mosquito or tick).

The compounds of the invention are particularly active against dengue virus replication. For dengue virus, four distinct, but closely related serotypes are known (DENV-1, -2, -3, and -4). Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control dengue disease, the only available methods at present are mosquito eradication strategies to control the vector. Although progress is being made in the development of vaccines for dengue, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titres. In both primary and secondary infections, higher viral titres are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyperendemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

When using one or more compounds of the invention and of the formulae as defined herein:
  the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.
  the therapeutically effective amount of the preparation of the compound(s), especially for the treatment of viral infections in humans and other mammals, preferably is a flaviviral replication inhibiting amount of the formulae as defined herein and corresponds to an amount which ensures a plasma level of between 1 μg/ml and 100 mg/ml, optionally of 10 mg/ml.

The present invention further relates to a method for preventing or treating viral infections in a subject or patient by administering to the patient in need thereof a therapeutically effective amount of the compounds of the present invention. The therapeutically effective amount of the compound(s), especially for the treatment of viral infections in humans and other mammals, preferably is a flaviviral replication inhibiting amount. The suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic, and, when it is higher than 2.0, the combination is defined as antagonistic.

This principle may be applied to a combination of different antiviral drugs of the invention or to a combination of the antiviral drugs of the invention with other drugs that exhibit anti-viral activity or that stimulate the immune response.

The invention thus relates to a pharmaceutical composition or combined preparation having synergistic effects against a viral infection and containing:
Either:
A)
(a) a combination of two or more of the compounds of the present invention, and
(b) optionally one or more pharmaceutical excipients or pharmaceutically acceptable carriers, for simultaneous, separate or sequential use in the treatment or prevention of a flaviviral infection
or
B)
(c) one or more anti-viral agents and/or immune stimulating agents, and
(d) at least one of the compounds of the present invention, and
(e) optionally one or more pharmaceutical excipients or pharmaceutically acceptable carriers, for simultaneous, separate or sequential use in the treatment or prevention of a flaviviral infection.

Suitable anti-viral agents for inclusion into the synergistic antiviral compositions or combined preparations of this invention include ribavirin.

Suitable immune stimulating agents for inclusion into the synergistic antiviral compositions or combined preparations of this invention include interferon.

The pharmaceutical composition or combined preparation with synergistic activity against viral infection according to this invention may contain the compounds of the present invention over a broad content range depending on the contemplated use and the expected effect of the preparation. Generally, the content of the compound of the invention for inclusion into the synergistic antiviral compositions of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of Flaviviral infections, more preferably Dengue viral infections. The invention therefore relates to the use of a composition comprising:
(a) one or more compounds of the formulae described herein, and
(b) one or more Picornaviral enzyme inhibitors as biologically active agents in respective proportions such as to provide a synergistic effect against a Flaviviral infection, particularly an Dengueviral infection in a mammal, for instance in the form of a combined preparation for simultaneous, separate or sequential use in viral infection therapy.

More generally, the invention relates to the compounds of formula (A), (B), (C), (D-1), (D-2), (E), (F), and (G) and all embodiments thereof being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

More generally, the invention relates to the compounds of formula (A), (B), (C), (D-1), (D-2), (E), (F), (G), (H), (I), (J), and all embodiments thereof being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $NH_4^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing Li+, Na+, and K. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_{4+}$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_{4+}$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived from a physiologically acceptable acid or base, are within the scope of the present invention.

Preferable anions to form pharmaceutically acceptable acid addition salts are acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like.

Preferable cations to form pharmaceutically acceptable basic salts are benzathine, chloroprocaine, choline, diethanolamine, ethylenediamine, meglumine, procaine, and the like; and those formed with metallic cations such as aluminum, calcium, lithium, magnesium, potassium, sodium, zinc, and the like.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

The compounds of the invention may be formulated with conventional carriers and excipients, which will be selected in accordance with standard practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts.

Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone, it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulphatesulphate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this invention relates to various precursor or "prodrug" forms of the compounds of the present invention. It may be desirable to formulate the compounds of the present invention in the form of a chemical species which itself is not significantly biologically-active, but which when delivered to the animal will undergo a chemical reaction catalyzed by the normal function of the body of the animal, inter alia, enzymes present in the stomach or in blood serum, said chemical reaction having the effect of releasing a compound as defined herein. The term "pro-drug" thus relates to these species which are converted in vivo into the active pharmaceutical ingredient.

The prodrugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present invention the term "therapeutically suitable prodrug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound of the invention, which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention may be prepared according to the general procedure outlined in the following schemes.

Scheme 1: all A, B, C, $R^1$ and LG are as described for the compounds of the present invention according to formula (A) wherein cycle C has a structure as formula (a1) and its embodiments and formulae.

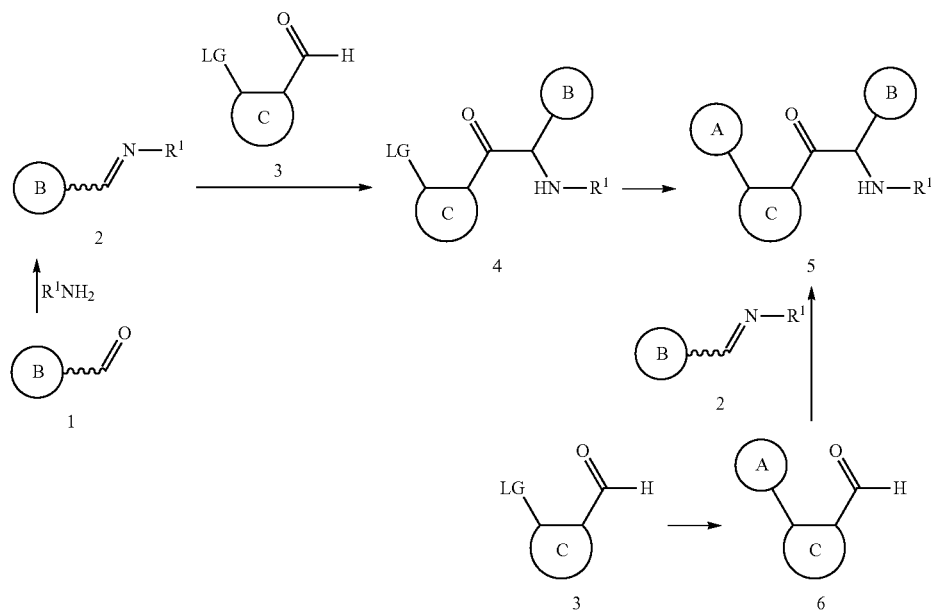

Aldehydes of formula 1 (commercially available or synthesized) may be reacted with amines of formula $R^1NH_2$ to provide imines of formula 2 which may then be reacted with intermediates of formula 3 (commercially available or synthesized by procedures known to the skilled in the art or as set forth in the examples below), in the presence of a catalyst such as 3-benzyl-5-(2-hydroxyethyl)-4-methylthiazol-3-ium chloride to provide intermediates of formula 4. More detailed information can be found in Chem. Commun., 2007, 852-854. Compounds of formula 4 may then be converted into desired compounds of formula 5 via Palladium-catalyzed coupling reactions (e.g. Suzuki, Stille, Negishi and the like). Alternatively, intermediates of formula 3 may be converted into intermediates of formula 6 via Palladium-catalyzed coupling reactions (e.g. Suzuki, Stille, Negishi and the like) which may further be reacted with imines of formula 2 under N-heterocyclic carbenes catalysis to provide the desired compounds of formula 5 following procedures known to the skilled in the art or as set forth in the examples below.

In another embodiment, compounds of the present invention may also be synthesized according to the general procedure outlined in the following scheme.

Scheme 2: all A, B, C, R¹, R² and LG are as described for the compounds of the present invention according to formula (A) wherein cycle C has a structure as formula (a1) and its embodiments and formulae.

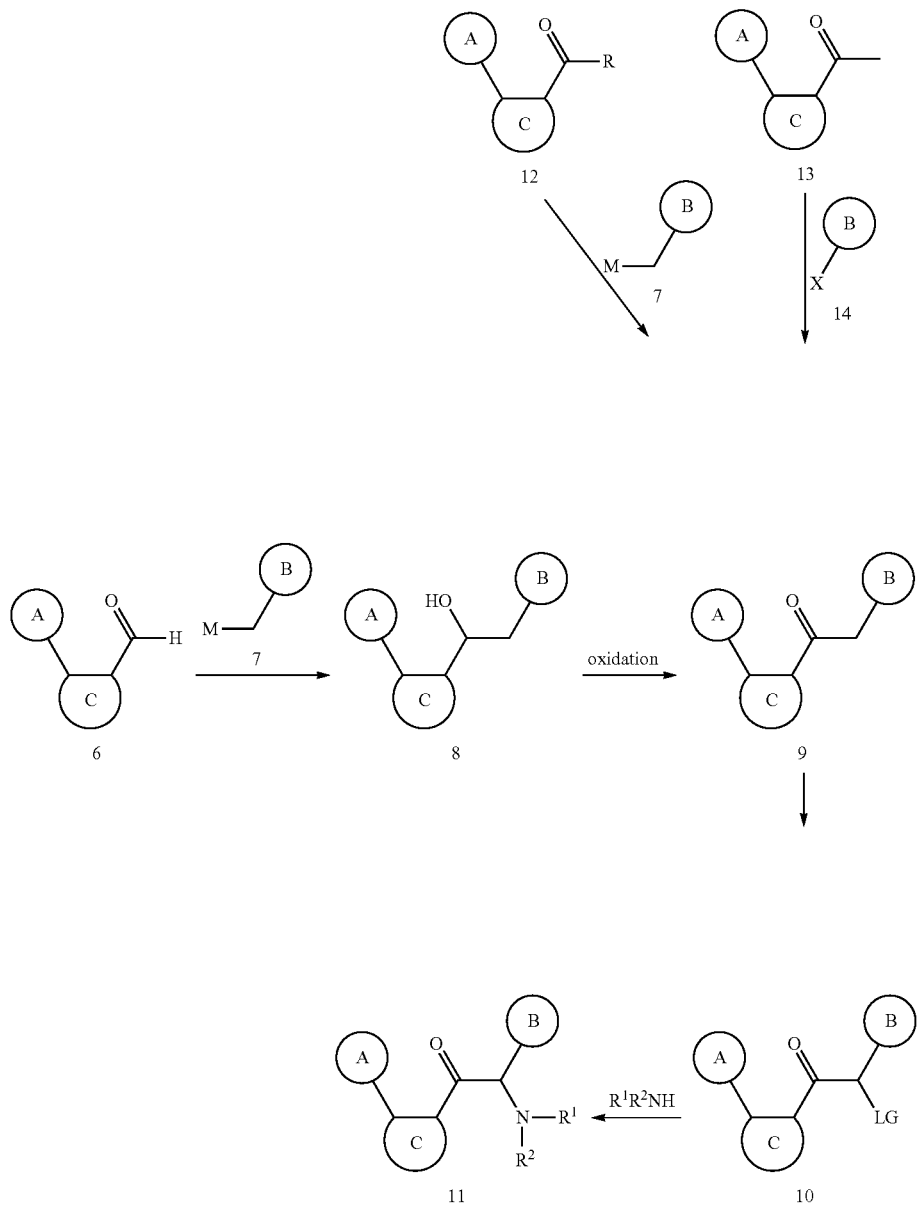

Derivatives of formula 6 (commercially available or synthesized by procedures known to the skilled in the art) may be reacted with Grignard or organolithium derivatives of formula 7 wherein M is MgX (X being and halogen selected from chlorine, bromine and iodine) or Lithium to provide intermediates of formula 8 which may be oxidized in intermediates of formula 9 following reactions known to the skilled in the art. Intermediates of formula 9 may be converted into intermediates of formula 10 wherein LG is an halogen selected from chlorine, bromine or iodine following reactions known to the skilled in the art or as set forth in the examples below. Compounds of interest having a genera formula 11 may finally be obtained from intermediates of formula 10 by leaving group displacement with amines of formula R¹R²NH (commercially available or synthesized).

Alternatively, intermediates of formula 9 may be prepared by condensation of organometallic derivatives of formula 7 with intermediates of formula 12 wherein R is a chlorine atom or —N(CH₃)OCH₃ (Weinreb amide) as known to the skilled in the art. Intermediates of formula 9 may also be prepared by α-arylation of ketones of formula 13 with intermediates of formula 14, wherein X is an halogen selected from chlorine, bromine or iodine, in the presence of a catalyst (e.g. Pd₂dba₃, Pd(OAc)₂, Pd(dba)₂ and the like), a ligand (e.g. BINAP, Xantphos, PtBu₃ and the like) and a base (e.g. NaOtBu, K₃PO₄ and the like). More information can be found in the following references: *J. Am. Chem. Soc.* 1997, 11108-11109 and *J. Am. Chem. Soc.* 1999, 1473-1478.

In another embodiment, compounds of the present invention may also be synthesized according to the general procedure outlined in the following scheme.

Scheme 3: all A, B, C, R¹, R², and LG are as described for the compounds of the present invention according to formula (A) wherein cycle C has a structure as fromuls (a2) or (a3) and its embodiments and formulae.

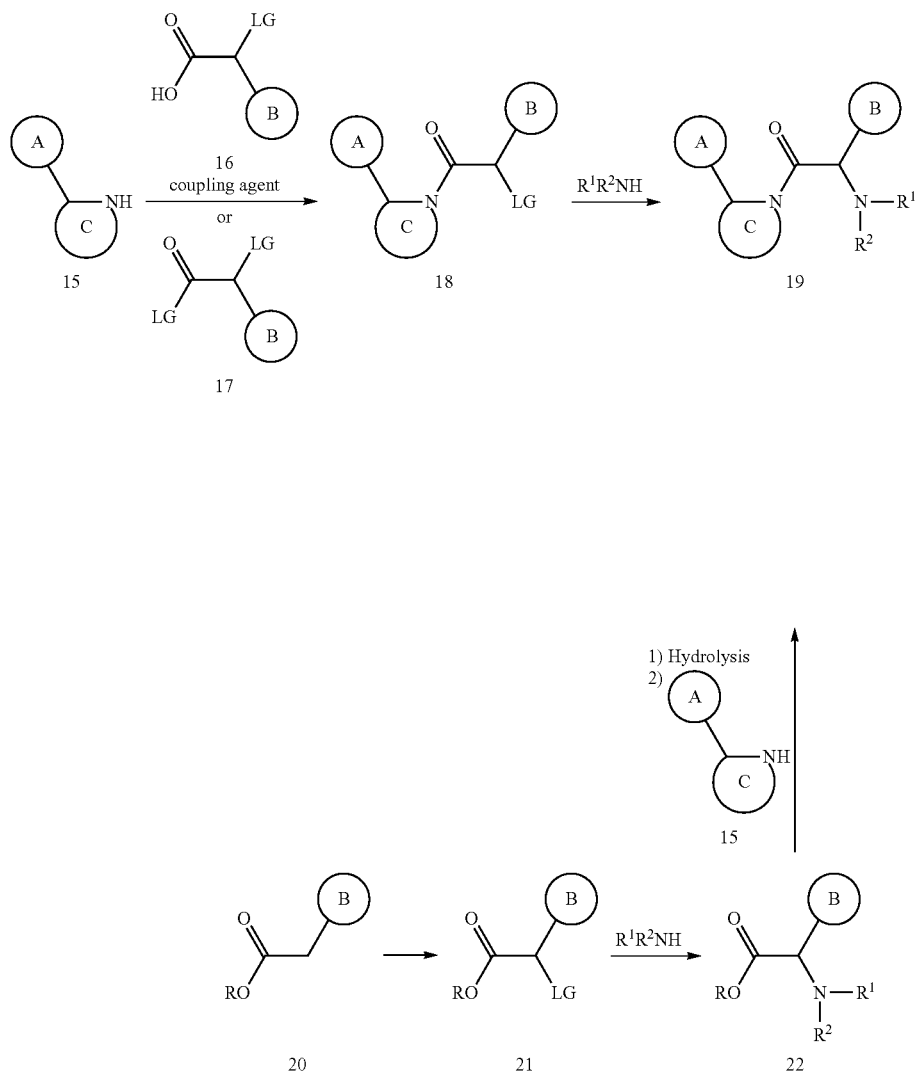

Intermediates of formula 15 may be converted into intermediates of formula 18 following standard amide bond formation with intermediates of formula 16 or with intermediates of formula 17 wherein LG is a chlorine or bromine (preferably a chlorine). The leaving group LG of intermediates of formula 18 may then be displaced by amines of formula $R^1R^2NH$ to provide the desired compounds of formula 19. Alternatively, 2-substituted acetic acid derivatives of formula 20, wherein R is an ester protecting group (e.g. methyl, ethyl, t-butyl and the like), may be converted in intermediates of formula 21 by halogenation reactions known to the skilled in the art or as set forth in the examples below. Intermediates of formula 21 may then be reacted with amines of formula $R^1R^2NH$ to provide intermediates of formula 22 which can be converted into desired compounds of formula 19 following standard hydrolysis and peptide bond formation. Abbreviations used in the description, particularly in the schemes and examples, are as follows:
DIBALH Diisobutylaluminium hydride
DMAP 4-Dimethylaminopyridine
DME Dimethoxyethane
DMF N,N-Dimethylformamide
DMSO Dimethylsulfoxide
h Hour
HATU O-(7-Azabenzotriazol-1-yl)-N,N,N',N'-tetramethyl-uronium hexafluorophosphate
HPLC High performance liquid chromatography
min Minute
NBS N-Bromosuccinimide
THF Tetrahydrofuran
TLC Thin layer chromatography
$t_r$ retention time

EXAMPLES

The following examples are provided for the purpose of illustrating the present invention and by no means should be interpreted to limit the scope of the present invention.

Part A represents the preparation of the compounds (intermediates and final compounds) whereas Part B represents the pharmacological examples.

TABLE 1

Structures of example compounds of the invention and their respective codes.

| Code | Structure |
| --- | --- |
| CPD-001 | 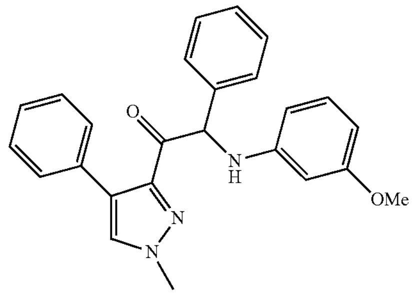 |
| CPD-002 | 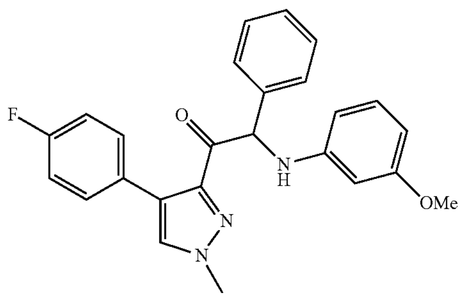 |
| CPD-003 | 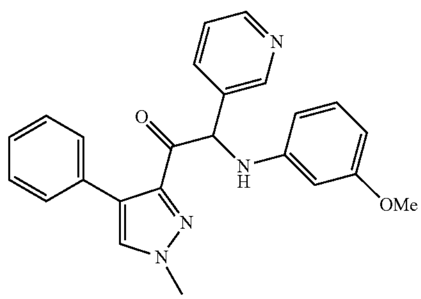 |
| CPD-004 | 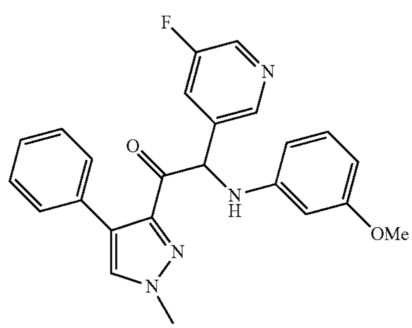 |
| CPD-005 | 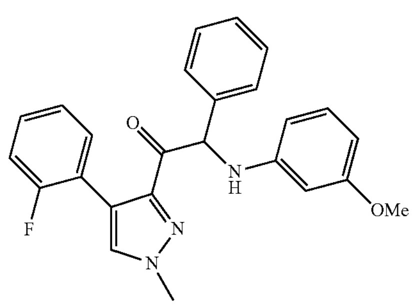 |

TABLE 1-continued
Structures of example compounds of the invention and their respective codes.
| Code | Structure |
|---|---|
| CPD-006 | 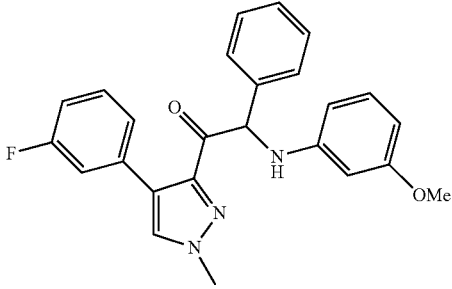 |
| CPD-007 | 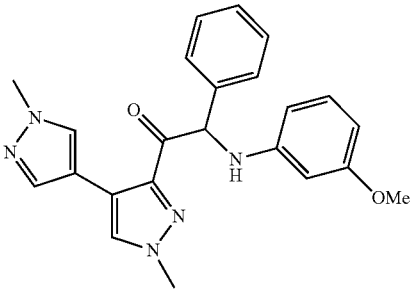 |
| CPD-008 | 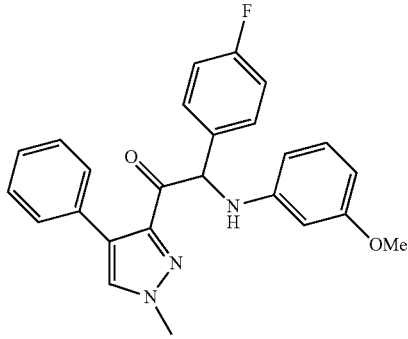 |
| CPD-009 | 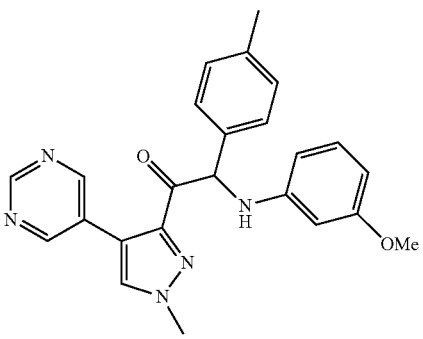 |

TABLE 1-continued

Structures of example compounds of the invention and their respective codes.

| Code | Structure |
|---|---|
| CPD-010 | 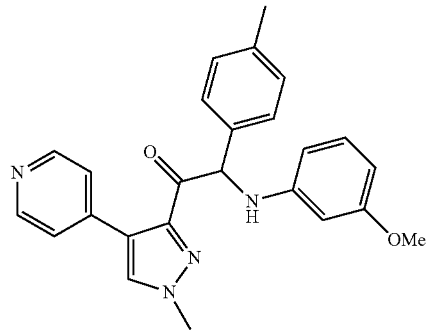 |
| CPD-011 | 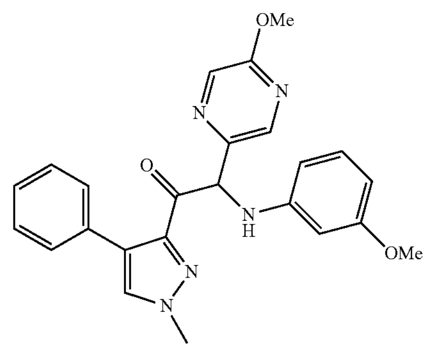 |
| CPD-012 | 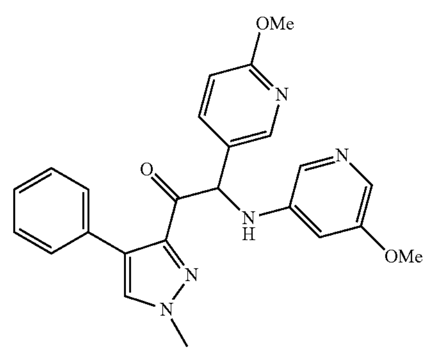 |
| CPD-013 | 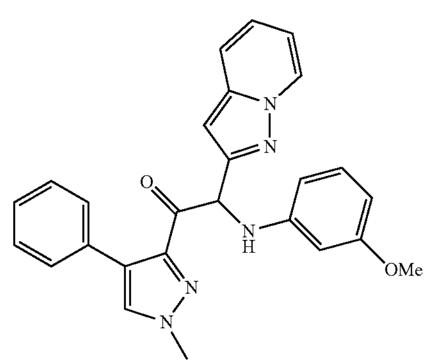 |

TABLE 1-continued
Structures of example compounds of the invention and their respective codes.
| Code | Structure |
|---|---|
| CPD-014 | 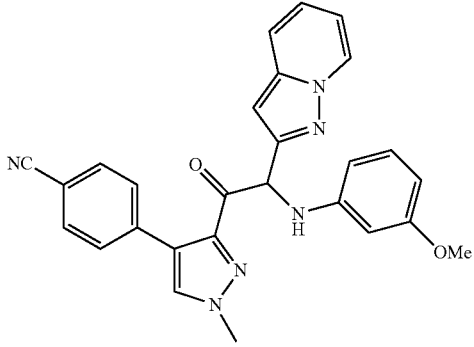 |
| CPD-015 | 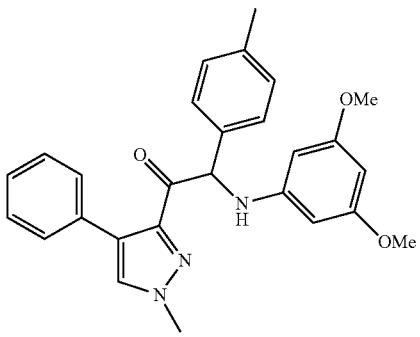 |
| CPD-016 | 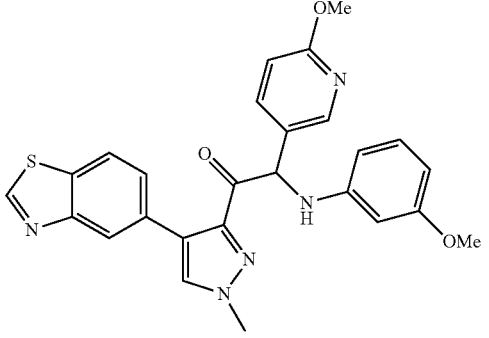 |
| CPD-017 | 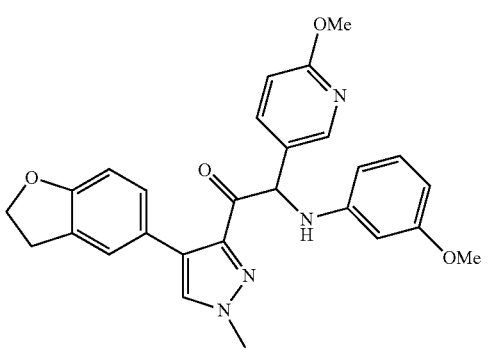 |

TABLE 1-continued

Structures of example compounds of the invention and their respective codes.

| Code | Structure |
|------|-----------|
| CPD-018 | 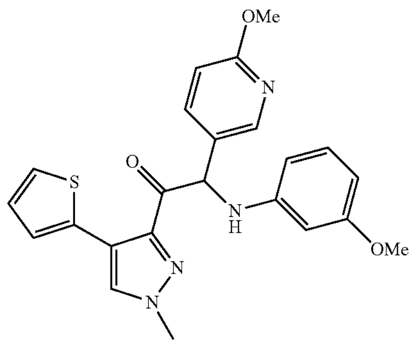 |
| CPD-019 | 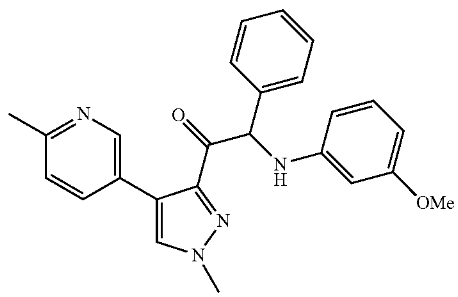 |
| CPD-020 | 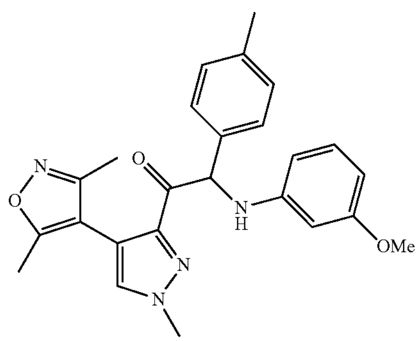 |
| CPD-021 | | enantiomer 1; tr = 8.6 min

TABLE 1-continued
Structures of example compounds of the invention and their respective codes.
| Code | Structure |
|---|---|
| CPD-022 | 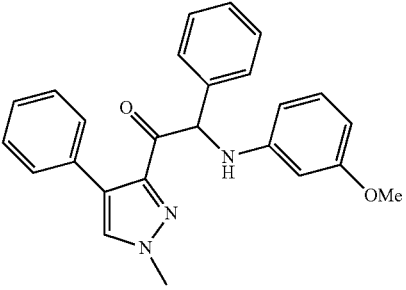<br>enantiomer 2; tr = 14.2 min |
| CPD-023 | 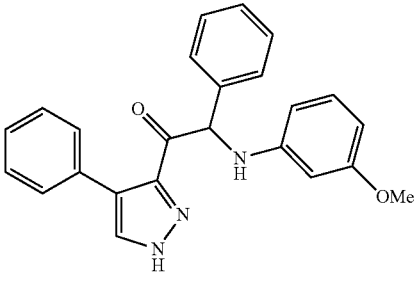 |
| CPD-024 | 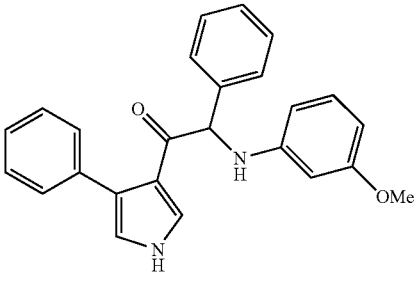 |
| CPD-025 | 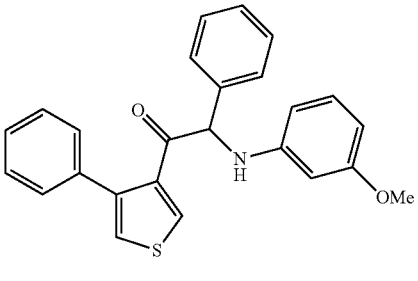 |
| CPD-026 | 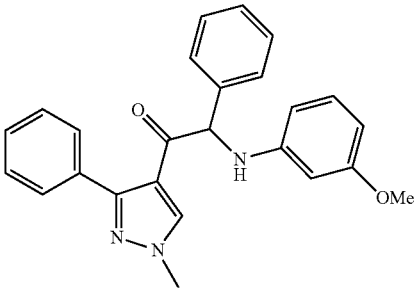 |

TABLE 1-continued
Structures of example compounds of the invention and their respective codes.
| Code | Structure |
|---|---|
| CPD-027 | 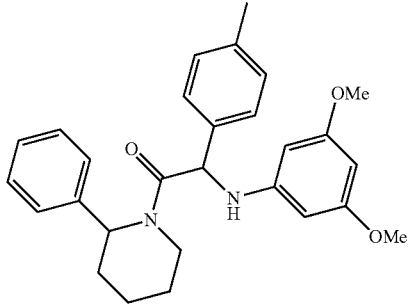 |
| CPD-028 | 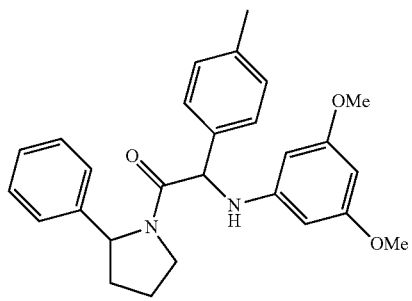 |
| CPD-029 | 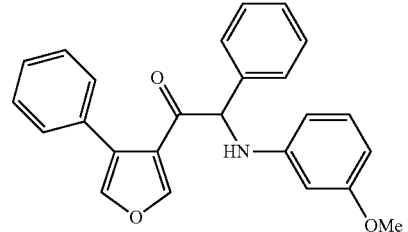 |
| CPD-030 | 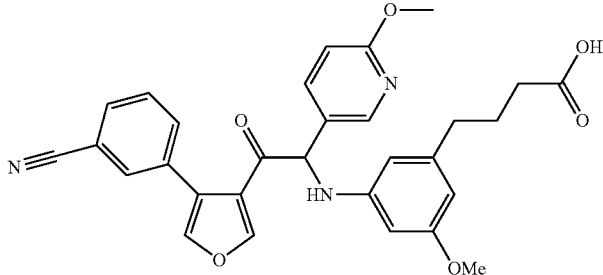 |
| CPD-031 | 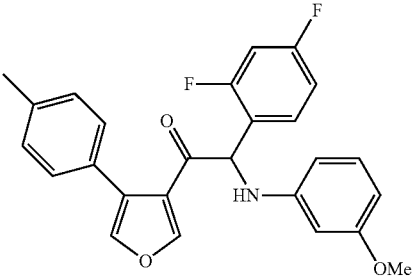 |

TABLE 1-continued

Structures of example compounds of the invention and their respective codes.

| Code | Structure |
| --- | --- |
| CPD-032 | 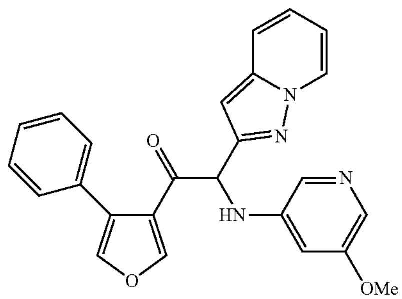 |
| CPD-033 | 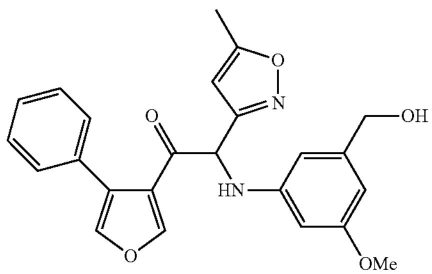 |
| CPD-034 | 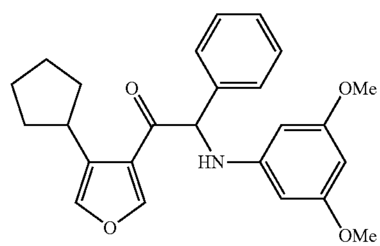 |
| CPD-035 | 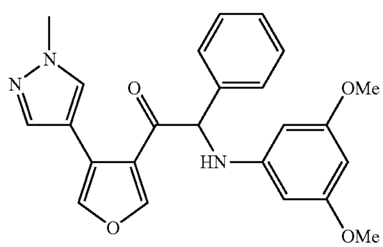 |
| CPD-036 | 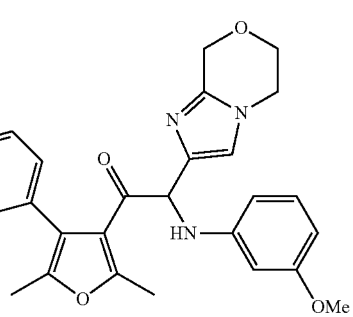 |

TABLE 1-continued

Structures of example compounds of the invention and their respective codes.

| Code | Structure |
|---|---|
| CPD-037 | 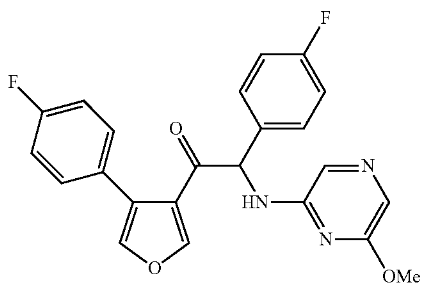 |
| CPD-038 | 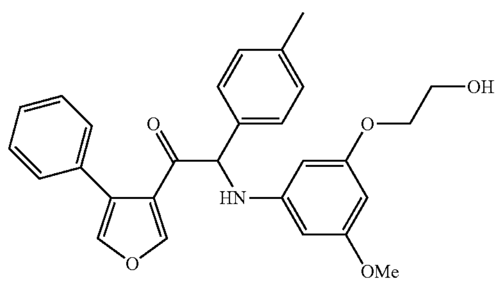 |
| CPD-039 | 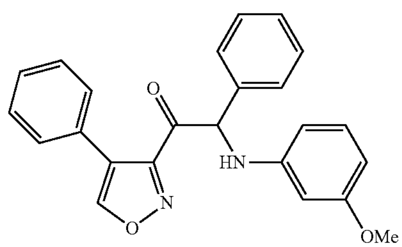 |
| CPD-040 | 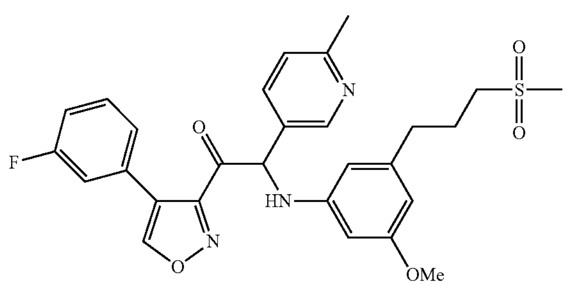 |
| CPD-041 | 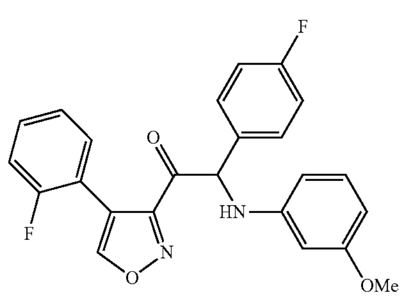 |

TABLE 1-continued

Structures of example compounds of the invention and their respective codes.

| Code | Structure |
| --- | --- |
| CPD-042 | 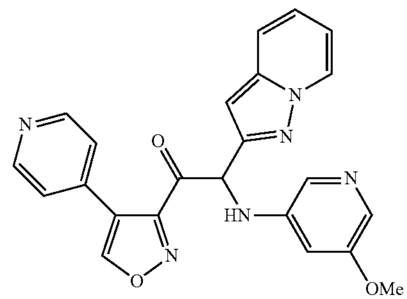 |
| CPD-043 | 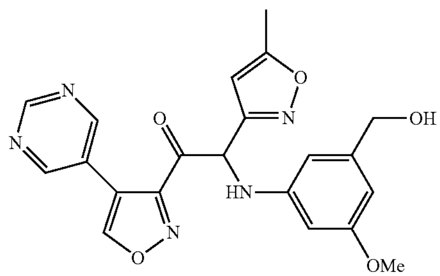 |
| CPD-044 | 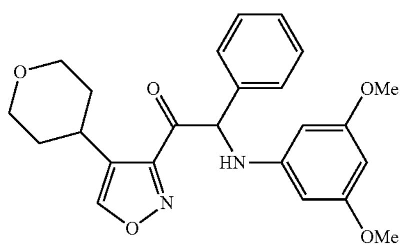 |
| CPD-045 | 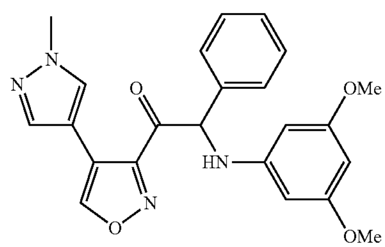 |
| CPD-046 | 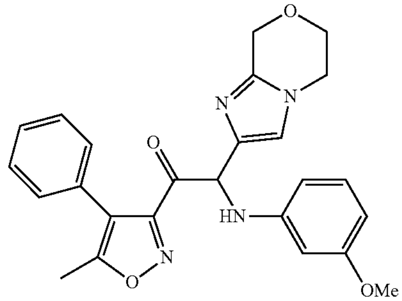 |

TABLE 1-continued

Structures of example compounds of the invention and their respective codes.

| Code | Structure |
|---|---|
| CPD-047 | 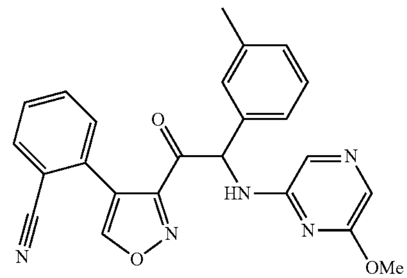 |
| CPD-048 | 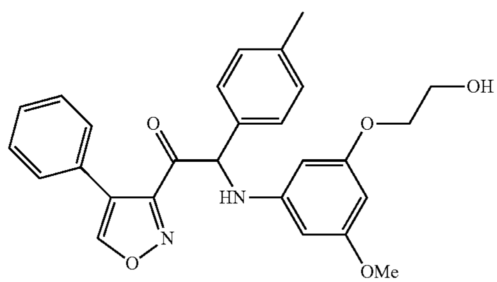 |
| CPD-049 | 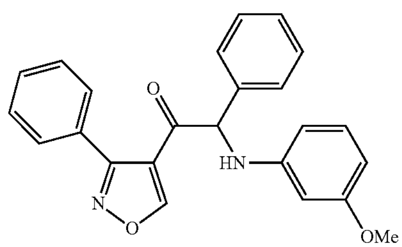 |
| CPD-050 | 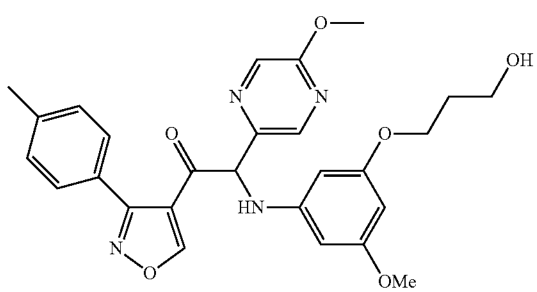 |
| CPD-051 | 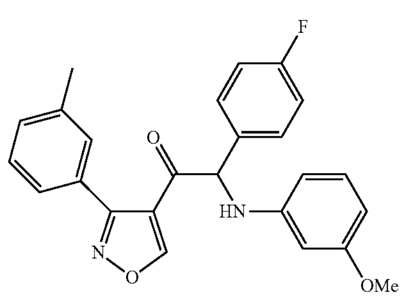 |

TABLE 1-continued

Structures of example compounds of the invention and their respective codes.

| Code | Structure |
| --- | --- |
| CPD-052 | 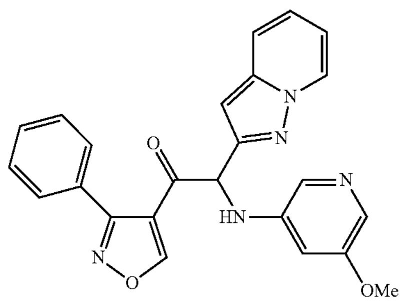 |
| CPD-053 | 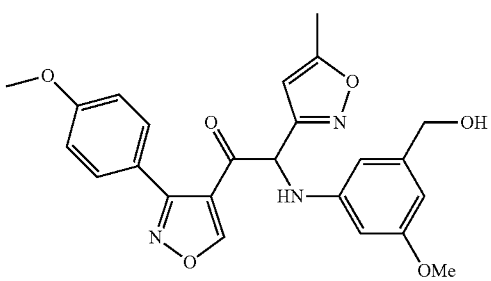 |
| CPD-054 | 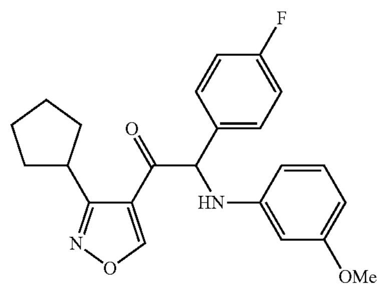 |
| CPD-055 | 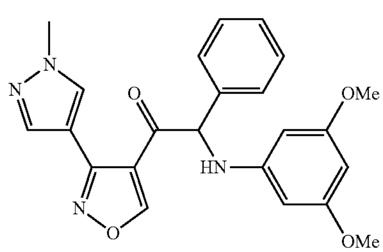 |
| CPD-056 | 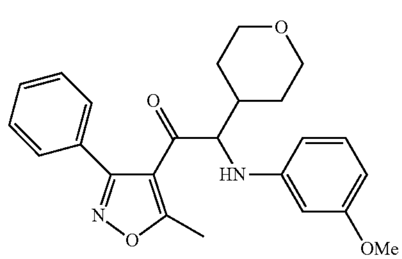 |

TABLE 1-continued
Structures of example compounds of the invention and their respective codes.
| Code | Structure |
|---|---|
| CPD-057 | 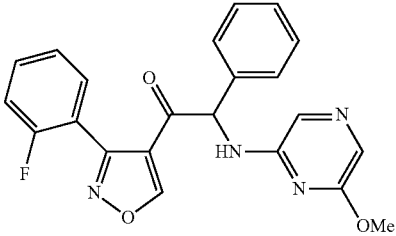 |
| CPD-058 | 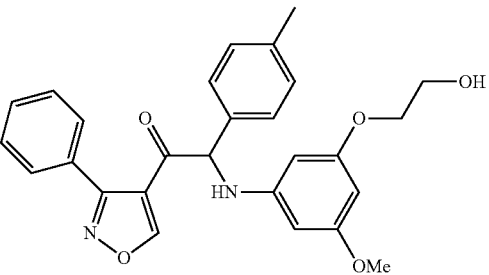 |
| CPD-059 | 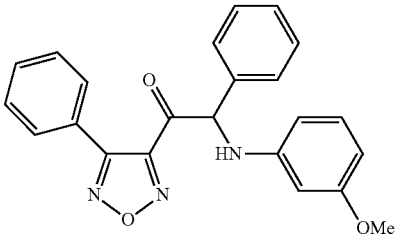 |
| CPD-060 | 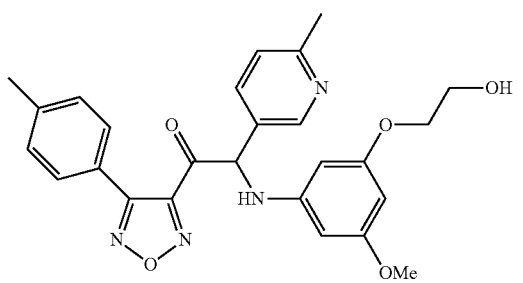 |
| CPD-061 | 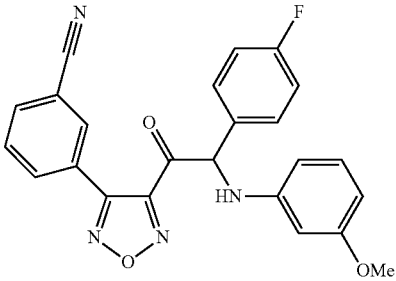 |

TABLE 1-continued

Structures of example compounds of the invention and their respective codes.

| Code | Structure |
| --- | --- |
| CPD-062 | 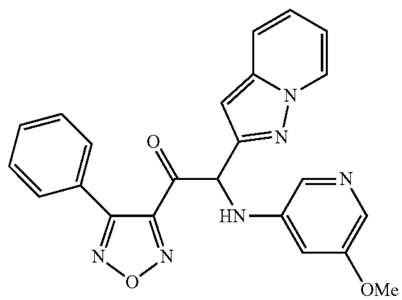 |
| CPD-063 | 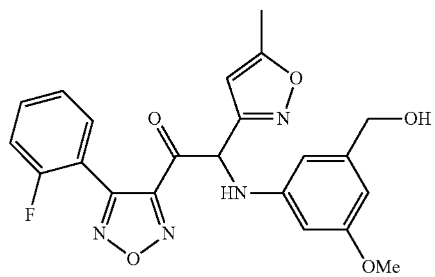 |
| CPD-064 | 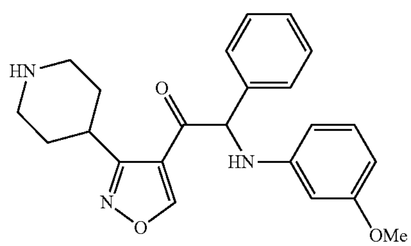 |
| CPD-065 | 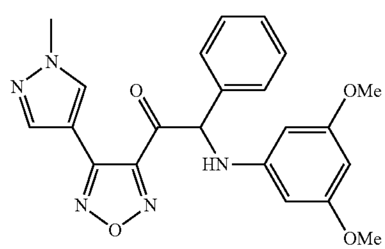 |
| CPD-066 | 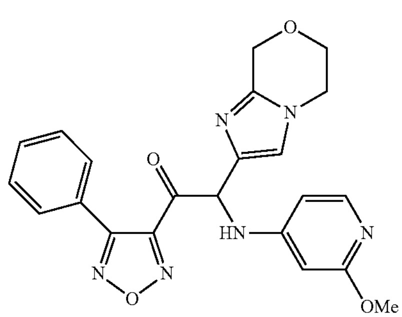 |

TABLE 1-continued

Structures of example compounds of the invention and their respective codes.

| Code | Structure |
|---|---|
| CPD-067 | 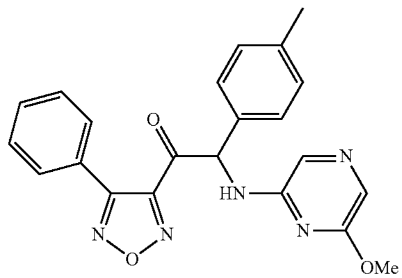 |
| CPD-068 | 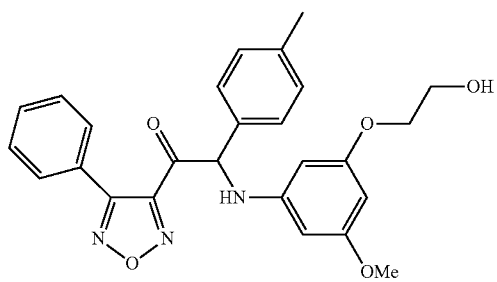 |
| CPD-069 | 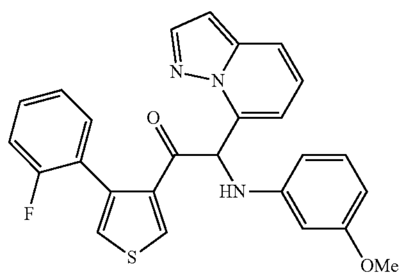 |
| CPD-070 | 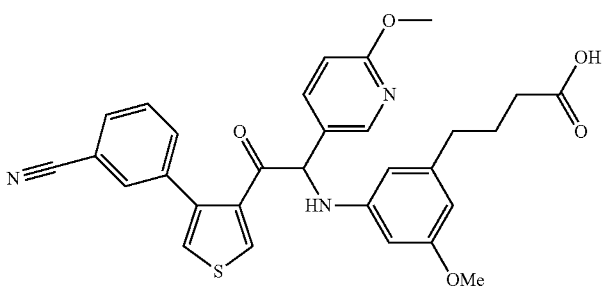 |
| CPD-071 | 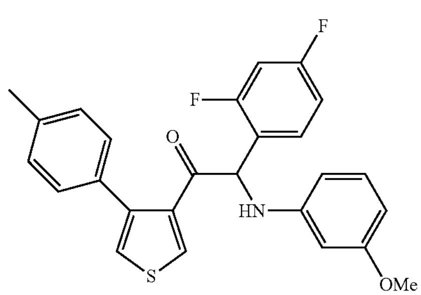 |

TABLE 1-continued

Structures of example compounds of the invention and their respective codes.

| Code | Structure |
|---|---|
| CPD-072 | 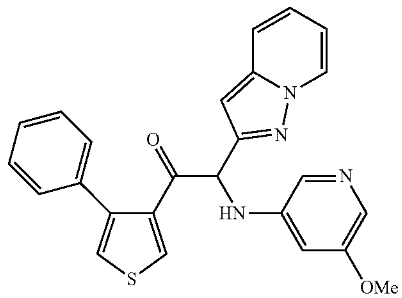 |
| CPD-073 | 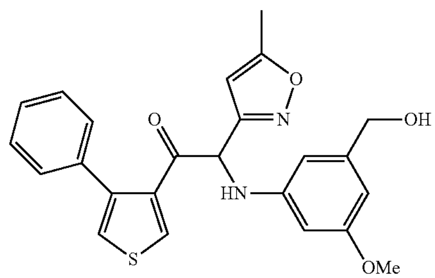 |
| CPD-074 | 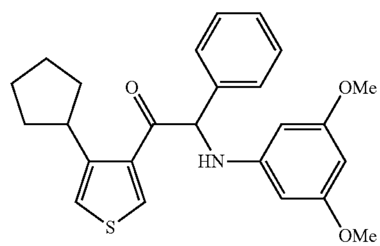 |
| CPD-075 | 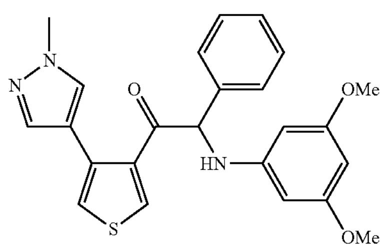 |
| CPD-076 | 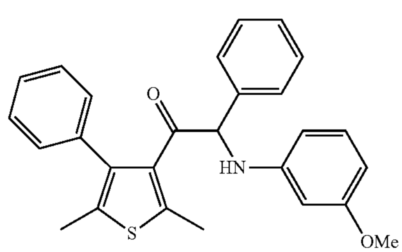 |

TABLE 1-continued

Structures of example compounds of the invention and their respective codes.

| Code | Structure |
| --- | --- |
| CPD-077 | 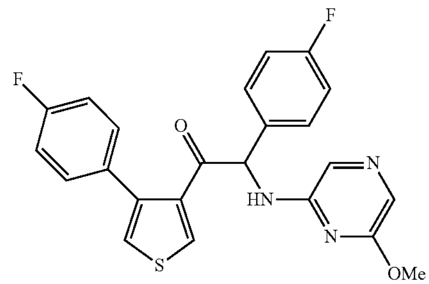 |
| CPD-078 | 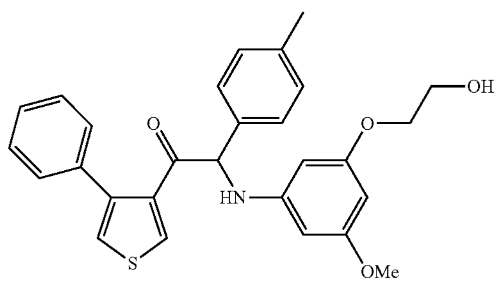 |
| CPD-079 | 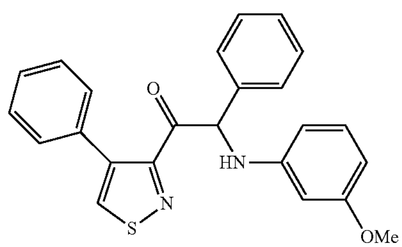 |
| CPD-080 | 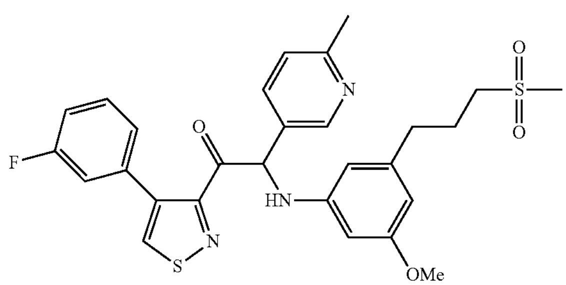 |
| CPD-081 | 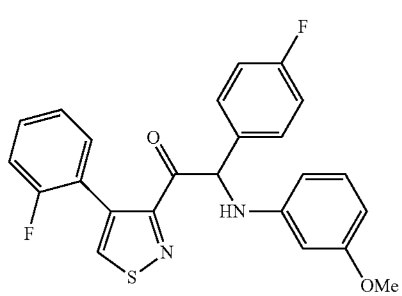 |

TABLE 1-continued

Structures of example compounds of the invention and their respective codes.

| Code | Structure |
|------|-----------|
| CPD-082 | 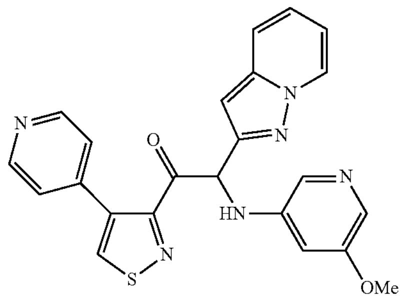 |
| CPD-083 | 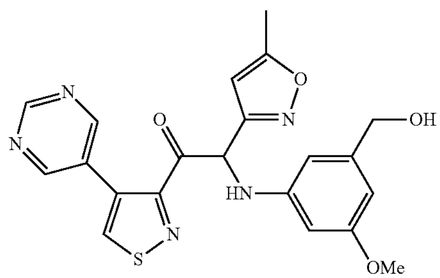 |
| CPD-084 | 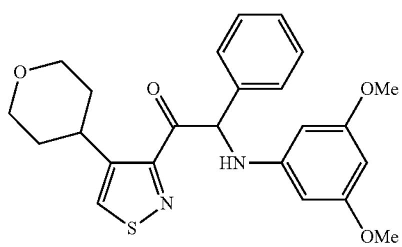 |
| CPD-085 | 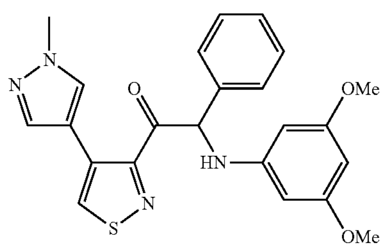 |
| CPD-086 | 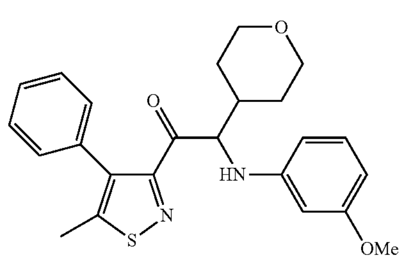 |

TABLE 1-continued

Structures of example compounds of the invention and their respective codes.

| Code | Structure |
| --- | --- |
| CPD-087 | 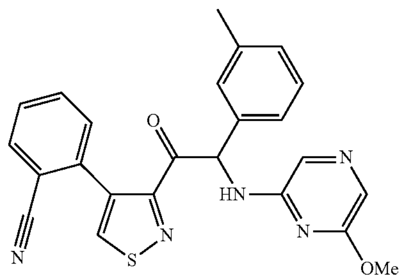 |
| CPD-088 | 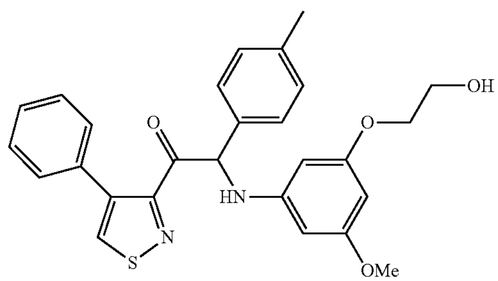 |
| CPD-089 | 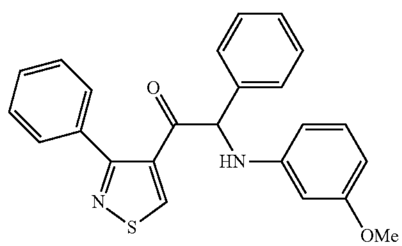 |
| CPD-090 | 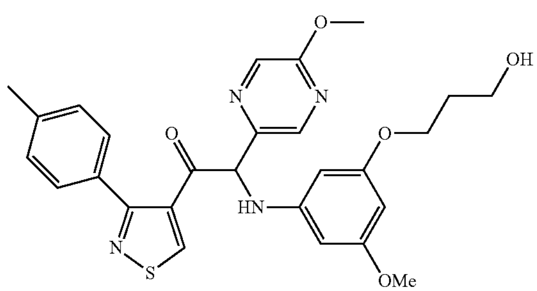 |
| CPD-091 | 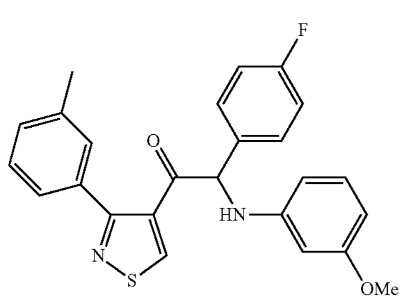 |

TABLE 1-continued

Structures of example compounds of the invention and their respective codes.

| Code | Structure |
| --- | --- |
| CPD-092 | 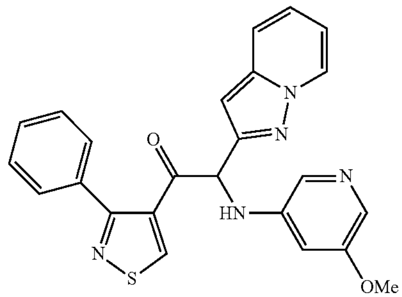 |
| CPD-093 | 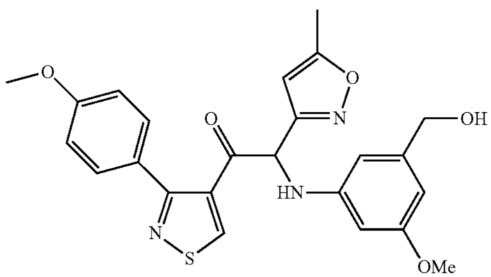 |
| CPD-094 | 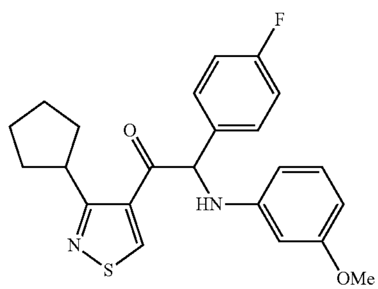 |
| CPD-095 | 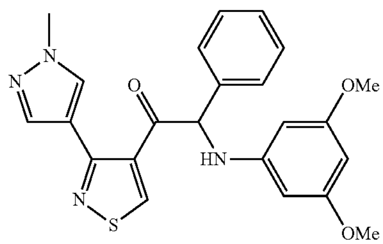 |
| CPD-096 | 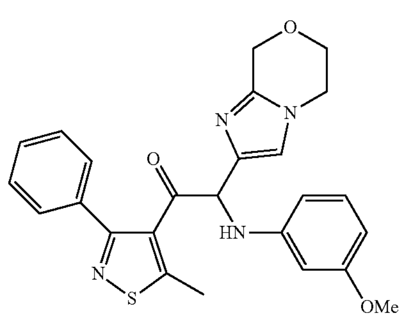 |

TABLE 1-continued
Structures of example compounds of the invention and their respective codes.
| Code | Structure |
|---|---|
| CPD-097 | 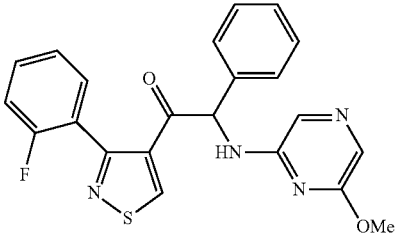 |
| CPD-098 | 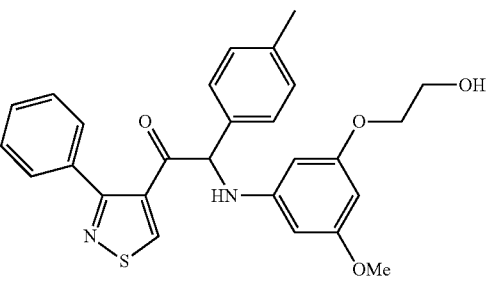 |
| CPD-099 | 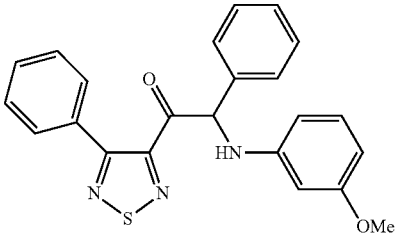 |
| CPD-100 | 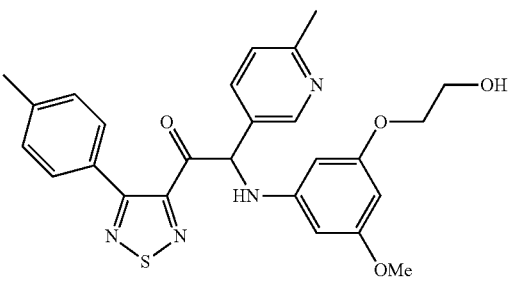 |
| CPD-101 | 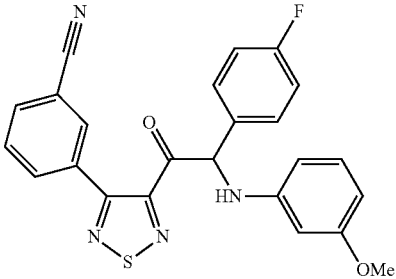 |

TABLE 1-continued

Structures of example compounds of the invention and their respective codes.

| Code | Structure |
| --- | --- |
| CPD-102 | 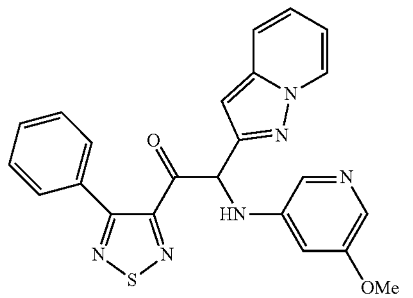 |
| CPD-103 | 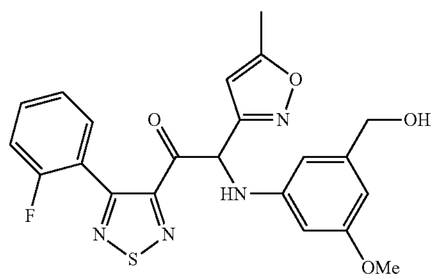 |
| CPD-104 | 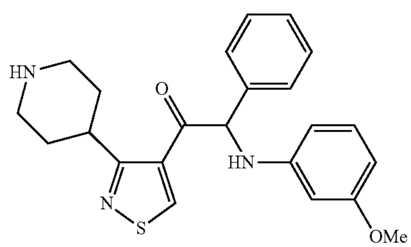 |
| CPD-105 | 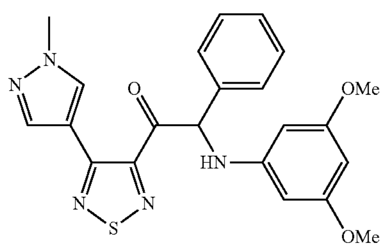 |
| CPD-106 | 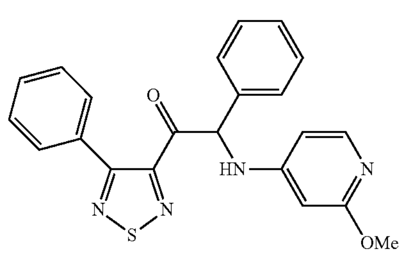 |

TABLE 1-continued
Structures of example compounds of the invention and their respective codes.
| Code | Structure |
|---|---|
| CPD-107 | 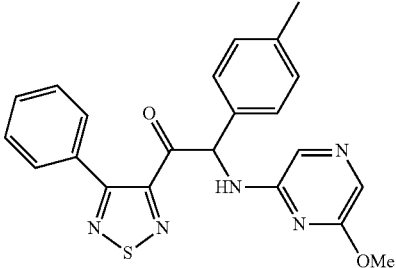 |
| CPD-108 | 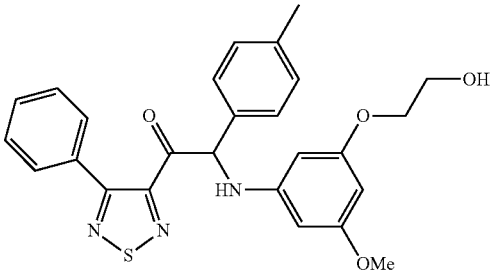 |
| CPD-109 | 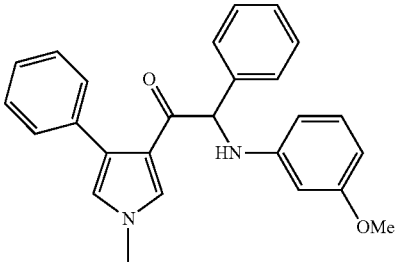 |
| CPD-110 | 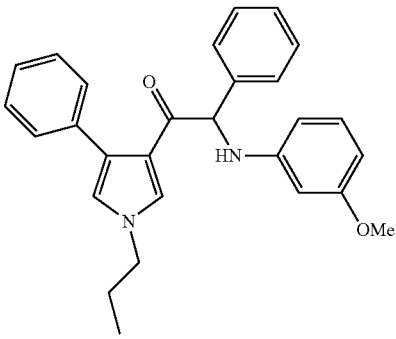 |
| CPD-111 | 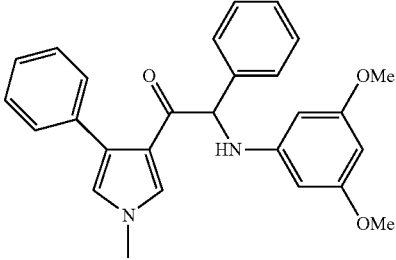 |

TABLE 1-continued

Structures of example compounds of the invention and their respective codes.

| Code | Structure |
| --- | --- |
| CPD-112 | 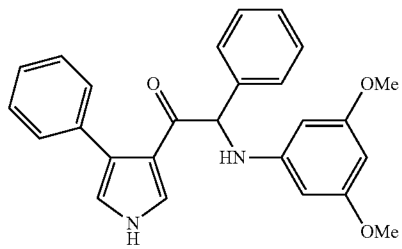 |
| CPD-113 | 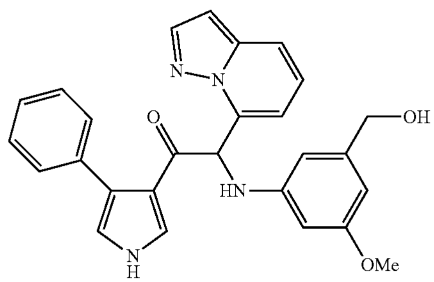 |
| CPD-114 | 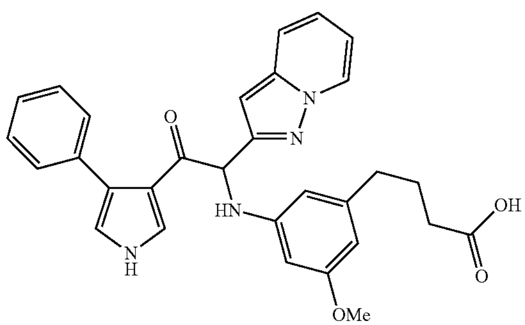 |
| CPD-115 | 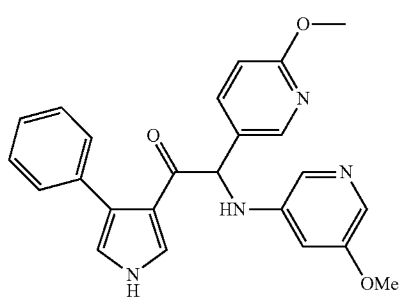 |
| CPD-116 | 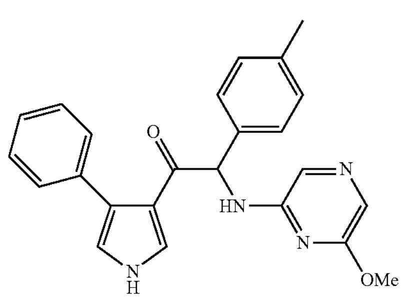 |

TABLE 1-continued
Structures of example compounds of the invention and their respective codes.
| Code | Structure |
| --- | --- |
| CPD-117 | 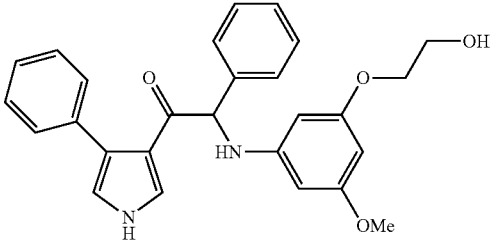 |
| CPD-118 | 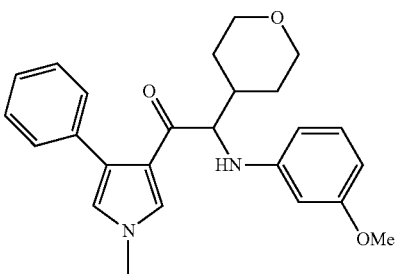 |
| CPD-119 | 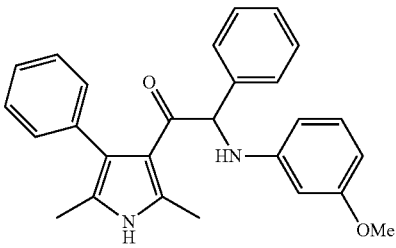 |
| CPD-120 | 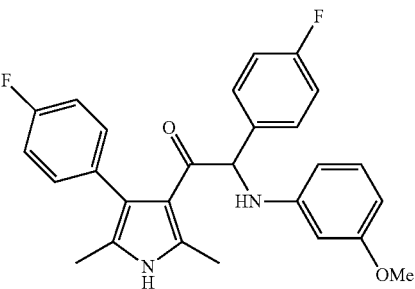 |
| CPD-121 | 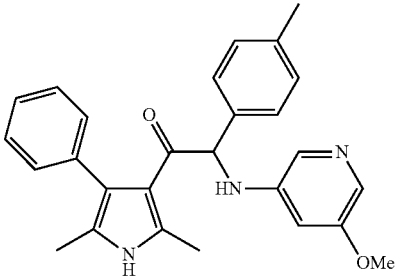 |

TABLE 1-continued

Structures of example compounds of the invention and their respective codes.

| Code | Structure |
|---|---|
| CPD-122 | 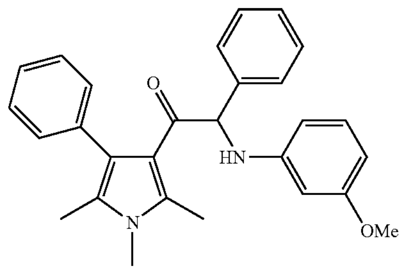 |
| CPD-123 | 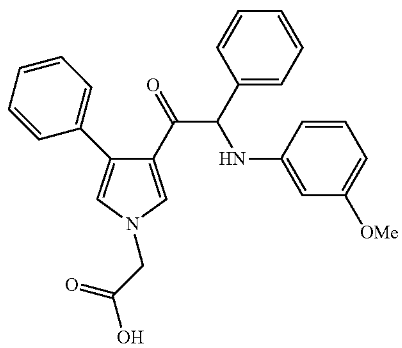 |
| CPD-124 | 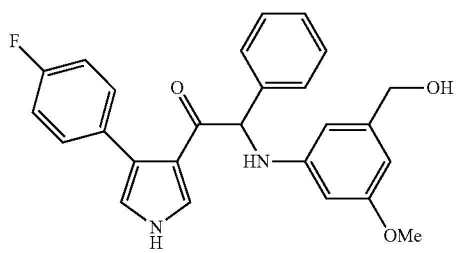 |
| CPD-125 | 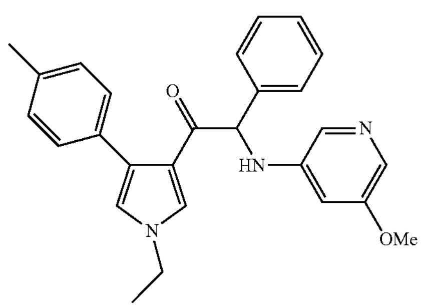 |
| CPD-126 | 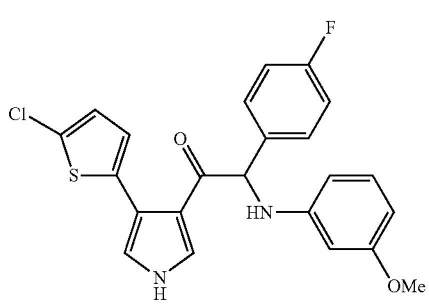 |

TABLE 1-continued

Structures of example compounds of the invention and their respective codes.

| Code | Structure |
| --- | --- |
| CPD-127 | 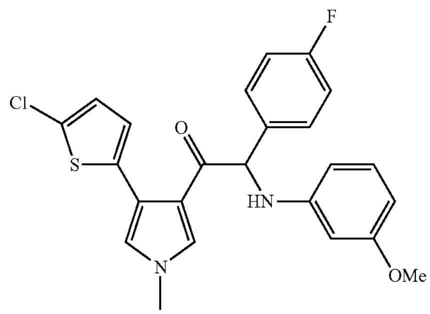 |
| CPD-128 | 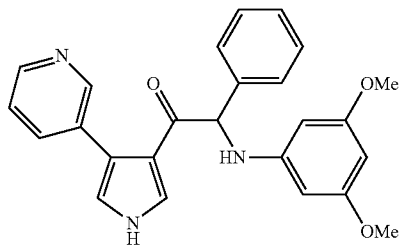 |
| CPD-129 | 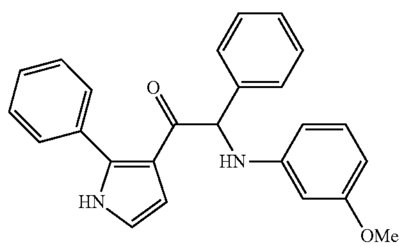 |
| CPD-130 | 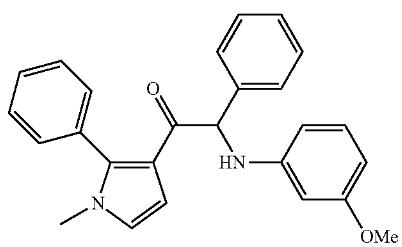 |
| CPD-131 | 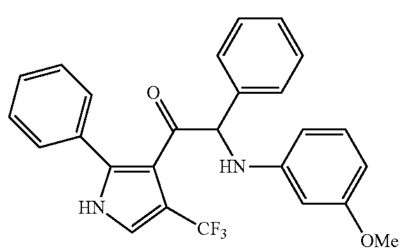 |

TABLE 1-continued

Structures of example compounds of the invention and their respective codes.

| Code | Structure |
|---|---|
| CPD-132 | 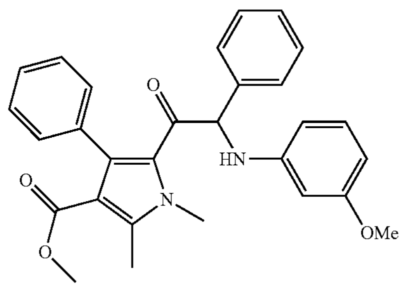 |
| CPD-133 | 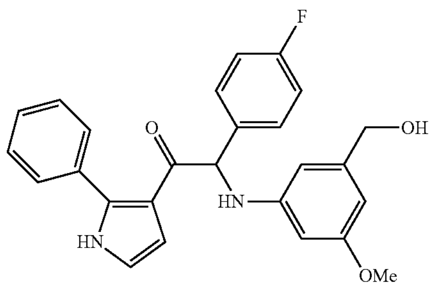 |
| CPD-134 | 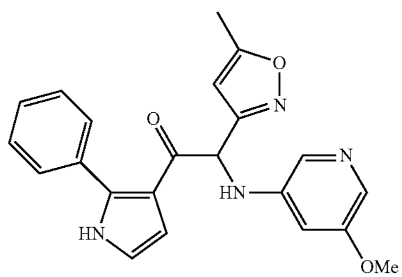 |
| CPD-135 | 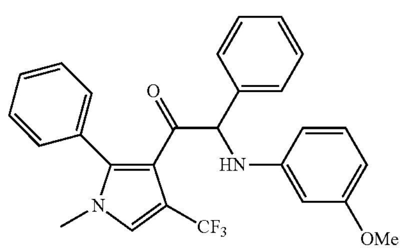 |
| CPD-136 | 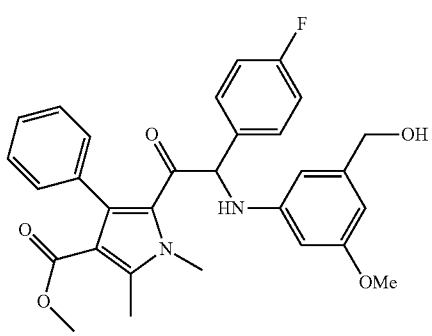 |

TABLE 1-continued
Structures of example compounds of the invention and their respective codes.
| Code | Structure |
|---|---|
| CPD-137 | 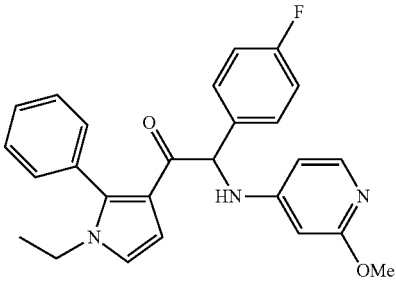 |
| CPD-138 | 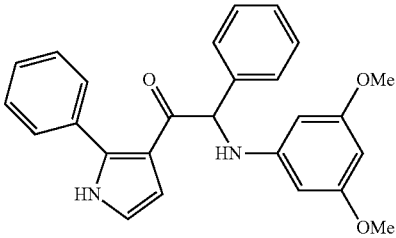 |
| CPD-139 | 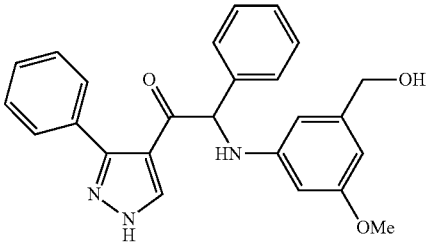 |
| CPD-140 | 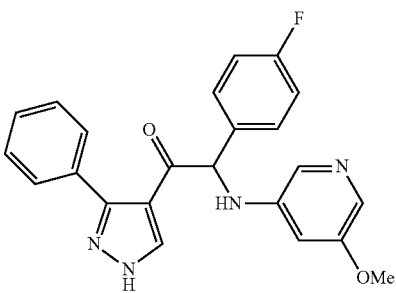 |
| CPD-141 | 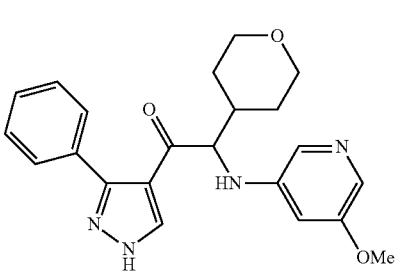 |

203
204
TABLE 1-continued
Structures of example compounds of the invention and their respective codes.
| Code | Structure |
| --- | --- |
| CPD-142 | 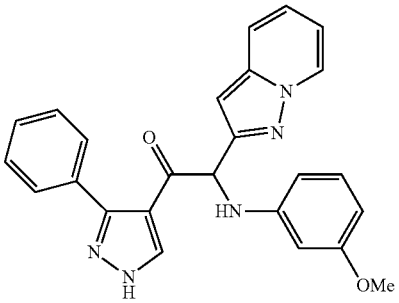 |
| CPD-143 | 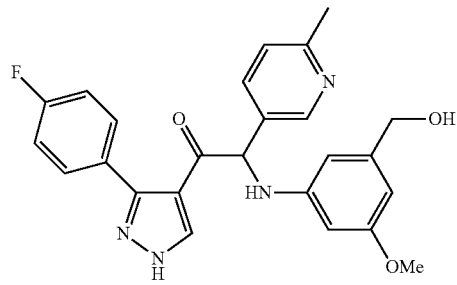 |
| CPD-144 | 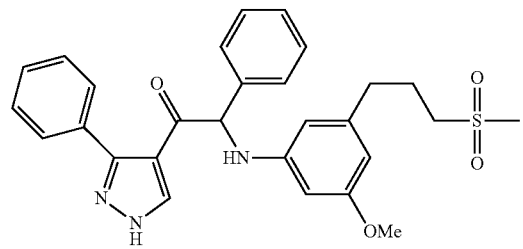 |
| CPD-145 | 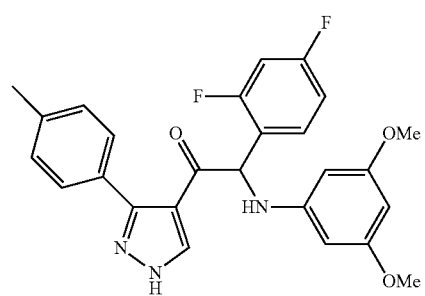 |
| CPD-146 | 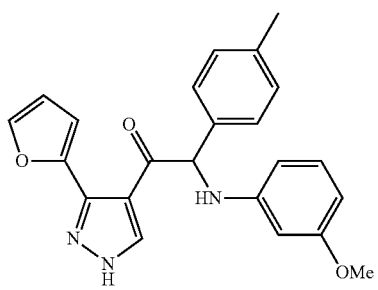 |

TABLE 1-continued

Structures of example compounds of the invention and their respective codes.

| Code | Structure |
|---|---|
| CPD-147 | 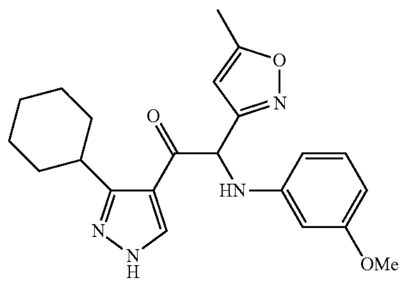 |
| CPD-148 | 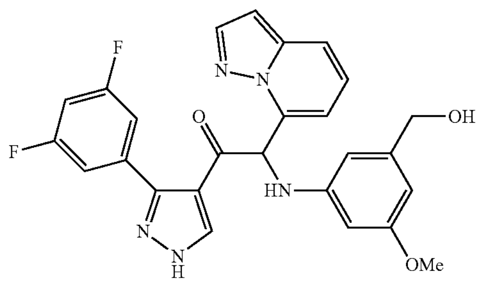 |
| CPD-149 | 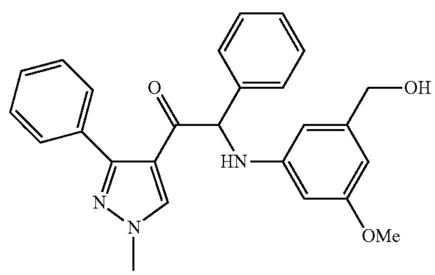 |
| CPD-150 | 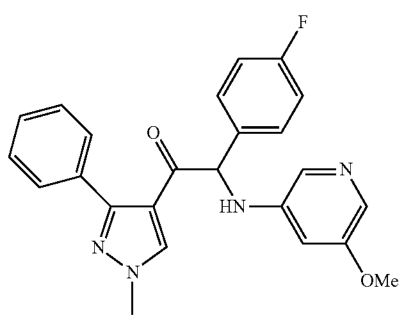 |
| CPD-151 | 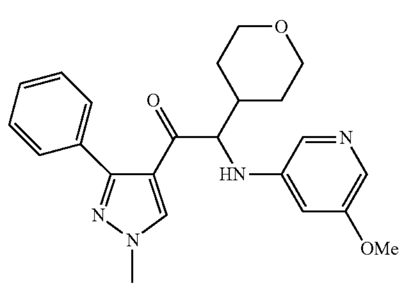 |

TABLE 1-continued

Structures of example compounds of the invention and their respective codes.

| Code | Structure |
| --- | --- |
| CPD-152 | 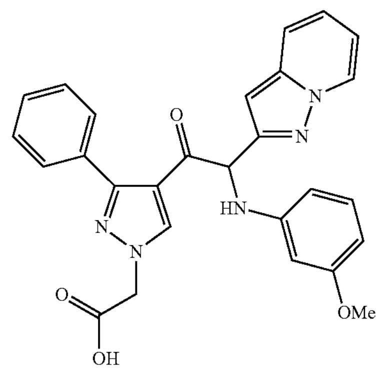 |
| CPD-153 | 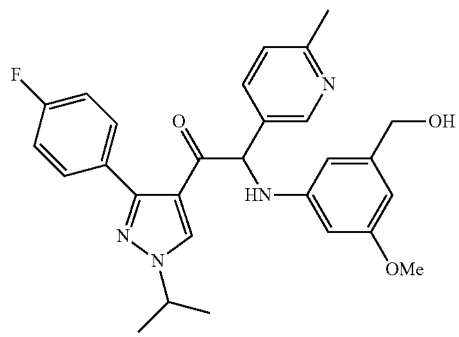 |
| CPD-154 | 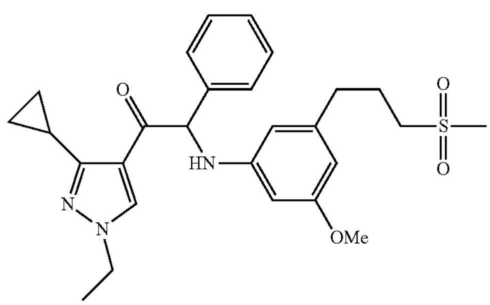 |
| CPD-155 | 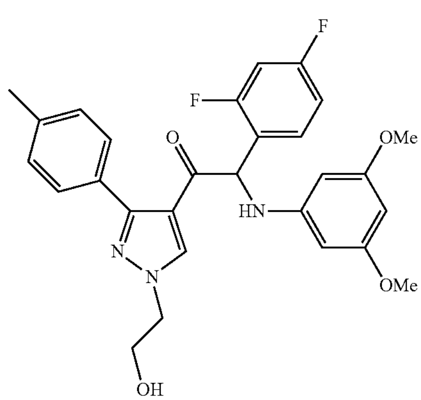 |

TABLE 1-continued
Structures of example compounds of the invention and their respective codes.
| Code | Structure |
|---|---|
| CPD-156 | 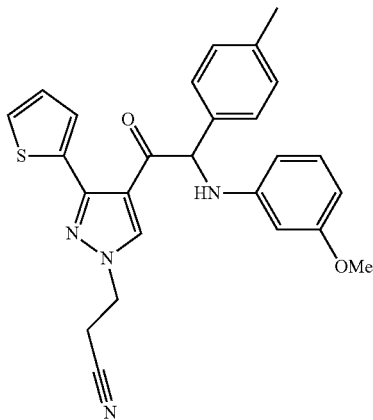 |
| CPD-157 | 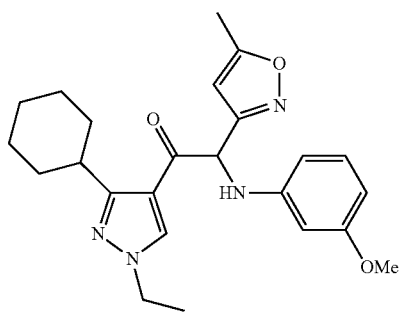 |
| CPD-158 | 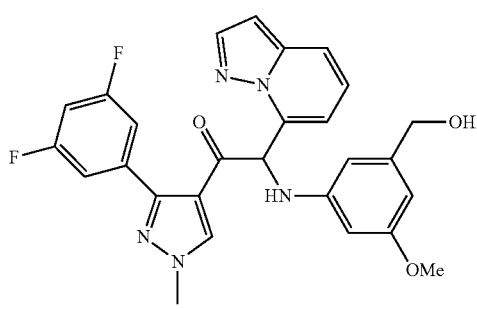 |
| CPD-159 | 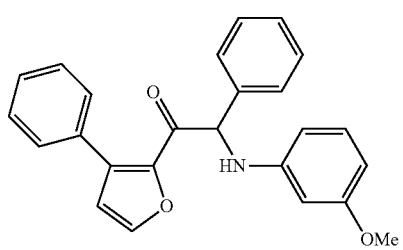 |

TABLE 1-continued

Structures of example compounds of the invention and their respective codes.

| Code | Structure |
|---|---|
| CPD-160 | 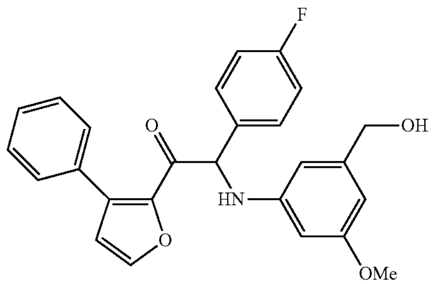 |
| CPD-161 | 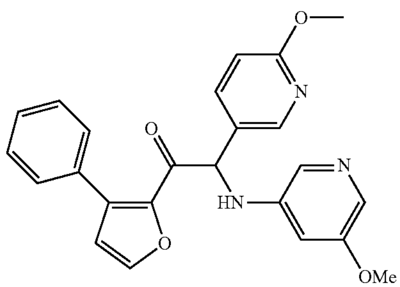 |
| CPD-162 | 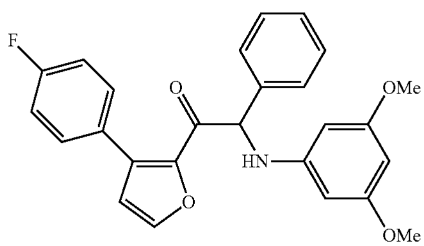 |
| CPD-163 | 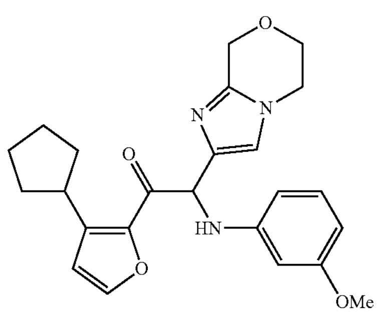 |
| CPD-164 | 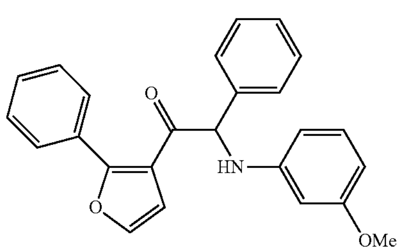 |

TABLE 1-continued
Structures of example compounds of the invention and their respective codes.
| Code | Structure |
|---|---|
| CPD-165 | 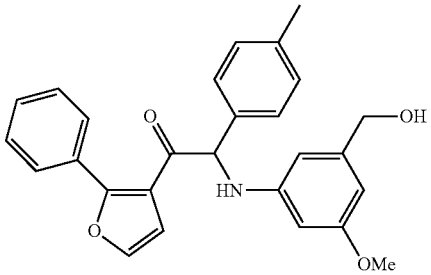 |
| CPD-166 | 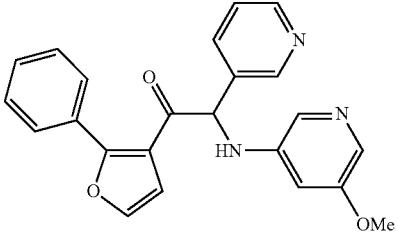 |
| CPD-167 | 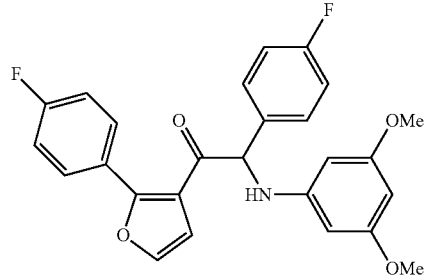 |
| CPD-168 | 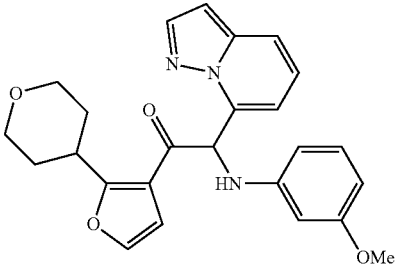 |
| CPD-169 | 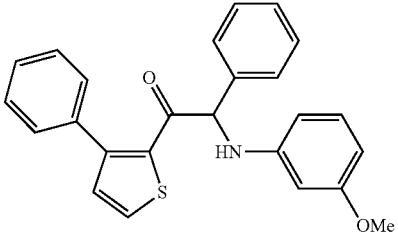 |

TABLE 1-continued
Structures of example compounds of the invention and their respective codes.
| Code | Structure |
|---|---|
| CPD-170 | 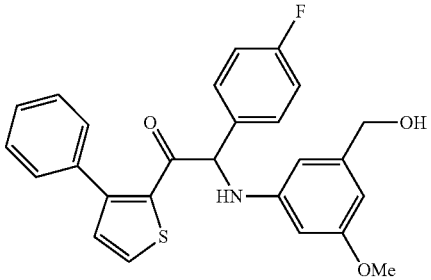 |
| CPD-171 | 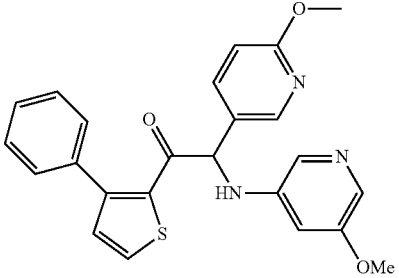 |
| CPD-172 | 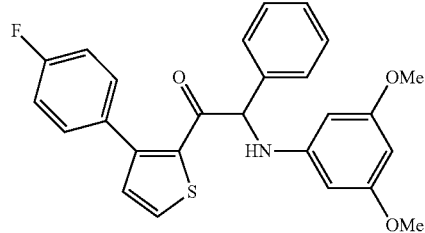 |
| CPD-173 | 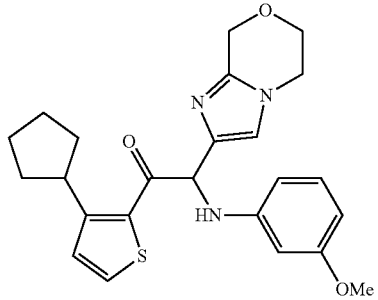 |
| CPD-174 | 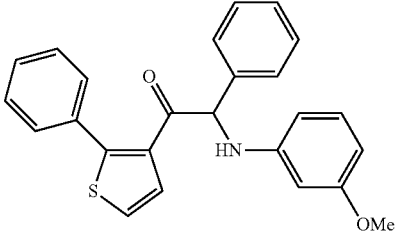 |

TABLE 1-continued
Structures of example compounds of the invention and their respective codes.
| Code | Structure |
|---|---|
| CPD-175 | 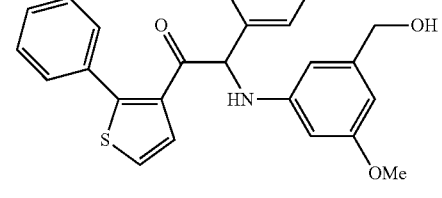 |
| CPD-176 | 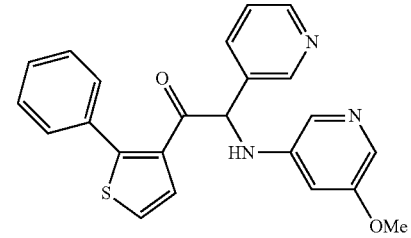 |
| CPD-177 | 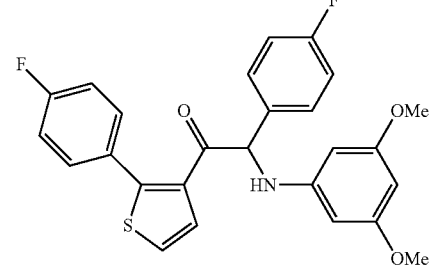 |
| CPD-178 | 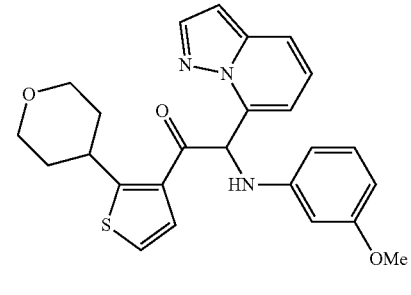 |
| CPD-179 | 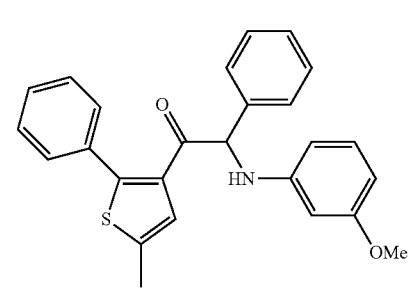 |

TABLE 1-continued
Structures of example compounds of the invention and their respective codes.
| Code | Structure |
| --- | --- |
| CPD-180 | 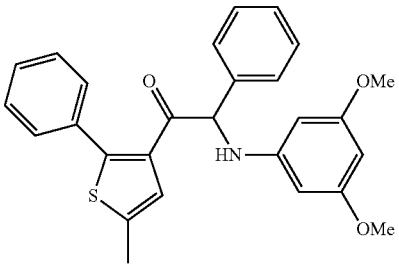 |
| CPD-181 | 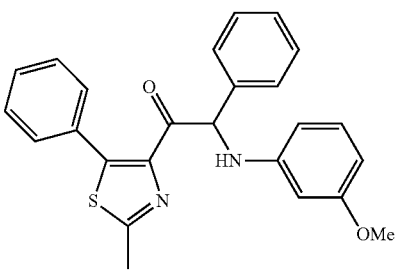 |
| CPD-182 | 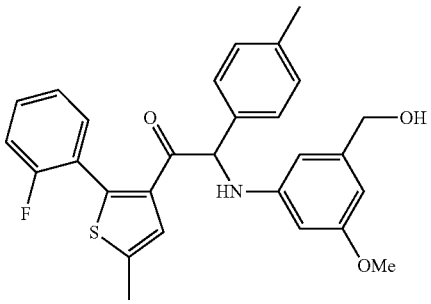 |
| CPD-183 | 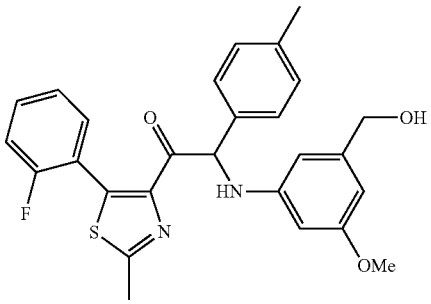 |
| CPD-184 | 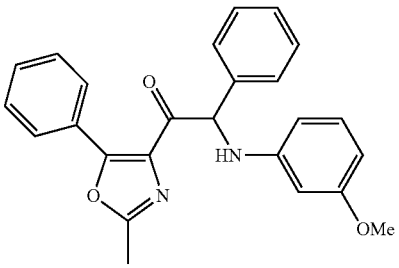 |

TABLE 1-continued
Structures of example compounds of the invention and their respective codes.
| Code | Structure |
|---|---|
| CPD-185 | 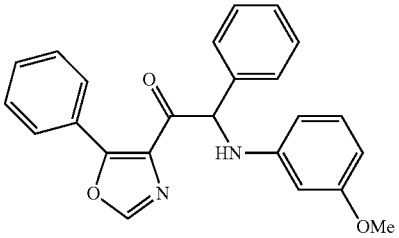 |
| CPD-186 | 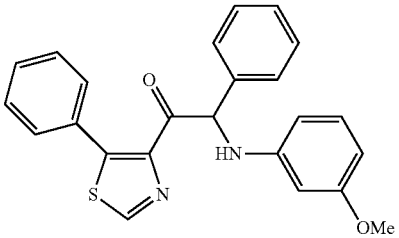 |
| CPD-187 | 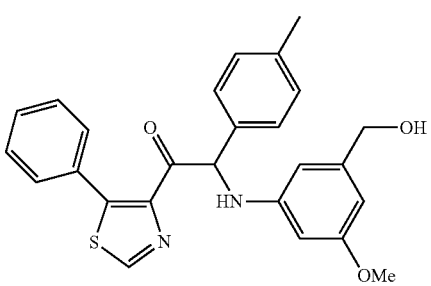 |
| CPD-188 | 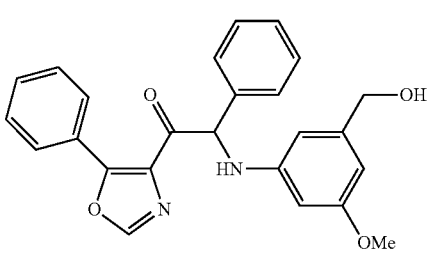 |
| CPD-189 | 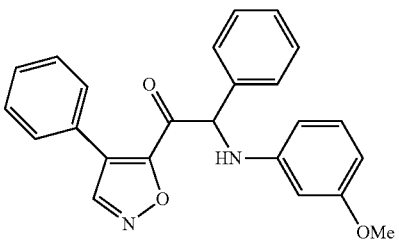 |
| CPD-190 | 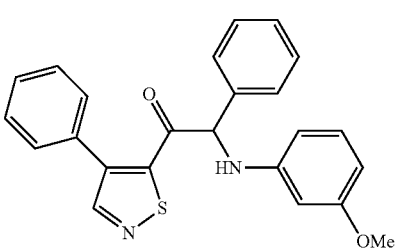 |

TABLE 1-continued

Structures of example compounds of the invention and their respective codes.

| Code | Structure |
|---|---|
| CPD-191 | 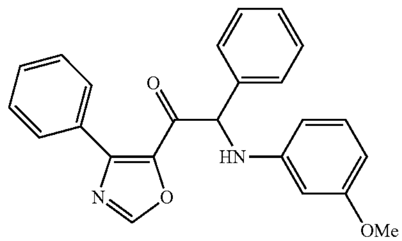 |
| CPD-192 | 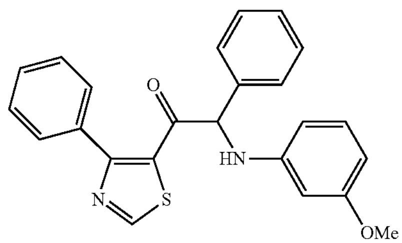 |
| CPD-193 | 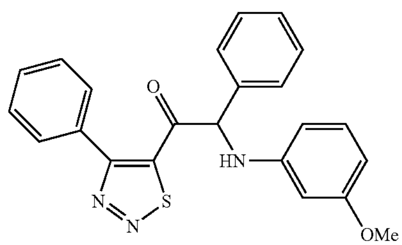 |
| CPD-194 | 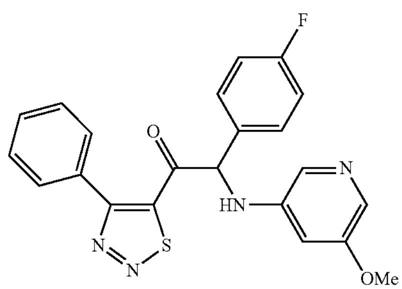 |
| CPD-195 | 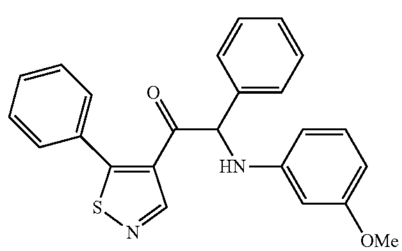 |
| CPD-196 | 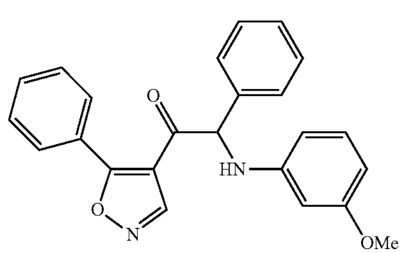 |

TABLE 1-continued

Structures of example compounds of the invention and their respective codes.

| Code | Structure |
|---|---|
| CPD-197 | 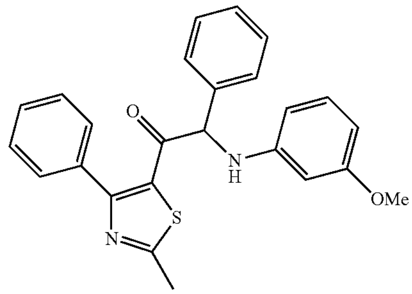 |
| CPD-198 | 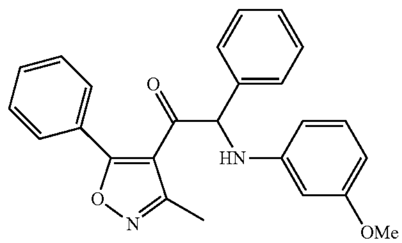 |
| CPD-199 | 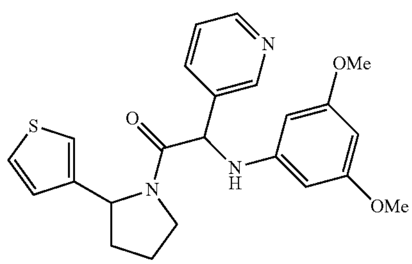 |
| CPD-200 | 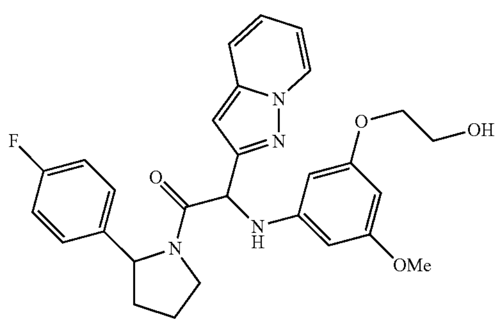 |
| CPD-201 | 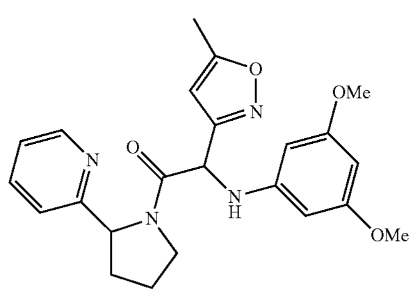 |

TABLE 1-continued
Structures of example compounds of the invention and their respective codes.
| Code | Structure |
|---|---|
| CPD-202 | 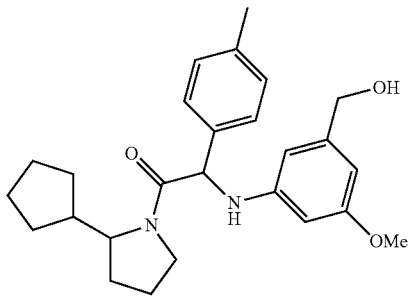 |
| CPD-203 | 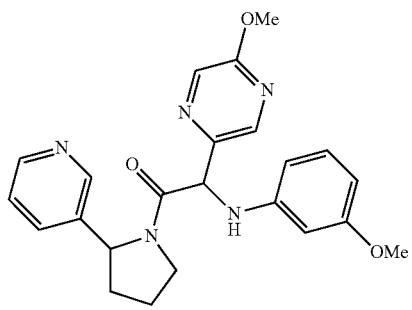 |
| CPD-204 | 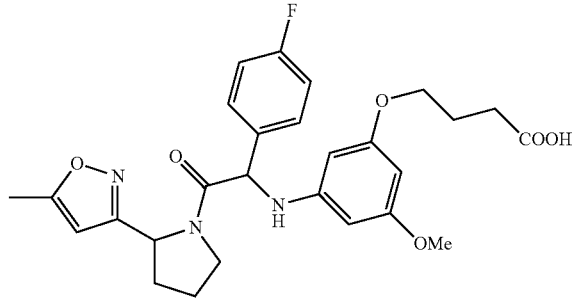 |
| CPD-205 | 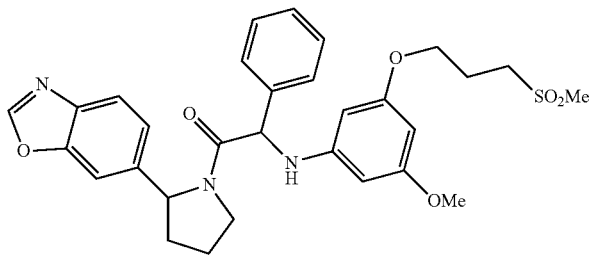 |
| CPD-206 | 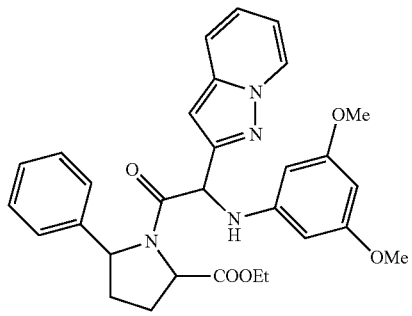 |

TABLE 1-continued

Structures of example compounds of the invention and their respective codes.

| Code | Structure |
|---|---|
| CPD-207 | 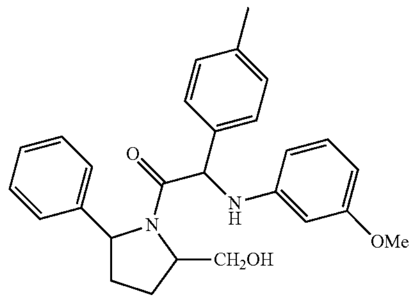 |
| CPD-208 | 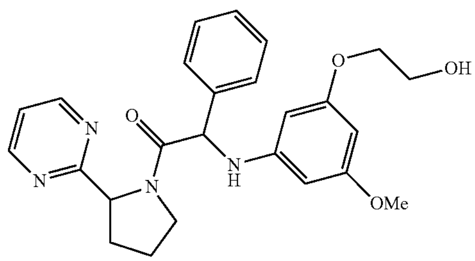 |
| CPD-209 | 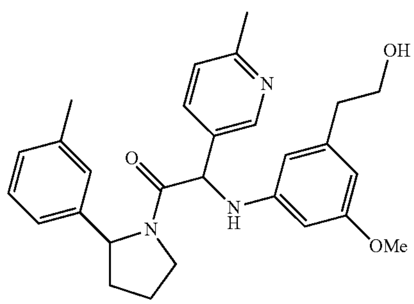 |
| CPD-210 | 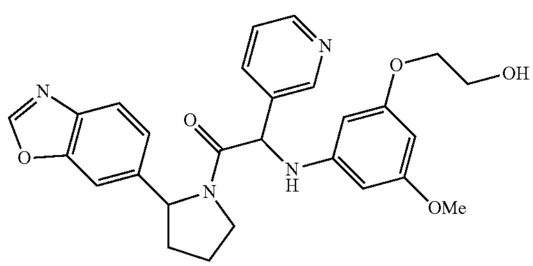 |
| CPD-211 | 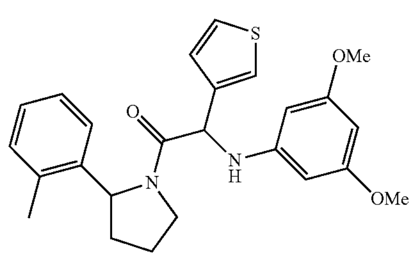 |

TABLE 1-continued

Structures of example compounds of the invention and their respective codes.

| Code | Structure |
|---|---|
| CPD-212 | 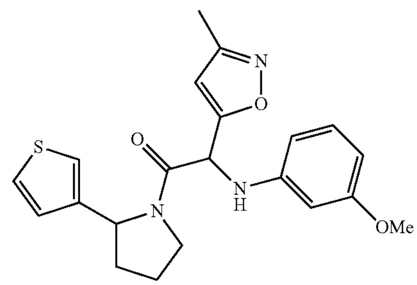 |
| CPD-213 | 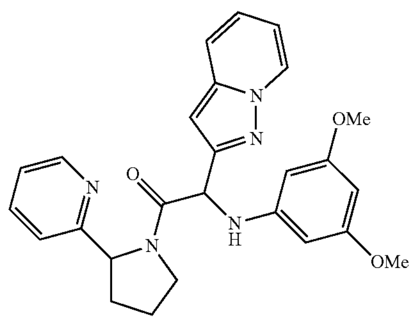 |
| CPD-214 | 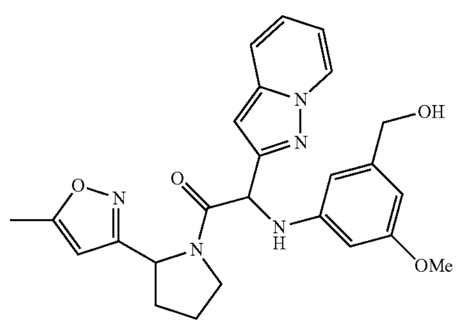 |
| CPD-215 | 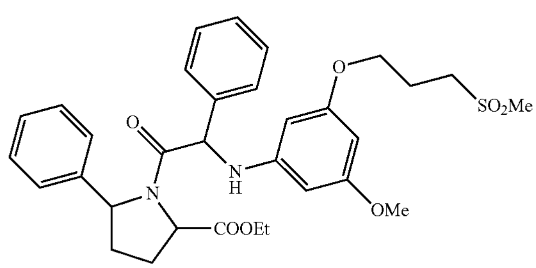 |
| CPD-216 | 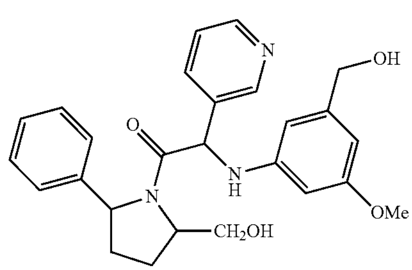 |

TABLE 1-continued
Structures of example compounds of the invention and their respective codes.
| Code | Structure |
|---|---|
| CPD-217 | 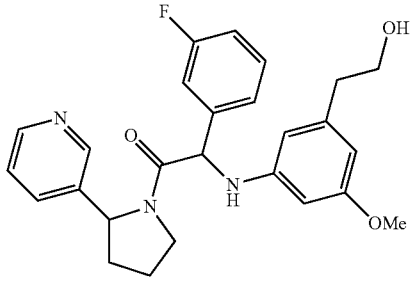 |
| CPD-218 | 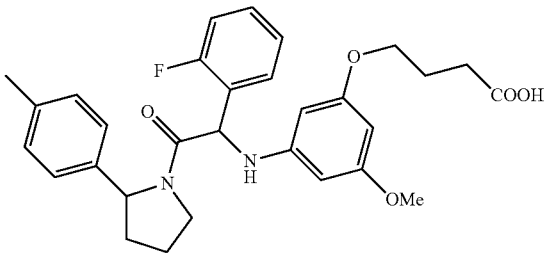 |
| CPD-219 | 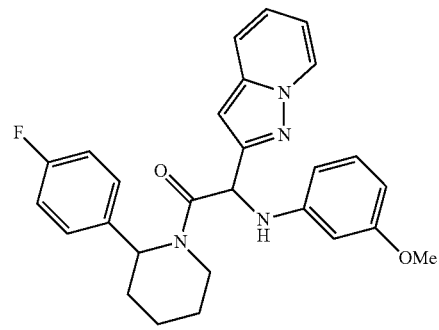 |
| CPD-220 | 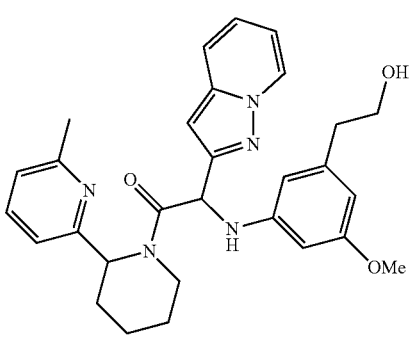 |
| CPD-221 | 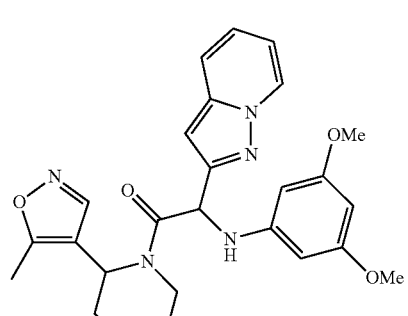 |

TABLE 1-continued
Structures of example compounds of the invention and their respective codes.
| Code | Structure |
| --- | --- |
| CPD-222 | 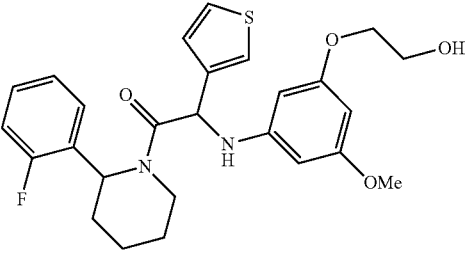 |
| CPD-223 | 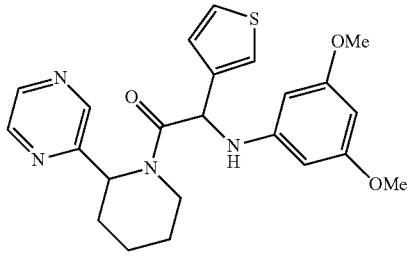 |
| CPD-224 | 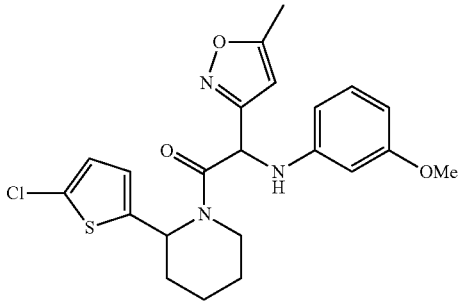 |
| CPD-225 | 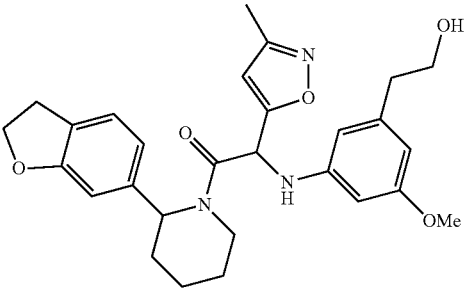 |
| CPD-226 | 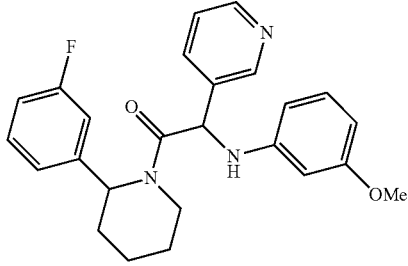 |

TABLE 1-continued

Structures of example compounds of the invention and their respective codes.

| Code | Structure |
| --- | --- |
| CPD-227 | 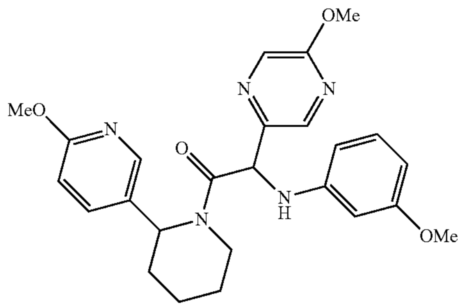 |
| CPD-228 | 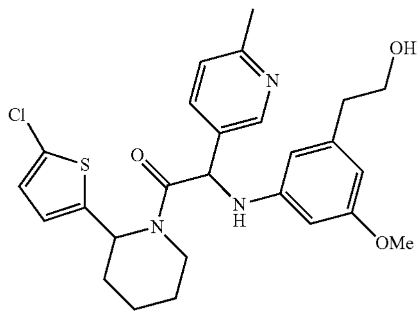 |
| CPD-229 | 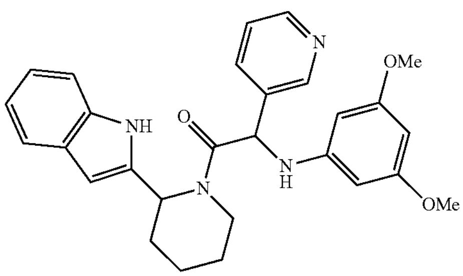 |
| CPD-230 | 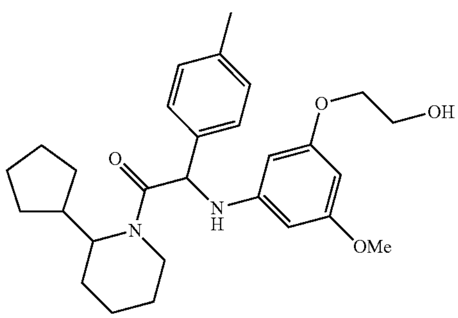 |
| CPD-231 | 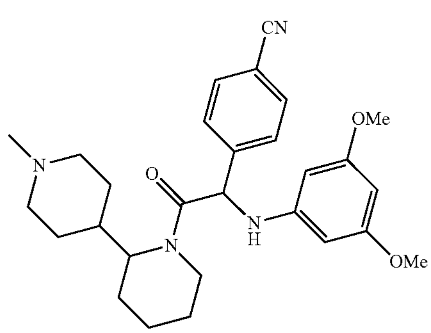 |

TABLE 1-continued

Structures of example compounds of the invention and their respective codes.

| Code | Structure |
| --- | --- |
| CPD-232 | 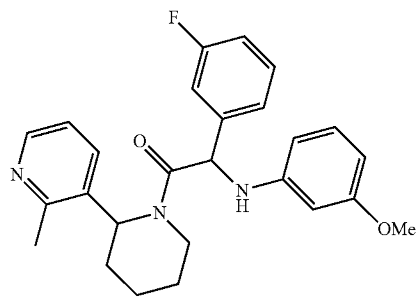 |
| CPD-233 | 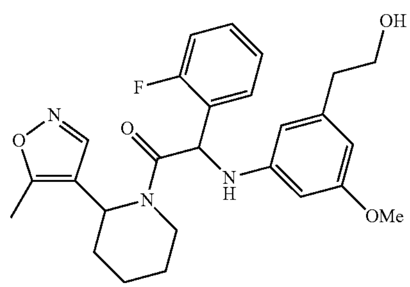 |
| CPD-234 | 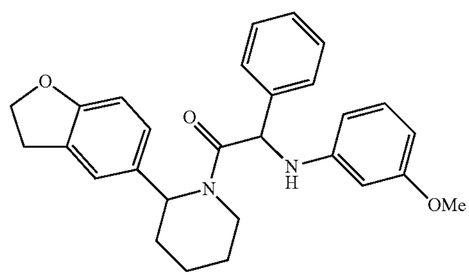 |
| CPD-235 | 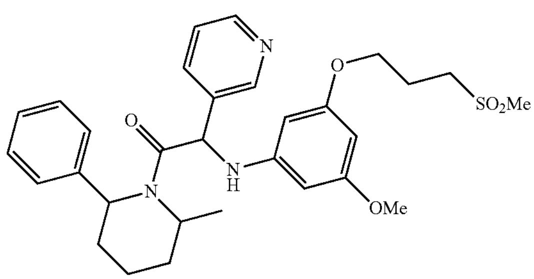 |
| CPD-236 | 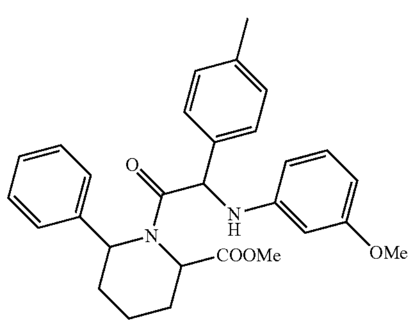 |

241
242
TABLE 1-continued
Structures of example compounds of the invention and their respective codes.
| Code | Structure |
|---|---|
| CPD-237 | 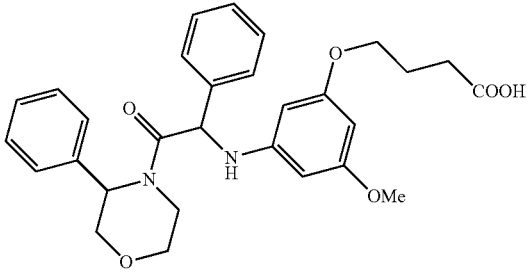 |
| CPD-238 | 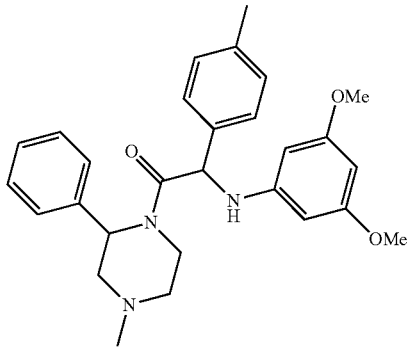 |
| CPD-239 | 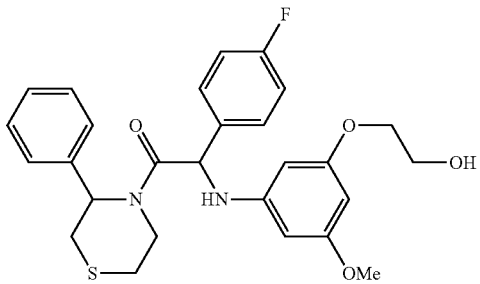 |
| CPD-240 | 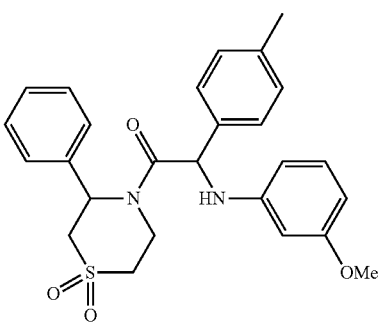 |
| CPD-241 | 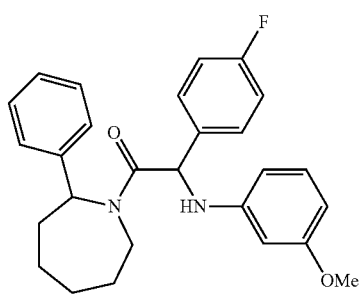 |

TABLE 1-continued

Structures of example compounds of the invention and their respective codes.

| Code | Structure |
| --- | --- |
| CPD-242 | 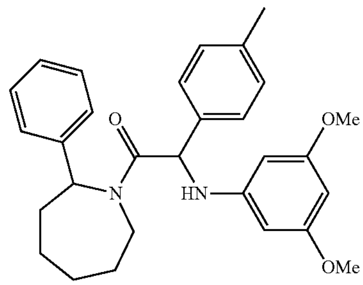 |
| CPD-243 | 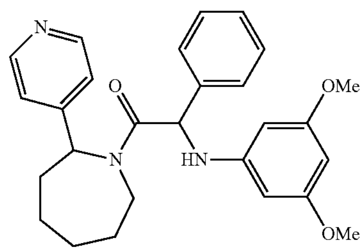 |
| CPD-244 | 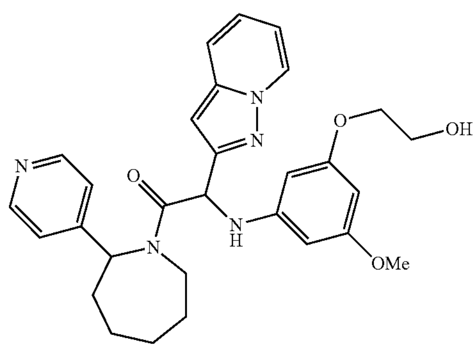 |
| CPD-245 | 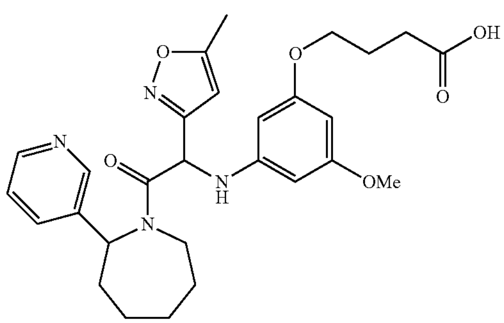 |
| CPD-246 | 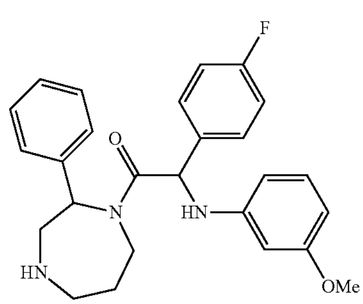 |

TABLE 1-continued
Structures of example compounds of the invention and their respective codes.
| Code | Structure |
|---|---|
| CPD-247 | 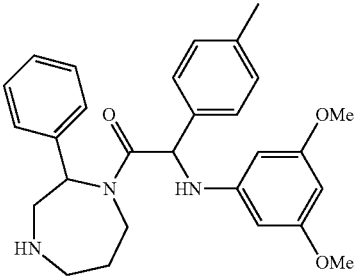 |
| CPD-248 | 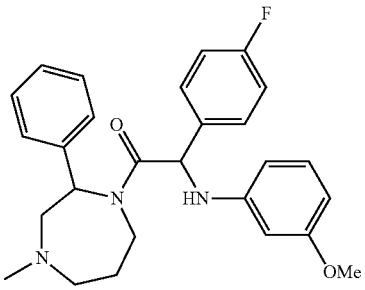 |
| CPD-249 | 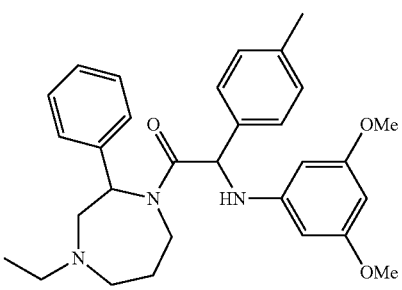 |
| CPD-250 | 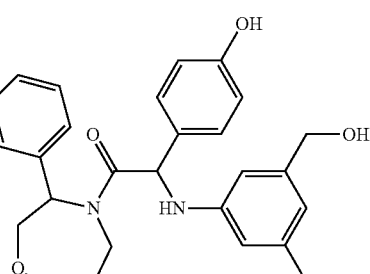 |
| CPD-251 | 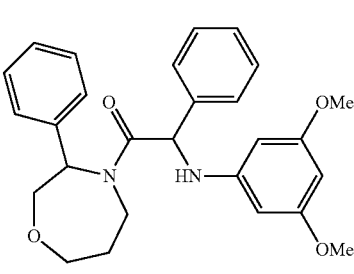 |

TABLE 1-continued
Structures of example compounds of the invention and their respective codes.
| Code | Structure |
|---|---|
| CPD-252 | 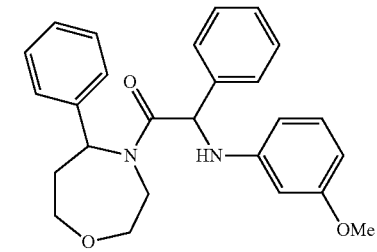 |
| CPD-253 | 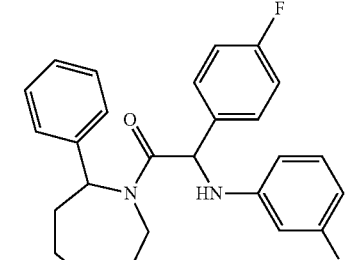 |
| CPD-254 | 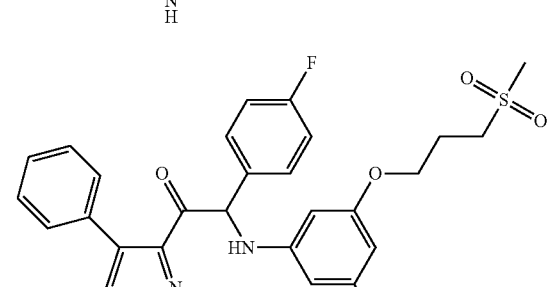 |
| CPD-255 | 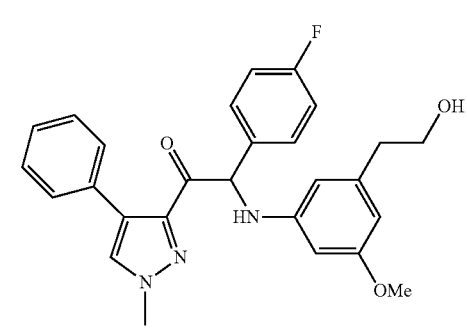 |
| CPD-256 | 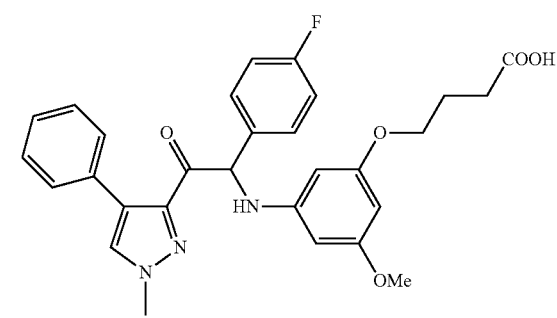 |

TABLE 1-continued
Structures of example compounds of the invention and their respective codes.
| Code | Structure |
|---|---|
| CPD-257 | 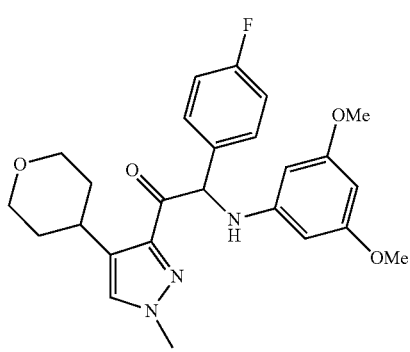 |
| CPD-258 | 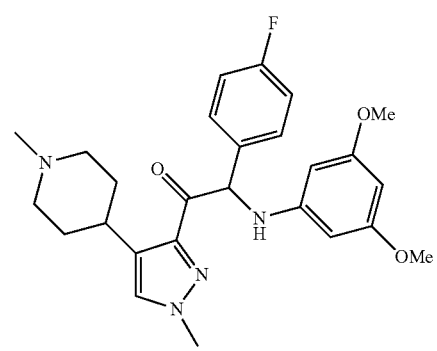 |
| CPD-259 | 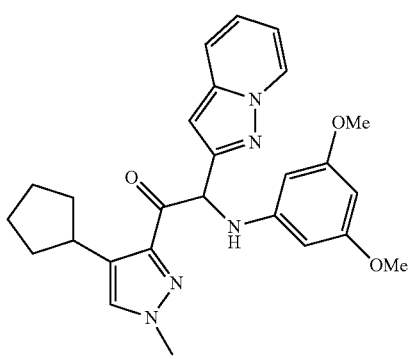 |
| CPD-260 | 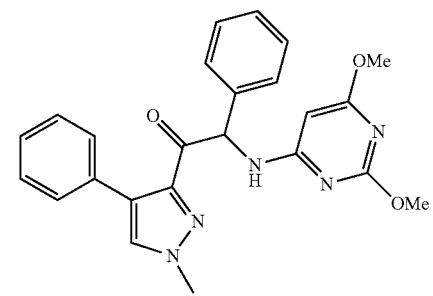 |

TABLE 1-continued

Structures of example compounds of the invention and their respective codes.

| Code | Structure |
|---|---|
| CPD-261 | 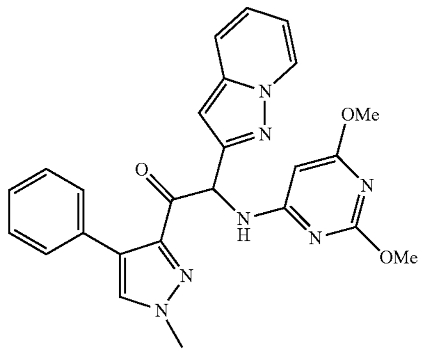 |
| CPD-262 | 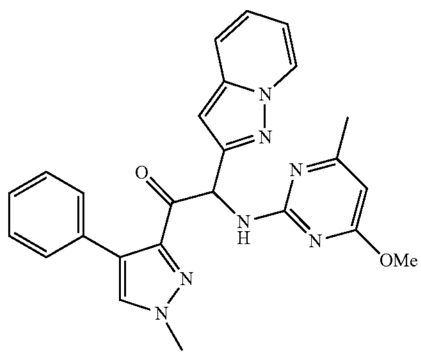 |
| CPD-263 | 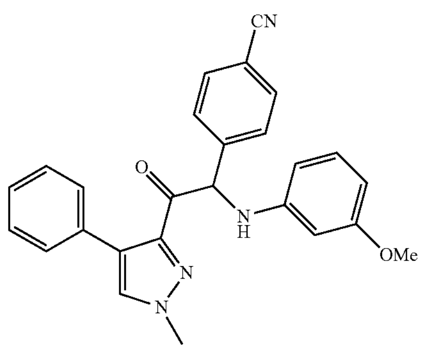 |
| CPD-264 | 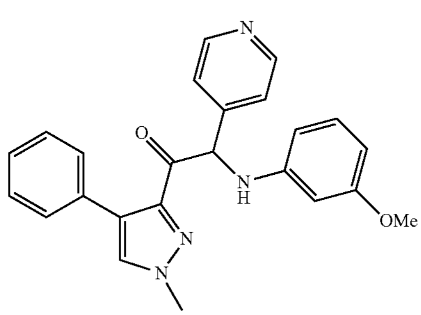 |

TABLE 1-continued

Structures of example compounds of the invention and their respective codes.

| Code | Structure |
| --- | --- |
| CPD-265 | 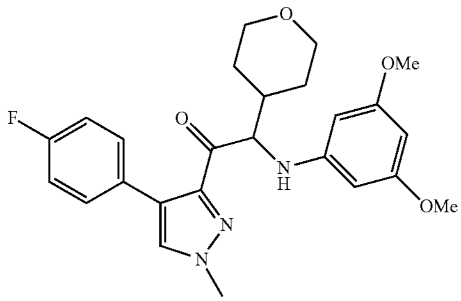 |
| CPD-266 | 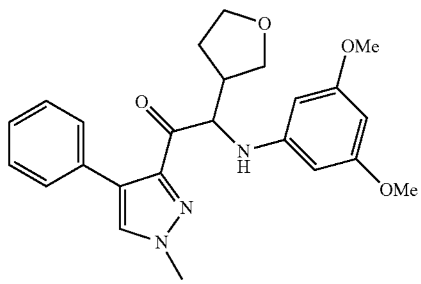 |
| CPD-267 | 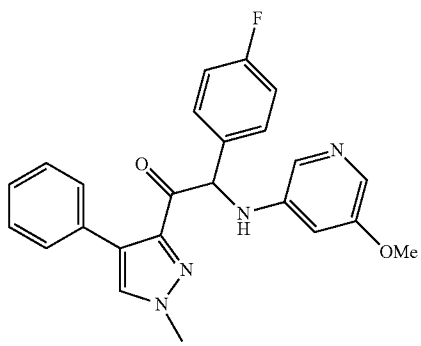 |
| CPD-268 | 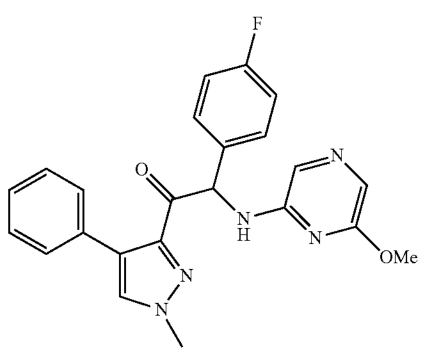 |

TABLE 1-continued
Structures of example compounds of the invention and their respective codes.
| Code | Structure |
| --- | --- |
| CPD-269 | 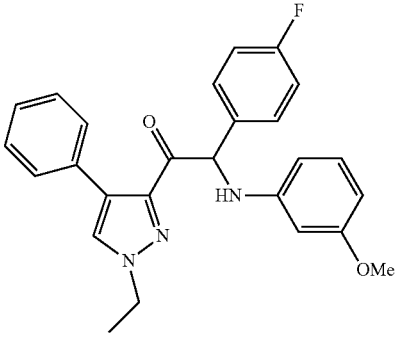 |
| CPD-270 | 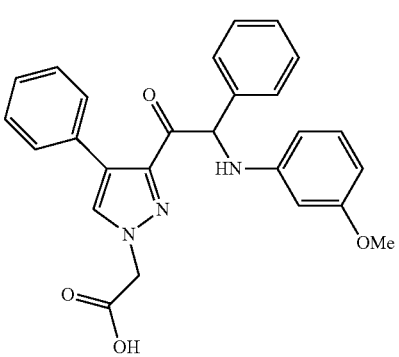 |
| CPD-271 | 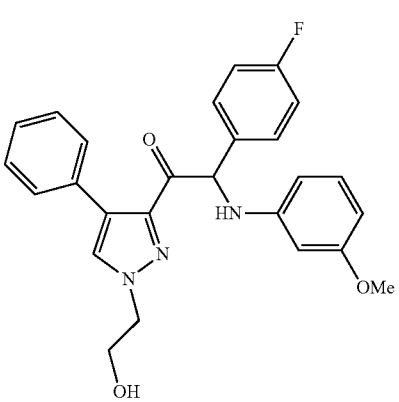 |
| CPD-272 | 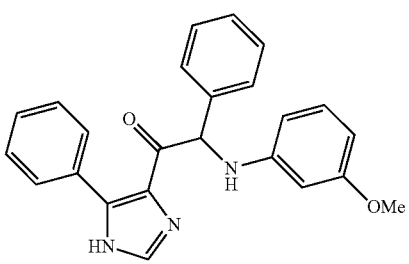 |

TABLE 1-continued

Structures of example compounds of the invention and their respective codes.

| Code | Structure |
|---|---|
| CPD-273 | 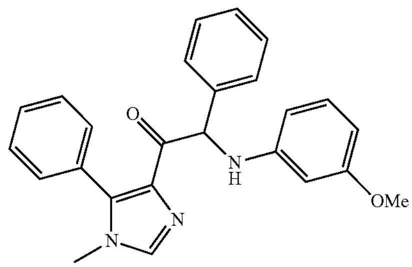 |
| CPD-274 | 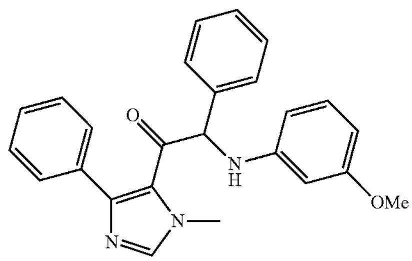 |
| CPD-275 | 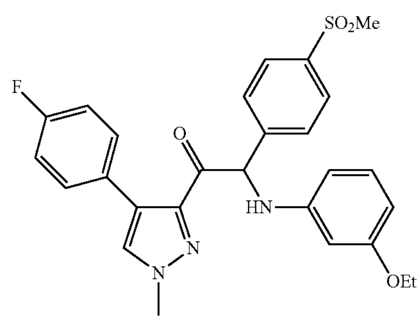 |
| CPD-276 | 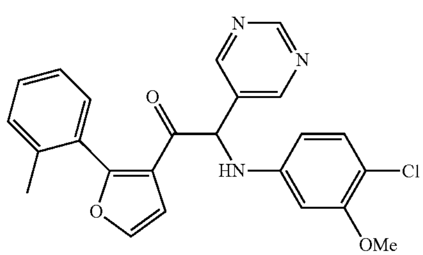 |
| CPD-277 | 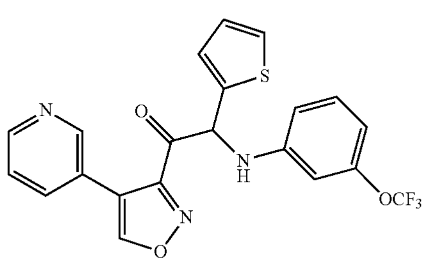 |

TABLE 1-continued

Structures of example compounds of the invention and their respective codes.

| Code | Structure |
| --- | --- |
| CPD-278 | 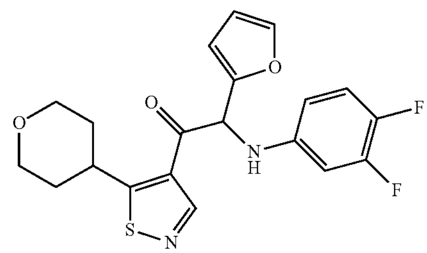 |
| CPD-279 | 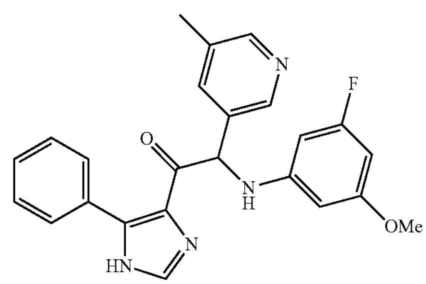 |
| CPD-280 | 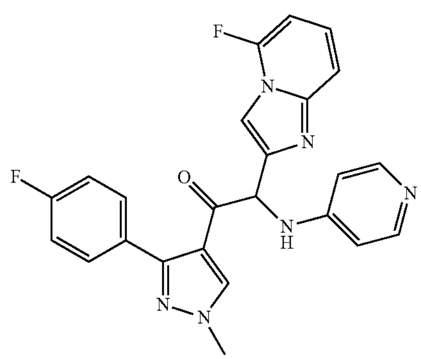 |
| CPD-281 | 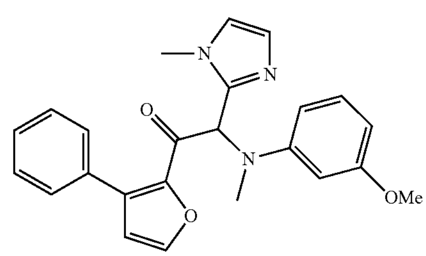 |
| CPD-282 | 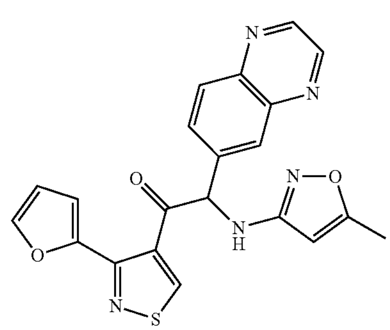 |

TABLE 1-continued

Structures of example compounds of the invention and their respective codes.

| Code | Structure |
| --- | --- |
| CPD-283 | 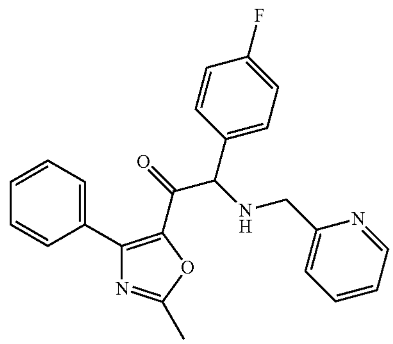 |
| CPD-284 | 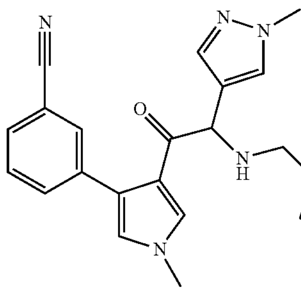 |
| CPD-285 | 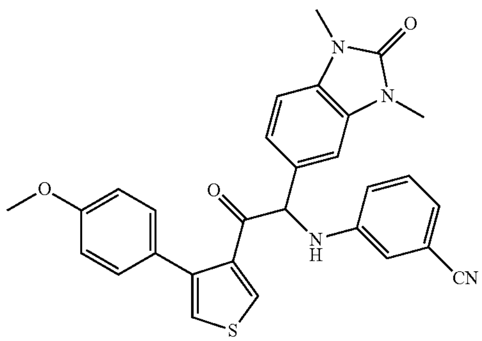 |
| CPD-286 | 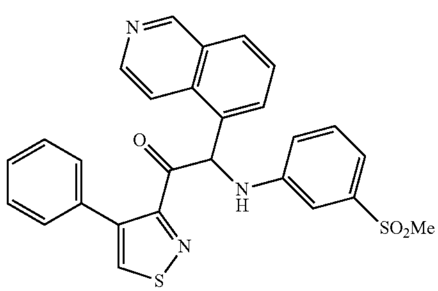 |
| CPD-287 | 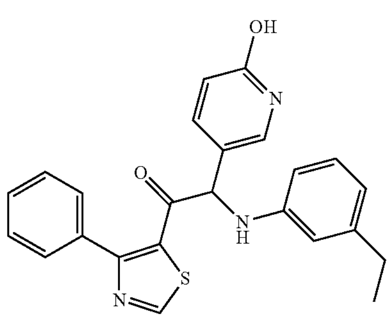 |

TABLE 1-continued

Structures of example compounds of the invention and their respective codes.

| Code | Structure |
|---|---|
| CPD-288 | 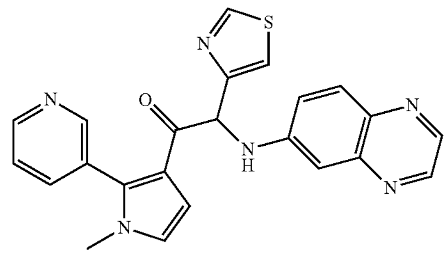 |
| CPD-289 | 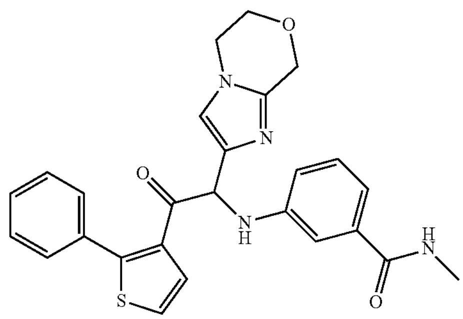 |
| CPD-290 | 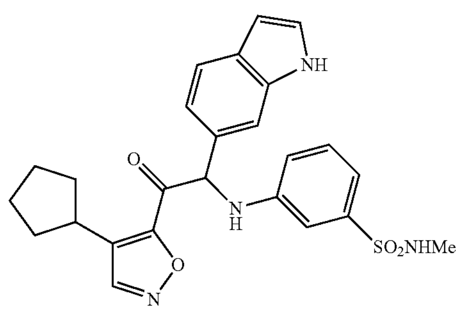 |
| CPD-291 | 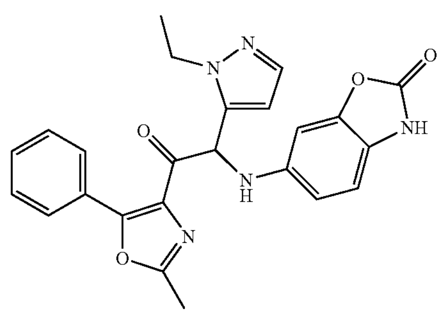 |
| CPD-292 | 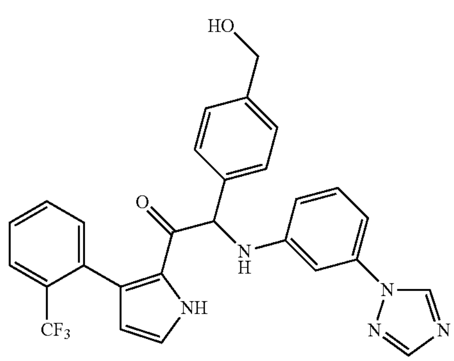 |

TABLE 1-continued

Structures of example compounds of the invention and their respective codes.

| Code | Structure |
| --- | --- |
| CPD-293 | 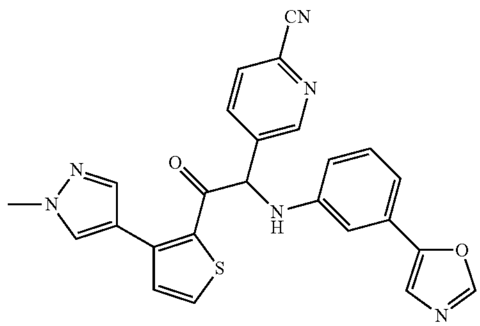 |
| CPD-294 | 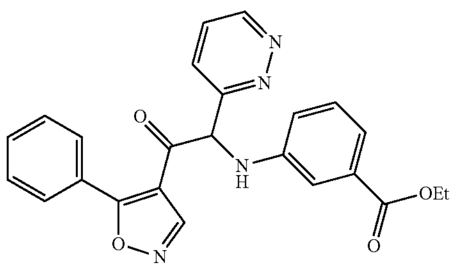 |
| CPD-295 | 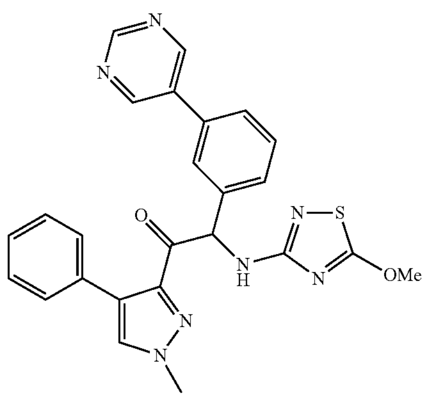 |
| CPD-296 | 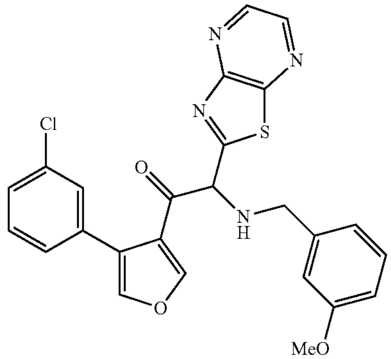 |

TABLE 1-continued

Structures of example compounds of the invention and their respective codes.

| Code | Structure |
| --- | --- |
| CPD-297 | 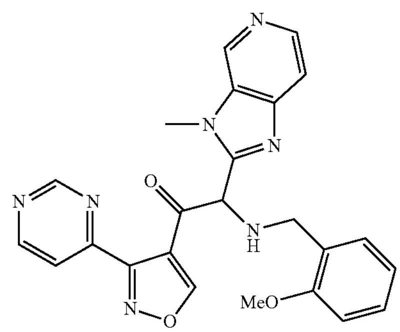 |
| CPD-298 | 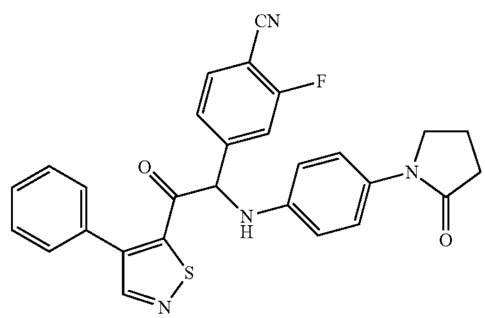 |
| CPD-299 | 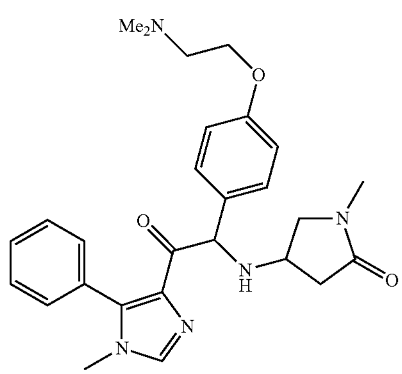 |
| CPD-300 | 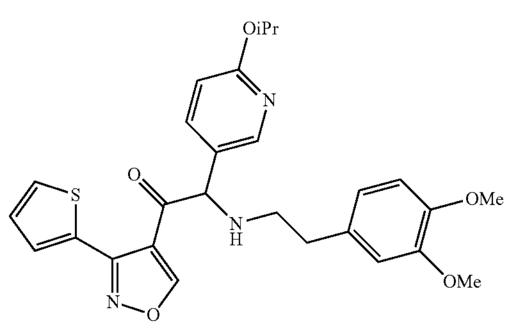 |

TABLE 1-continued

Structures of example compounds of the invention and their respective codes.

| Code | Structure |
|---|---|
| CPD-301 | 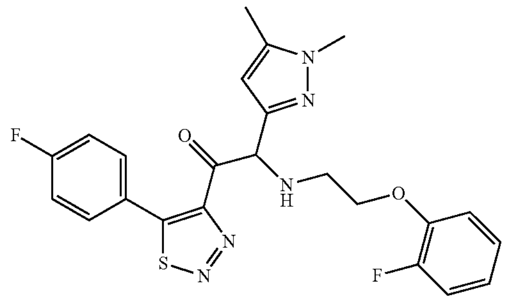 |
| CPD-302 | 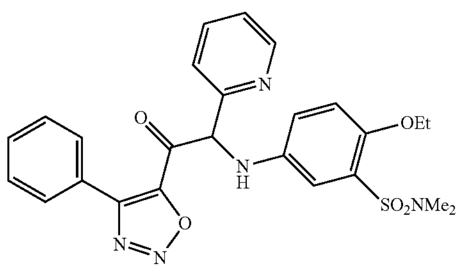 |
| CPD-303 | 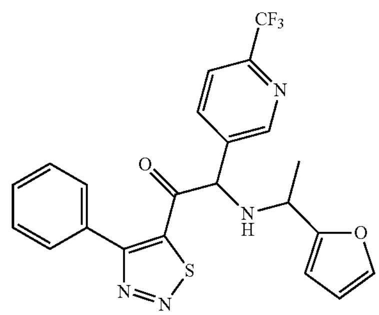 |
| CPD-304 | 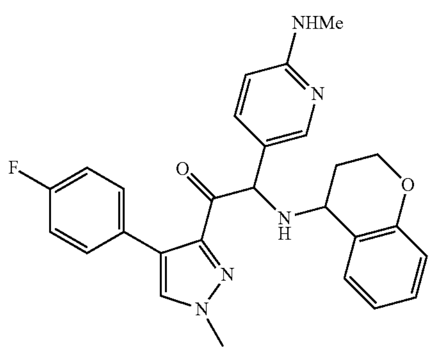 |
| CPD-305 | 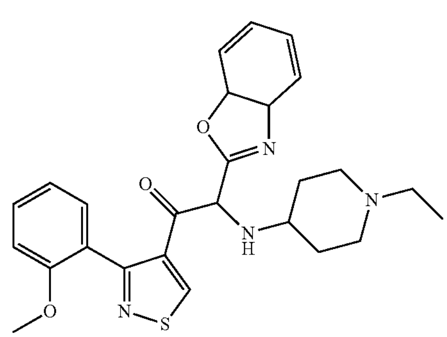 |

TABLE 1-continued

Structures of example compounds of the invention and their respective codes.

| Code | Structure |
|------|-----------|
| CPD-306 | 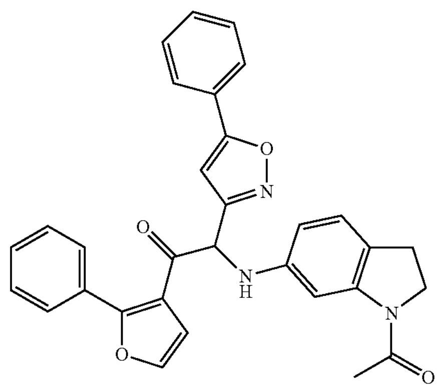 |
| CPD-307 | 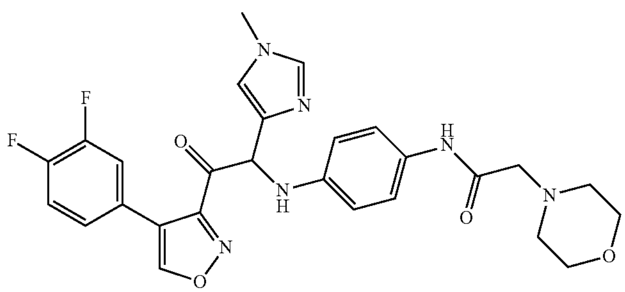 |
| CPD-308 | 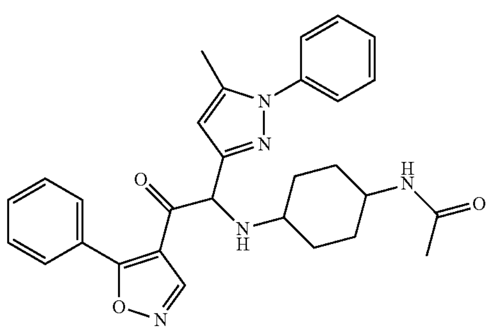 |
| CPD-309 | 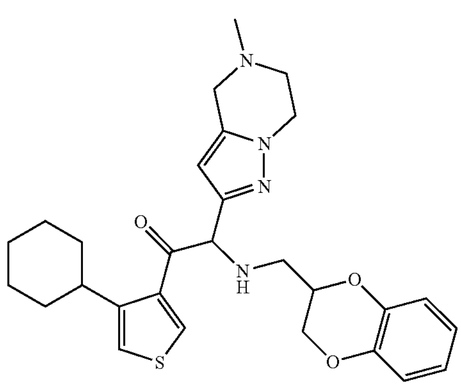 |

TABLE 1-continued

Structures of example compounds of the invention and their respective codes.

| Code | Structure |
| --- | --- |
| CPD-310 | 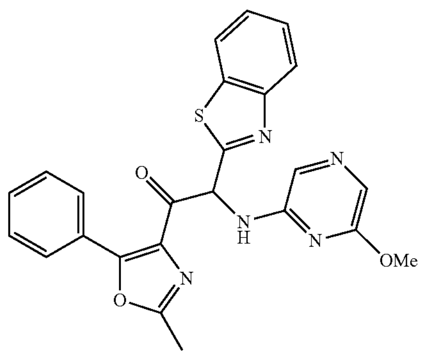 |
| CPD-311 | 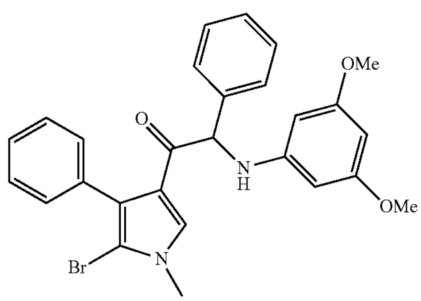 |
| CPD-312 | 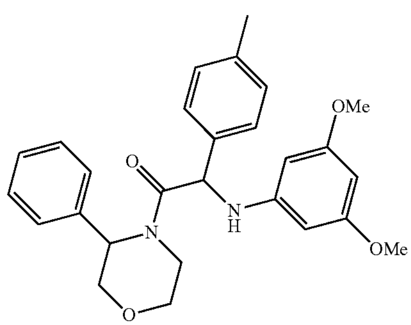 |
| CPD-313 | 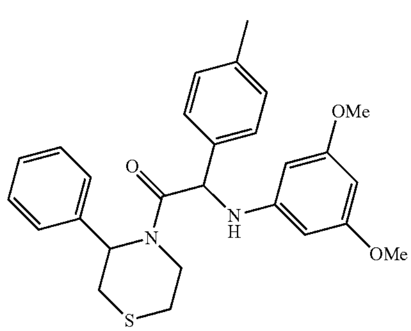 |

TABLE 1-continued

Structures of example compounds of the invention and their respective codes.

| Code | Structure |
|---|---|
| CPD-314 | (structure) |

Part A

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a XBridge Prep C18 column (19×100 mm; 5 µm) equipped with a XBridge C18 guard column (19×10 mm; 5 µm) or with a SunFire Prep C18 ODB column (19×100 mm; 5 µm) equipped with a SunFire C18 guard column (19×10 mm; 5 µm).

Elutions were carried out with the methods described in the following tables, and detection wavelengths were fixed at 210 and 254 nm.

Method 1

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Formic Acid LC-MS grade 0.1% in milliQ water
Solvent B: Acetonitrile HPLC grade.

Method 2

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Ammonium Acetate puriss p.a. for HPLC 10 mM in milliQ water, adjusted at pH10 with Ammonium Hydroxide puriss p.a. for HPLC
Solvent B: Acetonitrile HPLC grade.

All the enantiomer separations mentioned in this experimental part have been carried out with the following system: a Waters 2489 UV/Visible Detector, a Waters 2545 Binary Gradient Module, a Waters Fraction Collector III and a Waters Dual Flex Injector. The separations were performed with a ChiralPak IC column (20×250 mm; 5 µm) equipped with a ChiralPak IC guard column (10×20 mm; 5 µm). Elutions were carried out with the isocratic method described below, and detection wavelengths were fixed at 210 and 254 nm.

Method 3:
Eluant: n-heptane/dichloromethane/ethanol/diethylamine: 90/10/1/0.1
Flow rate: 20 mL/min General procedures used in the synthesis of compounds of the invention:

General Procedure A:

To a solution of a carboxylic acid in dichloromethane was added an amine, triethylamine and HATU. The reaction mixture was stirred at room temperature overnight. The reaction mixture was diluted with dichloromethane and washed with a 1N hydrochloric acid solution. The phases were separated. The organic phase was washed with a saturated sodium bicarbonate solution, water and brine, dried over sodium sulfate, filtered and concentrated under reduced pressure. The residue was purified by flash chromatography on silica gel.

General Procedure B:

A mixture of an aldehyde and an amine was heated in a sealed tube at 60° C. for 6 h. The formation of the imine was quantitative and the imine was used in the next step without further purification.

General Procedure C:

A mixture of an aldehyde and an amine in ethanol was heated at 60-70° C. for 5-20 h. The formation of the imine was quantitative and the solution of the imine in ethanol was used in the next step without further purification.

General Procedure D: Umpolung

To a solution of 3-benzyl-5-(2-hydroxyethyl)-4-methyl-thiazol-3-ium chloride in ethanol was added triethylamine and the mixture was stirred at 60-70° C. for 10 min. To the resulting yellow solution were added an aldehyde and a solution of an imine in ethanol. The reaction mixture was stirred in a sealed tube at 60-70° C. for 18-120 h. The reaction mixture was concentrated under reduced pressure and the residue was purified by flash chromatography on silica gel.

General Procedure E:

To a solution of 3-benzyl-5-(2-hydroxyethyl)-4-methyl-thiazol-3-ium chloride in ethanol was added triethylamine and the reaction mixture was stirred at 60-70° C. for 10 min.

To the resulting yellow solution were added an aldehyde and a solution of an imine in ethanol. The reaction mixture was stirred in a sealed tube at 60-70° C. for 18-120 h, after which the reaction mixture was irradiated in a microwave oven at 160° C. for 4 min. The reaction mixture was concentrated under reduced pressure and the residue was purified by flash chromatography on silica gel.

General Procedure F:

To a degassed mixture of an aryl or heteroaryl halide, a boronic acid or a boronic ester and a base (e.g. potassium fluoride or sodium carbonate) in a mixture of an organic solvent (e.g. DME or dioxane) and water was added tetrakis(triphenylphosphine)palladium(0). The reaction mixture was refluxed overnight. After cooling to room temperature, the reaction mixture was filtered through celite. The filtrate was diluted with ethyl acetate and washed with water. The phases were separated. The organic phase was washed with brine, dried over sodium sulfate, filtered and concentrated under reduced pressure. The residue was purified by flash chromatography on silica gel.

General Procedure G:

To a degassed mixture of an aryl or heteroaryl halide, a boronic acid or a boronic ester and a base (e.g. potassium fluoride or sodium carbonate) in a mixture of an organic solvent (e.g. DME or dioxane) and water was added tetrakis(triphenylphosphine)palladium(0). The reaction mixture was irradiated in a microwave oven at 130° C. for 20 min. After cooling to room temperature, the reaction mixture was filtered through celite. The filtrate was diluted with ethyl acetate and washed with water. The phases were separated. The organic phase was washed with brine, dried over sodium sulfate, filtered and concentrated under reduced pressure. The residue was purified by flash chromatography on silica gel.

Example 1: Preparation of 2-((3-methoxyphenyl)amino)-1-(1-methyl-4-phenyl-1H-pyrazol-3-yl)-2-phenylethanone Step 1:

1-Methyl-4-phenyl-1H-pyrazole-3-carbaldehyde was prepared according to general procedure F from 4-bromo-1-methyl-1H-pyrazole-3-carbaldehyde (0.100 g; 0.529 mmol), benzeneboronic acid (0.077 g; 0.635 mmol), sodium carbonate (0.135 g; 1.274 mmol) and tetrakis(triphenylphosphine)palladium(0) (0.031 g; 0.026 mmol) in a mixture of DME (4 mL) and water (1.6 mL). Purification by flash chromatography on silica gel using a gradient of ethyl acetate (10% to 100%) in heptane furnished 0.093 g (94%) of the desired compound as a yellow solid. ESI/APCI(+): 187 (M+H).

Step 2:

N-Benzylidene-3-methoxyaniline was prepared according to general procedure B from a mixture of benzaldehyde (0.101 mL; 0.996 mmol) and m-anidisine (0.112 mL; 1.073 mmol).

Step 3:

2-((3-Methoxyphenyl)amino)-1-(1-methyl-4-phenyl-1H-pyrazol-3-yl)-2-phenylethanone was prepared according to general procedure D from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (1 mL), 1-methyl-4-phenyl-1H-pyrazole-3-carbaldehyde (0.093 g; 0.499 mmol) and a solution of N-benzylidene-3-methoxyaniline (0.499 mmol) in ethanol (1 mL), heated at 70° C. for 24 h. Purification by flash chromatography on silica gel using a gradient of ethyl acetate (5% to 80%) in heptane followed by a second purification by flash chromatography on silica gel using a gradient of ethyl acetate (10% to 60%) in heptane furnished 0.030 g (14%) of the desired compound as a white solid. ESI/APCI(+): 398 (M+H). ESI/APCI(−): 396 (M−H).

Example 2: Preparation of 1-(4-(4-fluorophenyl)-1-methyl-1H-pyrazol-3-yl)-2-((3-methoxyphenyl)amino)-2-phenylethanone Step 1:

1-(4-Bromo-1-methyl-1H-pyrazol-3-yl)-2-((3-methoxyphenyl)amino)-2-phenylethanone was prepared according to general procedure D from a mixture of 3-benzyl-5-(2-hydroxyethyl)-4-methylthiazol-3-ium chloride (0.135 g; 0.500 mmol) and triethylamine (0.069 mL; 0.498 mmol) in ethanol (0.735 mL), 4-bromo-1-methyl-1H-pyrazole-3-carboxaldehyde (0.205 g, 1.085 mmol) and a solution of N-benzylidene-3-methoxyaniline (0.996 mmol) in ethanol (0.735 mL), heated at 70° C. for 18 h. Purification by flash chromatography on silica gel using a gradient of ethyl acetate (0% to 70%) in heptane furnished 0.266 g (67%) of the desired compound as a yellow solid. ESI/APCI(+): 400, 402 (M+H). $^1$H NMR (DMSO-$d_6$) δ 8.13 (1H, s); 7.49 (2H, d); 7.33 (2H, m); 7.25 (1H, m); 6.93 (1H, t); 6.44 (1H, d); 6.25 (3H, m); 6.14 (1H, d); 4.00 (3H, s); 3.64 (3H, s).

Step 2:

1-(4-(4-Fluorophenyl)-1-methyl-1H-pyrazol-3-yl)-2-((3-methoxyphenyl)amino)-2-phenylethanone was prepared according to general procedure F from 1-(4-bromo-1-methyl-1H-pyrazol-3-yl)-2-((3-methoxyphenyl)amino)-2-phenylethanone (0.100 g; 0.250 mmol), 4-fluorophenylboronic acid (0.052 g; 0.372 mmol), potassium fluoride (0.058 g; 0.998 mmol) and tetrakis(triphenylphosphine)palladium (0) (0.029 g; 0.025 mmol) in a mixture of dioxane (4 mL) and water (1 mL). Purification by flash chromatography on silica gel using a gradient of ethyl acetate (20% to 50%) in heptane furnished 0.073 g (70%) of the desired compound as a white foam. ESI/APCI(+): 416 (M+H). ESI/APCI(−): 414 (M−H). $^1$H NMR (DMSO-$d_6$) δ 8.06 (1H, s); 7.52 (2H, d); 7.1-7.4 (7H, m); 6.92 (1H, t); 6.35 (2H, m); 6.28 (2H, m); 6.12 (1H, d); 4.03 (3H, s); 3.61 (3H, s).

Example 3: Preparation of 2-((3-methoxyphenyl)amino)-1-(1-methyl-4-phenyl-1H-pyrazol-3-yl)-2-(pyridin-3-yl)ethanone Step 1:

A solution of 3-methoxy-N-(pyridin-3-ylmethylene)aniline in ethanol was prepared according to general procedure C from a mixture of nicotinaldehyde (0.047 mL; 0.500 mmol) and m-anidisine (0.056 mL; 0.500 mmol) in ethanol (0.5 mL), heated at 60° C. for 6 h.

Step 2:

2-((3-Methoxyphenyl)amino)-1-(1-methyl-4-phenyl-1H-pyrazol-3-yl)-2-(pyridin-3-yl)ethanone was prepared according to general procedure D from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (1 mL), 1-methyl-4-phenyl-1H-pyrazole-3-carbaldehyde (0.093 g; 0.499 mmol) and a solution of 3-methoxy-N-(pyridin-3-ylmethylene)aniline (0.500 mmol) in ethanol (0.5 mL), heated at 70° C. for 18 h. Purification by flash chromatography on silica gel using a gradient of ethyl acetate (2% to 20%) in dichloromethane followed by precipitation from diethyl ether furnished 0.060 g (30%) of the desired compound as a white solid. ESI/APCI(+): 399

(M+H). ESI/APCI(–): 397 (M–H). $^1$H NMR (DMSO-d$_6$) δ 8.75 (1H, s); 8.45 (1H, d); 8.08 (1H, s); 7.88 (1H, d); 7.21-7.43 (6H, m); 6.95 (1H, t); 6.55 (1H, d); 6.40 (1H, d); 6.30 (2H, m); 6.15 (1H, d); 4.04 (3H, s); 3.62 (3H, s).

Example 4: Preparation of 2-(5-fluoropyridin-3-yl)-2-((3-methoxyphenyl)amino)-1-(1-methyl-4-phenyl-1H-pyrazol-3-yl)ethanone Step 1:
A solution of N-((5-fluoropyridin-3-yl)methylene)-3-methoxyaniline in ethanol was prepared according to general procedure C from a mixture of 5-fluoronicotinaldehyde (0.062 g; 0.504 mmol) and m-anidisine (0.056 mL; 0.500 mmol) in ethanol (0.5 mL), heated at 60° C. for 6 h.

Step 2:
2-(5-Fluoropyridin-3-yl)-2-((3-methoxyphenyl)amino)-1-(1-methyl-4-phenyl-1H-pyrazol-3-yl)ethanone was prepared according to general procedure D from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (1 mL), 1-methyl-4-phenyl-1H-pyrazole-3-carbaldehyde (0.093 g; 0.499 mmol) and a solution of N-((5-fluoropyridin-3-yl)methylene)-3-methoxyaniline (0.500 mmol) in ethanol (0.5 mL), heated at 70° C. for 18 h. Purification by flash chromatography on silica gel using a gradient of ethyl acetate (2% to 20%) in dichloromethane followed by precipitation from ethanol furnished 0.055 g (26%) of the desired compound as a beige solid. ESI/APCI(+): 417 (M+H). ESI/APCI(–): 415 (M–H). $^1$H NMR (DMSO-d$_6$) δ 8.65 (1H, s); 8.47 (1H, d); 8.10 (1H, s); 7.83 (1H, d); 7.23-7.47 (5H, m); 6.96 (1H, t); 6.56-6.67 (1H, m); 6.44-6.53 (1H, m); 6.32 (2H, m); 6.18 (1H, d); 4.05 (3H, s); 3.63 (3H, s).

Example 5: Preparation of 1-(4-(2-fluorophenyl)-1-methyl-1H-pyrazol-3-yl)-2-((3-methoxyphenyl)amino)-2-phenylethanone 1-(4-(2-Fluorophenyl)-1-methyl-1H-pyrazol-3-yl)-2-((3-methoxyphenyl)amino)-2-phenylethanone was prepared according to general procedure F from 1-(4-bromo-1-methyl-1H-pyrazol-3-yl)-2-((3-methoxyphenyl)amino)-2-phenylethanone (0.100 g; 0.250 mmol), (2-fluorophenyl)boronic acid (0.052 g; 0.372 mmol), potassium fluoride (0.058 g; 0.998 mmol) and tetrakis(triphenylphosphine)palladium(0) (0.029 g; 0.025 mmol) in a mixture of DME (3 mL) and water (0.75 mL). Purification by flash chromatography on silica gel using a gradient of ethyl acetate (2% to 40%) in heptane furnished 0.095 g (91%) of the desired compound as a beige solid. ESI/APCI(+): 416 (M+H). ESI/APCI(–): 414 (M–H). $^1$H NMR (DMSO-d$_6$) δ 8.03 (1H, s); 7.51 (2H, d); 7.20-7.41 (5H, m); 7.17 (2H, d); 6.92 (1H, t); 6.34-6.44 (1H, m); 6.21-6.33 (3H, m); 6.12 (1H, d); 4.04 (3H, s); 3.61 (3H, s).

Example 6: Preparation of 1-(4-(3-fluorophenyl)-1-methyl-1H-pyrazol-3-yl)-2-((3-methoxyphenyl)amino)-2-phenylethanone 1-(4-(3-Fluorophenyl)-1-methyl-1H-pyrazol-3-yl)-2-((3-methoxyphenyl)amino)-2-phenylethanone was prepared according to general procedure F from 1-(4-bromo-1-methyl-1H-pyrazol-3-yl)-2-((3-methoxyphenyl)amino)-2-phenylethanone (0.100 g; 0.250 mmol), (3-fluorophenyl)boronic acid (0.052 g; 0.372 mmol), potassium fluoride (0.058 g; 0.998 mmol) and tetrakis(triphenylphosphine)palladium(0) (0.029 g; 0.025 mmol) in a mixture of DME (3 mL) and water (0.75 mL). Purification by flash chromatography on silica gel using a gradient of ethyl acetate (2% to 40%) in heptane furnished 0.092 g (89%) of the desired compound as a beige solid. ESI/APCI(+): 416 (M+H). ESI/APCI(–): 414 (M–H). $^1$H NMR (DMSO-d$_6$) δ 8.15 (1H, s); 7.51 (2H, d); 7.34 (3H, m); 7.22 (3H, m); 7.06 (1H, t); 6.93 (1H, t); 6.46 (1H, d); 6.24-6.39 (3H, m); 6.13 (1H, d); 4.04 (3H, s); 3.62 (3H, s).

Example 7: Preparation of 1-(1,1'-dimethyl-1H,1'H-[4,4'-bipyrazol]-3-yl)-2-((3-methoxyphenyl)amino)-2-phenylethanone 1-(1,1'-Dimethyl-1H,1'H-[4,4'-bipyrazol]-3-yl)-2-((3-methoxyphenyl)amino)-2-phenylethanone was prepared according to general procedure F from 1-(4-bromo-1-methyl-1H-pyrazol-3-yl)-2-((3-methoxyphenyl)amino)-2-phenylethanone (0.100 g; 0.250 mmol), 1-methyl-1H-pyrazole-4-boronic acid pinacol ester (0.078 g; 0.375 mmol), potassium fluoride (0.058 g; 0.998 mmol) and tetrakis(triphenylphosphine)palladium(0) (0.029 g; 0.025 mmol) in a mixture of DME (3 mL) and water (0.75 mL). Purification by flash chromatography on silica gel using a gradient of ethyl acetate (2% to 20%) in dichloromethane furnished 0.074 g (74%) of the desired compound as a beige solid. ESI/APCI(+): 402 (M+H). ESI/APCI(–): 400 (M–H). $^1$H NMR (DMSO-d$_6$) δ 8.14 (2H, s); 7.75 (1H, s); 7.51 (2H, m); 7.17-7.36 (3H, m); 6.93 (1H, t); 6.40 (2H, m); 6.30 (2H, s); 6.13 (1H, d); 4.01 (3H, s); 3.82 (3H, s); 3.62 (3H, s).

Example 8: Preparation of 2-(4-fluorophenyl)-2-((3-methoxyphenyl)amino)-1-(1-methyl-4-phenyl-1H-pyrazol-3-yl)ethanone Step 1:
A solution of N-(4-fluorobenzylidene)-3-methoxyaniline in ethanol was prepared according to general procedure C from a mixture of 4-fluorobenzaldehyde (0.126 g; 1.015 mmol) and m-anidisine (0.109 mL; 0.974 mmol) in ethanol (0.5 mL), heated at 60° C. for 18 h.

Step 2:
2-(4-Fluorophenyl)-2-((3-methoxyphenyl)amino)-1-(1-methyl-4-phenyl-1H-pyrazol-3-yl)ethanone was prepared according to general procedure D from a mixture of 3-benzyl-5-(2-hydroxyethyl)-4-methylthiazol-3-ium chloride (0.116 g; 0.430 mmol) and triethylamine (0.080 mL; 0.574 mmol) in ethanol (0.5 mL), 1-methyl-4-phenyl-1H-pyrazole-3-carbaldehyde (0.160 g; 0.859 mmol) and a solution of N-(4-fluorobenzylidene)-3-methoxyaniline (0.974 mmol) in ethanol (1.5 mL), heated at 60° C. for 18 h. Purification by flash chromatography on silica gel using a gradient of ethyl acetate (0% to 40%) in heptane furnished 0.174 g (48%) of the desired compound as a yellow oil. ESI/APCI(+): 416 (M+H).

Example 9: Preparation of 2-((3-methoxyphenyl)amino)-1-(1-methyl-4-(pyrimidin-5-yl)-1H-pyrazol-3-yl)-2-(p-tolyl)ethanone Step 1:
A solution of 3-methoxy-N-(4-methylbenzylidene)aniline in ethanol was prepared according to general procedure C from a mixture of p-tolualdehyde (0.279 mL; 2.57 mmol) and m-anidisine (0.277 mL; 2.48 mmol) in ethanol (1.5 mL), heated at 60° C. for 6 h.

Step 2:

1-(4-Bromo-1-methyl-1H-pyrazol-3-yl)-2-((3-methoxyphenyl)amino)-2-(p-tolyl)ethanone was prepared according to general procedure D from a mixture of 3-benzyl-5-(2-hydroxyethyl)-4-methylthiazol-3-ium chloride (0.330 g; 1.22 mmol) and triethylamine (0.250 mL; 1.79 mmol) in ethanol (1.5 mL), 4-bromo-1-methyl-1H-pyrazole-3-carboxaldehyde (0.455 g, 2.41 mmol) and a solution of 3-methoxy-N-(4-methylbenzylidene)aniline (2.48 mmol) in ethanol (3 mL), heated at 60° C. for 18 h. Purification by flash chromatography on silica gel using a gradient of ethyl acetate (0% to 50%) in heptane furnished 0.612 g (61%) of the desired compound as a yellow wax that slowly solidified. ESI/APCI(+): 414, 416 (M+H).

Step 3: 2-((3-Methoxyphenyl)amino)-1-(1-methyl-4-(pyrimidin-5-yl)-1H-pyrazol-3-yl)-2-(p-tolyl)ethanone was prepared according to general procedure F from 1-(4-bromo-1-methyl-1H-pyrazol-3-yl)-2-((3-methoxyphenyl)amino)-2-(p-tolyl)ethanone (0.120 g; 0.290 mmol), pyrimidin-5-ylboronic acid (0.056 g; 0.452 mmol), potassium fluoride (0.072 g; 1.239 mmol) and tetrakis(triphenylphosphine)palladium (0) (0.035 g; 0.030 mmol) in a mixture of dioxane (4 mL) and water (1 mL). Purification by flash chromatography on silica gel using a gradient of ethyl acetate (50% to 100%) in heptane followed by purification by solid phase extraction on C18-reversed phase column using a gradient of acetonitrile (10% to 60%) in water furnished 0.090 g (75%) of the desired compound as a yellow foam. ESI/APCI(+): 414 (M+H).

Example 10: Preparation of 2-((3-methoxyphenyl)amino)-1-(1-methyl-4-(pyridin-4-yl)-1H-pyrazol-3-yl)-2-(p-tolyl)ethanone 2-((3-Methoxyphenyl)amino)-1-(1-methyl-4-(pyridin-4-yl)-1H-pyrazol-3-yl)-2-(p-tolyl)ethanone was prepared according to general procedure F from 1-(4-bromo-1-methyl-1H-pyrazol-3-yl)-2-((3-methoxyphenyl)amino)-2-(p-tolyl)ethanone (0.123 g; 0.297 mmol), pyridine-4-ylboronic acid (0.057 g; 0.464 mmol), potassium fluoride (0.076 g; 1.308 mmol) and tetrakis(triphenylphosphine)palladium (0) (0.032 g; 0.028 mmol) in a mixture of dioxane (4 mL) and water (1 mL). The residue was purified by flash chromatography on silica gel using a gradient of ethyl acetate (50% to 100%) in heptane. Further purification by solid phase extraction on C18-reversed phase column using a gradient of acetonitrile (10% to 60%) in water followed by purification by preparative HPLC (XBrigde column; method 1) furnished 0.045 g (37%) of the desired compound as a yellow solid. ESI/APCI(+): 413 (M+H).

Example 11: Preparation of 2-((3-methoxyphenyl)amino)-2-(5-methoxypyrazin-2-yl)-1-(1-methyl-4-phenyl-1H-pyrazol-3-yl)ethanone Step 1:
A solution of 3-methoxy-N-((5-methoxypyrazin-2-yl)methylene)aniline in ethanol was prepared according to general procedure C from a mixture of 5-methoxypyrazine-2-carbaldehyde (0.139 g; 1.006 mmol) and m-anidisine (0.110 mL; 0.983 mmol) in ethanol (0.5 mL), heated at 60° C. for 18 h.

Step 2:
2-((3-Methoxyphenyl)amino)-2-(5-methoxypyrazin-2-yl)-1-(1-methyl-4-phenyl-1H-pyrazol-3-yl)ethanone was prepared according to general procedure D from a mixture of 3-benzyl-5-(2-hydroxyethyl)-4-methylthiazol-3-ium chloride (0.116 g; 0.430 mmol) and triethylamine (0.080 mL; 0.574 mmol) in ethanol (0.5 mL), 1-methyl-4-phenyl-1H-pyrazole-3-carbaldehyde (0.162 g; 0.870 mmol) and a solution of 3-methoxy-N-((5-methoxypyrazin-2-yl)methylene)aniline (0.983 mmol) in ethanol (1.5 mL), heated at 60° C. for 18 h. The residue was purified by flash chromatography on silica gel using a gradient of ethyl acetate (0% to 60%) in heptane. Further purification by solid phase extraction on C18-reversed phase column using a gradient of acetonitrile (10% to 55%) in water followed by purification by preparative HPLC (XBridge column; method 1) furnished 0.118 g (32%) of the desired compound as a yellow solid. ESI/APCI(+): 430 (M+H).

Example 12: Preparation of 2-(6-methoxypyridin-3-yl)-2-((5-methoxypyridin-3-yl)amino)-1-(1-methyl-4-phenyl-1H-pyrazol-3-yl)ethanone Step 1:
A solution of 5-methoxy-N-((6-methoxypyridin-3-yl)methylene)pyridin-3-amine in ethanol was prepared according to general procedure C from a mixture of 6-methoxynicotinaldehyde (0.126 g; 0.919 mmol) and 5-methoxypyridin-3-amine (0.114 g; 0.918 mmol) in ethanol (1 mL), heated at 60° C. for 6 h.

Step 2:
2-(6-Methoxypyridin-3-yl)-2-((5-methoxypyridin-3-yl)amino)-1-(1-methyl-4-phenyl-1H-pyrazol-3-yl)ethanone was prepared according to general procedure D from a mixture of 3-benzyl-5-(2-hydroxyethyl)-4-methylthiazol-3-ium chloride (0.126 g; 0.460 mmol) and triethylamine (0.064 mL; 0.462 mmol) in ethanol (1.5 mL), 1-methyl-4-phenyl-1H-pyrazole-3-carbaldehyde (0.171 g; 0.918 mmol) and a solution of 5-methoxy-N-((6-methoxypyridin-3-yl)methylene)pyridin-3-amine (0.918 mmol) in ethanol (1 mL), heated at 70° C. for 18 h. The residue was purified by flash chromatography on silica gel using a gradient of ethyl acetate (30% to 100%) in dichloromethane. Further purification by flash chromatography on silica gel using a gradient of methanol (0% to 7%) in dichloromethane furnished 0.030 g (8%) of the desired compound as a beige solid. ESI/APCI(+): 430 (M+H). ESI/APCI(−): 428 (M−H).

Example 13: Preparation of 2-((3-methoxyphenyl)amino)-1-(1-methyl-4-phenyl-1H-pyrazol-3-yl)-2-(pyrazolo[1,5-a]pyridin-2-yl)ethanone Step 1:
A solution of 3-methoxy-N-(pyrazolo[1,5-a]pyridin-2-ylmethylene)aniline in ethanol was prepared according to general procedure C from a mixture of pyrazolo[1,5-a]pyridine-2-carbaldehyde (0.073 g; 0.499 mmol) and m-anidisine (0.056 mL; 0.501 mmol) in ethanol (0.5 mL), heated at 60° C. for 6 h.

Step 2:
1-(4-Bromo-1-methyl-1H-pyrazol-3-yl)-2-((3-methoxyphenyl)amino)-2-(pyrazolo[1,5-a]pyridin-2-yl)ethanone was prepared according to general procedure D from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1.5 mL), 4-bromo-1-methyl-1H-pyrazole-3-carboxaldehyde (0.189 g, 1.000 mmol) and a solution of 3-methoxy-N-(pyrazolo[1,5-a]pyridin-2-ylmethylene)aniline (0.999 mmol) in ethanol (1 mL), heated at 70° C. for 18 h. Purification by flash chromatography on silica gel using a gradient of ethyl acetate (15% to 70%) in heptane furnished 0.277 g (63%) of the desired compound as a beige solid. ESI/APCI(+): 440, 442 (M+H).

Step 3:
2-((3-Methoxyphenyl)amino)-1-(1-methyl-4-phenyl-1H-pyrazol-3-yl)-2-(pyrazolo[1,5-a]pyridin-2-yl)ethanone was prepared according to general procedure F from 1-(4-bromo-1-methyl-1H-pyrazol-3-yl)-2-((3-methoxyphenyl)amino)-2-(pyrazolo[1,5-a]pyridin-2-ypethanone (0.100 g; 0.227 mmol), benzeneboronic acid (0.041 g; 0.341 mmol), potassium fluoride (0.053 g; 0.908 mmol) and tetrakis(triphenylphosphine)palladium(0) (0.026 g; 0.023 mmol) in a mixture of DME (3 mL) and water (0.75 mL). Purification by flash chromatography on silica gel using a gradient of ethyl acetate (15% to 70%) in heptane furnished 0.074 g (76%) of the desired compound as a beige solid. ESI/APCI(+): 438 (M+H). $^1$H NMR (DMSO-$d_6$) δ 8.61 (1H, d); 8.06 (1H, s); 7.64 (1H, d); 7.46 (2H, m); 7.23-7.40 (3H, m); 7.18 (1H, t); 6.96 (1H, t); 6.78 (1H, t); 6.62 (2H, m); 6.38 (2H, m); 6.30 (1H, d); 6.15 (1H, d); 4.01 (3H, s); 3.63 (3H, s).

Example 14: Preparation of 4-(3-(2-((3-methoxyphenyl)amino)-2-(pyrazolo[1,5-a]pyridin-2-yl)acetyl)-1-methyl-1H-pyrazol-4-yl)benzonitrile 4-(3-(2-((3-Methoxyphenyl)amino)-2-(pyrazolo[1,5-a]pyridin-2-ypacetyl)-1-methyl-1H-pyrazol-4-yl)benzonitrile was prepared according to general procedure G from 1-(4-bromo-1-methyl-1H-pyrazol-3-yl)-2-((3-methoxyphenyl)amino)-2-(pyrazolo[1,5-a]pyridin-2-ypethanone (0.080 g; 0.182 mmol), 4-cyanophenylboronic acid (0.040 g; 0.273 mmol), potassium fluoride (0.042 g; 0.727 mmol) and tetrakis(triphenylphosphine)palladium(0) (0.021 g; 0.018 mmol) in a mixture of DME (3 mL) and water (0.75 mL). Purification by flash chromatography on silica gel using a gradient of ethyl acetate (15% to 70%) in heptane furnished 0.057 g (68%) of the desired compound as a beige solid. ESI/APCI(+): 463 (M+H). ESI/APCI(−): 461 (M−H). $^1$H NMR (DMSO-$d_6$) δ 8.61 (1H, d); 8.22 (1H, s); 7.83 (2H, m); 7.57-7.74 (3H, m); 7.12-7.25 (1H, m); 6.96 (1H, t); 6.85 (1H, t); 6.55-6.70 (2H, m); 6.37 (3H, m); 6.16 (1H, d); 4.01 (3H, s); 3.63 (3H, s).

Example 15: Preparation of 2-((3,5-dimethoxyphenyl)amino)-1-(1-methyl-4-phenyl-1H-pyrazol-3-yl)-2-(p-tolyl)ethanone Step 1:
A solution of 3,5-dimethoxy-N-(4-methylbenzylidene)aniline in ethanol was prepared according to general procedure C from a mixture of p-tolualdehyde (0.118 mL; 1.000 mmol) and 3,5-dimethoxyaniline (0.153 g; 0.999 mmol) in ethanol (2 mL), heated at 60° C. for 6.5 h.

Step 2:
1-(4-Bromo-1-methyl-1H-pyrazol-3-yl)-2-((3,5-dimethoxyphenyl)amino)-2-(p-tolypethanone was prepared according to general procedure D from a mixture of 3-benzyl-5-(2-hydroxyethyl)-4-methylthiazol-3-ium chloride (0.135 g; 0.500 mmol) and triethylamine (0.069 mL; 0.498 mmol) in ethanol (0.735 mL), 4-bromo-1-methyl-1H-pyrazole-3-carboxaldehyde (0.205 g, 1.085 mmol) and a solution of 3,5-dimethoxy-N-(4-methylbenzylidene)aniline (0.999 mmol) in ethanol (2 mL) and dichloromethane (1 mL), heated at 70° C. for 25 h. Purification by flash chromatography on silica gel using a gradient of ethyl acetate (0% to 100%) in heptane furnished 0.063 g (15%) of the desired compound as a yellow foam. ESI/APCI(+): 444, 446 (M+H).

Step 3:
2-((3,5-Dimethoxyphenyl)amino)-1-(1-methyl-4-phenyl-1H-pyrazol-3-yl)-2-(p-tolypethanone was prepared according to general procedure F from 1-(4-bromo-1-methyl-1H-pyrazol-3-yl)-2-((3,5-dimethoxyphenyl)amino)-2-(p-tolypethanone (0.063 g; 0.142 mmol), benzeneboronic acid (0.066 g; 0.213 mmol), potassium fluoride (0.030 g; 0.516 mmol) and tetrakis(triphenylphosphine)palladium(0) (0.016 g; 0.014 mmol) in a mixture of dioxane (2.3 mL) and water (0.6 mL). Purification by flash chromatography on silica gel using a gradient of ethyl acetate (20% to 60%) in heptane furnished 0.028 g (45%) of the desired compound as a beige solid. ESI/APCI(+): 442 (M+H); 464 (M+Na). ESI/APCIN: 440 (M−H). $^1$H NMR (DMSO-$d_6$) δ 8.04 (1H, s); 7.2-7.4 (7H, m); 7.12 (2H, m); 6.30 (2H, m); 5.91 (2H, s); 5.72 (1H, s); 4.02 (3H, s); 3.60 (3H, s); 1.99 (3H, s).

Example 16: Preparation of 1-(4-(benzo[d]thiazol-5-yl)-1-methyl-1H-pyrazol-3-yl)-2-((3-methoxyphenyl)amino)-2-(6-methoxypyridin-3-yl)ethanone Step 1:
A solution of 3-methoxy-N-((6-methoxypyridin-3-yl)methylene)aniline in ethanol was prepared according to general procedure C from a mixture of 6-methoxypyridine-3-carboxaldehyde (0.411 g; 2.98 mmol) and m-anisidine (0.336 mL; 3.00 mmol) in ethanol (6 mL), heated at 60° C. for 6.5 h.

Step 2:
1-(4-Bromo-1-methyl-1H-pyrazol-3-yl)-2-((3-methoxyphenyl)amino)-2-(6-methoxypyridin-3-yl)ethanone was prepared according to general procedure D from a mixture of 3-benzyl-5-(2-hydroxyethyl)-4-methylthiazol-3-ium chloride (0.405 g; 1.50 mmol) and triethylamine (0.207 mL; 1.49 mmol) in ethanol (2.2 mL), 4-bromo-1-methyl-1H-pyrazole-3-carboxaldehyde (0.615 g, 3.25 mmol) and a solution of 3-methoxy-N-((6-methoxypyridin-3-yl)methylene)aniline (2.98 mmol) in ethanol (6 mL), heated at 70° C. for 22 h. Purification by flash chromatography on silica gel using a gradient of ethyl acetate (40% to 100%) in heptane furnished 0.776 g (60%) of the desired compound as a yellow solid. ESI/APCI(+): 431, 433 (M+H). $^1$H NMR (DMSO-$d_6$) δ 8.28 (1H, s); 8.14 (1H, s); 7.75 (1H, d); 6.94 (1H, t); 6.80 (1H, d); 6.47 (1H, d); 6.27 (2H, s); 6.1-6.25 (2H, m); 3.99 (3H, s); 3.80 (3H, s); 3.62 (3H, s).

Step 3:
1-(4-(Benzo[d]thiazol-5-yl)-1-methyl-1H-pyrazol-3-yl)-2-((3-methoxyphenyl)amino)-2-(6-methoxypyridin-3-yl)ethanone was prepared according to general procedure F from 1-(4-bromo-1-methyl-1H-pyrazol-3-yl)-2-((3-methoxyphenyl)amino)-2-(6-methoxypyridin-3-yl)ethanone (0.120 g; 0.278 mmol), benzothiazole-5-boronic acid pinacol ester (0.109 g; 0.417 mmol), potassium fluoride (0.058 g; 0.998 mmol) and tetrakis(triphenylphosphine)palladium(0) (0.032 g; 0.028 mmol) in a mixture of dioxane (4.5 mL) and water (1.1 mL). Purification by flash chromatography on silica gel using a gradient of ethyl acetate (20% to 80%) in heptane followed by purification by preparative TLC using ethyl acetate (70%) in heptane as eluent furnished 0.042 g (31%) of the desired compound as a yellow foam. ESI/APCI(+): 486 (M+H); 508 (M+Na). ESI/APCI(−): 484 (M−H). $^1$H NMR (DMSO-$d_6$) δ 9.40 (1H, s); 8.33 (1H, s); 8.21 (1H, s); 8.14 (1H, m); 7.79 (1H, d); 7.50 (1H, d); 6.95 (1H, t); 6.80 (1H, d); 6.33 (2H, m); 6.30 (2H, s); 6.17 (1H, d); 4.06 (3H, s); 3.80 (3H, s); 3.63 (3H, s).

Example 17: Preparation of 1-(4-(2,3-dihydrobenzofuran-5-yl)-1-methyl-1H-pyrazol-3-yl)-2-((3-methoxyphenyl)amino)-2-(6-methoxypyridin-3-yl)ethanone 1-(4-(2,3-Dihydrobenzofuran-5-yl)-1-methyl-1H-pyrazol-3-yl)-2-((3-methoxyphenyl)amino)-2-(6-methoxypyridin-3-yl)ethanone was prepared according to general procedure F from 1-(4-bromo-1-methyl-1H-pyrazol-3-yl)-2-((3-methoxyphenyl)amino)-2-(6-methoxypyridin-3-yl)ethanone (0.120 g; 0.278 mmol), 2,3-dihydro-1-benzofuran-5-ylboronic acid (0.068 g; 0.415 mmol), potassium fluoride (0.058 g; 0.998 mmol) and tetrakis(triphenylphosphine)palladium(0) (0.032 g; 0.028 mmol) in a mixture of dioxane (4.5 mL) and water (1.1 mL). Purification by flash chromatography on silica gel using a gradient of ethyl acetate (30% to 70%) in heptane followed by a second purification by flash chromatography using a gradient of ethyl acetate (30% to 70%) in heptane furnished 0.034 g (26%) of the desired compound as a white solid. ESI/APCI(+): 471 (M+H); 493 (M+Na). ESI/APCI(−): 469 (M−H). $^1$H NMR (DMSO-$d_6$) δ 8.29 (1H, s); 7.97 (1H, s); 7.76 (1H, d); 7.29 (1H, s); 7.12 (1H, d); 6.94 (1H, t); 6.75 (2H, m); 6.43 (1H, m); 6.29 (3H, m); 6.14 (1H, d); 4.52 (2H, t); 4.01 (3H, s); 3.79 (3H, s); 3.62 (3H, s); 3.15 (2H, t).

Example 18: Preparation of 2-((3-methoxyphenyl)amino)-2-(6-methoxypyridin-3-yl)-1-(1-methyl-4-(thiophen-2-yl)-1H-pyrazol-3-ypethanone 2-((3-Methoxyphenyl)amino)-2-(6-methoxypyridin-3-yl)-1-(1-methyl-4-(thiophen-2-yl)-1H-pyrazol-3-yl)ethanone was prepared according to general procedure F from 1-(4-bromo-1-methyl-1H-pyrazol-3-yl)-2-((3-methoxyphenyl)amino)-2-(6-methoxypyridin-3-yl)ethanone (0.120 g; 0.278 mmol), thiophene-2-boronic acid (0.053 g; 0.414 mmol), potassium fluoride (0.058 g; 0.998 mmol) and tetrakis(triphenylphosphine)palladium(0) (0.032 g; 0.028 mmol) in a mixture of dioxane (4.5 mL) and water (1.1 mL). Purification by flash chromatography on silica gel using a gradient of ethyl acetate (20% to 60%) in heptane followed by crystallization from ethyl acetate and heptane furnished 0.015 g (12%) of the desired compound as a yellow solid. ESI/APCI(+): 435 (M+H). $^1$H NMR (DMSO-$d_6$) δ 8.29 (1H, s); 8.25 (1H, s); 7.78 (1H, d); 7.49 (2H, m); 7.05 (1H, t); 6.95 (1H, t); 6.76 (2H, d); 6.50 (1H, d); 6.30 (3H, m); 6.15 (1H, d); 4.02 (3H, s); 3.79 (3H, s); 3.62 (3H, s).

Example 19: Preparation of 2-((3-methoxyphenyl)amino)-1-(1-methyl-4-(6-methylpyridin-3-yl)-1H-pyrazol-3-yl)-2-phenylethanone 2-((3-Methoxyphenyl)amino)-1-(1-methyl-4-(6-methylpyridin-3-yl)-1H-pyrazol-3-yl)-2-phenylethanone was prepared according to general procedure G from 1-(4-bromo-1-methyl-1H-pyrazol-3-yl)-2-((3-methoxy phenyl)amino)-2-phenylethanone (0.120 g; 0.300 mmol), 2-methyl-5-(4,4,5,5-tetramethyl-1,3,2-dioxaborolan-2-yl)pyridine (0.104 g; 0.475 mmol), potassium fluoride (0.070 g; 1.205 mmol) and tetrakis(triphenylphosphine)palladium(0) (0.044 g; 0.038 mmol) in a mixture of dioxane (4 mL) and water (1 mL). Purification by flash chromatography on silica gel using a gradient of ethyl acetate (50% to 100%) in heptane followed by purification by preparative HPLC (XBridge column; method 1) furnished 0.071 g (57%) of the desired compound as a yellow solid. ESI/APCI(+): 413 (M+H).

Example 20: Preparation of 1-(4-(3,5-dimethylisoxazol-4-yl)-1-methyl-1H-pyrazol-3-yl)-2-((3-methoxyphenyl)amino)-2-(p-tolyl)ethanone 1-(4-(3,5-Dimethylisoxazol-4-yl)-1-methyl-1H-pyrazol-3-yl)-2-((3-methoxyphenyl)amino)-2-(p-tolypethanone was prepared according to general procedure F from 1-(4-bromo-1-methyl-1H-pyrazol-3-yl)-2-((3-methoxyphenyl)amino)-2-(p-tolypethanone (0.120 g; 0.290 mmol), (3,5-dimethylisoxazol-4-yl)boronic acid (0.062 g; 0.440 mmol), potassium fluoride (0.070 g; 1.205 mmol) and tetrakis(triphenylphosphine)palladium(0) (0.035 g; 0.030 mmol) in a mixture of dioxane (4 mL) and water (1 mL). The residue was purified by flash chromatography on silica gel using a gradient of ethyl acetate (50% to 100%) in heptane. Further purification by flash chromatography on silica gel using a gradient of ethyl acetate (0% to 50%) in heptane followed by purification by preparative HPLC (XBridge column; method 1) furnished 0.045 g (36%) of the desired compound as a yellow solid. ESI/APCI(+): 431 (M+H).

Example 21: Enantiomers separation of 2-((3-methoxyphenyl)amino)-1-(1-methyl-4-phenyl-1H-pyrazol-3-yl)-2-phenylethanone leading to (−)-2-((3-methoxyphenyl)amino)-1-(1-methyl-4-phenyl-1H-pyrazol-3-yl)-2-phenylethanone and (+)-2-((3-methoxyphenyl)amino)-1-(1-methyl-4-phenyl-1H-pyrazol-3-yl)-2-phenylethanone 2-((3-Methoxyphenyl)amino)-1-(1-methyl-4-phenyl-1H-pyrazol-3-yl)-2-phenylethanone was separated into its enantiomers and purified by preparative HPLC (ChiralPak column; method 3). Under these conditions, the two enantiomers were obtained:
faster eluting enantiomer: $t_r$=8.6 min; ee>95%
slower eluting enantiomer $t_r$=14.2 min; ee>95%.

Example 22: Preparation of 2-((3-methoxyphenyl)amino)-2-phenyl-1-(4-phenyl-1H-pyrazol-3-yl)ethanone Step 1:
4-Phenyl-1H-pyrazole-3-carbaldehyde was prepared according to general procedure F from 4-bromo-1H-pyrazole-3-carbaldehyde (0.200 g; 1.14 mmol), benzeneboronic acid (0.209 g; 1.71 mmol), potassium fluoride (0.266 g; 4.57 mmol) and tetrakis(triphenylphosphine)palladium(0) (0.132 g; 0.114 mmol) in a mixture of DME (16 mL) and water (4 mL). Purification by flash chromatography on silica gel using a gradient of ethyl acetate (5% to 50%) in heptane furnished 0.078 g (40%) of the desired compound as a white solid. ESI/APCI(−): 171 (M−H).
Step 2:
2-((3-Methoxyphenyl)amino)-2-phenyl-1-(4-phenyl-1H-pyrazol-3-yl)ethanone was prepared according to general procedure D from a mixture of 3-benzyl-5-(2-hydroxyethyl)-4-methylthiazol-3-ium chloride (0.110 g; 0.407 mmol) and triethylamine (0.057 mL; 0.407 mmol) in ethanol (1 mL), 4-phenyl-1H-pyrazole-3-carbaldehyde (0.140 g, 0.813 mmol) and a solution of N-benzylidene-3-methoxyaniline (0.813 mmol) in ethanol (1 mL), heated at 70° C. for 18 h. The residue was purified by flash chromatography on silica gel using a gradient of ethyl acetate (5% to 50%) in heptane. Further purification by flash chromatography on silica gel using a gradient of ethyl acetate (2% to 40%) in heptane followed by purification by preparative HPLC (XBridge column; method 2) furnished 0.012 g (4%) of the desired compound as a beige solid. ESI/APCI(−): 171 (M−H).

Example 23: Preparation of 2-((3-methoxyphenyl)amino)-2-phenyl-1-(4-phenyl-1H-pyrrol-3-yl)ethanone Step 1:
To a solution of ethyl 4-phenyl-1H-pyrrole-3-carboxylate (0.500 g; 2.32 mmol) in acetonitrile (15 mL) were added di-tert-butyl dicarbonate (0.610 g; 2.79 mmol) and DMAP (0.026 g; 0.213 mmol). The reaction mixture was stirred overnight at room temperature and was concentrated under reduced pressure. The residue was partitioned between dichloromethane and a saturated ammonium chloride solution. The phases were separated. The organic phase was washed with a 1M sodium bicarbonate solution and brine, dried over magnesium sulfate, filtered and concentrated under reduced pressure. The residue was purified by flash chromatography on silica gel using ethyl acetate (30%) in heptane as eluant to furnish 0.643 g (88%) of 1-tert-butyl 3-ethyl 4-phenyl-1H-pyrrole-1,3-dicarboxylate as a white solid. $^1$H NMR (DMSO-d$_6$) δ 7.82 (1H, s); 7.45-7.33 (6H, m); 4.16 (2H, q); 1.59 (9H, s); 1.19 (3H, t).
Step 2:
To a solution of 1-tert-butyl 3-ethyl 4-phenyl-1H-pyrrole-1,3-dicarboxylate (0.643 g; 2.04 mmol) in dichloromethane (20 mL) cooled at −78° C. was added a 1M DIBALH solution in hexane (4.50 mL; 4.50 mmol). The reaction mixture was allowed to warm to 0° C. and stirring was continued for 1 h. The reaction mixture was diluted with ethyl acetate and a 1N Rochelle salt solution was added. After 30 min stirring at room temperature, the phases were separated. The organic phase was washed with brine, dried over magnesium sulfate, filtered and concentrated under reduced pressure to furnish 0.505 g (91%) of tert-butyl 3-(hydroxymethyl)-4-phenyl-1H-pyrrole-1-carboxylate as a pale pink oil. The crude product was used in the next step without further purification.
Step 3:
A mixture of tert-butyl 3-(hydroxymethyl)-4-phenyl-1H-pyrrole-1-carboxylate (0.505 g; 1.85 mmol) and manganese dioxide (1.650 g; 19.0 mmol) in DMSO (8 mL) was stirred at 50° C. for 6 h. The reaction mixture was allowed to cool to room temperature and stirring was continued for 60 h. The solution was filtered through celite. The filtrate was diluted with ethyl acetate and was washed with water. The organic phase was washed with brine, dried over magnesium sulfate, filtered and concentrated under reduced pressure. Purification by flash chromatography on silica gel using a gradient of ethyl acetate (0% to 20%) in heptane furnished 0.149 g (30%) of tert-butyl 3-formyl-4-phenyl-1H-pyrrole-1-carboxylate as a white solid. $^1$H NMR (DMSO-d$_6$) δ: 9.88 (1H, s); 8.20 (1H, d); 7.58 (2H, d); 7.53 (1H, d); 7.41-7.32 (3H, m); 1.61 (9H, s).
Step 4:
2-((3-Methoxyphenyl)amino)-2-phenyl-1-(4-phenyl-1H-pyrrolo-3-yl)ethanone was prepared according to general procedure E from a mixture of 3-benzyl-5-(2-hydroxyethyl)-4-methylthiazolium chloride (0.070 g; 0.259 mmol) and triethylamine (0.060 mL; 0.430 mmol) in ethanol (1 mL), tert-butyl 3-formyl-4-phenyl-1H-pyrrole-4-carboxylate (0.149 g; 0.549 mmol) and N-benzylidene-3-methoxyaniline (0.601 mmol) in ethanol (1.5 mL). Purification by flash chromatography on silica gel using a gradient of ethyl acetate (0% to 50%) in heptane followed by purification by preparative HPLC (XBridge column, method 1) furnished 0.010 g (5%) of the desired compound. ESI/APCI(+): 383 (M+H). ESI/APCIN: 381 (M−H).

Example 24: Preparation of 2-((3-methoxyphenyl)amino)-2-phenyl-1-(4-phenylthiophen-3-yl)ethanone Step 1:
1-(4-Bromothiophen-3-yl)-2-((3-methoxyphenyl)amino)-2-phenylethanone was prepared according to general procedure D from a mixture of 3-benzyl-5-(2-hydroxyethyl)-4-methylthiazol-3-ium chloride (0.135 g; 0.500 mmol) and triethylamine (0.069 mL; 0.498 mmol) in ethanol (0.735 mL), 4-bromothiophene-3-carboxaldehyde (0.229 g, 1.199 mmol) and a solution of N-benzylidene-3-methoxy aniline (0.996 mmol) in ethanol (0.735 mL), heated at 70° C. for 64 h. The residue was purified by flash chromatography on silica gel using a gradient of ethyl acetate (0% to 100%) in heptane. Further purification by flash chromatography on silica gel using a gradient of ethyl acetate (10% to 50%) in heptane followed by crystallization from ethyl acetate and heptane furnished 0.014 g (15%) of the desired compound as a yellow solid. ESI/APCI(+): 402, 404 (M+H).
Step 2:
2-((3-Methoxyphenyl)amino)-2-phenyl-1-(4-phenylthiophen-3-yl)ethanone was prepared according to general procedure F from 1-(4-bromothiophen-3-yl)-2-((3-methoxyphenyl)amino)-2-phenylethanone (0.058 g; 0.144 mmol), benzeneboronic acid (0.026 g; 0.213 mmol), potassium fluoride (0.033 g; 0.568 mmol) and tetrakis(triphenylphosphine)palladium(0) (0.017 g; 0.015 mmol) in a mixture of dioxane (2.3 mL) and water (0.6 mL). Purification by flash chromatography on silica gel using a gradient of ethyl acetate (10% to 30%) in heptane followed by purification by preparative HPLC (XBridge column; method 1) furnished 0.028 g (49%) of the desired compound as a white foam. ESI/APCI(+): 400 (M+H); 422 (M+Na). ESI/APCIN: 398 (M−H). $^1$H NMR (DMSO-d$_6$) δ 8.98 (1H, d); 7.49 (3H, m); 7.35 (2H, m); 7.26 (4H, m); 6.91 (3H, m); 6.33 (3H, m); 6.18 (1H, d); 6.11 (1H, d); 3.62 (3H, s).

Example 25: Preparation of 2-((3-methoxyphenyl)amino)-1-(1-methyl-3-phenyl-1H-pyrazol-4-yl)-2-phenylethanone 2-((3-Methoxyphenyl)amino)-1-(1-methyl-3-phenyl-1H-pyrazol-4-yl)-2-phenylethanone was prepared according to general procedure D from a mixture of 3-benzyl-5-(2-hydroxyethyl)-4-methylthiazol-3-ium chloride (0.091 g; 0.337 mmol) and triethylamine (0.070 mL; 0.502 mmol) in ethanol (0.5 mL), 1-methyl-3-phenyl-1H-pyrazole-4-carbaldehyde (0.122 g; 0.655 mmol) and a solution of N-benzylidene-3-methoxyaniline (0.757 mmol) in ethanol (1.5 mL), heated at 60° C. for 16 h. Purification by flash chromatography on silica gel using a gradient of ethyl acetate (0% to 50%) in heptane followed purification by preparative HPLC (XBridge column; method 20% acid) furnished 0.053 g (20%) of the desired compound as a white solid. ESI/APCI(+): 398 (M+H). ESI/APCI(−): 396 (M−H).

Example 26: Preparation of 2-((3,5-dimethoxyphenyl)amino)-1-(2-phenylpiperidin-1-yl)-2-(p-tolypethanone Step 1:
To a solution of ethyl p-tolylacetate (2.97 mL; 16.8 mmol) in carbon tetrachloride (17 mL) was added portionwise NBS (3.30 g; 18.5 mmol). After addition of a few drops of a 48% hydrobromic acid solution, the reaction mixture was refluxed for 4 h. The reaction mixture was cooled to room temperature and filtered. The solids were washed with carbon tetrachloride and the filtrate was concentrated under reduced pressure. The residue was dissolved in acetonitrile (42 mL). After addition of 3,5-dimethoxyaniline (6.50 g; 42.4 mmol), the reaction mixture was refluxed overnight and was concentrated under reduced pressure. The residue was partitioned between ethyl acetate and a 1N hydrochloric acid solution. The organic phase was washed with a saturated sodium bicarbonate solution, water and brine, dried over sodium sulfate, filtered and concentrated under reduced pressure. The residue was purified by flash chromatography on silica gel using a gradient of ethyl acetate (20% to 90%) in heptane to furnish 0.737 g (13%) of ethyl 2-((3,5-dimethoxyphenyl)amino)-2-(p-tolyl)acetate as a white solid. ESI/APCI(+): 330 (M+H). $^1$H NMR (DMSO-d$_6$) δ 7.38 (2H, m); 7.18 (2H, m); 6.27 (1H, d); 5.89 (2H, s); 5.77 (1H, s); 5.12 (1H, d); 4.10 (2H, m); 3.63 (6H, s); 2.29 (3H, s); 1.13 (3H, t).

Step 2:

To a mixture of ethyl 2-((3,5-dimethoxyphenyl)amino)-2-(p-tolyl)acetate (0.721 g; 2.19 mmol) in methanol (9 mL), THF (9 mL) and water (9 mL) was added lithium hydroxide (0.280 g; 11.7 mmol). The reaction mixture was stirred at room temperature for 2.5 h. The organic solvents were removed under reduced pressure. The residue was acidified with a 3M hydrochloric acid solution and extracted with ethyl acetate. The organic phase was dried over sodium sulfate, filtered and concentrated under reduced pressure to furnish quantitatively 0.663 g of 2-((3,5-dimethoxyphenyl)amino)-2-(p-tolyl)acetic acid as a beige solid. ESI/APCI(+): 302 (M+H). ESI/APCI(−): 300 (M−H). $^1$H NMR (DMSO-d$_6$) δ 12.8 (1H, brs); 7.36 (2H, m); 7.15 (2H, m); 6.20 (1H, brs); 5.86 (2H, s); 5.73 (1H, s); 4.99 (1H, s); 3.60 (6H, s); 2.28 (3H, s).

Step 3:

2-((3,5-Dimethoxyphenyl)amino)-1-(2-phenylpiperidin-1-yl)-2-(p-tolyl)ethanone was prepared according to general procedure A from 2-((3,5-dimethoxyphenyl)amino)-2-(p-tolyl)acetic acid (0.070 g; 0.232 mmol), 2-phenylpiperidine (0.040 g; 0.248 mmol), triethylamine (0.150 mL; 1.082 mmol) and HATU (0.090 g; 0.237 mmol) in dichloromethane (3 mL). Purification by flash chromatography on silica gel using a gradient of ethyl acetate (0% to 20%) in heptane furnished 0.040 g (39%) of the desired compound as a white solid. ESI/APCI(+): 445 (M+H).

Example 27: Preparation of 2-((3,5-dimethoxyphenyl)amino)-1-(2-phenylpyrrolidin-1-yl)-2-(p-tolyl)ethanone 2-((3,5-Dimethoxyphenyl)amino)-1-(2-phenylpyrrolidin-1-yl)-2-(p-tolyl)ethanone was prepared according to general procedure A from 2-((3,5-dimethoxyphenyl)amino)-2-(p-tolyl)acetic acid (0.080 g; 0.265 mmol), 2-phenylpyrrolidine (0.041 g; 0.278 mmol), triethylamine (0.220 mL; 1.587 mmol) and HATU (0.101 g; 0.265 mmol) in dichloromethane (2.9 mL). Purification by flash chromatography on silica gel using a gradient of ethyl acetate (20% to 60%) in heptane furnished 0.070 g (61%) of the desired compound as a white foam. ESI/APCI(+): 431 (M+H); 453 (M+Na).

Example 28: Preparation of 2-((3-methoxyphenyl)amino)-1-(2-methyl-4-phenylthiazol-5-yl)-2-phenylethanone 2-((3-Methoxyphenyl)amino)-1-(2-methyl-4-phenylthiazol-5-yl)-2-phenylethanone was prepared according to general procedure D from a mixture of 3-benzyl-5-(2-hydroxyethyl)-4-methylthiazol-3-ium chloride (0.135 g; 0.500 mmol) and triethylamine (0.069 mL; 0.498 mmol) in ethanol (0.735 mL), 2-methyl-4-phenyl-1,3-thiazole-5-carboxaldehyde (0.244 g; 1.200 mmol) and a solution of N-benzylidene-3-methoxyaniline (0.996 mmol) in ethanol (2 mL), heated at 70° C. for 16 h. Purification by flash chromatography on silica gel using a gradient of ethyl acetate (20% to 50%) in heptane followed by purification by crystallization from ethyl acetate and heptane furnished 0.013 g (3%) of the desired compound as a white powder. ESI/APCI(+): 415 (M+H). ESI/APCI(−): 413 (M−H). $^1$H NMR (DMSO-d$_6$) δ 7.48 (2H, m); 7.43 (3H, m); 7.31 (5H, m); 6.92 (1H, t); 6.60 (1H, d); 6.16 (3H, m); 5.58 (1H, d); 3.61 (3H, s); 2.70 (3H, s).

Example 29: Preparation of 2-((3,5-dimethoxyphenyl)amino)-1-(4-methyl-2-phenylpiperazin-1-yl)-2-(p-tolyl)ethanone 2-((3,5-Dimethoxyphenyl)amino)-1-(4-methyl-2-phenylpiperazin-1-yl)-2-(p-tolyl)ethanone was prepared according to general procedure A from 2-((3,5-dimethoxyphenyl)amino)-2-(p-tolyl)acetic acid (0.080 g; 0.265 mmol), 1-methyl-3-phenylpiperazine (0.040 g; 0.227 mmol), triethylamine (0.150 mL; 1.082 mmol) and HATU (0.101 g; 0.265 mmol) in dichloromethane (2 mL). Purification by flash chromatography on silica gel using a gradient of ethyl acetate (0% to 20%) in heptane followed by purification by preparative HPLC (XBridge column, method 1) furnished 0.019 g (18%) of the desired compound under its formic acid salt form. ESI/APCI(+): 460 (M+H).

Example 30: Preparation of 2-((3,5-dimethoxyphenyl)amino)-1-(2-phenylazepan-1-yl)-2-(p-tolyl)ethanone 2-((3,5-Dimethoxyphenyl)amino)-1-(2-phenylazepan-1-yl)-2-(p-tolyl)ethanone was prepared according to general procedure A from 2-((3,5-dimethoxyphenyl)amino)-2-(p-tolyl)acetic acid (0.080 g; 0.265 mmol), 2-phenylazepane (0.049 g; 0.280 mmol), triethylamine (0.220 mL; 1.587 mmol) and HATU (0.101 g; 0.265 mmol) in dichloromethane (2.9 mL). Purification by flash chromatography on silica gel using a gradient of ethyl acetate (10% to 30%) in heptane furnished 0.060 g (49%) of the desired compound as a white foam. ESI/APCI(+): 459 (M+H).

Example 31: Preparation of 1-(5-bromo-1-methyl-4-phenyl-1H-pyrrol-3-yl)-2-((3,5-dimethoxyphenyl)amino)-2-phenylethan-1-one Step 1:

To a suspension of sodium hydride (0.049 g; 1.225 mmol) in DMF (1.1 mL) cooled at 0° C. was added dropwise a solution of ethyl 4-phenylpyrrole-3-carboxylate (0.210 g; 0.976 mmol) in DMF (2 mL). After 1 h at room temperature, a solution of methyl iodide (0.072 mL; 1.157 mmol) in DMF (1.9 mL) was added. The reaction mixture was stirred at room temperature overnight. The reaction mixture was poured into cold water and was extracted with ethyl acetate. The organic phase was washed with a saturated sodium bicarbonate solution, water and brine, dried over sodium sulfate, filtered and concentrated under reduced pressure. The residue was purified by flash chromatography on silica gel using a gradient of ethyl acetate (10% to 40%) in heptane to furnish 0.175 g (78%) of ethyl 1-methyl-4-phenyl-1H- pyrrole-3-carboxylate as a yellow oil. ESI/APCI(+): 230 (M+H). $^1$H NMR (DMSO-d$_6$) δ 7.47 (1H, s); 7.41 (2H, m); 7.30 (2H, m); 7.21 (1H, t); 6.91 (1H, s); 4.09 (2H, q); 3.67 (3H, s); 1.19 (3H, t).

Step 2:

To a solution of ethyl 1-methyl-4-phenyl-1H-pyrrole-3-carboxylate (0.170 g; 0.741 mmol) in THF (2.5 mL) cooled at −40° C. were added N,O-dimethylhydroxylamine hydrochloride (0.187 g; 1.917 mmol) and a 2M isopropylmagnesium chloride solution in THF (2 mL; 4.0 mmol). The reaction mixture was allowed to warm to 0° C. over 5 h. The reaction was quenched by addition of a saturated ammonium chloride solution. The reaction mixture was diluted with ethyl acetate. The phases were separated. The organic phase was washed with water and brine, dried over sodium sulfate, filtered and concentrated under reduced pressure. The residue was purified by flash chromatography on silica gel using a gradient of ethyl acetate (30% to 85%) in heptane to furnish 0.148 g (82%) of N-methoxy-N,1-dimethyl-4-phenyl-1H-pyrrole-3-carboxamide as a white oil. ESI/APCI(+): 245 (M+H). $^1$H NMR (DMSO-d$_6$) δ 7.28 (4H, m); 7.15 (2H, m); 6.95 (1H, s); 3.66 (3H, s); 3.53 (3H, s); 3.09 (3H, s).

Step 3:

To a solution of N-methoxy-N,1-dimethyl-4-phenyl-1H-pyrrole-3-carboxamide (0.138 g; 0.565 mmol) in THF (4 mL) cooled at −70° C. was added a 1M benzylmagnesium chloride solution in THF (1.7 mL; 1.7 mmol). The reaction mixture was stirred at −70° C. for 3 h. A 1M benzylmagnesium chloride solution in THF (1.7 mL; 1.7 mmol) was added again. After 3 h at −70° C., a 1M benzylmagnesium chloride solution in THF (1.7 mL; 1.7 mmol) and the reaction mixture was allowed to slowly warm to room temperature and was stirred at room temperature overnight. The reaction was quenched by addition of a saturated ammonium chloride solution. The reaction mixture was diluted with ethyl acetate. The phases were separated. The organic phase was washed with a saturated sodium bicarbonate solution, water and brine, dried over sodium sulfate, filtered and concentrated under reduced pressure. The residue was purified by flash chromatography on silica gel using a gradient of ethyl acetate (20% to 60%) in heptane to furnish 0.095 g (61%) of 1-(1-methyl-4-phenyl-1H-pyrrol-3-yl)-2-phenylethan-1-one as a white oil. ESI/APCI(+): 276 (M+H). $^1$H NMR (DMSO-d$_6$) δ 7.89 (1H, d); 7.1-7.3 (10H, m); 6.92 (1H, d); 3.99 (2H, s); 3.70 (3H, s).

Step 4:

To a solution of 1-(1-methyl-4-phenyl-1H-pyrrol-3-yl)-2-phenylethan-1-one (0.090 g; 0.327 mmol) in THF (4 mL) cooled at 0° C. was added a solution of phenyltrimethylammonium tribromide (0.176 g; 0.468 mmol) in THF (4.9 mL). The reaction mixture was stirred at 0° C. for 1 h and at room temperature for 3 h. A solution of phenyltrimethylammonium tribromide (0.050 g; 0.133 mmol) in THF (1.4 mL) was added and stirring was continued for 3.5 h. 3,5-Dimethoxyaniline (0.507 g; 3.310 mmol) was added and the reaction mixture was stirred at room temperature for 64 h and was refluxed for 6.5 h. The reaction mixture was concentrated under reduced pressure. The residue was partitioned between ethyl acetate and a 1N hydrochloric acid solution. The organic phase was washed with water and brine, dried over sodium sulfate, filtered and concentrated under reduced pressure. Purification by flash chromatography on silica gel using a gradient of ethyl acetate (20% to 60%) in heptane followed by crystallization from ethyl acetate and heptane furnished 0.021 g (13%) of 1-(5-bromo-1-methyl-4-phenyl-1H-pyrrol-3-yl)-2-((3,5-dimethoxyphenyl)amino)-2-phenylethan-1-one as a beige powder. ESI/APCI(+): 505, 507 (M+H). ESI/APCI(−): 503, 505 (M−H). $^1$H NMR (DMSO-d$_6$) δ 8.53 (1H, s); 7.51 (2H, m); 7.2-7.4 (6H, m); 7.11 (2H, m); 6.22 (1H, m); 5.94 (2H, s); 5.83 (1H, m); 5.72 (1H, s); 3.72 (3H, s); 3.62 (6H, s).

Example 32: Preparation of 2-((3,5-dimethoxyphenyl)amino)-1-(3-phenylmorpholino)-2-(p-tolyl)ethan-1-one 2-((3,5-Dimethoxyphenyl)amino)-1-(3-phenylmorpholino)-2-(p-tolyl)ethanone was prepared according to general procedure A from 2-((3,5-dimethoxyphenyl)amino)-2-(p-tolyl)acetic acid (0.061 g; 0.202 mmol), 3-phenylmorpholine (0.040 g; 0.245 mmol), triethylamine (0.115 mL; 0.825 mmol) and HATU (0.087 g; 0.229 mmol) in dichloromethane (2 mL). Purification by flash chromatography on silica gel using a gradient of ethyl acetate (0% to 30%) in heptane furnished 0.029 g (24%) of the desired compound as a white solid. ESI/APCI(+): 447 (M+H).

Example 33: Preparation of 2-((3,5-dimethoxyphenyl)amino)-1-(3-phenylthiomorpholino)-2-(p-tolyl)ethan-1-one 2-((3,5-Dimethoxyphenyl)amino)-1-(3-phenylthiomorpholino)-2-(p-tolyl)ethan-1-one was prepared according to general procedure A from 2-((3,5-dimethoxyphenyl)amino)-2-(p-tolyl)acetic acid (0.080 g; 0.265 mmol), 3-phenylthiomorpholine (0.050 g; 0.279 mmol), triethylamine (0.220 mL; 1.587 mmol) and HATU (0.101 g; 0.265 mmol) in dichloromethane (2.9 mL). Purification by flash chromatography on silica gel using a gradient of ethyl acetate (10% to 40%) in heptane furnished 0.011 g (9%) of the less polar stereoisomers as a white solid and 0.047 g (39%) of the more polar stereoisomers as a white foam. ESI/APCI(+): 463 (M+H).

Example 34: Preparation of 2-((3,5-dimethoxyphenyl)amino)-1-(1,1-dioxido-3-phenylthiomorpholino)-2-(p-tolyl)ethan-1-one 2-((3,5-Dimethoxyphenyl)amino)-1-(1,1-dioxido-3-phenylthiomorpholino)-2-(p-tolyl)ethan-1-one was prepared according to general procedure A from 2-((3,5-dimethoxyphenyl)amino)-2-(p-tolyl)acetic acid (0.080 g; 0.265 mmol), 3-phenyl-1λ$^6$,4-thiomorpholine-1,1-dione (0.058 g; 0.275 mmol), triethylamine (0.220 mL; 1.587 mmol) and HATU (0.101 g; 0.265 mmol) in dichloromethane (2.9 mL). Purification by flash chromatography on silica gel using a gradient of ethyl acetate (30% to 70%) in heptane furnished 0.067 g (51%) of 2-((3,5-dimethoxyphenyl)amino)-1-(1,1-dioxido-3-phenylthiomorpholino)-2-(p-tolyl)ethan-1-one as a white foam. ESI/APCI(+): 495 (M+H). ESI/APCI(−): 493 (M−H).

Without being limiting, some more examples of compounds of the present invention which can be prepared by using similar protocols as described herein are shown in table 1.

Part B

Example 35: Antiviral Activity of the Compounds of the Invention

For Dengue virus: Vero-B or Vero-M cells (5×10$^4$) were seeded in 96-well plates. One day later, culture medium was replaced with 100 μL assay medium containing a 2× serial dilution of the compound (concentration range: 50 μg/mL 0.004 µg/mL) and 100 µL of dengue virus inoculum (DENV). Following a 2 hour incubation period, the cell monolayer was washed 3 times with assay medium to remove residual, non-adsorbed virus and cultures were further incubated for either 4 days (DENV-2 NGC), 5 days (DENV-4 strain H241) or 7 days (DENV-1 Djibouti strain D1/H/IMTSSA/98/606 and DENV-3 strain H87 prototype) in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation.

The antiviral activity of the compounds against DENV-2 NGC is also tested in adenocarcinomic human alveolar basal epithelial cells (A549 cells), using the above described protocol with the difference that less cells/well were seeded ($2 \times 10^4$ cells/well).

For the yellow fever virus: Vero-B cells ($5 \times 10^4$) are seeded in 96-well plates. One day later, culture medium is replaced with 100 µL assay medium containing a 2× serial dilution of the compound (concentration range 50 µg/mL 0.004 µg/mL) and 100 µL of yellow fever virus inoculum (YFV-17D). Following a 2 hour incubation period, the cell monolayer is washed 3 times with assay medium to remove residual, non-adsorbed virus and cultures are further incubated for 4 days in the presence of the compound (inhibitor). Supernatant is harvested and viral RNA load determined by real-time quantitative RT-PCR. The 50% effective concentration ($EC_{50}$), which is defined as the compound concentration that is required to inhibit viral RNA replication by 50%, is determined using logarithmic interpolation.

Quantitative Reverse Transcriptase-PCR (RT-qPCR)

RNA was isolated from 100 µL (or in some circumstances 150 µL) supernatant with the NucleoSpin 96 Virus kit (Macherey-Nagel, Duren, Germany) as described by the manufacturer. The sequences of the TaqMan primers (DENV-For, DENV-Rev, YFV-For, YFV-Rev; Table 2) and TaqMan probes (DENV-Probe and YFV-Probe; Table 2) were selected from non-structural gene 3 (NS3) or NS5, of the respective flaviviruses using Primer Express software (version 2.0; Applied Biosystems, Lennik, Belgium). The TaqMan probe was fluorescently labelled with 6-carboxyfluorescein (FAM) at the 5' end as the reporter dye, and with minor groove binder (MGB) at the 3' end as the quencher (Table 2). One-step, quantitative RT-PCR was performed in a total volume of 25 µL, containing 13.9375 µL $H_2O$, 6.25 µL master mix (Eurogentec, Seraing, Belgium), 0.375 µL forward primer, 0.375 µL reverse primer, 1 µL probe, 0.0625 µL reverse transcriptase (Eurogentec) and 3 µL sample. RT-PCR was performed using the ABI 7500 Fast Real-Time PCR System (Applied Biosystems, Branchburg, N.J., USA) using the following conditions: 30 min at 48° C. and 10 min at 95° C., followed by 40 cycles of 15 s at 95° C. and 1 min at 60° C. The data was analyzed using the ABI PRISM 7500 SDS software (version 1.3.1; Applied Biosystems). For absolute quantification, standard curves were generated using 10-fold dilutions of template preparations of known concentrations.

TABLE 2

Primers and probes used for real-time, quantitative RT-PCR.

| Primer/Probe | Sequence (5'→3')[a] | Source[b] | Target |
|---|---|---|---|
| DENV-For | TCGGAGCCGGAGTTTACAAA (SEQ ID N. 1) | DENV NGC | 2 NS3 |
| DENV-Rev | TCTTAACGTCCGCCCATGAT (SEQ ID N. 2) | | |
| DENV-Probe | *FAM*-ATTCCACACAATGTGGCAT-*MGB* (SEQ ID N. 3) | | |
| DenS | GGATAGACCAGAGATCCTGCTGT (SEQ ID N. 4) | DENV-1,-3,-4 | NS5 |
| DenAS1-3 | CATTCCATTTTCTGGCGTTC (SEQ ID N. 5) | DENV-1,-3 | |
| DenAS4 | CAATCCATCTTGCGGCGCTC (SEQ ID N. 6) | DENV-4 | |
| DEN_1-3 probe | *FAM*-CAGCATCATTCCAGGCACAG-*MGB* (SEQ ID N. 7) | DENV-1,-3 | |
| DEN_4 probe | *FAM*-CAACATCAATCCAGGCACAG-*MGB* (SEQ ID N. 8) | DENV-4 | |
| YFV-For | TGGCATATTCCAGTCAACCTTCT (SEQ ID N. 9) | YFV-17D | NS3 |
| YFV-Rev | GAAGCCCAAGATGGAATCAACT (SEQ ID N. 10) | | |
| YFV-Probe | *FAM*-TTCCACACAATGTGGCATG-*MGB* (SEQ ID N. 11) | | |

[a]Reporter dye (FAM) and quencher (MGB/TAMRA) elements are indicated in bold and italics.
[b]The nucleotide sequence and position of the primers and probes within the genome were deduced from the nucleotide sequence of DENV 2 NGC (GenBank accession no. M29095; Irie et al., 1989), dengue virus serotype 1 Djibouti strain D1/H/IMTSSA/98/606 (Genbank Accession Number AF298808), dengue virus serotype 3 strain H87 prototype (c93130), dengue virus serotype 4 strain H241 (no sequences available) and YFV-17D (GenBank accession no. X03700; Rice et al., 1985).

Cytotoxicity Assay

Potential cytotoxic effects of the compounds were evaluated in uninfected quiescent Vero-B or Vero-M cells. Cells were seeded at $5 \times 10^4$ cells/well in a 96-well plate in the presence of two-fold serial dilutions (ranging from 50 µg/mL 0.004 µg/mL) of compound and incubated for 4 to 7 days. Culture medium was discarded and 100 µL 3-(4,5-dimethylthiazol-2-yl)-5-(3-carboxymethoxyphenyl)-2-(4-sulfophenyl)-2H-tetrazolium/phenazinemethosulfate (MTS/PMS; Promega, Leiden, The Netherlands) in PBS was added to each well. Following a 2-hour incubation period at 37° C., the optical density was determined at 498 nm. Cytotoxic activity was calculated using the following formula: % cell viability=$100 \times (OD_{Compound}/OD_{CC})$, where $OD_{Compound}$ and $OD_{CC}$ correspond to the optical density at 498 nm of the uninfected cell cultures treated with compound and that of uninfected, untreated cell cultures, respectively. The 50% cytotoxic concentration (i.e., the concentration that reduces the total cell number with 50%; $CC_{50}$) was calculated using linear interpolation.

A similar protocol was used to assess cytotoxicity in A549 cells with the difference that cells were seeded at $2 \times 10^4$ cells/well.

Table 3 shows the activity against DENV-2 in Vero-B cells and the cytotoxicity of some example compounds of the invention.

TABLE 3

| Code | EC$_{50}$ (μM) | CC$_{50}$ (μM) | SI |
| --- | --- | --- | --- |
| CPD-001 | 0.323 | >125 | >390 |
| CPD-002 | 0.095 | >120 | >1273 |
| CPD-003 | 1.665 | >125 | >75 |
| CPD-004 | 1.553 | >120 | >77 |
| CPD-005 | 0.383 | >120 | >314 |
| CPD-006 | 0.517 | >120 | >233 |
| CPD-007 | 15.543 | >125 | >8 |
| CPD-008 | 0.096 | >120 | >1248 |
| CPD-009 | 3.289 | >120 | >37 |
| CPD-010 | 2.109 | >121 | >57 |
| CPD-011 | 0.745 | >116 | >156 |
| CPD-012 | 71.251 | >116 | >2 |
| CPD-013 | 0.343 | >114 | >333 |
| CPD-014 | 2.292 | >108 | >47 |
| CPD-015 | 0.016 | >113 | >7257 |
| CPD-016 | 1.874 | >103 | >55 |
| CPD-017 | 1.636 | >106 | >65 |
| CPD-018 | 1.266 | >115 | >91 |
| CPD-019 | 39.881 | 80 | 2 |
| CPD-020 | 13.171 | >116 | >9 |
| CPD-023 | 0.443 | >130 | >294 |
| CPD-024 | 0.207 | 25 | 121 |
| CPD-027 | 1.215 | >112 | >93 |
| CPD-028 | 0.221 | >116 | >526 |
| CPD-238 | 2.817 | >99 | >35 |
| CPD-242 | 1.156 | >109 | >94 |
| CPD-311 | 0.047 | >99 | >2092 |
| CPD-312 | 5.646 | >112 | >20 |
| CPD-313 | 0.951 | >108 | >114 |
| CPD-314 | 4.468 | >101 | >23 |

Table 4 shows the activity against DENY-1 in Vero-B cells and the cytotoxicity of some example compounds of the invention.

TABLE 4

| Code | EC$_{50}$ (μM) | CC$_{50}$ (μM) | SI |
| --- | --- | --- | --- |
| CPD-001 | 2.642 | >126 | >48 |
| CPD-002 | 2.094 | >120 | >57 |
| CPD-003 | 7.012 | 104 | 15 |
| CPD-004 | 9.777 | >120 | >12 |
| CPD-008 | 2.639 | >120 | >46 |
| CPP-013 | 2.240 | >114 | >51 |
| CPD-015 | 0.132 | >113 | >859 |
| CPD-023 | 0.939 | 31 | 33 |
| CPD-024 | 1.526 | 30 | 20 |
| CPD-025 | 3.630 | >125 | >34 |
| CPD-026 | 2.390 | >126 | >53 |
| CPD-027 | 2.085 | >112 | >54 |
| CPD-028 | 17.188 | 70 | 4 |
| CPD-311 | 0.016 | >99 | >6350 |

Table 5 shows the activity against DENV-3 in Vero-B cells and the cytotoxicity of some example compounds of the invention.

TABLE 5

| Code | EC$_{50}$ (μM) | CC$_{50}$ (μM) | SI |
| --- | --- | --- | --- |
| CPD-001 | 2.116 | >126 | >59 |
| CPD-002 | 0.794 | >120 | >151 |
| CPD-008 | 1.010 | >120 | >119 |
| CPD-015 | 0.188 | >113 | >604 |
| CPD-024 | 1.906 | >131 | >69 |
| CPD-027 | 7.230 | 10 | 1 |
| CPD-311 | 0.266 | >99 | >371 |

Table 6 shows the activity against DENV-4 in Vero-M cells and the cytotoxicity of some example compounds of the invention.

TABLE 6

| Code | EC$_{50}$ (μM) | CC$_{50}$ (μM) | SI |
| --- | --- | --- | --- |
| CPD-002 | 8.208 | >120 | >15 |
| CPD-008 | 4.742 | >120 | >25 |
| CPD-015 | 3.148 | >113 | >36 |
| CPD-024 | 1.595 | 10 | 6 |
| CPD-028 | 6.666 | >116 | >17 |

Example 36: In Vivo Activity of the Compounds of the Invention Against Dengue Infection A dengue viremia model in mice as described in Schul W, Liu W, Xu H Y, Flamand M, Vasudevan S G. J. Infect Dis. 2007; 95(5):665-74) (included herein by reference) can be used to examine the in vivo efficacy of compounds. In this model, AG129 mice (lacking alpha/beta interferon and gamma interferon receptors) are intraperitoneally inoculated with 2×10$^6$ plaque-forming units (PFU) of DENV-2 (strain TSV01) on day 0. The infected mice (6 or 8 animals per group) are immediately treated with the compound to test at one or more selected doses via IP, IV or SC injection or via oral administration and the vehicle as a control for three consecutive days. On day 4, blood samples are taken, and viral titers are determined using a plaque assay.

A dengue mortality model in AG129 mice (lacking alpha/beta interferon and gamma interferon receptors) as described in Tan et al (PLoS Negl Trop Dis 2010; 4(4) and Ann Acad Med Singapore 2011; 40:523-32) (included herein by reference) was established to examine the in vivo efficacy of a compound of the invention. Female AG129 mice (B&K Universal, UK), 7-9 weeks old, are divided randomly in 3 test groups (n=4 or 5 per group): 1 infected group that only receives vehicle and 2 infected groups that are treated either with the test compound of the invention (60 mg/kg/day, sc, twice daily, dissolved in a 10% DMSO, 5% Solutol in Saline (0.9%)) or with a reference compound (e.g. Celgosivir (100 mg/kg/day; ip, twice daily, dissolved in 0.9% NaCl)). The mice are subcutaneously inoculated on day 0 with 1×10$^7$ plaque-forming units (PFU) of the non-mouse-adapted DENV-2 strain D2Y98P, a highly infectious strain in AG129 mice, which results in severe disease and eventually death within 2 weeks. The infected mice are subsequently treated BID for multiple consecutive days (e.g. 17 consecutive days) with either vehicle, reference compound (e.g. Celgosivir) or the compound of the invention. Mice are euthanized as soon as they have signs of virus-induced paralysis and/or have lost >=30% bodyweight.

The invention claimed is:

1. A compound of formula (A),

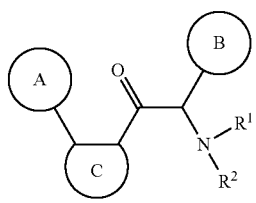

wherein, cycle C is

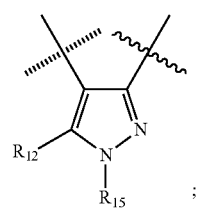

wherein the wavy line (∿) indicates the point of attachment to the carbonyl of the main formula (A) and the hashed line (∥∥∥) indicates the point of attachment to the cycle A of the main formula (A);

cycle A is selected from

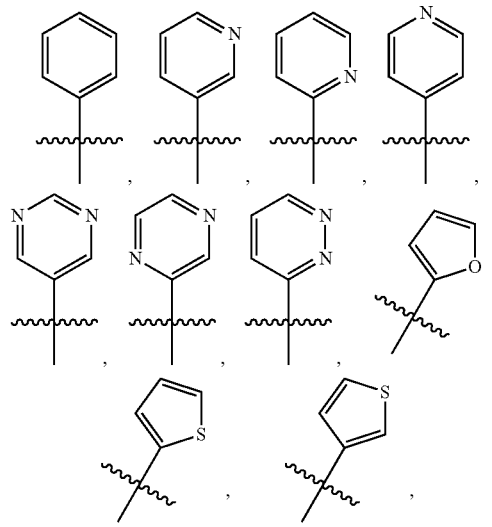

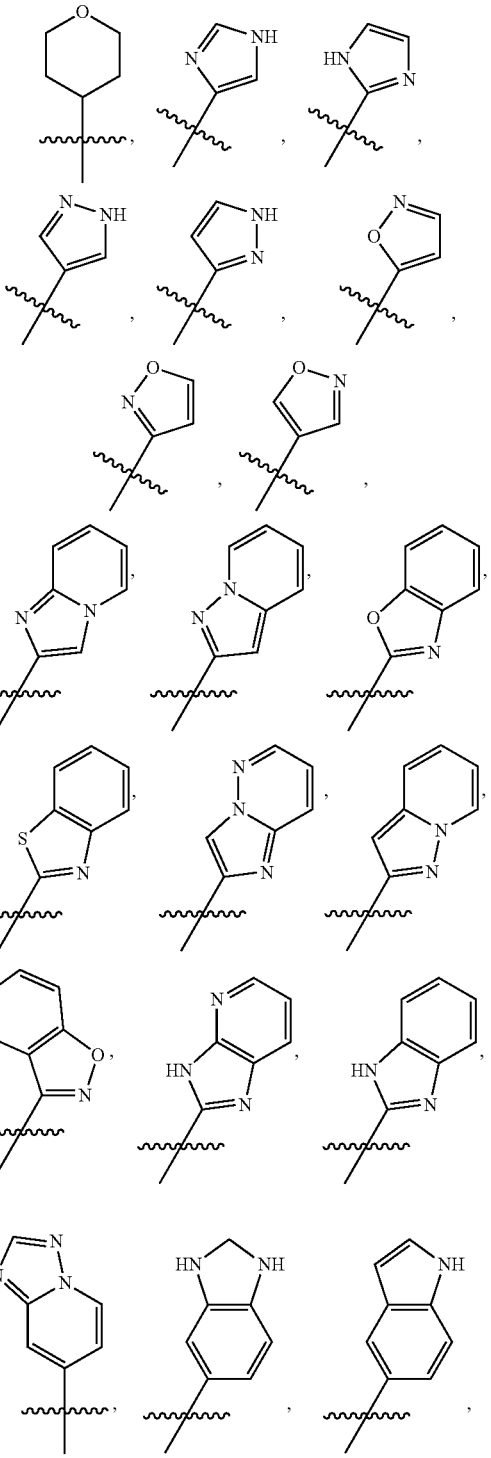

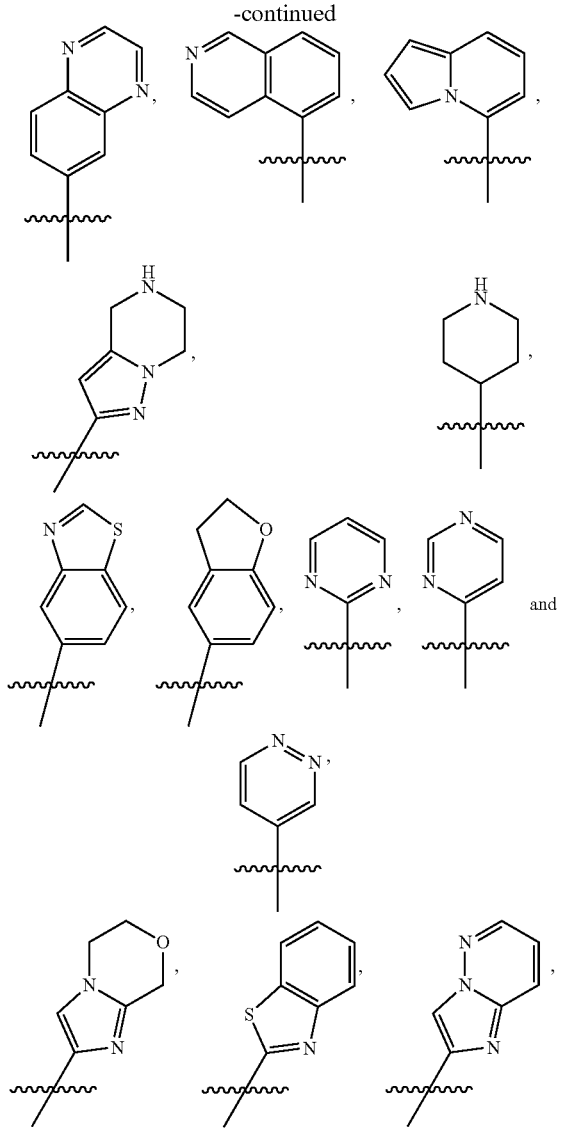
wherein the wavy line (~~~) indicates the point of attachment to the atom of cycle C, and wherein the depicted cycles may be optionally substituted with one, two, or three substituents selected from alkyl, —OCH₃, halogen, trifluoromethyl, —OCF₃, or cyano;
cycle B is selected from
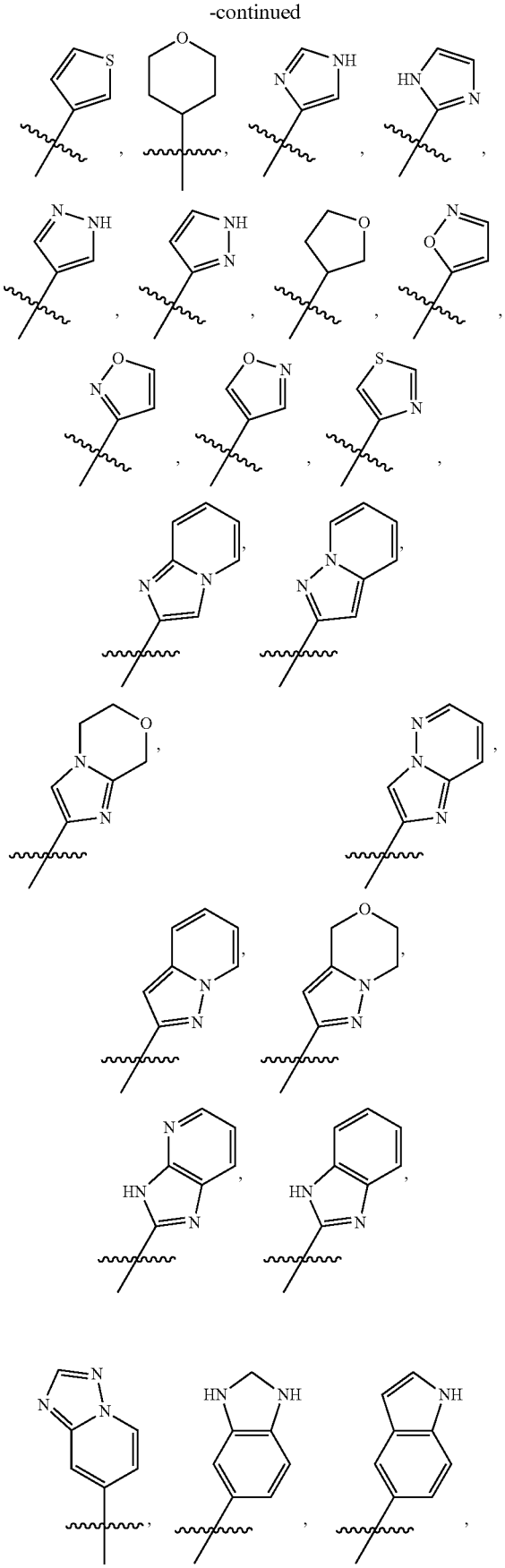

-continued

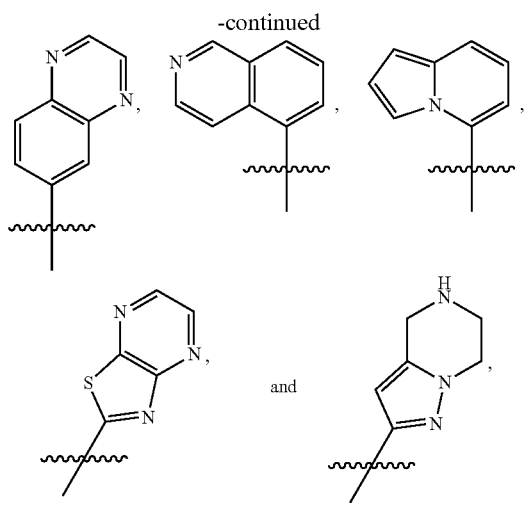

and wherein the wavy line (∿∿) indicates the point of attachment to the carbon atom of the main formula (A), and wherein the depicted cycles may be optionally substituted with one, two, or three $Z^{1a}$;

$R^1$ is selected from, aryl, and heterocycle,
and wherein said, aryl, and heterocycle are optionally substituted with one, two, or three $Z^{1b}$;

$R^2$ is hydrogen;

$R^{12}$ is hydrogen;

$R^{15}$ is selected from hydrogen; $C_{1-6}$alkyl; and $C_{3-7}$cycloalkyl;

each $Z^{1a}$ and $Z^{1b}$ is independently selected from the group consisting of halogen, hydroxyl, —$OZ^2$, =O, —$S(=O)_2Z^3$, —$S(=O)_2NZ^4Z^5$, trifluoromethyl, trifluoromethoxy, —$NZ^4C(=O)Z^2$, cyano, $C(=O)OZ^2$, $C_{1-6}$ alkyl, heteroC$_{1-6}$ alkyl, aryl, and heterocycle;
and wherein said $C_{1-6}$ alkyl, aryl, and heterocycle are optionally substituted with one, two, or three substituents selected from $C_{1-6}$ alkyl, hydroxyl, =O, halogen, trifluoromethyl, —$OCF_3$, and —$C(O)OH$;

each $Z^2$ is $C_{1-6}$ alkyl;

each $Z^3$ is independently selected from hydroxyl, and $C_{1-6}$alkyl;

each $Z^4$ and $Z^5$ is independently selected from hydrogen, and $C_{1-6}$alkyl;

or an isomer, solvate, or salt thereof;

wherein the term "heterocycle" as used herein means a saturated, unsaturated or aromatic ring system of 3 to 18 atoms including at least one N, O, or S.

2. A pharmaceutical composition comprising a pharmaceutically acceptable carrier, and as active ingredient an effective amount of the compound according to claim 1 or a pharmaceutically acceptable salt thereof.

3. The compound of claim 1, wherein the compound has structure according to formula (E1)

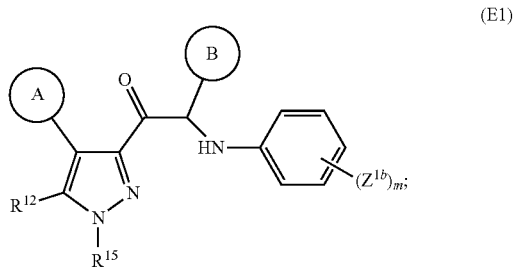

wherein each of cycle A, cycle B, $R^{12}$, $R^{15}$ and $Z^{1b}$ is as described for formula (A) in claim 1.

4. The compound of claim 1, wherein the isomer is a stereo-isomer or a tautomer.

5. The compound of claim 1, wherein the salt is a pharmaceutically acceptable salt.

* * * * *